United States Patent
Hirvelae et al.

(10) Patent No.: US 7,524,853 B2
(45) Date of Patent: *Apr. 28, 2009

(54) COMPOUNDS AND THEIR USE IN THERAPY

(75) Inventors: Leena Hirvelae, Oulu (FI); Nina Johansson, Turku (FI); Pasi Koskimies, Turku (FI); Olli Taneli Pentikaeinen, Lieto (FI); Tommi Nyroenen, Helsinki (FI); Tiina Annamaria Salminen, Koski (FI); Mark Stuart Johnson, Turku (FI); Pekka Lehtovuori, Espoo (FI); Pauli Saarenketo, Piikkioe (FI); Bartholomeus Johannes Van Steen, Utrecht (NL); Heinrich-Hubert Thole, Hannover (DE); Mikko Unkila, Kaarina (FI); Josef Messinger, Sehnde (DE); Johanna Kiviniemi, Turku (FI); Lila Pirkkala, Turku (FI); Bettina Husen, Hannover (DE)

(73) Assignees: Solvay Pharmaceuticals B.V., Weesp (NL); Solvay Pharmaceuticals GmbH, Hannover (DE)

( * ) Notice: Subject to any disclaimer, the term of this patent is extended or adjusted under 35 U.S.C. 154(b) by 315 days.

This patent is subject to a terminal disclaimer.

(21) Appl. No.: 11/011,744

(22) Filed: Dec. 15, 2004

(65) Prior Publication Data

US 2005/0176742 A1    Aug. 11, 2005

Related U.S. Application Data

(63) Continuation-in-part of application No. 10/861,907, filed on Jun. 7, 2004.

(60) Provisional application No. 60/477,047, filed on Jun. 10, 2003.

(30) Foreign Application Priority Data

Dec. 13, 2004    (WO) ................ PCT/EP2004/053424

(51) Int. Cl.
| | |
|---|---|
| A01N 43/54 | (2006.01) |
| A61K 31/505 | (2006.01) |
| C07D 239/00 | (2006.01) |
| C07D 471/00 | (2006.01) |
| C07D 487/00 | (2006.01) |
| C07D 491/00 | (2006.01) |

(52) U.S. Cl. ...................................... 514/267; 544/250
(58) Field of Classification Search ................ 549/43; 514/712, 708, 709, 267; 544/251, 250
See application file for complete search history.

(56) References Cited

U.S. PATENT DOCUMENTS 5,597,823 A  *  1/1997  Meyer et al. ................. 514/250

FOREIGN PATENT DOCUMENTS

| WO | WO 96/22992 A1 | 8/1996 |
| WO | WO 03/017973 | 3/2003 |
| WO | WO 03/022835 | 3/2003 |
| WO | WO 2004/080271 A2 | 9/2004 |
| WO | WO 2004/110459 A1 | 12/2004 |
| WO | WO 2005/032527 A2 | 4/2005 |

OTHER PUBLICATIONS

Manhas, et al., Heterocyclic Compounds. 4. Synthesis and Antiinflammatory Activity of Some Substituted Thienopyrimidones, Journal of Medicinal Chemistry, pp. 106-107, vol. 15, No. 1 (1971).*
Manhas, et al., Heterocyclic Compounds. VI. Synthesis of Polynuclear Thienopyrimidine Derivatives (1), J. Heterocyclic Chemistry, 13, 903 (1976).*
Shishoo, C.J., et al., Studies on the Synthesis of 2-(2-Arylvinyl)thieno[2,3-d]pyrimidines and 5-(2-Arylvinyl)triazolothieno[3,2-e]pyrimidines, J. Heterocyclic Chem., 22 825 (1985).*
Smith et al., Inhibitors of Steroidogenesis as Agents for the Treatment of Hormone-dependent Cancers, Expert Opinion on Therapeutic Patents, vol. 11(5), pp. 789-824 (2001).*
Manhas, et al., Heterocyclic Compounds. 4. Synthesis and Antiinflammatory Activity of Some Substituted Thienopyrimidones, Journal of Medicinal Chemistry, pp. 106-107, vol. 15, No. 1 (1971).*
Manhas, et al., Heterocyclic Compounds. 4. Synthesis and Antiinflammatory Activity of Some Substituted Thienopyrimidones, Journal of Medicinal Chemistry, pp. 106-107, vol. 15, No. 1 (1971).*
Bulun, et al., "Estrogen biosynthesis in endometriosis; molecular basis and clinical relevance," *J. Molecular Endocrinology*, 25:35-42 (2000).
Chetrie, et al., "The selective estrogen enzyme modulator (SEEM) in breast cancer," *J. Steroid Biochem. & Molecular Biol.*, 76:95-104 (2001).
Zeitoun, et al., "Aromatase: a key molecule in the pathophysiology of endometriosis and a therapeutic target," *Fertility and Sterility*, 72(6):961-969 (1999).

* cited by examiner

*Primary Examiner*—James O Wilson
*Assistant Examiner*—Erich A Leeser
(74) *Attorney, Agent, or Firm*—Crowell & Moring LLP

(57) ABSTRACT

Thiophenepyrimidinone compounds and their use in therapy, especially for use in the treatment and/or prevention of a steroid hormone dependent diseases or disorders, such as steroid hormone dependent diseases or disorders requiring inhibition of 17β-hydroxysteroid dehydrogenase enzymes.

40 Claims, No Drawings

COMPOUNDS AND THEIR USE IN THERAPY

CROSS REFERENCE TO RELATED APPLICATION

This application claims priority from the international patent application PCT/EP 2004/053424, filed Dec. 13, 2004 and is a continuation-in-part of U.S. patent application Ser. No. 10/861,907, filed Jun. 7, 2004, which claimed priority from U.S. provisional patent application No. 60/477,047, filed Jun. 10, 2003.

FIELD OF THE INVENTION

The present invention relates to novel substituted thiophenepyrimidinone derivatives which represent inhibitory compounds of the 17β-hydroxysteroid dehydrogenase enzymes, preferably of the 17β-hydroxysteroid dehydrogenase type 1 (17β-HSD1), type 2 (17β-HSD2) or type 3 (17β-HSD3) enzyme, to their salts, to pharmaceutical preparations containing these compounds and to processes for the preparation of these compounds. Furthermore, the invention concerns the therapeutic use of said thiophenepyrimidinone derivatives, particularly their use in the treatment or prevention of steroid hormone dependent diseases or disorders, such as steroid hormone dependent diseases or disorders requiring the inhibition of 17β-hydroxysteroid dehydrogenase enzymes, in particular 17β-HSD type I enzymes, and/or requiring the modulation of the endogenous 17β-estradiol and/or testosterone concentration.

BACKGROUND OF THE INVENTION

The publications and other materials used herein to illuminate the background of the invention, and in particular, cases to provide additional details respecting the practice, are incorporated by reference.

Mammalian 17β-Hydroxysteroid dehydrogenases (17β-HSDs) are NAD(H) or NADP(H) dependent enzymes which catalyze—besides other reactions—the final steps in male and female sex hormone biosynthesis. These enzymes convert inactive 17-keto-steroids into their active 17β-hydroxy-forms or catalyze the oxidation of the 17β-hydroxy-forms into the 17-keto-steroids. Because both estrogens and androgens have the highest affinity for their receptors in the 17β-hydroxy form, 17β-HSD enzymes play an essential role in the tissue-selective regulation of the activity of sex steroid hormones.

At present, 10 human members of the 17β-HSD enzyme family have been described (types 1-5, 7, 8, 10, 11 and 12). The human 17β-HSD family members share less than 30% similarity in their primary structure. The 17β-HSDs are expressed in distinct, though in some cases, overlapping patterns. The different types of 17β-HSDs also differ in their substrate and cofactor specificities. In intact cells in culture, the 17β-HSDs catalyze the reaction in a unidirectional way: types 1, 3, 5 and 7 use NADP(H) as a cofactor and catalyze the reductive reaction (activation), while types 2, 4, 8 and 10 catalyze the oxidative reaction (inactivation) using NAD(H) as a cofactor. [see e.g. Labrie et al. (2000) Trends Endocrinol Metab., 11:421-7].

Due to their essential role in the tissue-selective regulation of the activity of sex steroid hormones 17β-HSDs can be involved in the occurrence and development of estrogen-sensitive pathologies (f. ex. breast, ovarian, uterine and endometrium cancers etc.) and androgen-sensitive pathologies (f. ex. prostate cancer, benign prostatic hyperplasia, acne, hirsutism, etc). Furthermore, many types of 17β-HSD have been shown to be involved in the pathogenesis of particular human disorders. For example, 17β-HSD3 is known to be involved in the development of pseudohermaphroditism, the 17β-HSD8 plays a role in polycystic kidney disease and the 17β-HSD4 is related to the occurrence of bifunctional enzyme deficiency. Therefore treatment of sex steroid-sensitive diseases by administration of specific inhibitors of the 17β-HSDs enzymes have been suggested, optionally in combination with potent and specific antiestrogens and antiandrogens [Labrie F et al. (1997) Steroids, 62:148-58].

Due to the fact that each type of 17β-HSD has a selective substrate affinity, directional (reductive or oxidative) activity in intact cells, and a particular tissue distribution, the selectivity of drug action could be achieved by targeting a particular 17β-HSD isozyme. By individual modulation of the particular 17β-HSDs it is possible to influence or even control the local and paracrine concentration of estrogens and androgens in different target tissues.

The best characterized member of the 17β-HSD family is the type 1 17β-HSD [EC 1.1.1.62]. This enzyme could be crystallized in different states of functionality (e.g. with and without ligand and/or co-factor). The 17β-HSD1 catalyzes in vitro the reduction as well as the oxidation between estrone (E1) and estradiol (E2). However, under physiological in vivo conditions the enzyme only catalyzes the reductive reaction from the estrone (E1) to the estradiol (E2). The 17β-HSD1 was found to be expressed in a variety of hormone-dependent tissues, e.g. placenta, mammary gland tissue or uterus and endometrium tissue, respectively. Estradiol itself is, especially in comparison to the significantly less active estrone, a very potent hormone, which regulates the expression of a variety of genes by binding to the nuclear estrogen receptor and plays an essential role in the proliferation and differentiation of the target cell. Physiological as well as pathological cell proliferations can be estradiol dependent. Especially many breast cancer cells are stimulated by a locally raised estradiol concentration. Furthermore, the occurrence or course of benign pathologies such as endometriosis, uterine leiomyomas (fibroids or myomas), adenomyosis, menorrhagia, metrorrhagia and dysmenorrhea is dependent from the existence of significantly high estradiol levels.

Endometriosis is a well-known gynaecological disorder that affects 10 to 15% of women in the reproductive age. It is a benign disease defined as the presence of viable endometrial gland and stroma cells outside the uterine cavity. It is most frequently found in the pelvic area. In women developing endometriosis, the endometrial cells entering the peritoneal cavity by retrograde menstruation (the most likely mechanism) have the capacity to adhere to and invade the peritoneal lining, and are then able to implant and grow. The implants respond to steroid hormones of the menstrual cycle in a similar way as the endometrium in the uterus. The infiltrating lesions and the blood from these lesions which are unable to leave the body cause inflammation of the surrounding tissue. The most common symptoms of endometriosis are dysmenorrhoea, dyspareunia and (chronic) abdominal pain. The occurrence of these symptoms is not related to the extent of the lesions. Some women with severe endometriosis are asymptomatic, while women with mild endometriosis may have severe pain. Endometriosis is found in up to 50% of the women with infertility. However, currently no causal relation has been proven between mild endometriosis and infertility. Moderate to severe endometriosis can cause tubal damage and adhesions leading to infertility. The aims of treatment of endometriosis are pain relief, resolution of the endometriotic tissue and restoration of fertility (if desired). The two common treatments are surgery or anti-inflammatory and/or hormonal therapy or a combination thereof.

Uterine leiomyomas (fibroids or myomas), benign clonal tumours, arise from smooth muscle cells of the human uterus. They are clinically apparent in up to 25% of women and are the single, most common indication for hysterectomy. They cause significant morbidity, including prolonged and heavy menstrual bleeding, pelvic pressure and pain, urinary problems, and, in rare cases, reproductive dysfunction. The pathophysiology of myomas is not well understood. Myomas are found submucosally (beneath the endometrium), intramurally (within the myometrium) and subserosally (projecting out of the serosal compartment of the uterus), but mostly are mixed forms of these 3 different types. The presence of estrogen receptors in leiomyoma cells has been studied by Tamaya et al. [Tamaya et al. (1985) Acta Obstet Gynecol Scand., 64:307-9]. They have shown that the ratios of estrogen receptor compared to progesterone and androgen receptor levels were higher in leiomyomas than in the corresponding normal myometrium. Surgery has long been the main treatment for myomas. Furthermore, medical therapies that have been proposed to treat myomas include administration of a variety of steroids such as the androgenic steroids danazol or gestrinone, GnRH agonists and progestogens, whereby the administration is often associated a variety of serious side-effects.

Everything that has been said above in relation to the treatment of uterine leiomyomas and endometriosis equally applies to other benign gynaecological disorders, notably adenomyosis, functional menorrhagia and metrorrhagia. These benign gynaecological disorders are all estrogen sensitive and are treated in a comparable way as described herein before in relation to uterine leiomyomas and endometriosis. The available pharmaceutical treatments, however, suffer from the same major drawbacks, i.e. they have to be discontinued once the side-effects become more serious than the symptoms to be treated and symptoms reappear after discontinuation of the therapy.

Since the aforementioned malign and benign pathologies are all 17β-estradiol dependent, a reduction of the endogenous 17β-estradiol concentration in the respective tissue will result in an impaired or reduced proliferation of 17β-estradiol cells in said tissues. Therefore, it may be concluded that selective inhibitors of the 17β-HSD1 enzyme are well suited for their use to impair endogenous productions of estrogens, in particular of 17β-estradiol, in myomas, endometriotic, a adenomyotic and endometrial tissue. The application of a compound acting as selective inhibitor on the 17β-HSD1 which preferentially catalyzes the reductive reaction will result in a lowered intracellular estradiol-concentration since the reductive conversion of the estrone into the active estradiol is reduced or suppressed. Therefore, reversible or even irreversible inhibitors of the 17β-HSD1 may play a significant role in the prophylaxis and/or treatment of steroid-hormone, in particular 17β-estradiol, dependent disorders or diseases. Furthermore, the reversible or even irreversible inhibitors of the 17β-HSD1 should have no or only pure antagonistic binding activities to the estradiol receptor, in particular to the estrogen receptor α subtype, since agonistic binding of the estrogen receptor would lead to activation and therefore—by regulation of a variety of genes—to the proliferation and differentiation of the target cell. In contrast, antagonists of the estrogen receptor, so called anti-estrogens, bind competitively to the specific receptor protein thus preventing access of endogenous estrogens to their specific binding site. At present it is described in the literature that several malignant disease as breast cancer, prostate carcinoma, ovarian cancer, uterine cancer, endometrial cancer and endometrial hyperplasia may be treated by the administration of a selective 17β-HSD1 inhibitor. Furthermore, a selective 17β-HSD1 inhibitor may be useful for the prevention of the aforementioned hormone-dependent cancers, especially breast cancer.

Several reversible or irreversible inhibitors of the 17β-HSD1 enzyme of steroidal and even non-steroidal origin are already known from the literature. The characteristics of these inhibitory molecules, which mainly have a substrate or cofactor-like core structure, have been reported in the literature [reviewed in: Poirier D. (2003) Curr Med Chem. 10:453-77]. The recently published international application WO 2004/085457 discloses a variety of estron derivatives with different subsituents in C3, C6, C16 and/or C17 position as potent 17β-HSD1 inhibitors].

A further well characterized member of the 17β-HSD family is the 17β-HSD type 3 enzyme (17β-HSD3). The 17β-HSD3 has a distinct feature compared to other 17HSDs: it is found to be expressed almost exclusively in the testis, whereas the other isoenzymes are expressed more widely in several tissues. 17β-HSD3 has a crucial role in androgen biosynthesis. It converts 4-androstene-3,17-one (A) to testosterone (T). The biological significance of the 17β-HSD3 is of undeniable physiological importance. Mutations in the gene for 17β-HSD3 have found to lead to decreased T formation in the fetal testis and consequently to a human intersex disorder termed male pseudohermaphroditism [Geissler W M et al. (1994) Nat Genet., 7:34-9].

With regard to the indication prostate cancer, the primary cancer cells mostly retain their responsiveness to androgens in their regulation of proliferation, differentiation, and programmed cell death for some period. At present, androgen deprivation is the only effective systemic hormonal therapy available for prostate cancer. The development of selective inhibitors against 17β-HSD3 is a new therapeutic approach for the treatment of androgen dependent disease [Labrie et al. (2000) Trends Endocrinol Metab., 11:421-7]. Furthermore, Oefelein et al. reported that the depot GnRH analogue fails, in nearly 20% of cases, to achieve castrate levels of T in men [Oefelein M G & Cornum R (2000) J Urol.; 164:726-9]. In order to improve the response rate to endocrine therapy for men with prostate cancer it may be important to selectively inhibit testicular 17β-HSD3 activity. Besides prostate cancer, many other androgen-sensitive diseases, i.e. diseases whose onset or progress is aided by androgenic activity, may be treated by selectively inhibiting 17β-HSD3 activity. These diseases include but are not limited to benign prostatic hyperplasia, prostatitis, acne, seborrhea, hirsutism, androgenic alopecia, precocious puberty, adrenal hyperplasia, and polycystic ovarian syndrome. Furthermore, considering the fact that 17β-HSD3 is found mainly in the testis, the development of potent inhibitors could be of interest for blocking spermatogenesis and as an anti-fertility agent for males.

Several reversible or irreversible inhibitors of the 17β-HSD3 enzymes of steroidal and even non-steroidal origin are already known from the literature. The characteristics of these inhibitory molecules have been reported in the literature [reviewed in: Poirier D. (2003) Curr Med Chem. 10:453-77]. For example, U.S. Pat. No. 6,541,463 discloses androsterone derived inhibitors for 17β-HSD3. These derivatives have been synthesised by parallel solid- and liquid-phase chemistry and some of these compounds showed 2 to 18-fold higher inhibition activity than that of the natural substrate of the enzyme, A-dione, used itself as a inhibitor. Furthermore, the international patent application WO 01/42181 discloses benzyl-tetralins, the chemical structure of which is related to that of the phytoestrogen biochanin, as 17β-HSD3 inhibitors. Furthermore, international patent applications WO 98/32724, WO 98/30556 and WO 99/12540 disclose tetralone, benzopyrane and benzofuranone derivatives, which have a 17β-HSD inhibitory activity, for the treatment of hormone sensitive diseases.

Microsomal 17β-hydroxysteroid dehydrogenase of human endometrium and placenta (designated 17β-HSD type 2 or 17β-HSD2) was cloned by expression cloning, and found to be equally active using androgens and estrogens as substrates for oxidation [Andersson S. (1995) J. Steroid Biochem. Molec. Biol., 55:533-534]. The recombinant 17β-HSD2 converts the highly active 17β-hydroxysteroids such as estradiol (E2), testosterone (T), and dehydrotestosterone (DHT) to their inactive keto forms. In addition, the 17β-HSD2 can, to a lesser extent, also convert 20β-hydroxyprogesterone (20βP) to progesterone (P). The broad tissue distribution together with the predominant oxidative activity of 17β-HSD2 suggest that the enzyme may play an essential role in the inactivation of highly active 17β-hydroxysteroids, resulting in diminished sex hormone action in target tissues. Dong and colleagues showed significant 17β-HSD2 activity in cultured human osteoblasts and osteoblast-like osteosarcoma cells MG63 and TE85, but not in SaOS-2 [Dong Y et al. (1998) J. Bone Min. Res., 13:1539-1546]. The potential for interconversion of E1 to E2, T to A, and DHT to A by bone cells could therefore represent important mechanism for the local regulation of intracellular ligand supply for the estrogen and androgen receptors in the osteoblasts and other steroid sensitive cells. This modulation of steroid levels may be employed for a wide variety of indications, including the following: for the prevention and treatment of osteoporosis, for the treatment of ovarian cancer, for the treatment of breast cancer, for the treatment of endometrial cancer, for the treatment of endometriosis, for the treatment of prostate cancer and/or for the treatment of androgen-dependent hair-loss.

Several reversible or irreversible inhibitors of the 17β-HSD2 enzymes of steroidal and even non-steroidal origin are already known from the literature. The characteristics of these inhibitory molecules have been reported in the literature [reviewed in: Poirier D. (2003) Curr Med Chem. 10:453-77]. In addition, the international patent application WO 02/26706 discloses 17β-HSD2 inhibitors of non-steroidal origin.

Some thienopyrimidinones derivatives that are described as being useful in therapy have already been disclosed in the literature: The Japanese patent publication JP48042271 B (Yoshitomi Pharmaceutical industries Ltd.) disclose compounds useful as central nervous depressants and anti-inflammatory agents. The U.S. Pat. No. 5,597,823 (Abbott Laboratories, Inc.) describes adrenergic antagonist useful in the treatment of benign prostate hyperplasia. The Japanese patent application JP62132884 (Mitsubishi Chem. Ind. Ltd.) discloses Benzylthienopyrimidinones useful as cardiovascular agents. Manhas et al describe the synthesis and antiinflammatory activity of some substituted thienopyrimidinones [Manhas MS et al. (1972) J Med Chem. 15(1):106-7]. Gadad et al. describe the synthesis and antihyperlipaemic activity of some 2-aminomethyl-3-aryl-5,6,7,8-tetrahydrobenzo(b)/5,6-dimethylthieno (2,3-d)-pyrimidin-4-ones [Gadad AK et al. (1996) Arzneimittelforschung. 46(10):981-5]. Manjunath et al. describe the synthesis and evaluation of 2-chloromethyl-3-N-substituted arylthieno(2,3-d)pyrimidin-4-ones and derivatives for central nervous system depressant activity [Manjunath K S et al. (1997) Arzneimittelforschung. 47(9):1005-8].

Furthermore, several other thienopyrimidinones derivatives have been described but were not related to any medical use so far. For example, the compounds (3-Benzyl-7-tert-butyl-4-oxo-3,4,5,6,7,8-hexahydro-benzo[4,5]thieno[2,3-d]pyrimidin-2-yl)-acetic acid methyl ester (CAS reg. no 423749-31-9) and 2,3-Dibenzyl-7-tert-butyl-5,6,7,8-tetrahydro-3H-benzo[4,5]thieno[2,3-d]pyrimidin-4-one (CAS reg. no 372974-51-1) are commercially available.

However, according to the inventors' knowledge none of the already known compounds described above has been described as useful in the treatment and/or prevention of a steroid hormone dependent disease or disorder, particularly a steroid hormone dependent disease or disorder requiring the inhibition of the 17β-hydroxysteroid dehydrogenase (17HSD) type 1, type 2 or type 3 enzyme.

In addition, closely related thienopyrimidinone derivatives are disclosed in unpublished international applications PCT/EP 2004/006230 and PCT/EP 2004/006231 being useful in the treatment and/or prevention of a steroid hormone dependent disease or disorder, particularly a steroid hormone dependent disease or disorder requiring the inhibition of the 17β-hydroxysteroid dehydrogenase (17HSD) type 1, type 2 or type 3 enzyme. However, at least some of these compounds are quite insoluble and have difficulties in membrane permeability.

As a consequence, there is still a need for the development of improved compounds that are selectively inhibiting the 17β-HSD1, 17β-HSD3 and/or 17β-HSD2 enzyme, while desirably failing to inhibit substantially other members of the 17β-HSD protein family, or other catalysts of sex steroid degradation or activation. In particular, it is an aim of the present invention to develop selective inhibitors of the 17β-HSD1 enzyme, whereby in addition the compounds have no or only pure antagonistic binding affinities to the estrogen receptor (both subtypes α and β).

SUMMARY OF THE INVENTION

Therefore, it is an object of the present invention to develop novel inhibitors of the 17β-HSD1 and 17β-HSD2 enzyme, which have valuable pharmacological properties and which are suited for the treatment of estrogen dependent diseases and disorders. It is a further object of the present invention to develop novel inhibitors of the 17β-HSD3 enzyme, which have valuable pharmacological properties and which are suited for the treatment of androgen dependent diseases and disorders.

It has now been found that the thiophenepyrimidinone derivatives of the present invention would be valuable in therapy, especially in the treatment or prevention of steroid hormone dependent diseases or disorders, such as steroid hormone dependent diseases or disorders requiring the inhibition of 17β-hydroxysteroid dehydrogenase (HSD) enzymes. In particular, compounds of formula (I) represent potent inhibitors of the 17β-HSD1, 17β-HSD3 and/or 17β-HSD2 enzyme and possess valuable pharmacological properties for the treatment and/or prophylaxis of malignant steroid dependent diseases or disorders such as breast cancer, prostate carcinoma, ovarian cancer, uterine cancer, endometrial cancer and endometrial hyperplasia, but also for the treatment and/or prophylaxis of benign steroid dependent diseases or disorders such as endometriosis, uterine fibroids, uterine leiomyoma, adenomyosis, dysmenorrhea, menorrhagia, metrorrhagia, prostadynia, benign prostatic hyperplasia, prostatitis, acne, seborrhea, hirsutism, androgenic alopecia, precocious puberty, adrenal hyperplasia, polycystic ovarian syndrome, or urinary dysfunction. Further estrogen-dependent diseases which may be treated and/or prevented with an effective amount of a compound of the invention are multiple sclerosis, rheumatoid arthritis, Alzheimer's disease, colon cancer, tissue wounds, skin wrinkles and cataracts. Furthermore, compounds of formula (I) may be useful for the prevention and treatment of osteoporosis, and for blocking spermatogenesis and as an anti-fertility agent for males.

Accordingly, the present invention relates to the use of a compound having the structural formula (I)

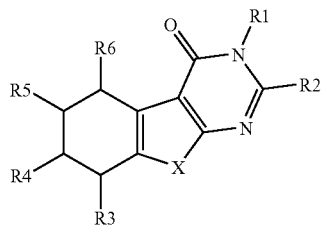

(I)

wherein
X is S, SO or $SO_2$
R1 and R2 are individually selected from the group consisting of alkyl, substituted alkyl, aryl, substituted aryl, heteroaryl, substituted heteroaryl, cycloheteroalkyl, substituted cycloheteroalkyl, eroalkyl, arylalkyl, substituted arylalkyl, heteroarylalkyl, substituted heteroarylalkyl, cycloheteroalkyl-alkyl, substituted cycloheteroalkyl-alkyl,
or R2 itself may be independently selected from acyl, carboxyl, or amido,
whereby R1 and R2 cannot be simultaneously unsubstituted alkyl,
the hydrocarbon chain —C(R3)-C(R4)-C(R5)-C(R6)- of the six-membered ring is saturated or contains one or two double bonds between the carbon atoms;
R3 and R4 are individually selected from the group consisting of hydrogen, oxo, halogen or dihalogen, acyl, alkyl, substituted alkyl, hydroxyl, carboxyl, amido, amino, nitrile, thio, alkoxy, acyloxy, aryloxy, alkylthio and arylthio; and
R5 and R6 are individually selected from the group consisting of hydrogen, halogen, alkyl, substituted alkyl, arylalkyl, substituted arylalkyl, hydroxyl, alkoxy, aryloxy, acyl or carboxyl,
or a pharmaceutically acceptable salt thereof,
for the manufacture of a medicament for the treatment and/or prevention of a steroid hormone dependent disease or disorder, preferably for a steroid hormone dependent disease or disorder requiring the inhibition of a 17β-hydroxysteroid dehydrogenase (17β-HSD) enzyme, most preferably requiring the inhibition of the 17β-HSD type 1, 17β-HSD type 2 or 17β-HSD type 3 enzyme.

According to another aspect, the invention concerns a compound of formula (I)

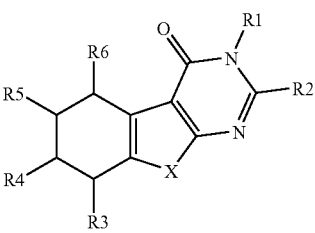

(I)

wherein
X is S, SO or $SO_2$
R1 and R2 are individually selected from the group consisting of alkyl, substituted alkyl, aryl, substituted aryl, heteroaryl, substituted heteroaryl, cycloheteroalkyl, substituted cycloheteroalkyl, arylalkyl, substituted arylalkyl, heteroarylalkyl, substituted heteroarylalkyl, cycloheteroalkyl-alkyl, substituted cycloheteroalkyl-alkyl,
or R2 itself may be independently selected from acyl, carboxyl, or amido,
whereby R1 and R2 cannot be simultaneously unsubstituted alkyl, and
whereby R2 has to be different from methyl if all substituents R3, R5 and R6 simultaneously represent hydrogen and R4 represents hydrogen or methyl;
R3 and R4 are individually selected from the group consisting of hydrogen, oxo, halogen or dihalogen, acyl, alkyl, substituted alkyl, hydroxyl, carboxyl, amido, amino, nitrile, thio, alkoxy, acyloxy, aryloxy, alkylthio and arylthio;
R5 and R6 are individually selected from the group consisting of hydrogen, halogen, alkyl, substituted alkyl, arylalkyl, substituted arylalkyl, hydroxyl, alkoxy, aryloxy, acyl or carboxyl, and
the hydrocarbon chain —C(R3)-C(R4)-C(R5)-C(R6)- of the six-membered ring is saturated or contains one or two double bonds between the carbon atoms;
whereby the six-membered ring comprising the hydrocarbon chain —C(R3)-C(R4)-C(R5)-C(R6)- has to be an aromatic ring if all the substituents R3, R4, R5 and R6 are simultaneously hydrogen;
or a pharmaceutically acceptable salt thereof,
for use in therapy.

According to a third aspect, the invention concerns a novel compound of formula (I)

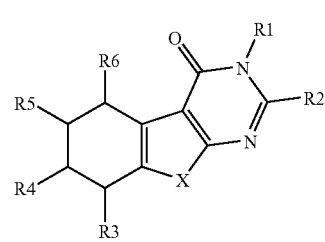

(I)

wherein
X is S, SO or $SO_2$
R1 and R2 are individually selected from the group consisting of alkyl, substituted alkyl, aryl, substituted aryl, heteroaryl, substituted heteroaryl, cycloheteroalkyl, substituted cycloheteroalkyl, arylalkyl, substituted arylalkyl, heteroarylalkyl, substituted heteroarylalkyl, cycloheteroalkyl-alkyl, substituted cycloheteroalkyl-alkyl,
or R2 itself may be independently selected from acyl, carboxyl, or amido,
whereby R1 and R2 cannot be simultaneously unsubstituted alkyl, and
whereby R2 has to be different from methyl if all substituents R3, R5 and R6 simultaneously represent hydrogen and R4 represents hydrogen or methyl;
R3 and R4 are individually selected from the group consisting of hydrogen, oxo, halogen or dihalogen, acyl, alkyl, substituted alkyl, hydroxyl, carboxyl, amido, amino, nitrile, thio, alkoxy, acyloxy, aryloxy, alkylthio and arylthio;

R5 and R6 are individually selected from the group consisting of hydrogen, halogen, alkyl, substituted alkyl, arylalkyl, substituted arylalkyl, hydroxyl, alkoxy, aryloxy, acyl or carboxyl; and the hydrocarbon chain —C(R3)-C(R4)-C(R5)-C(R6)- of the six-membered ring is saturated or contains one or two double bonds between the carbon atoms;

whereby the six membered ring comprising the hydrocarbon chain —C(R3)-C(R4)-C(R5)-C(R6)- has to be an aromatic ring if all the substituents R3, R4, R5 and R6 are simultaneously hydrogen;

or a pharmaceutically acceptable salt thereof, under the proviso that said compound is not (3-Benzyl-7-tert-butyl-4-oxo-3,4,5,6,7,8-hexahydro-benzo[4,5]thieno[2,3-d]pyrimidin-2-yl)-acetic acid methyl ester or 2,3-Dibenzyl-7-tert-butyl-5,6,7,8-tetrahydro-3H-benzo[4,5]thieno[2,3-d]pyrimidin-4-one.

According to a fourth aspect, the invention concerns a pharmaceutical composition comprising as active agent a compound of formula (I) as defined herein, for which no use in therapy earlier has been disclosed, and at least a pharmaceutically acceptable carrier.

According to a fifth aspect, the invention concerns the use of a compound of formula (I) as defined herein for the treatment or prevention of a steroid hormone dependent disease or disorder. Preferably, the steroid hormone dependent disease or disorder is a disease or disorder requiring the inhibition of a 17β-hydroxysteroid dehydrogenase enzyme, preferably of the 17β-HSD type 1, 17β-HSD type 2 or 17β-HSD type 3.

DETAILED DESCRIPTION

Definitions

The following terms are used to describe various constituents of the chemical composition useful in this invention. The terms are defined as follows:

As used herein, the terms "comprising" and "including" are used herein in their open, non-limiting sense.

The word "compound" shall here be understood to cover any and all isomers (e. g., enantiomers, stereoisomers, diastereomers, rotomers, and tautomers), racemates or any mixture of isomers, prodrugs, and any pharmaceutically acceptable salt of said compound.

Where the plural form is used for compounds, salts, and the like, this is taken to mean also a single compound, salt, or the like.

The term "substituted" means that the specified group or moiety bears one or more substituents. Where any group may carry multiple substituents and a variety of possible substituents is provided, the substituents are independently selected and need not be the same. The term "unsubstituted" means that the specified group bears no substituents. The term "optionally substituted" means that the specified group is unsubstituted or substituted by one or more substituents.

Any asymmetric carbon atoms may be present in the (R)-, (S)- or (R,S)-configuration, preferably in the (R)- or (S)-configuration, whichever is most active. Substituents at a double bond or a ring may be present in cis- (.=Z-) or trans (=E-) form.

The compounds of the present invention may contain asymmetric centers on the molecule, depending upon the nature of the various substituents. In certain instances, asymmetry may also be present due to restricted rotation about the central bond adjoining the two aromatic rings of the specified compounds. It is intended that all isomers (including enantiomers and diastereomers), either by nature of asymmetric centers or by restricted rotation as described above, as separated, pure or partially purified isomers or racemic mixtures thereof, be included within the ambit of the instant invention.

The term "halogen" refers to fluorine (F, Fluoro-), bromine (Br, Bromo-), chlorine (Cl, Chloro), and iodine (J, Iodo-) atoms. Preferred in the context of the present invention are Br, Cl and F.

The terms "dihalogen", "trihalogen" and "perhalogen" refer to two, three and four substituents, respectively, each individually selected from the group consisting of fluorine, bromine, chlorine, and iodine atoms.

The term "hydroxyl" refers to the group —OH
The term "oxo" refers to the group =O
The term "thio" refers to the group =S
The term "thiol" refers to the group —SH
The term "sulfonyl" refers to the group —S(O)$_{1-2}$—
The term "sulfamoyl" refers to the group —SO$_2$—NH$_2$
The term "nitro" refers to the group —NO$_2$
The term "nitrile" or "cyano" refers to the group —CN For the purpose of the present invention, the carbon content of various hydrocarbon containing moieties is indicated by a prefix designating the minimum and maximum number of carbon atoms in the moiety, i.e., the prefix $C_i$-$C_j$ defines the number of carbon atoms present from the integer "i" to the integer "j" inclusive. Thus $C_1$-$C_4$-alkyl refers to alkyl of 1-4 carbon atoms, inclusive, or methyl, ethyl, propyl, butyl and isomeric forms thereof.

The term "alkyl" stands for a hydrocarbon radical which may be linear, cyclic or branched, with single or multiple branching, whereby the alkyl group comprises 1 to 12 carbon atoms. In one embodiment, the term "alkyl" stands for a linear or branched (with single or multiple branching) alkyl chain of 1 to 8 carbon atoms, exemplified by the term ($C_1$-$C_8$)alkyl, more preferably of 1 to 4 carbon atoms exemplified by the term ($C_1$-$C_4$)alkyl. The term ($C_1$-$C_8$)alkyl is further exemplified by such groups as methyl; ethyl; n-propyl; isopropyl; n-butyl; sec-butyl; isobutyl; tert-butyl; n-pentyl; isopentyl; neopentyl; tert-pentyl; 2- or 3-methylpentyl; n-hexyl; isohexyl, and the like. The alkyl group may be partially unsaturated, forming such groups as, for example, propenyl (allyl), methyl-propenyl, butenyl, pentenyl, pentinyl, hexenyl, octadienyl, and the like. The term "alkyl" further comprises cycloalkyl groups, preferably cyclo($C_3$-$C_8$)alkyl which refers to cyclopropyl, cyclobutyl, cyclopentyl, cyclohexyl, cycloheptyl, cyclooctyl and isomeric forms thereof such as methylcyclopropyl; 2- or 3-methylcyclobutyl; 2-, or 3-methylcyclopentyl, and the like. The cycloalkyl group may also be partly unsaturated, forming such groups as, for example, cyclohexenyl, cyclopentenyl, cyclooctadienyl, and the like. Furthermore, the term "alkyl" comprises a cycloalkyl-alkyl group comprising 4 to 12 carbon atoms, preferably "cyclo($C_3$-$C_8$)alkyl-($C_1$-$C_4$)alkyl" which refers to a alkyl group of 1 to 4 carbon atoms as described above substituted with a cyclo($C_3$-$C_8$)alkyl group as described above, forming such groups as for example cyclopropylmethyl, cyclohexylmethyl, cyclopentylethyl or cyclohexenylethyl.

The term "substituted alkyl" refers to alkyl as just described and substituted by up to five, more preferably by up to three, most preferably by one or two substituents independently selected from the group consisting of halogen, hydroxyl, thiol, nitro, nitrile, alkoxy, aryloxy, acyloxy, amino, amido, acylamino, alkylthio, arylthio, acyl, carboxyl, sulfamoyl, sulfonamide, and alkylsulfonyl, as defined herein. These groups may be attached to any carbon atom of the alkyl moiety. Substituted alkyl is preferably substituted with hydroxyl, halogen, $C_1$-$C_4$-alkoxy, arylacyl, preferably phenylacyl, phenoxy, benzyloxy, $C_1$-$C_4$-alkylthio, an alkylamino group —NR"$_2$, a carboxyl group —(C=O)—OR", an alkylacyloxy group —O—CO—R, or a heteroaryl acyloxy group —O—CO-HetAr, wherein R" represents hydrogen or $C_1$-$C_4$-alkyl. Preferably substituted alkyl refers to substituted $C_1$-$C_4$-alkyl.

Halogenated alkyl, halogenated alkoxy and halogenated alkylthio are substituents in which the alkyl moieties (preferably ($C_1$-$C_6$)alkyl, more preferably ($C_1$-$C_4$)alkyl, and most preferably methyl) are substituted either partially or in full with halogens, generally with chlorine and/or fluorine. Preferred examples of such substituents are trifluoromethyl, trifluoromethoxy, trifluoromethylthio, dichloromethyl, pentafluoroethyl, dichloropropyl, fluoromethyl and difluoromethyl.

The term "alkoxy" refers to a group —OR, where R may be alkyl, arylalkyl, substituted arylalkyl, heteroarylalkyl or substituted heteroarylalkyl as defined herein, wherein the alkyl chain may be optionally further substituted as defined herein. Preferably, the term "alkoxy" refers to —O—($C_1$-$C_4$)alkyl (or ($C_1$-$C_4$)alkoxy), with the ($C_1$-$C_4$)alkyl group as defined above, or to —O—($C_1$-$C_4$)alkyl-phenyl, preferably benzoxy or phenethyloxy, optionally substituted in the aryl group with up to five independently selected substituents, in particular hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy; the number of said substituents being up to five for halogen, and up to three for any combination of said other substituents.

The term "aryloxy" refers to a group —OAr, where Ar may be aryl, substituted aryl, heteroaryl or substituted heteroaryl as defined herein. Preferably, Ar represents aryl as defined herein, which is optionally substituted in the aryl group with up to five independently selected substituents, in particular hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy; the number of said substituents being up to five for halogen, and up to three for any combination of said other substituents. Preferably, aryloxy refers to phenoxy, optionally substituted as defined above.

The term "acyloxy" refers to a group —O—CO—R, where R may be alkyl, arylalkyl, substituted arylalkyl, heteroarylalkyl, substituted heteroarylalkyl, aryl, substituted aryl, heteroaryl or substituted heteroaryl as defined herein, wherein the alkyl chain may be optionally further substituted as defined herein.

The term "alkylacyloxy" represents a preferred selection of the term "acyloxy" and refers to the group —O—CO—$C_1$-$C_{12}$-alkyl, preferably to —O—CO—$C_1$-$C_8$-alkyl, and most preferably to —O—CO—$C_1$-$C_4$-alkyl.

The term "arylacyloxy" represents a preferred selection of the term "acyloxy" and refers to the group —O—CO—Ar, wherein Ar represents aryl as defined herein, preferably phenyl, which is optionally substituted in the aryl group with up to five independently selected substituents, in particular hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy; the number of said substituents being up to five for halogen, and up to three for any combination of said other substituents The term "heteroaryl-acyloxy" represents a preferred selection of the term "acyloxy" and refers to the group —O—CO-HetAr, wherein HetAr represents heteroaryl as defined herein, preferably thienyl, furyl or pyridinyl.

The term "acyl" refers to a group —(C=O)—R, where R may be hydrogen, alkyl, aryl or aryl-($C_1$-$C_4$)-alkyl (both optionally substituted in the aryl group with independently selected substituents as defined herein), heteroaryl or heteroaryl-($C_1$-$C_4$)-alkyl (both optionally substituted in the heteroaryl group with up to three independently selected substituents as defined herein), as defined herein. Preferably, the term "acyl" refers to a group —(C=O)—R', where R' represents hydrogen, ($C_1$-$C_4$)alkyl, phenyl, or phenyl-($C_1$-$C_4$)alkyl, preferably benzyl.

The term "carbonyl" represents a preferred selection of the term "acyl" and refers to the group —CHO.

The term "alkylacyl" represents a preferred selection of the term "acyl" and refers to a group —(C=O)-alkyl, preferably —(C=O)($C_1$-$C_4$)alkyl.

The term "arylacyl" represents a preferred selection of the term "acyl" and refers to the group —CO—Ar, wherein Ar represents aryl as defined herein, preferably phenyl, which is optionally substituted in the aryl group as defined herein.

The term "heteroarylacyl" represents a preferred selection of the term "acyl" and refers to the group —CO-HetAr, wherein HetAr represents heteroaryl as defined herein, preferably thienyl, furyl or pyridinyl.

The term "carboxyl" refers to a group —(C=O)—OR, where R may be hydrogen, alkyl, substituted alkyl, aryl or aryl-($C_1$-$C_4$)-alkyl (both optionally substituted in the aryl group with independently selected substituents as defined herein), heteroaryl or heteroaryl-($C_1$-$C_4$)-alkyl (both optionally substituted in the heteroaryl group with independently selected substituents as defined herein), as defined herein. Preferably, the term "carboxyl" refers to a group —(C=O)—OR', where R' represents hydrogen, ($C_1$-$C_4$)alkyl, phenyl, or ($C_1$-$C_4$)alkyl-phenyl, preferably benzyl; whereby the phenyl moiety may be optionally substituted with substituents independently selected from the group consisting of hydroxyl, halogen, ($C_1$-$C_4$)alkoxy, ($C_1$-$C_4$)-alkyl, halogenated ($C_1$-$C_4$) alkyl and halogenated ($C_1$-$C_4$)alkoxy, the number of said substituents being up to five for halogen, and up to three for any combination of said other substituents.

The term "alkylcarboxyl" represents a preferred selection of the term "carboxyl" and refers to a group —(C=O)—OR, where R is hydrogen or $C_1$-$C_4$ alkyl.

The terms "alkylthio" ("alkylsulfanyl") and "alkylsulfonyl" refers to a group —SR and —S(O)$_{n=1-2}$—R, respectively, where R may be alkyl, substituted alkyl, arylalkyl, substituted arylalkyl, heteroarylalkyl or substituted heteroarylalkyl, as defined herein. Preferably, the term "alkylthio" ("alkylsulfanyl") refers to a group —SR'and the term "alkylsulfonyl" refers to a group —S(O)$_{n=1-2}$—R', respectively, where R' represents ($C_1$-$C_4$)alkyl, or ($C_1$-$C_4$)alkyl-phenyl, preferably benzyl; optionally substituted in the alkyl chain with up to threee substituents as defined herein, preferably hydroxyl, ($C_1$-$C_4$)-alkoxy or halogen.

The term "arylthio" ("arylsulfanyl") and "arylsulfonyl" refers to a group —S—Ar and —S(O)$_{n=1-2}$—Ar, respectively, where Ar represents aryl, substituted aryl, heteroaryl or substituted heteroaryl, as defined herein. Preferably Ar represents aryl, which is optionally substituted in the aryl group with independently selected substituents as defined herein, in particular hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy, the number of said substituents being up to five for halogen, and up to three for any combination of said other substituents. Preferably, arylthio refers to phenylsulfanyl, optionally substituted as defined above.

The term "amino" refers to the group —NRR', where R and R' may independently be hydrogen, alkyl (optionally substituted in the alkyl chain with up to five independently selected substituents as defined herein, in particular hydroxyl, halogen or ($C_1$-$C_4$)-alkoxy), aryl or aryl-($C_1$-$C_4$)-alkyl (both optionally substituted in the aryl group with up to five independently selected substituents as defined herein, in particular hydroxyl, halogen, ($C_1$-$C_4$)-alkyl, ($C_1$-$C_4$)-alkoxy, halogenated ($C_1$-

$C_4$)-alkyl, or halogenated ($C_1$-$C_4$)-alkoxy, the number of said substituents being up to five for halogen, and up to three for any combination of said other substituents), heteroaryl or heteroaryl-($C_1$-$C_4$)-alkyl (both optionally substituted in the heteroaryl group with up to three independently selected substituents as defined herein), as defined herein.

The term "alkylamino" represents a preferred selection of the term "amino" and refers to the group —NRR', where R and R' may independently be hydrogen or ($C_1$-$C_4$)alkyl.

The term "amido" refers to the group —(C=O)—NRR', where R and R' may independently be hydrogen, alkyl (optionally substituted in the alkyl chain with up to five independently selected substituents as defined herein, in particular hydroxyl, halogen or ($C_1$-$C_4$)-alkoxy), aryl or aryl-($C_1$-$C_4$)-alkyl (both optionally substituted in the aryl group with independently selected substituents as defined herein, in particular hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy, the number of said substituents being up to five for halogen, and up to three for any combination of said other substituents), heteroaryl or heteroaryl-($C_1$-$C_4$)-alkyl (both optionally substituted in the heteroaryl group with up to three independently selected substituents as defined herein), as defined herein.

The term "alkylamido" represents a preferred selection of the term "amido" and refers to the group —(C=O)—NRR', where R and R' may be independently selected from hydrogen or ($C_1$-$C_4$)alkyl.

The term "acylamino" refers to the group —NR—CO—R', where R and R' may independently be hydrogen, alkyl (optionally substituted in the alkyl chain with up to five independently selected substituents as defined herein, in particular hydroxyl, halogen or ($C_1$-$C_4$)-alkoxy), aryl or aryl-($C_1$-$C_4$)-alkyl (both optionally substituted in the aryl group with independently selected substituents as defined herein, in particular hydroxyl, halogen, ($C_1$-$C_4$)-alkyl, ($C_1$-$C_4$)-alkoxy, halogenated ($C_1$-$C_4$)-alkyl, or halogenated ($C_1$-$C_4$)-alkoxy, the number of said substituents being up to five for halogen, and up to three for any combination of said other substituents), heteroaryl or heteroaryl-($C_1$-$C_4$)-alkyl (both optionally substituted in the heteroaryl group with up to three independently selected substituents as defined herein), as defined herein.

The term "carbonylamino" represents a preferred selection of the term "acylamino" and refers to the group —NR—CO—$CH_2$—R', where R and R' may be independently selected from hydrogen or ($C_1$-$C_4$)alkyl.

The term "sulfonamide" refers to the group —$SO_2$—NRR', wherein R and R' may independently be selected from hydrogen or ($C_1$-$C_4$)alkyl.

The term "aryl" refers to an aromatic carbocyclic group comprising 6 to 14, more preferably 6 to 10, carbon atoms and having at least one aromatic ring or multiple condensed rings in which at least one ring is aromatic. Preferably, aryl is phenyl, naphthyl, indanyl, indenyl, fluorenyl, 1,2,3,4-tetrahydro-naphthalen-1-yl or even biphenyl.

The term "heteroaryl" refers to an aromatic carbocyclic group of having a single 4 to 8 membered ring or multiple condensed rings comprising 6 to 14, more preferably 6 to 10, ring atoms and containing at least one heteroatom, such as N, O or S, within at least one ring, the number of N atoms being 0-3 and the number of O and S atoms each being 0-1; in which group at least one heterocyclic ring is aromatic. Examples of such groups include pyrrolyl, thienyl, furyl, imidazolyl, thiazolyl, isothiazolyl, oxazolyl, isoxazolyl, pyrazolyl, pyridinyl, pyrimidinyl, pyrazinyl, indolyl, quinolinyl, isoquinolinyl, benzoimidazolyl, 1,3-dihydro-benzoimidazolyl, benzofuran, benzo[b]thiophene and the like. Preferably, heteroaryl is quinolinyl, furyl, benzoimidazolyl, pyridinyl, thienyl, indolyl, benzo[b]thiophene, pyridinyl, imidazolyl, pyrazolyl or thiazolyl.

The aryl and the heteroaryl group may optionally be substituted by substituents independently selected from the group consisting of halogen, hydroxyl, ($C_1$-$C_6$)alkoxy, ($C_1$-$C_6$)alkyl, halogenated ($C_1$-$C_6$)alkyl, halogenated ($C_1$-$C_6$) alkoxy, oxo, thiol, nitro, nitrile, sulfamoyl, sulfonamide, carboxyl, aryloxy or arylalkyloxy (both optionally substituted in the aryl moiety with indepndently selected substituents as defined herein), ($C_1$-$C_6$)alkylthio, arylthio or arylalkylthio (both optionally substituted in the aryl moiety with independently selected substituents as defined herein), amino, amido, acyl, and acylamino, as defined herein, the number of said substituents being up to five for halogen, and up to three for any combination of said other substituents. The heteroaryl group may further be optionally substituted with an aryl or an aryloxy group, which aryl group may be optionally substituted in the aryl moiety with substituents, especially hydroxyl, halogen, ($C_1$-$C_6$)alkoxy, ($C_1$-$C_6$)alkyl, halogenated ($C_1$-$C_6$)alkyl or halogenated ($C_1$-$C_6$)alkoxy, the number of said substituents being up to five for halogen, and up to three for any combination of said other substituents. The aryl group may further be optionally substituted with a heteroaryl group.

Substituted aryl is preferably substituted by substituents selected from the group consisting of ($C_1$-$C_6$)alkoxy, preferably methoxy, hydroxyl, ($C_1$-$C_4$)alkyl, halogen, halogenated ($C_1$-$C_4$)alkyl, preferably halogenated methyl, most preferably trifluoromethyl, halogenated ($C_1$-$C_6$)alkoxy, and sulfonamide, the number of said substituents being up to five for halogen, and up to four, preferably up to three, for any combination of said other substituents. Preferably substituted aryl is substituted phenyl.

The aryl may be further substituted by two groups which are attached to adjacent carbon atoms and are combined into a saturated or partly unsaturated cyclic 5, 6, 7, or 8 membered ring system, optionally containing up to three heteroatoms, such as N, O or S, the number of N atoms being 0-3 and the number of O and S atoms each being 0-2. Preferably, the two groups which are attached to adjacent carbon atoms, are combined into a saturated cyclic 5 or 6 membered ring system, optionally containing up to three heteroatoms, such as N or O, the number of N atoms being 0-3 and the number of O atoms each being 0-2. This cyclic ring system may optionally be further substituted by an oxo group. Preferred examples of such a substituted aryl groups are benzo[1,3]dioxol, 2,3-dihydrobenzofuran, 3H-isobenzofuran-1-one and 1,3-dihydro-benzoimidazol-2-one.

Substituted heteroaryl is preferably substituted by up to three, preferably up to two substituents selected from the group consisting of halogen, ($C_1$-$C_4$)-alkoxy, ($C_1$-$C_4$)-alkyl, preferably methyl, ($C_1$-$C_4$)-alkyl-carboxyl, preferably carboxylmethylester, halogenated ($C_1$-$C_4$)-alkyl, preferably halogenated methyl, halogenated ($C_1$-$C_4$)-alkoxy, phenoxy (optionally substituted with up to three, preferably one halogen), benzyloxy, benzyl or phenyl.

The term "cycloheteroalkyl" refers to a four- to eight-membered heterocyclic ring containing at least one heteroatom, such as N, O or S, the number of N atoms being 0-3 and the number of O and S atoms each being 0-1, which system may be saturated, partly unsaturated or hydroaromatic, and which ring can be part of a multiple condensed ring-system in which some rings may be aromatic. Examples of such cycloheteroalkyls include pyrrolidinyl, tetrahydrofuryl, tetrahydrothiophenyl, tetrahydropyridinyl, dioxolyl, azetidinyl, thiazolidinyl, oxazolidinyl, piperidinyl, morpholinyl, thiomorpholinyl, piperazinyl, azepanyl, diazepanyl, oxazepanyl, thiazepanyl, dihydro-1H-pyrrolyl, 1,3-dihydro-benzoimidazolyl and the like. Preferred examples of such cycloheteroalkyl groups are pyrrolidinyl, morpholinyl, tetrahydrofuryl, piperidinyl or dioxolyl.

The cycloheteroalkyl group may optionally be substituted by up to three substituents, in dependently selected from the group consisting of oxo, alkyl, aryl or aryl-($C_1$-$C_4$)-alkyl (both optionally substituted in the aryl group with independently selected substituents as defined herein), hydroxyl, ($C_1$-$C_6$)alkoxy, halogenated ($C_1$-$C_6$)alkyl, halogenated ($C_1$-$C_6$) alkoxy, carboxyl-($C_1$-$C_6$)alkyl, thiol, nitrile, sulfamoyl, sulfonamide, carboxyl, aryloxy or arylalkyloxy (both optionally substituted in the aryl moiety with independently selected substituents as defined herein), ($C_1$-$C_6$)alkylthio, arylthio or arylalkylthio (both optionally substituted in the aryl moiety with independently selected substituents as defined herein), amino, amido, acyl, and acylamino, as defined herein. These groups may be attached to any carbon atom of the cycloheteroalkyl moiety. Substituted cycloheteroalkyl is preferably substituted with oxo, ($C_1$-$C_4$)alkyl, preferably methyl, phenyl and/or ($C_1$-$C_4$)alkylphenyl, in particular benzyl.

The term "arylalkyl" refers to an alkyl group substituted with up to three independently selected aryl groups; preferably the term "arylalkyl" refers to "aryl-($C_1$-$C_4$)-alkyl" or diaryl-($C_1$-$C_4$)-alkyl, whereby the aryl is an aryl group as defined above. Arylalkyl is preferably benzyl (—CH2-Phenyl) or phenethyl (—$CH_2$—$CH_2$-Phenyl).

The term "substituted arylalkyl" refers to an arylalkyl group as defined above, wherein the aryl group is substituted as defined above.

The term "heteroarylalkyl" refers to an alkyl group substituted with up to three independently selected heteroaryl groups; preferably the term "heteroarylalkyl" refers to "heteroaryl-($C_1$-$C_4$)-alkyl", whereby the heteroaryl is a heteroaryl group as defined above.

The term "substituted heteroarylalkyl" refers to a heteroarylalkyl group as defined above, wherein the heteroaryl group is substituted as defined above.

The term "cycloheteroalkyl-alkyl" refers to an alkyl group substituted with up to three independently selected cycloheteroalkyl groups; preferably the term "cycloheteroalkylalkyl" refers to "cycloheteroalkyl-($C_1$-$C_4$)-alkyl", whereby the cycloheteroalkyl is a cycloheteroalkyl group as defined above. Preferably, "cycloheteroalkyl-alkyl" is morpholinylethyl, morpholinylpropyl, piperidinylethyl, tetrahydrofurylmethyl or pyrrolidinylpropyl.

The term "substituted cycloheteroalkyl-alkyl" refers to a cycloheteroalkyl-alkyl group as defined above, wherein the cycloheteroalkyl-alkyl group is substituted as defined above. Preferably, "substituted cycloheteroalkyl-alkyl" is dimethyl-[1,3]-dioxolylmethyl or 2-oxo-pyrrolidinyl-propyl.

The term "pro-drug" as used herein, represents derivatives of the compounds of the invention that are drug precursors which, following administration to a patient, release the drug in vivo via a chemical or physiological process. In particular, pro-drugs are derivatives of the compounds of the invention in which functional groups carry additional substituents which may be cleaved under physiological conditions in vivo and thereby releasing the active principle of the compound (e. g., a pro-drug on being brought to a physiological pH or through an enzyme action is converted to the desired drug form).

The term "pharmaceutically acceptable salts" refers to salt forms that are pharmacologically acceptable and substantially non-toxic to the subject being administered the compounds of the invention. Pharmaceutically acceptable salts of compounds of formula I include conventional and stoichiometrical acid-addition salts or base-addition salts formed from suitable non-toxic organic or inorganic acids or inorganic bases. Acid addition salts, for example, from compounds of formula I with a basic nitrogen atom are formed preferably with organic or inorganic acids. Suitable inorganic acids are, for example, halogenic acids such as hydrochloric acid, sulfuric acid, or phosphoric acid. Suitable organic acids are, for example, carboxylic, phosphonic, or sulfonic acids, for example acetic acid, propionic acid, glycolic acid, lactic acid, hydroxybutyric acid, malic acid, malenic acid, malonic acid, salicylic acid, fumaric acid, succinic acid, adipic acid, tartaric acid, citric acid, glutaric acid, 2- or 3-glycerophosphoric acid and other mineral and carboxylic acids well known to those skilled in the art. The salts are prepared by contacting the free base forms with a sufficient amount of the desired acid to produce a salt in the conventional manner. Compounds containing acidic substituents may also form salts with inorganic or organic bases. Examples of suitable bases for salt formation include, but are not limited to, inorganic bases such as alkali or alkaline earth-metal (e.g., sodium, potassium, lithium, calcium, or magnesium) hydroxides, and those derived from ammonium hydroxides (e.g., a quaternary ammonium hydroxide such as tetramethylammonium hydroxide). Also contemplated are salts formed with pharmaceutical acceptable amines such as ammonia, alkyl amines, hydroxyal-kylamines, N-methylglucamine, benzylamines, piperidines, and pyrrolidines and the like. Certain compounds will be acidic in nature, e. g. those compounds which possess a carboxyl or phenolic hydroxyl group. Salts of phenols can be made by heating acidic compounds with any of the above mentioned bases according to procedures well known to those skilled in the art.

As used herein, the term "composition" is intended to encompass a product comprising the specified ingredients in the specified amounts, as well as any product which results, directly or indirectly, from combination of the specified ingredients in the specified amounts.

The phrase "effective amount" as used herein, means an amount of a compound or composition which is sufficient enough to significantly and positively modify the symptoms and/or conditions to be treated (e. g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically acceptable excipient(s)/carrier(s) utilized, and like factors within the knowledge and expertise of the attending physician.

Preferred Embodiments

According to a preferred embodiment of the present invention, the substituents R1 to R6 are defined as follows:

R1 and R2 may be individually selected from the group consisting of (i) —$C_1$-$C_{12}$-alkyl, which alkyl can be linear, cyclic, branched or partially unsaturated, and which can be optionally substituted with one, two or three substituents individually selected from the group consisting of hydroxyl, $C_1$-$C_{12}$-alkoxy, thiol, $C_1$-$C_{12}$-alkylthio, aryloxy, arylacyl, —CO—OR, —O—CO—R, heteroaryl-acyloxy, and —N(R)$_2$;

whereby said aryl group is phenyl or naphthyl, and can be optionally substituted with one, two or three halogen;

whereby said heteroaryl group is thienyl, furyl or pyridinyl (ii) aryl and aryl-$C_1$-$C_{12}$-alkyl, which aryl is preferably selected from the group consisting of phenyl, biphenyl, naphthyl, indanyl, indenyl and fluorenyl, whereby the alkyl moiety can be optionally substituted with one or two hydroxyl groups, and whereby the aryl moiety can be optionally substituted with up to five substituents individually selected from the group consisting of halogen, hydroxyl, $C_1$-$C_{12}$-alkoxy, nitro, nitrile, $C_1$-$C_{12}$-alkyl, halogenated $C_1$-$C_{12}$-alkyl, —$SO_2$—$N(R)_2$, and $C_1$-$C_{12}$-alkylsulphonyl;

or which aryl may be optionally substituted by two groups which are attached to adjacent carbon atoms and are combined into a saturated cyclic 5, 6 or 7 membered ring system, optionally containing one, two or three heteroatoms, such as N or O, the number of N atoms being 0-3 and the number of O atoms each being 0-2, whereby the cyclic ring system may optionally be further substituted by an oxo group;

(iii) heteroaryl and heteroaryl-$C_1$-$C_{12}$-alkyl, which heteroaryl is preferably selected from the group consisting of pyrrolyl, thienyl, furyl, imidazolyl, thiazolyl, isothiazolyl, oxazolyl, isoxazolyl, pyrazolyl, pyridinyl, pyrimidinyl, pyrazinyl, indolyl, quinolinyl, isoquinolinyl, ben-zoimidazolyl, 1,3-dihydro-benzoimidazolyl, benzofuran, and benzo[b]thiophene, whereby the heteroaryl group can be optionally substituted with one, two or three substituents individually selected from the group consisting of halogen, $C_1$-$C_{12}$-alkyl, halogenated $C_1$-$C_8$-alkyl, —CO—OR, aryl or aryloxy, whereby the aryl group is selected from phenyl or naphthyl and can be optionally substituted with one, two or three halogen atoms;

(iv) cycloheteroalkyl and cycloheteroalkyl-$C_1$-$C_8$-alkyl, which cycloheteroalkyl moiety is preferably selected from the group consisting of piperidinyl, pyrrolidinyl, tetrahydrofuryl, dioxolyl, morpholinyl, tetrahydrothiophenyl, tetrahydropyridinyl, azetidinyl, thiazolidinyl, oxazolidinyl, thiomorpholinyl, piperazinyl, azepanyl, diazepanyl, oxazepanyl, thiazepanyl, dihydro-1H-pyrrolyl, and 1,3-dihydro-benzoimidazolyl, whereby the cycloheteroalkyl moiety can be optionally substituted with one or two substituents individually selected from the group consisting of oxo, $C_1$-$C_{12}$-alkyl, hydroxyl, $C_1$-$C_{12}$-alkoxy and aryl-$C_1$-$C_{12}$-alkyl;

or R2 itself may be independently selected from —CO—R, —CO—O—R, or —CO—N(R)$_2$;

R3 and R4 are individually selected from the group consisting of hydrogen, oxo, thio, halogen or dihalogen, —CO—R, preferably CHO, —CO—O—R, nitrile, —CO—N(R)$_2$, —O—CO—R, —O—R, —S—R, —N(R)$_2$, —$C_1$-$C_{12}$-alkyl, which alkyl can be linear, cyclic, branched or partially unsaturated, and which alkyl can be optionally substituted with one, two or three substituents individually selected from the group consisting of hydroxyl, $C_1$-$C_{12}$-alkoxy, thiol, and —N(R)$_2$; and R5 and R6 are individually selected from the group consisting of hydrogen, halogen, —O—R, —CO—O—R, —CO—R, $C_1$-$C_{12}$-alkyl, which alkyl can be linear, cyclic, branched or partially unsaturated, and which alkyl can be optionally substituted with one, two or three substituents individually selected from the group consisting of hydroxyl, $C_1$-$C_{12}$-alkoxy, thiol, $C_1$-$C_{12}$-alkylthio, —CO—OR and —CO—NHR; and aryl and aryl-$C_1$-$C_{12}$-alkyl, which aryl is preferably phenyl or naphthyl, whereby the aryl moiety can be optionally substituted with up to five substituents individually selected from the group consisting of halogen, hydroxyl, $C_1$-$C_{12}$-alkoxy, nitro, nitrile, $C_1$-$C_{12}$-alkyl, halogenated $C_1$-$C_{12}$-alkyl, wherein R represents hydrogen, $C_1$-$C_{12}$-alkyl, $C_1$-$C_4$-alkylphenyl or phenyl, optionally substituted in the phenyl moiety with one, two or three substituents selected from the group consisting of halogen, hydroxyl, and $C_1$-$C_4$-alkoxy, preferably methoxy.

According to a preferable embodiment, at least one of the substituents R3 to R6 shall be different from hydrogen, particularly in case the six-membered ring comprising the hydrocarbon chain —C(R3)-C(R4)-C(R5)-C(R6)- is not an aromatic ring.

Especially preferable compounds are those where the six-membered ring comprising the hydrocarbon chain —C(R3)-C(R4)-C(R5)-C(R6)- is an aromatic ring.

Particularly preferable compounds of formula (I) are those where R2 is selected from the group consisting of (i) —$C_1$-$C_8$-alkyl, which alkyl can be linear, cyclic, branched or partially unsaturated, which can be optionally substituted with up to three substituents individually selected from the group consisting of hydroxyl, $C_1$-$C_8$-alkoxy, thiol, $C_1$-$C_8$-alkylthio, aryloxy, —CO—O—$C_1$-$C_8$-alkyl, and —O—CO—R';

whereby said aryl group is phenyl or naphthyl, and can be optionally substituted with one, two or three halogen atoms;

(ii) aryl and aryl-$C_1$-$C_8$-alkyl, which aryl is preferably selected from the group consisting of phenyl, biphenyl, naphthyl, indanyl, indenyl and fluorenyl, whereby the aryl moiety can be optionally substituted with one to five substituents individually selected from the group consisting of halogen, hydroxyl, $C_1$-$C_8$-alkoxy, nitro, nitrile, halogenated $C_1$-$C_8$-alkyl, —$SO_2$—$N(R')_2$, (iii) heteroaryl and heteroaryl-$C_1$-$C_8$-alkyl, which is preferably selected from the group consisting of pyrrolyl, thienyl, furyl, imidazolyl, thiazolyl, isothiazolyl, oxazolyl, isoxazolyl, pyrazolyl, pyridinyl, pyrimidinyl, pyrazinyl, indolyl, quinolinyl, isoquinolinyl, benzoimidazolyl, 1,3-dihydro-benzoimidazolyl, benzofuran, and benzo[b]thiophene, whereby the heteroaryl group can be optionally substituted with up to three substituents individually selected from the group consisting of halogen, $C_1$-$C_8$-alkyl, halogenated $C_1$-$C_8$-alkyl, aryl or aryloxy, whereby the aryl group is selected from phenyl or naphthyl and can be optionally substituted with one, two or three halogen atoms;

(iv) —CO—R', (v) —CO—N(R')$_2$, and (vi) —CO—O—R';

wherein R' represents hydrogen or $C_1$-$C_8$-alkyl.

Most preferable compounds of formula (I) are those where R2 is
a) a residue of formula (II)

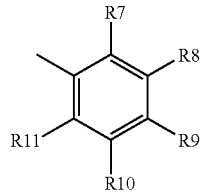

wherein
R7 is hydrogen, halogen, hydroxyl or $C_1$-$C_4$-alkoxy, preferably methoxy,
R8 is hydrogen, $C_1$-$C_4$-alkoxy, preferably methoxy, hydroxyl, nitrile, halogen, or halogenated $C_1$-$C_4$-alkyl, preferably trifluormethyl,
R9 is hydrogen, $C_1$-$C_4$-alkoxy, preferably methoxy, hydroxyl, nitrile, halogen, or N,N-di-$C_1$-$C_4$-alkyl-sulphonamide
R10 is hydrogen, $C_1$-$C_4$-alkoxy, preferably methoxy, hydroxyl, nitrile, halogen, or halogenated $C_1$-$C_4$-alkyl, preferably trifluormethyl
R11 is hydrogen, halogen, hydroxyl or $C_1$-$C_4$-alkoxy, preferably methoxy
or b)
(i) —$C_1$-$C_8$-alkyl, which alkyl can be linear, cyclic, branched or partially unsaturated;
(ii) —$C_1$-$C_4$-alkyl, substituted with one or two substituents selected from the group consisting of
—CO—O—R";
—O—R";
—O—Ar, whereby Ar is phenyl optionally substituted with halogen;
—O—CO—R",
phenyl or biphenyl, optionally substituted in the phenyl moiety with up to three $C_1$-$C_4$-alkoxy, preferably methoxy, groups;
(iii) —CO—O—R",
(iv) —CO—R", preferably —CHO
(v) -naphthyl,
(vi) -heteroaryl,
whereby the heteroaryl group can be optionally substituted by one or two substituents individually selected from the group consisting of halogen, $C_1$-$C_4$-alkyl, halogenated $C_1$-$C_4$-alkyl, preferably trifluormethyl, phenyl and phenoxy,
whereby the phenyl group can be optionally substituted with one to three halogen;
wherein R" represents hydrogen or $C_1$-$C_4$-alkyl, preferably methyl or ethyl.
Even more preferred are R2 substituents that represent
(i) —$C_3$-$C_8$-alkyl, which alkyl is linear, cyclic or branched,
(ii) —$C_1$-$C_4$-alkyl, optionally substituted with one or two substituents independently selected from the group consisting of $C_1$-$C_4$-alkoxy and hydroxyl,
(iii) phenyl-$C_1$-$C_4$-alkyl,
wherein the phenyl group is optionally substituted with one or two $C_1$-$C_4$-alkoxy groups,
(iv) heteroaryl,
which heteroaryl moiety is selected from the group consisting of furyl, pyridinyl, thienyl, thiazolyl and pyrimidinyl, and
(v) a residue of formula (II)

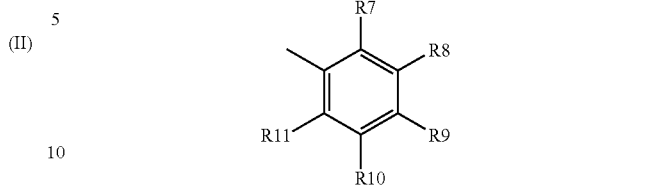

wherein
R7 is hydrogen, $C_1$-$C_4$-alkoxy or halogen,
R8 is hydrogen, halogen, $C_1$-$C_4$-alkoxy, or hydroxyl,
R9 is hydrogen, hydroxyl or $C_1$-$C_4$-alkoxy,
R10 is hydrogen, halogen, $C_1$-$C_4$-alkoxy, or hydroxyl, and
R11 is hydrogen, $C_1$-$C_4$-alkoxy or halogen.
Preferred R2 substituents are those where R2 is selected from the group consisting of a residue of formula (II)

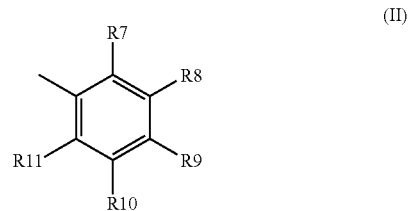

wherein
R7 is hydrogen, bromo, chloro, or fluoro,
R8 is hydrogen, $C_1$-$C_4$-alkoxy, preferably methoxy, or hydroxyl,
R9 is hydrogen, $C_1$-$C_4$-alkoxy, preferably methoxy, or hydroxyl,
R10 is hydrogen, $C_1$-$C_4$-alkoxy, preferably methoxy, or hydroxyl,
R11 is hydrogen;
—$C_3$-$C_6$-alkyl, which alkyl can be linear, cyclic, or branched; optionally substituted with an —O—CO—($C_1$-$C_4$)-alkyl or —CO—O—($C_1$-$C_4$)-alkyl group; and
-heteroaryl which can be selected from the group consisting of thienyl, furyl, pyridinyl, benzothienyl, and pyrazoloyl.
Mostly preferred R2 substituents are those where R2 is methoxyphenyl, trimethoxyphenyl, 2-bromo-3,4,5-trimethoxyphenyl, 2-chloro-3,4,5-trimethoxyphenyl, thienyl, or propyl.
Particularly preferable compounds of formula (I) are those where R1 is selected from the group consisting of
(i) —$C_1$-$C_8$-alkyl, which alkyl can be linear, cyclic, branched or partially unsaturated,
which can be optionally substituted with up to three substituents individually selected from the group consisting of hydroxyl, $C_1$-$C_8$-alkoxy, thiol, —$NH_2$, $C_1$-$C_8$-alkylthio, aryloxy, arylacyl, —CO—O—$C_1$-$C_8$-alkyl, $C_1$-$C_8$-alkylacyloxy, heteroaryl-acyloxy, and $C_1$-$C_8$-alkylamino;
whereby said aryl group is phenyl or naphthyl, and can be optionally substituted with up to three halogen;
whereby said heteroaryl group is thienyl, furyl or pyridinyl,
(ii) aryl and aryl-$C_1$-$C_8$-alkyl, which aryl moiety is preferably selected from the group consisting of phenyl, biphenyl, naphthyl, indanyl, indenyl, and fluorenyl, wherein the alkyl moiety can be optionally substituted with one or two hydroxyl groups, and
wherein the aryl moiety can be optionally substituted with up to five substituents individually selected from the group consisting of halogen, hydroxyl, $C_1$-$C_8$-alkoxy, $C_1$-$C_8$-alkylsulphonyl, —$SO_2$—N($C_1$-$C_8$-alkyl)$_2$, $C_1$-$C_8$-alkyl, halogenated $C_1$-$C_8$-alkyl;
or which aryl may be optionally substituted by two groups which are attached to adjacent carbon atoms and are combined into a saturated cyclic 5 or 6 membered ring system, optionally containing up to three heteroatoms, such as N or O, the number of N atoms being 0-3 and the number of O atoms each being 0-2,
whereby the cyclic ring system may optionally be further substituted by an oxo group;
(iii) heteroaryl and heteroaryl-$C_1$-$C_8$-alkyl, which heteroaryl moiety is preferably selected from the group consisting of quinolinyl, thiazolyl, pyrimidinyl, furyl, pyridinyl, thienyl, pyrrolyl, imidazolyl, isothiazolyl, oxazolyl, isoxazolyl, pyrazolyl, pyrazinyl, indolyl, isoquinolinyl, benzoimidazolyl, 1,3-dihydro-benzoimidazolyl, benzofuran, and benzo[b]thiophene,
whereby the heteroaryl group can be optionally substituted with up to three substituents individually selected from the group consisting of halogen, $C_1$-$C_8$-alkyl, and —CO—O—$C_1$-$C_8$-alkyl;
(iv) cycloheteroalkyl and cycloheteroalkyl-$C_1$-$C_8$-alkyl, which cycloheteroalkyl moiety is preferably selected from the group consisting of piperidinyl, pyrrolidinyl, tetrahydrofuryl, dioxolyl, morpholinyl, tetrahydrothiophenyl, tetrahydropyridinyl, azetidinyl, thiazolidinyl, oxazolidinyl, thiomorpholinyl, piperazinyl, azepanyl, diazepanyl, oxazepanyl, thiazepanyl, dihydro-1H-pyrrolyl, and 1,3-dihydro-benzoimidazolyl,
whereby the cycloheteroalkyl moiety can be optionally substituted with up to two substituents individually selected from the group consisting of oxo, $C_1$-$C_8$-alkyl, hydroxyl, $C_1$-$C_8$-alkoxy and aryl-$C_1$-$C_8$-alkyl.

Most preferable compounds of formula (I) are those where R1 is selected from the group consisting of
(i) —$C_1$-$C_8$-alkyl, which alkyl can be linear, cyclic or branched,
(ii) —$C_1$-$C_4$-alkyl, substituted with one or two substituents independently selected from the group consisting of —O—R"; —O—Ar, —O—CO-HetAr, —CO—Ar, —CO—O—R", and —N(R")$_2$,
(iii) aryl and aryl-$C_1$-$C_4$-alkyl, which aryl moiety is preferably selected from the group consisting of phenyl, indanyl, and fluorenyl,
wherein the alkyl moiety can be optionally substituted with a hydroxyl group; and
wherein the aryl moiety can be optionally substituted with up to three substituents individually selected from the group consisting of
halogen, —O—R"; —$SO_2$—R", —$SO_2$—N(R")$_2$,
or which aryl may be optionally substituted by two groups which are attached to adjacent carbon atoms and are combined into a saturated cyclic 5 or 6 membered ring system, optionally containing up to two O atoms,
whereby the cyclic ring system may optionally be further substituted by an oxo group;
(iv) heteroaryl and heteroaryl-$C_1$-$C_4$-alkyl, which heteroaryl moiety is preferably selected from the group consisting of quinolinyl, thiazolyl, pyrimidinyl, furyl, pyridinyl, pyrazinyl, and thienyl,
whereby the heteroaryl group can be optionally substituted with one or two substituents individually selected from the group consisting of halogen, —$C_1$-$C_4$-alkyl, and —CO—O—R";
(v) cycloheteroalkyl and cycloheteroalkyl-$C_1$-$C_4$-alkyl, which cycloheteroalkyl moiety is preferably selected from the group consisting of piperidinyl, morpholinyl, pyrrolidinyl, tetrahydrofuryl, and dioxolyl,
whereby the cycloheteroalkyl moiety can be optionally substituted with one or two substituents individually selected from the group consisting of oxo, $C_1$-$C_4$-alkyl, preferably methyl, and —$C_1$-$C_4$-alkyl-Ar, preferably benzyl or phenethyl.
wherein
Ar represent phenyl, optionally substituted with halogen or $C_1$-$C_4$-alkoxy, preferably methoxy,
HetAr represents thienyl, furyl, pyridinyl, and
R" represents hydrogen or $C_1$-$C_4$-alkyl, preferably methyl or ethyl.

More preferred R1 substituents are those where R1 is selected from the group consisting of
(i) —$C_1$-$C_4$-alkyl, optionally substituted with one or two hydroxy groups,
(ii) phenyl-$C_1$-$C_4$-alkyl,
wherein the phenyl group is optionally substituted with one or two $C_1$-$C_4$-alkoxy groups,
or wherein the phenyl group is substituted by two groups which are attached to adjacent carbon atoms and are combined into a saturated cyclic 5 or 6-membered ring system, optionally containing one or two O-atoms;
(iii) heteroaryl or heteroaryl-$C_1$-$C_4$-alkyl,
which heteroaryl moiety is selected from the group consisting of furyl, pyridinyl, thienyl, thiazolyl and pyrimidinyl,
wherein the heteroaryl group is optionally substituted with $C_1$-$C_4$-alkyl, and
(iv) cycloheteroalkyl-$C_1$-$C_4$-alkyl;
which cycloheteroalkyl moiety is selected from the group consisting of tetrahydrofuryl, piperidinyl, morpholinyl, and pyrrolidinyl.

Further preferred R1 substituents are those where R1 is selected from the group consisting of
(i) —$C_3$-$C_8$-alkyl, which alkyl can be linear, cyclic or branched,
(ii) —$C_1$-$C_4$-alkyl, substituted with one or two substituents independently selected from the group consisting of $C_1$-$C_4$-alkoxy, hydroxyl, and —O—CO-HetAr,
(iii) phenyl-$C_1$-$C_4$-alkyl,
wherein the aryl moiety can be optionally substituted with up to three substituents individually selected from the group consisting of halogen, $C_1$-$C_4$-alkoxy, and hydroxyl,
(iv) heteroaryl-$C_1$-$C_4$-alkyl, which heteroaryl moiety is selected from the group consisting of pyrimidinyl, furyl, pyridinyl, and thienyl,
whereby the heteroaryl group can be optionally substituted with one or two substituents individually selected from the group consisting of halogen, $C_1$-$C_4$-alkoxy, and hydroxyl, and
(v) cycloheteroalkyl-$C_1$-$C_4$-alkyl, which cycloheteroalkyl moiety is selected from the group consisting of tetrahydrofuryl, piperidinyl, morpholinyl, and pyrrolidinyl, Mostly preferred R1 substituents are those where R1 is selected from the group consisting of isobutyl, 3-methylbutyl, benzyl, phenethyl, tetrahydrofurylmethyl, furylmethyl, 5-bromo-furan-2-ylmethyl, 5-bromo-2-methoxybenzyl, thiophene-2-carboxylic acid ethyl ester, and methoxyethyl.

Particularly preferable compounds of formula (I) are those, wherein R3 is selected from the group consisting of hydrogen, oxo, —O—R', —O—Ar, —O—CO—R', halogen, thio, —S—R', and —S—Ar,
wherein
R' represents hydrogen or $C_1$-$C_8$-alkyl,
Ar represents phenyl, optionally substituted with one or more substituents selected from the group consisting of halogen, hydroxy or $C_1$-$C_4$-alkoxy, preferably methoxy.

Most preferable compounds of formula (I) are those, where R3 is selected from the group consisting of hydrogen, oxo, —O—R", —O—Ar, —O—CO—R", halogen, thio, —S—R", and —S—Ar;
wherein
R" represents hydrogen or $C_1$-$C_4$-alkyl, preferably methyl or ethyl, and
Ar represent phenyl, optionally substituted with one or more substituents selected from the group consisting of halogen, hydroxy or methoxy.

Preferred R3 substituents are those where R3 is selected from the group consisting of hydrogen, hydroxyl, oxo, halogen, phenoxy, phenylthio, $C_1$-$C_4$-alkoxy, $C_1$-$C_4$-alkylthio, and —O—CO—$C_1$-$C_4$-alkyl.

Mostly preferred R3 substituents are those where R3 is selected from the group consisting of hydrogen, hydroxyl, oxo, chloro, bromo, —O—CO—$CH_3$, and —S-ethyl.

Particularly preferable compounds of formula (I) are those, wherein R4 is selected from the group consisting of hydrogen, $C_1$-$C_8$-alkyl, optionally substituted with hydroxyl; —CO—R', —CO—O—R', halogen and dihalogen,
wherein R' represents hydrogen or $C_1$-$C_8$-alkyl.

Most preferable compounds of formula (I) are those, where R4 is selected from the group consisting of hydrogen, $C_1$-$C_4$-alkyl, optionally substituted with hydroxyl; —CO—R", —CO—O—R", halogen and dihalogen
wherein R" represents hydrogen or $C_1$-$C_4$-alkyl, preferably methyl or ethyl.

Preferably, R4 is different from $C_1$-$C_4$-alkyl, in case R1 is benzyl.

Preferred R4 substituents are those where R4 is selected from the group consisting of hydrogen, halogen, carbonyl, and —CO—$C_1$-$C_4$-alkyl.

Mostly preferred R4 substituents are those where R4 is selected from the group consisting of hydrogen, bromo and carbonyl.

Particularly preferable compounds of formula (I) are those where R5 is selected from the group consisting of hydrogen, —COOR', phenyl-$C_1$-$C_4$-alkyl, $C_1$-$C_4$-alkyl, and $C_1$-$C_4$-alkyl substituted with —COOR', wherein R' represents H or $C_1$-$C_4$-alkyl.

Preferred compounds of formula (I) are further those wherein R5 is selected from the group consisting of hydrogen, —COOH, benzyl, $C_1$-$C_4$-alkyl, and $C_1$-$C_4$-alkyl substituted with —COOR', wherein R' represents H or $C_1$-$C_4$-alkyl.

Even more preferred are compopunds wherein R5 is selected from the group consisting of hydrogen, benzyl and $C_1$-$C_4$-alkyl.

Preferred R6 substituents are those where R6 is selected from the group consisting of hydrogen, halogen, —O—R', phenyl-$C_1$-$C_4$-alkyl, $C_1$-$C_4$-alkyl, and $C_1$-$C_4$-alkyl substituted with —COOR', wherein R' represents H or $C_1$-$C_4$-alkyl.

Mostly preferred R6 substituents are those where R6 is selected from the group consisting of hydrogen, halogen, preferably bromo, hydroxyl, benzyl, $C_1$-$C_4$-alkyl, and $C_1$-$C_4$-alkyl substituted with —COOR', wherein R' represents H or $C_1$-$C_4$-alkyl.

Even more preferred are compopunds wherein R6 is selected from the group consisting of hydrogen, benzyl and $C_1$-$C_4$-alkyl.

Preferred compounds of formula (I) are further those wherein X represents S.

Especially preferable compounds of formula (I) are the compounds of formula (I)

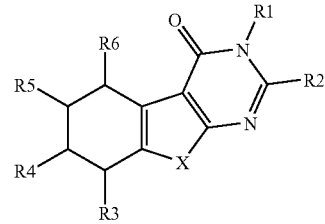

(I)

wherein
X is S, SO or $SO_2$
R1 is selected from the group consisting of:
(i) —$C_1$-$C_8$-alkyl, which alkyl can be linear, cyclic or branched,
(ii) —$C_1$-$C_4$-alkyl, substituted with one or two substituents independently selected from the group consisting of —O—R"; —O—Ar, —O—CO-HetAr, —CO—Ar, —CO—O—R", and —N(R")$_2$,
(iii) aryl and aryl-$C_1$-$C_4$-alkyl,
wherein the alkyl moiety can be optionally substituted with one hydroxyl group; and
wherein the aryl moiety can be optionally substituted with one, two or three substituents individually selected from the group consisting of halogen, —O—R"; —$SO_2$—R", —$SO_2$—N(R')$_2$.
or which aryl may be optionally substituted by two groups which are attached to adjacent carbon atoms and are combined into a saturated cyclic 5 or 6 membered ring system, optionally containing one or two O atoms,
wherein the cyclic ring system may optionally be further substituted by an oxo group;
(iv) heteroaryl and heteroaryl-$C_1$-$C_4$-alkyl,
wherein the heteroaryl group can be optionally substituted with one or two substituents individually selected from the group consisting of halogen, —$C_1$-$C_4$-alkyl, and —CO—O—R";
(v) cycloheteroalkyl and cycloheteroalkyl-$C_1$-$C_4$-alkyl,
wherein the cycloheteroalkyl moiety can be optionally substituted with one or two substituents individually selected from the group consisting of oxo, $C_1$-$C_4$-alkyl, and —$C_1$-$C_4$-alkyl-Ar;
R2 is selected from the group consisting of
a) a residue of formula (II)

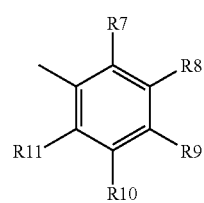

(II)

wherein
R7 is hydrogen, halogen, hydroxyl or $C_1$-$C_4$-alkoxy;
R8 is hydrogen, $C_1$-$C_4$-alkoxy, hydroxyl, nitrile, halogen, or halogenated $C_1$-$C_4$-alkyl;
R9 is hydrogen, $C_1$-$C_4$-alkoxy, hydroxyl, nitrile, halogen, or N,N-di-$C_1$-$C_4$-alkyl-sulphonamide;
R10 is hydrogen, $C_1$-$C_4$-alkoxy, hydroxyl, nitrile, halogen, or halogenated $C_1$-$C_4$-alkyl;
R11 is hydrogen, halogen, hydroxyl or $C_1$-$C_4$-alkoxy, and b)
(i) —$C_1$-$C_8$-alkyl, which alkyl can be linear, cyclic, branched or partially unsaturated;
(ii) —$C_1$-$C_4$-alkyl substituted with one or two substituents selected from the group consisting of —CO—O—R"; —O—R"; —O—Ar, wherein Ar is phenyl optionally substituted with halogen; —O—CO—R", and -phenyl or biphenyl, optionally substituted in the phenyl moiety with one, two or three $C_1$-$C_4$-alkoxy groups;
(iii) —CO—O—R",
(iv) —CO—R",
(v) -naphthyl, and
(vi) -heteroaryl
    wherein the heteroaryl group can be optionally substituted by one or two substituents individually selected from the group consisting of halogen, $C_1$-$C_4$-alkyl, halogenated $C_1$-$C_4$-alkyl, phenyl and phenoxy,
    wherein the phenyl group can be optionally substituted with one, two or three halogens;
R3 is selected from the group consisting of hydrogen, oxo, —O—R", —O—Ar, —O—CO—R", halogen, thio, —S—R", and —S—Ar;
R4 is selected from the group consisting of hydrogen, $C_1$-$C_4$-alkyl optionally substituted with hydroxyl, —CO—R", —CO—O—R", halogen and dihalogen,
R5 is selected from the group consisting of hydrogen, —COOR", phenyl-$C_1$-$C_4$-alkyl, $C_1$-$C_4$-alkyl, and $C_1$-$C_4$-alkyl substituted with —COOR",
R6 is selected from the group consisting of hydrogen, halogen, —O—R", phenyl-$C_1$-$C_4$-alkyl, $C_1$-$C_4$-alkyl, and $C_1$-$C_4$-alkyl substituted with —COOR";
wherein
    Ar represents phenyl optionally substituted with one or more substituents selected from the group consisting of halogen, hydroxy and methoxy,
    HetAr represents thienyl, furyl or pyridinyl, and
    R" represents hydrogen or $C_1$-$C_4$-alkyl, preferably methyl or ethyl.
Even more preferred are compounds of the general formula (I)

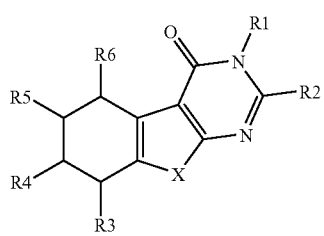

wherein
X is S,
R1 is selected from the group consisting of:
(i) —$C_3$-$C_8$-alkyl, which alkyl can be linear, cyclic or branched, (ii) —$C_1$-$C_4$-alkyl, substituted with one or two substituents independently selected from the group consisting of $C_1$-$C_4$-alkoxy, hydroxyl, and —O—CO-HetAr,
(iii) phenyl-$C_1$-$C_4$-alkyl,
    wherein the aryl moiety can be optionally substituted with up to three substituents individually selected from the group consisting of halogen, $C_1$-$C_4$-alkoxy, and hydroxyl,
(iv) heteroaryl-$C_1$-$C_4$-alkyl, which heteroaryl moiety is preferably selected from the group consisting of pyrimidinyl, furyl, pyridinyl, and thienyl,
    whereby the heteroaryl group can be optionally substituted with one or two substituents individually selected from the group consisting of halogen, $C_1$-$C_4$-alkoxy, and hydroxyl, and
(v) cycloheteroalkyl-$C_1$-$C_4$-alkyl, which cycloheteroalkyl moiety is preferably selected from the group consisting of tetrahydrofuryl, piperidinyl, morpholinyl, and pyrrolidinyl;
R2 is selected from the group consisting of
a) a residue of formula (II)

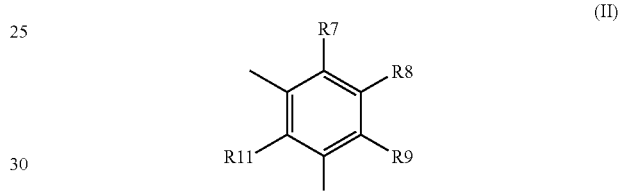

wherein
R7 is hydrogen, bromo, chloro, or fluoro,
R8 is hydrogen, $C_1$-$C_4$-alkoxy, preferably methoxy, or hydroxyl,
R9 is hydrogen, $C_1$-$C_4$-alkoxy, preferably methoxy, or hydroxyl,
R10 is hydrogen, $C_1$-$C_4$-alkoxy, preferably methoxy, or hydroxyl,
R11 is hydrogen,
and b)
(i) —$C_3$-$C_6$-alkyl, which alkyl can be linear, cyclic, or branched; optionally substituted with an —O—CO—($C_1$-$C_4$)-alkyl or —CO—O—($C_1$-$C_4$)-alkyl group;
(ii) -heteroaryl which can be selected from the group consisting of thienyl, furyl, pyridinyl, benzothienyl, and pyrazoloyl;
R3 is selected from the group consisting of hydrogen, oxo, hydroxyl, $C_1$-$C_4$-alkoxy, —O—CO—$C_1$-$C_4$-alkyl, and $C_1$-$C_4$-alkylthio;
R4 is selected from the group consisting of hydrogen, halogen, carbonyl, —CO—$C_1$-$C_4$-alkyl,
R5 is selected from the group consisting of hydrogen, —COOH, benzyl, $C_1$-$C_4$-alkyl, and $C_1$-$C_4$-alkyl substituted with —COOR', wherein R' represents H or $C_1$-$C_4$-alkyl; and
R6 is selected from the group consisting of hydrogen, bromo, hydroxyl, benzyl, $C_1$-$C_4$-alkyl, and $C_1$-$C_4$-alkyl substituted with —COOR', wherein R' represents H or $C_1$-$C_4$-alkyl.
A particularly preferred subgroup of the aforementioned group are compounds, wherein
R1 is selected from the group consisting of isobutyl, 3-methylbutyl, benzyl, tetrahydrofuryl-methyl, furylmethyl, 5-bromo-furan-2-ylmethyl, 5-bromo-2-methoxybenzyl, thiophene-2-carboxylic acid ethyl ester, and methoxyethyl;

R2 is selected from the group consisting of methoxyphenyl, trimethoxyphenyl, 2-bromo-3,4,5-trimethoxyphenyl, 2-chloro-3,4,5-trimethoxyphenyl, thienyl, and propyl;

R3 is selected from the group consisting of hydroxyl, oxo, —O—CO—CH$_3$, and —S-ethyl;

R4 is selected from the group consisting of hydrogen, bromo and carbonyl;

R5 is hydrogen, C$_1$-C$_4$-alkyl or benzyl, and

R6 is hydrogen or bromo.

In a further preferable subgroup the present invention comprises compounds, wherein R1 is linear, cyclic or branched —C$_3$-C$_8$-alkyl, R2 is trimethoxyphenyl, 2-bromo-3,4,5-trimethoxyphenyl, or 2-chloro-3,4,5-trimethoxyphenyl, R3 is hydrogen or hydroxyl, R4 is hydrogen, R5 is hydrogen, R6 is hydrogen, and wherein the six-membered ring comprising the hydrocarbon chain —C(R3)-C(R4)-C(R5)-C(R6)- is an aromatic ring.

The following compounds and their use, respectively, are especially preferred in the context of the present invention:

No. 1 3-Benzyl-2-(3,4,5-trimethoxyphenyl)-5,6,7,8-tetrahydro-3H-benzo[4,5]thieno[2,3-d]pyrimidin-4-one No. 2 3-Benzyl-6,7-dihydro-2-(3,4,5-trimethoxyphenyl)-3H,5H-benzo[4,5]thieno[2,3-d]pyrimidine-4,8-dione No. 3 3-Benzyl-8-chloro-4-oxo-2-(3,4,5-trimethoxyphenyl)-3,4,5,6-tetrahydro-benzo[4,5]thieno[2,3-d]pyrimidine-7-carbaldehyde No. 4 3-Benzyl-4-oxo-8-phenoxy-2-(3,4,5-trimethoxyphenyl)-3,4,5,6-tetrahydro-benzo[4,5]thieno[2,3-d]pyrimidine-7-carbaldehyde No. 5 3-Benzyl-4-oxo-8-phenoxy-2-(3,4,5-trimethoxyphenyl)-3,4-dihydro-benzo[4,5]thieno[2,3-d]pyrimidine-7-carbaldehyde No. 6 3-Benzyl-8-ethylsulfanyl-4-oxo-2-(3,4,5-trimethoxyphenyl)-3,4,5,6-tetrahydro-benzo[4,5]thieno[2,3-d]pyrimidine-7-carbaldehyde No. 7 3-Benzyl-8-ethoxy-4-oxo-2-(3,4,5-trimethoxyphenyl)-3,4,5,6-tetrahydro-benzo[4,5]thieno[2,3-d]pyrimidine-7-carbaldehyde No. 8 3-Benzyl-4-oxo-8-phenylsulfanyl-2-(3,4,5-trimethoxyphenyl)-3,4,5,6-tetrahydro-benzo[4,5]thieno[2,3-d]pyrimidine-7-carbaldehyde No. 9 3-Benzyl-4-oxo-8-phenylsulfanyl-2-(3,4,5-trimethoxyphenyl)-3,4-dihydro-benzo[4,5]thieno[2,3-d]pyrimidine-7-carbaldehyde No. 10 3-Phenyl-2-(3,4,5-trimethoxyphenyl)-5,6,7,8-tetrahydro-3H-benzo[4,5]thieno[2,3-d]pyrimidin-4-one No. 11 3-Phenyl-2-(3,4,5-trimethoxyphenyl)-6,7-dihydro-3H,5H-benzo[4,5]thieno[2,3-d]pyrimidine-4,8-dione No. 12 3-Benzyl-2-(p-methoxyphenyl)-5,6,7,8-tetrahydro-3H-benzo[4,5]thieno[2,3-d]pyrimidin-4-one No. 13 3-Benzyl-2-(p-methoxyphenyl)-6,7-dihydro-3H,5H-benzo[4,5]thieno[2,3-d]pyrimidine-4,8-dione No. 14 8-Chloro-2-(p-methoxyphenyl)-4-oxo-3-phenyl-3,4,5,6-tetrahydro-benzo[4,5]thieno[2,3-d]pyrimidine-7-carbaldehyde No. 15 3-Benzyl-2-(p-methoxyphenyl)-4-oxo-3,4,5,6-tetrahydro-benzo[4,5]thieno[2,3-d]pyrimidine-7-carboxylic acid ethyl ester No. 16 3-Benzyl-8-ethylsulfanyl-2-(p-methoxyphenyl)-4-oxo-3,4,5,6-tetrahydro-benzo[4,5]thieno[2,3-d]pyrimidine-7-carbaldehyde No. 17 3-Benzyl-2-(p-methoxyphenyl)-4-oxo-3,4-dihydro-benzo[4,5]thieno[2,3-d]pyrimidine-7-carbaldehyde No. 18 3-Benzyl-8-ethylsulfanyl-2-(p-methoxyphenyl)-4-oxo-3,4-dihydro-benzo[4,5]thieno[2,3-d]pyrimidine-7-carbaldehyde No. 19 3-Benzyl-8-ethylsulfanyl-7-hydroxymethyl-2-(p-methoxyphenyl)-3,4-dihydro-3H-benzo[4,5]thieno[2,3-d]pyrimidin-4-one No. 20 3-Benzyl-7-hydroxymethyl-2-(p-methoxyphenyl)-8-phenoxy-3H-benzo[4,5]thieno[2,3-d]pyrimidin-4-one No. 21 3-Benzyl-7-methyl-2-(p-methoxyphenyl)-8-phenoxy-3H-benzo[4,5]thieno[2,3-d]pyrimidin-4-one No. 22 3-Phenyl-2-(p-methoxyphenyl)-5,6,7,8-tetrahydro-3H-benzo[4,5]thieno[2,3-d]pyrimidin-4-one No. 23 3-Phenyl-2-(p-methoxyphenyl)-6,7-dihydro-3H,5H-benzo[4,5]thieno[2,3-d]pyrimidine-4,8-dione No. 24 2-Methyl-3-phenyl-5,6,7,8-tetrahydro-3H-benzo[4,5]thieno[2,3-d]pyrimidin-4-one No. 25 2-Methyl-3-phenyl-6,7-dihydro-3H,5H-benzo[4,5]thieno[2,3-d]pyrimidine-4,8-dione No. 26 2-(acetic acid methyl ester)-3-benzyl-5,6,7,8-tetrahydro-3H-benzo[4,5]thieno[2,3-d]pyrimidin-4-one No. 27 3-Benzyl-2-methoxymethyl-5,6,7,8-tetrahydro-3H-benzo[4,5]thieno[2,3-d]pyrimidin-4-one No. 28 3-Benzyl-2-hydroxymethyl-5,6,7,8-tetrahydro-3H-benzo[4,5]thieno[2,3-d]pyrimidin-4-one No. 29 Acetic acid 3-benzyl-4-oxo-3,4,5,6,7,8-hexahydro-benzo[4,5]thieno[2,3-d]pyrimidin-2-ylmethyl ester No. 30 Acetic acid 3-benzyl-4,8-dioxo-3,4,5,6,7,8-hexahydro-benzo[4,5]thieno[2,3-d]pyrimidin-2-ylmethyl ester No. 31 3-Benzyl-2-methoxymethyl-6,7-dihydro-3H,5H-benzo[4,5]thieno[2,3-d]pyrimidine-4,8-dione No. 32 3-Benzyl-4,8-dioxo-3,4,5,6,7,8-hexahydro-benzo[4,5]thieno[2,3-d]pyrimidine-2-carboxylic acid methyl ester No. 33 3-Benzyl-4,9,9-trioxo-4,5,6,7,8,9-hexahydro-3H-9 [ambda*6*-benzo[4,5]thieno[2,3-d]pyrimidine-2-carbaldehyde No. 34 3-Benzyl-8-chloro-2-methoxymethyl-4-oxo-3,4,5,6-tetrahydro-benzo[4,5]thieno[2,3-d]pyrimidine-7-carbaldehyde No. 36 2-Methoxymethyl-3-phenyl-5,6,7,8-tetrahydro-3H-benzo[4,5]thieno[2,3-d]pyrimidin-4-one No. 37 2-Methoxymethyl-3-phenyl-6,7-dihydro-3H,5H-benzo[4,5]thieno[2,3-d]pyrimidine-4,8-dione No. 38 2-Hydroxymethyl-3-phenyl-5,6,7,8-tetrahydro-3H-benzo[4,5]thieno[2,3-d]pyrimidin-4-one No. 39 Acetic acid 4-oxo-3-phenyl-3,4,5,6,7,8-hexahydro-benzo[4,5]thieno[2,3-d]pyrimidin-2-ylmethyl ester No. 40 4-Oxo-3-phenyl-3,4,5,6,7,8-hexahydro-benzo[4,5]thieno[2,3-d]pyrimidine-2-carboxylic acid ethyl ester No. 41 3-Benzyl-2-(3,4,5-trihydroxyphenyl)-5,6,7,8-tetrahydro-3H-benzo[4,5]thieno[2,3-d]pyrimidin-4-one No. 42 3-Phenyl-2-(3,5-dihydroxy-4-methoxyphenyl)-5,6,7,8-tetrahydro-3H-benzo[4,5]thieno[2,3-d]pyrimidin-4-one No. 43 3-Phenyl-2-(3,4,5-trihydroxyphenyl)-5,6,7,8-tetrahydro-3H-benzo[4,5]thieno[2,3-d]pyrimidin-4-one No. 44 7-Bromo-2-methyl-3-phenyl-6,7-dihydro-3H,5H-benzo[4,5]thieno[2,3-d]pyrimidine-4,8-dione No. 45 7,7-Dibromo-2-methyl-3-phenyl-6,7-dihydro-3H,5H-benzo[4,5]thieno[2,3-d]pyrimidine-4,8-dione No. 46 3-benzyl-7-bromo-2-(3,4,5-trimethoxyphenyl)-6,7-dihydro-3H,5H-benzo[4,5]thieno[2,3-d]pyrimidine-4,8-dione No. 47 3-benzyl-7-bromo-2-(2-bromo-3,4,5-trimethoxyphenyl)-6,7-dihydro-3H,5H-benzo[4,5]thieno[2,3-d]pyrimidine-4,8-dione No. 48 3-benzyl-7,7-dibromo-2-(2-bromo-3,4,5-trimethoxyphenyl)-6,7-dihydro-3H,5H-benzo[4,5]thieno[2,3-d]pyrimidine-4,8-dione No. 49 3-Benzyl-2-(2-bromo-3,4,5-trimethoxyphenyl)-8-hydroxy-3H-benzo[4,5]thieno[2,3-d]pyrimidin-4-one No. 50 Acetic acid 3-benzyl-2-(2-bromo-3,4,5-trimethoxyphenyl)-4-oxo-3,4-dihydro-benzo[4,5]thieno[2,3-d]pyrimidin-8-yl ester No. 51 3-benzyl-2-(2-bromo-3,4,5-trimethoxyphenyl)-3H-benzo[4,5]thieno[2,3-d]pyrimidin-4-one No. 52 3-benzyl-7-bromo-2-(2-bromo-3,4,5-trimethoxyphenyl)-8-hydroxy-3H-benzo[4,5]thieno[2,3-d]pyrimidin-4-one No. 53 3-Benzyl-8-hydroxy-2-(3,4,5-trimethoxyphenyl)-3H-benzo[4,5]thieno[2,3-d]pyrimidin-4-one No. 54 Acetic acid 3-benzyl-2-(3,4,5-trimethoxyphenyl)-4-oxo-3,4-dihydro-benzo[4,5]thieno[2,3-d]pyrimidin-8-yl ester No. 55 3-benzyl-7-bromo-9-oxo-2-(3,4,5-trimethoxyphenyl)-5,6,7,9-tetrahydro-3H-9lambda*4*-benzo[4,5]thieno[2,3-d]pyrimidine-4,8-dione No. 56 3-Benzyl-2-phenyl-5,6,7,8-tetrahydro-3H-benzo[4,5]thieno[2,3-d]pyrimidin-4-one No. 57 3-Benzyl-2-phenyl-6,7-dihydro-3H,5H-benzo[4,5]thieno[2,3-d]pyrimidine-4,8-dione No. 58 3-Benzyl-7-bromo-2-phenyl-6,7-dihydro-3H,5H-benzo[4,5]thieno[2,3-d]pyrimidine-4,8-dione No. 59 3-Benzyl-7,7-dibromo-2-phenyl-6,7-dihydro-3H,5H-benzo[4,5]thieno[2,3-d]pyrimidine-4,8-dione No. 60 3-Benzyl-8-hydroxy-2-phenyl-3H-benzo[4,5]thieno[2,3-d]pyrimidine-4-one No. 61 3-Benzyl-2-thiophen-2-yl-5,6,7,8-tetrahydro-3H-benzo[4,5]thieno[2,3-d]pyrimidin-4-one No. 62 3-Benzyl-2-thiophen-2-yl-6,7-dihydro-3H,5H-benzo[4,5]thieno[2,3-d]pyrimidine-4,8-dione No. 63 3-Benzyl-2-thiophen-2-yl-6,7-dihydro-3H,5H-benzo[4,5]thieno[2,3-d]pyrimidine-4,8-dione No. 64 3-Benzyl-2-(5-bromo-thiophen-2-yl)-6,7-dihydro-3H,5H-benzo[4,5]thieno[2,3-d]pyrimidine-4,8-dione No. 65 3-Benzyl-7-bromo-2-(5-bromothiophen-2-yl)-6,7-dihydro-3H,5H-benzo[4,5]thieno[2,3-d]pyrimidine-4,8-dione No. 66 3-Benzyl-7,7-dibromo-2-(5-bromothiophen-2-yl)-6,7-dihydro-3H,5H-benzo[4,5]thieno[2,3-d]pyrimidine-4,8-dione No. 67 3-Benzyl-8-hydroxy-2-thiophen-2-yl-3H-benzo[4,5]thieno[2,3-d]pyrimidine-4-one No. 68 3-Benzyl-2-(5-bromothiophen-2-yl)-8-hydroxy-3H-benzo[4,5]thieno[2,3-d]pyrimidin-4-one No. 69 Thiophene-2-carboxylic acid 2-(4-oxo-2-thiohen-2-yl-5,6,7,8-tetrahydro-4H-benzo[4,5]thieno[2,3-d]pyrimidin-3-yl)-ethyl ester No. 70 Thiophene-2-carboxylic acid 2-(4,8-dioxo-2-thiohen-2-yl-5,6,7,8-tetrahydro-4H-benzo[4,5]thieno[2,3-d]pyrimidin-3-yl)-ethyl ester No. 71 Thiophene-2-carboxylic acid 2-(7-bromo-4,8-dioxo-2-thiohen-2-yl-5,6,7,8-tetrahydro-4H-benzo[4,5]thieno[2,3-d]pyrimidin-3-yl)-ethyl ester No. 72 Thiophene-2-carboxylic acid 2-(7,7-dibromo-4,8-dioxo-2-thiohen-2-yl-5,6,7,8-tetrahydro-4H-benzo[4,5]thieno[2,3-d]pyrimidin-3-yl)-ethyl ester No. 73 Thiophene-2-carboxylic acid 2-(8-hydroxy4-oxo-2-thiohen-2-yl-4H-benzo[4,5]thieno[2,3-d]pyrimidin-3-yl)-ethyl ester No. 74 3-(2-Methoxyethyl)-2-thiophen-2-yl-5,6,7,8-tetrahydro-3H-benzo[4,5]thieno[2,3-d]pyrimidin-4-one No. 75 3-(2-Methoxyethyl)-2-thiophen-2-yl-6,7-dihydro-3H,5H-benzo[4,5]thieno[2,3-d]pyrimidine-4,8-dione No. 76 7-Bromo-3-(2-methoxyethyl)-2-thiophen-2-yl-6,7-dihydro-3H,5H-benzo[4,5]thieno[2,3-d]pyrimidine-4,8-dione No. 77 3-Benzyl-2-thiophen-2-yl-5,6,7,8-tetrahydro-3H-benzo[4,5]thieno[2,3-d]pyrimidin-4-one No. 78 3-Benzyl-2-(m-methoxyphenyl)-5,6,7,8-tetrahydro-3H-benzo[4,5]thieno[2,3-d]pyrimidin-4-one No. 79 3-Benzyl-2-(m-methoxyphenyl)-6,7-dihydro-3H,5H-benzo[4,5]thieno[2,3-d]pyrimidine-4,8-dione No. 80 3-Benzyl-7-bromo-2-(m-methoxyphenyl)-6,7-dihydro-3H,5H-benzo[4,5]thieno[2,3-d]pyrimidine-4,8-dione No. 81 3-Benzyl-7,7-dibromo-2-(m-methoxyphenyl)-6,7-dihydro-3H,5H-benzo[4,5]thieno[2,3-d]pyrimidine-4,8-dione No. 82 3-Benzyl-7,7-dibromo-2-(5-bromo-3-methoxyphenyl)-6,7-dihydro-3H,5H-benzo[4,5]thieno[2,3-d]pyrimidine-4,8-dione No. 83 3-Benzyl-8-hydroxy-2-(m-methoxyphenyl)-3H-benzo[4,5]thieno[2,3-d]pyrimidin-4-one No. 84 Acetic acid 3-benzyl-84-oxo-2-(m-methoxyphenyl)-3,4-dihydro-benzo[4,5]thieno[2,3-d]pyrimidin-8-yl ester No. 85 3-Butyl-2-(3,4,5-trimethoxyphenyl)-5,6,7,8-tetrahydro-3H-benzo[4,5]thieno[2,3-d]pyrimidin-4-one No. 86 3-Butyl-2-(3,4,5-trimethoxyphenyl)-6,7-dihydro-3H,5H-benzo[4,5]thieno[2,3-d]pyrimidine-4,8-dione No. 87 7-Bromo-3-butyl-2-(3,4,5-trimethoxyphenyl)-6,7-dihydro-3H,5H-benzo[4,5]thieno[2,3-d]pyrimidine-4,8-dione No. 88 3-Butyl-7,7-dibromo-2-(3,4,5-trimethoxyphenyl)-6,7-dihydro-3H,5H-benzo[4,5]thieno[2,3-d]pyrimidine-4,8-dione No. 89 3-Butyl-8-hydroxy-2-(3,4,5-trimethoxyphenyl)-3H-benzo[4,5]thieno[2,3-d]pyrimidin-4-one No. 90 7-Bromo-3-butyl-8-hydroxy-2-(3,4,5-trimethoxyphenyl)-3H-benzo[4,5]thieno[2,3-d]pyrimidin-4-one No. 91 3-Benzyl-8-methoxy-2-(2-bromo-3,4,5-trimethoxyphenyl)-3H-benzo[4,5]thieno[2,3-d]pyrimidin-4-one No. 92 3-Benzyl-7-bromo-8-hydroxy-2-phenyl-3H-benzo[4,5]thieno[2,3-d]pyrimidin-4-one No. 93 Acetic acid 3-benzyl-7-bromo-4-oxo-2-phenyl-3,4-dihydro-benzo[4,5]thieno[2,3-d]pyrimidin-8-yl ester No. 94 3-(2-Methoxybenzyl)-2-propyl-5,6,7,8-tetrahydro-3H-benzo[4,5]thieno[2,3-d]pyrimidin-4-one No. 95 3-(2-Methoxybenzyl)-2-propyl-6,7-dihydro-3H,5H-benzo[4,5]thieno[2,3-d]pyrimidine-4,8-dione No. 96 7-Bromo-3-(2-methoxybenzyl)-2-propyl-6,7-dihydro-3H,5H-benzo[4,5]thieno[2,3-d]pyrimidine-4,8-dione No. 97 7,7-Dibromo-3-(5-bromo-2-methoxybenzyl)-2-propyl-6,7-dihydro-3H,5H-benzo[4,5]thieno[2,3-d]pyrimidine-4,8-dione No. 98 3-Benzyl-3-(5-bromo-2-methoxybenzyl)-8-hydroxy-2-propyl-3H-benzo[4,5]thieno[2,3-d]pyrimidin-4-one No. 99 Acetic acid 3-benzyl-3-(5-bromo-2-methoxybenzyl)-4-oxo-2-propyl-3,4-dihydro-benzo[4,5]thieno[2,3-d]pyrimidin-8-yl ester No. 100 3-(5-Bromo-2-hydroxybenzyl)-8-hydroxy-2-propyl-3H-benzo[4,5]thieno[2,3-d]pyrimidin-4-one No. 101 3-Furan-2-ylmethyl-2-propyl-5,6,7,8-tetrahydro-3H-benzo[4,5]thieno[2,3-d]pyrimidin-4-one No. 102 3-Furan-2-ylmethyl-2-propyl-6,7-dihydro-3H,5H-benzo[4,5]thieno[2,3-d]pyrimidine-4,8-dione No. 103 7-Bromo-3-(5-bromofuran-2-ylmethyl)-2-propyl-6,7-dihydro-3H,5H-benzo[4,5]thieno[2,3-d]pyrimidine-4,8-dione No. 104 7,7-Dibromo-3-(5-bromofuran-2-ylmethyl)-2-propyl-6,7-dihydro-3H,5H-benzo[4,5]thieno[2,3-d]pyrimidine-4,8-dione No. 105 3-(5-Bromofuran-2-ylmethyl)-8-hydroxy-2-propyl-3H-benzo[4,5]thieno[2,3-d]pyrimidin-4-one No. 106 Acetic acid 3-(5-bromofuran-2-ylmethyl)-4-oxo-2-propyl-3,4-dihydro-benzo[4,5]thieno[2,3-d]pyrimidin-8-yl ester No. 107 7-Bromo-3-(5-bromofuran-2-ylmethyl)-8-hydroxy-2-propyl-3H-benzo[4,5]thieno[2,3-d]pyrimidin-4-one No. 108 3-(2-Methoxyethyl)-2-(3,4,5-trimethoxyphenyl)-5,6,7,8-tetrahydro-3H-benzo[4,5]thieno[2,3-d]pyrimidin-4-one No. 109 3-(2-Methoxyethyl)-2-(3,4,5-trimethoxyphenyl)-6,7-dihydro-3H,5H-benzo[4,5]thieno[2,3-d]pyrimidine-4,8-dione No. 110 7,7-Dibromo-2-(2-bromo-3,4,5-trimethoxyphenyl)-3-(2-methoxyethyl)-6,7-dihydro-3H,5H-benzo[4,5]thieno[2,3-d]pyrimidine-4,8-dione No. 111 7-Bromo-2-(2-bromo-3,4,5-trimethoxyphenyl)-3-(2-methoxyethyl)-6,7-dihydro-3H,5H-benzo[4,5]thieno[2,3-d]pyrimidine-4,8-dione No. 112 2-(2-Bromo-3,4,5-trimethoxyphenyl)-8-hydroxy-3-(2-methoxyethyl)-3H-benzo[4,5]thieno[2,3-d]pyrimidin-4-one No. 113 3-Isobutyl-2-(3,4,5-trimethoxyphenyl)-5,6,7,8-tetrahydro-3H-benzo[4,5]thieno[2,3-d]pyrimidin-4-one No. 114 3-Isobutyl-2-(3,4,5-trimethoxyphenyl)-6,7-dihydro-3H,5H-benzo[4,5]thieno[2,3-d]pyrimidine-4,8-dione No. 115 7-Bromo-3-isobutyl-2-(3,4,5-trimethoxyphenyl)-6,7-dihydro-3H,5H-benzo[4,5]thieno[2,3-d]pyrimidine-4,8-dione No. 116 7-Bromo-2-(2-bromo-3,4,5-trimethoxyphenyl)-3-isobutyl-6,7-dihydro-3H,5H-benzo[4,5]thieno[2,3-d]pyrimidine-4,8-dione No. 117 8-Hydroxy-3-isobutyl-2-(2-bromo-3,4,5-trimethoxyphenyl)-3H-benzo[4,5]thieno[2,3-d]pyrimidin-4-one No. 118 Acetic acid 2-(2-bromo-3,4,5-trimethoxyphenyl)-3-isobutyl-4-oxo-3,4-dihydro-benzo[4,5]-thieno[2,3-d]pyrimidin-8-yl ester No. 119 3-Furan-2-ylmethyl-2-(3,4,5-trimethoxylphenyl)-5,6,7,8-tetrahydro-3H-benzo[4,5]thieno[2,3-d]pyrimidin-4-one No. 120 3-Furan-2-ylmethyl-2-(3,4,5-trimethoxylphenyl)-6,7-dihydro-3H,5H-benzo[4,5]thieno[2,3-d]pyrimidine-4,8-dione No. 121 7-Bromo-3-(5-bromofuran-2-ylmethyl)-2-(2-bromo-3,4,5-trimethoxylphenyl)-6,7-dihydro-3H,5H-benzo[4,5]thieno[2,3-d]pyrimidine-4,8-dione No. 122 3-(5-Bromofuran-2-ylmethyl)-8-hydroxy-2-(3,4,5-trimethoxyphenyl)-3H-benzo[4,5]thieno[2,3-d]pyrimidin-4-one No. 123 3-Benzyl-7-chloro-2-(2-chloro-3,4,5-trimethoxyphenyl)-6,7-dihydro-3H,5H-benzo[4,5]thieno[2,3-d]pyrimidine-4,8-dione No. 124 3-Benzyl-2-(2-chloro-3,4,5-trimethoxyphenyl)-8-hydroxy-3H-benzo[4,5]thieno[2,3-d]pyrimidin-4-one No. 125 3-(2-Methylbutyl)-2-(3,4,5-trimethoxyphenyl)-5,6,7,8-tetrahydro-3H-benzo[4,5]thieno[2,3-d]pyrimidin-4-one No. 126 3-(2-Methylbutyl)-2-(3,4,5-trimethoxyphenyl)-6,7-dihydro-3H,5H-benzo[4,5]thieno[2,3-d]pyrimidine-4,8-dione No. 127 7-Bromo-3-(2-methylbutyl)-2-(3,4,5-trimethoxyphenyl)-6,7-dihydro-3H,5H-benzo[4,5]thieno[2,3-d]pyrimidine-4,8-dione No. 128 7,7-Dibromo-2-(2-bromo-3,4,5-trimethoxyphenyl)-3-(2-methylbutyl)-6,7-dihydro-3H,5-benzo[4,5]thieno[2,3-d]pyrimidine-4,8-dione No. 129 8-Hydroxy-3-(2-methylbutyl)-2-(3,4,5-trimethoxyphenyl)-3H-benzo[4,5]thieno[2,3-d]pyrimidin-4-one No. 130 3-(Tetrahydrofuran-2-ylmethyl)-2-(3,4,5-trimethoxyphenyl)-5,6,7,8-tetrahydro-3H-benzo[4,5]thieno[2,3-d]pyrimidin-4-one No. 131 3-(Tetrahydro-furan-2-ylmethyl)-2-(3,4,5-trimethoxyphenyl)-6,7-dihydro-3H,5H-benzo[4,5]thieno[2,3-d]pyrimidine-4,8-dione No. 132 7-Bromo-2-(2-bromo-3,4,5-trimethoxyphenyl)-3-(tetrahydrofuran-2-ylmethyl)-6,7-dihydro-3H,5H-benzo[4,5]thieno[2,3-d]pyrimidine-4,8-dione No. 133 2-(2-Bromo-3,4,5-trimethoxyphenyl)-8-hydroxy-3-(tetrahydrofuran-2-ylmethyl)-3H-benzo[4,5]thieno[2,3-d]pyrimidin-4-one No. 134 3-Butyl-2-thiophen-2-yl-6,7-dihydro-3H,5H-benzo[4,5]thieno[2,3-d]pyrimidine-4,8-dione No. 135 5-Bromo-3-isobutyl-2-(3,4,5-trimethoxyphenyl)-6,7-dihydro-3H,5H-benzo[4,5]thieno[2,3-d]pyrimidine-4,8-dione No. 136 3-Isobutyl-8-methoxy-2-(3,4,5-trimethoxyphenyl)-3H-benzo[4,5]thieno[2,3-d]pyrimidin-4-one No. 137 3-Benzyl-5-bromo-2-(3,4,5-trimethoxyphenyl)-6,7-dihydro-3H,5H-benzo[4,5]thieno[2,3-d]pyrimidine-4,8-dione No. 138 3-Benzyl-8-methoxy-2-(3,4,5-trimethoxyphenyl)-3H-benzo[4,5]thieno[2,3-d]pyrimidin-4-one No. 139 7-Chloro-2-(2-chloro-3,4,5-trimethoxyphenyl)-3-(tetrahydrofuran-2-ylmethyl)-6,7-dihydro-3H,5H-benzo[4,5]thieno[2,3-d]pyrimidine-4,8-dione No. 140 2-(2-Chloro-3,4,5-trimethoxyphenyl)-8-hydroxy-3-(tetrahydrofuran-2-ylmethyl)-3H-benzo[4,5]thieno[2,3-d]pyrimidin-4-one No. 141 7-Chloro-2-(2-chloro-3,4,5-trimethoxyphenyl)-3-(2-methylbutyl)-6,7-dihydro-3H,5H-benzo[4,5]thieno[2,3-d]pyrimidine-4,8-dione No. 142 7,7-Dichloro-2-(2-chloro-3,4,5-trimethoxyphenyl)-3-(2-methylbutyl)-6,7-dihydro-3H,5H-benzo[4,5]thieno[2,3-d]pyrimidine-4,8-dione No. 143 2-(2-Chloro-3,4,5-trimethoxyphenyl)-8-hydroxy-3-(2-methylbutyl)-3H-benzo[4,5]thieno[2,3-d]pyrimidin-4-one No. 144 3-Pyridin-3-ylmethyl-2-(3,4,5-trimethylphenyl)-5,6,7,8-tetrahydro-3H-benzo[4,5]thieno[2,3-d]pyrimidin-4-one No. 145 3-Benzyl-8-hydroxy-2-(3,4,5-trimethoxyphenyl)-5,6,7,8-tetrahydro-3H-benzo[4,5]thieno[2,3-d]pyrimidin-4-one No. 146 3-Benzyl-7-bromo-2-p-methoxyphenyl-6,7-dihydro-3H,5H-benzo[4,5]thieno[2,3-d]pyrimidine-4,8-dione No. 147 3-Benzyl-7,7-dibromo-2-p-methoxyphenyl-6,7-dihydro-3H,5H-benzo[4,5]thieno[2,3-d]pyrimidine-4,8-dione No. 148 7-Bromo-8-hydroxy-3-(2-methoxyethyl)-2-thiophen-2-yl-3H-benzo[4,5]thieno[2,3-d]pyrimidin-4-one No. 149 7-Bromo-8-hydroxy-3-(2-hydroxyethyl)-2-thiophen-2-yl-3H-benzo[4,5]thieno[2,3-d]pyrimidin-4-one No. 150 3-Benzyl-8-chloro-2-(2-chloro-3,4,5-trimethoxyphenyl)-4-oxo-3,4-dihydro-benzo[4,5]thieno[2,3-d]pyrimidine-7-carbaldehyde No. 151 8-Hydroxy-3-isobutyl-2-(3,4,5-trimethoxyphenyl)-3H-benzo[4,5]thieno[2,3-d]pyrimidin-4-one No. 618 3-Benzo[1,3]dioxol-5-ylmethyl-8-hydroxy-2-(2-methoxy-phenyl)-3H-benzo[4,5]thieno[2,3-d]pyrimidin-4-one
No. 633 3-Butyl-8-hydroxy-2-(2-methoxy-phenyl)-3H-benzo[4,5]thieno[2,3-d]pyrimidin-4-one
No. 637 3-Butyl-2-(2,4-difluoro-phenyl)-8-hydroxy-3H-benzo[4,5]thieno[2,3-d]pyrimidin-4-one
No. 674 2-(3,4-Dimethoxy-benzyl)-8-hydroxy-3-(2-pyridin-2-yl-ethyl)-3H-benzo[4,5]thieno[2,3-d]pyrimidin-4-one In a preferred embodiment, the invention relates to a compound selected from the group consisting of exemplary compounds
No. 16 3-Benzyl-8-ethylsulfanyl-2-(p-methoxyphenyl)-4-oxo-3,4,5,6-tetrahydro-benzo[4,5]thieno[2,3-d]pyrimidine-7-carbaldehyde
No. 17 3-Benzyl-2-(p-methoxyphenyl)-4-oxo-3,4-dihydro-benzo[4,5]thieno[2,3-d]pyrimidine-7-carbaldehyde
No. 18 3-Benzyl-8-ethylsulfanyl-2-(p-methoxyphenyl)-4-oxo-3,4-dihydro-benzo[4,5]thieno[2,3-d]pyrimidine-7-carbaldehyde
No. 67 3-Benzyl-8-hydroxy-2-thiophen-2-yl-3H-benzo[4,5]thieno[2,3-d]pyrimidine-4-one
No. 73 Thiophene-2-carboxylic acid 2-(8-hydroxy-4-oxo-2-thiohen-2-yl-4H-benzo[4,5]thieno[2,3-d]pyrimidin-3-yl)-ethyl ester
No. 89 3-Butyl-8-hydroxy-2-(3,4,5-trimethoxyphenyl)-3H-benzo[4,5]thieno[2,3-d]pyrimidin-4-one
No. 98 3-Benzyl-3-(5-bromo-2-methoxybenzyl)-8-hydroxy-2-propyl-3H-benzo[4,5]thieno[2,3-d]pyrimidin-4-one
No. 99 Acetic acid 3-benzyl-3-(5-bromo-2-methoxybenzyl)-4-oxo-2-propyl-3,4-dihydro-benzo[4,5]thieno[2,3-d]pyrimidin-8-yl ester
No. 105 3-(5-Bromofuran-2-ylmethyl)-8-hydroxy-2-propyl-3H-benzo[4,5]thieno[2,3-d]pyrimin-4-one
No. 106 Acetic acid 3-(5-bromofuran-2-ylmethyl)-4-oxo-2-propyl-3,4-dihydro-benzo[4,5]thieno[2,3-d]pyrimidin-8-yl ester
No. 117 8-Hydroxy-3-isobutyl-2-(2-bromo-3,4,5-trimethoxyphenyl)-3H-benzo[4,5]thieno[2,3-d]pyrimidin-4-one
No. 124 3-Benzyl-2-(2-chloro-3,4,5-trimethoxyphenyl)-8-hydroxy-3H-benzo[4,5]thieno[2,3-d]pyrimidin-4-one
No. 127 7-Bromo-3-(2-methylbutyl)-2-(3,4,5-trimethoxyphenyl)-6,7-dihydro-3H,5H-benzo[4,5]thieno[2,3-d]pyrimidine-4,8-dione
No. 129 8-Hydroxy-3-(2-methylbutyl)-2-(3,4,5-trimethoxyphenyl)-3H-benzo[4,5]thieno[2,3-d]pyrimidin-4-one
No. 135 5-Bromo-3-isobutyl-2-(3,4,5-trimethoxyphenyl)-6,7-dihydro-3H,5H-benzo[4,5]thieno[2,3-d]pyrimidine-4,8-dione
No. 140 2-(2-Chloro-3,4,5-trimethoxyphenyl)-8-hydroxy-3-(tetrahydrofuran-2-ylmethyl)-3H-benzo[4,5]thieno[2,3-d]pyrimidin-4-one
No. 143 2-(2-Chloro-3,4,5-trimethoxyphenyl)-8-hydroxy-3-(2-methylbutyl)-3H-benzo[4,5]thieno[2,3-d]pyrimidin-4-one
No. 148 7-Bromo-8-hydroxy-3-(2-methoxyethyl)-2-thiophen-2-yl-3H-benzo[4,5]thieno[2,3-d]pyrimidin-4-one
No. 633 3-Butyl-8-hydroxy-2-(2-methoxy-phenyl)-3H-benzo[4,5]thieno[2,3-d]pyrimidin-4-one
No. 637 3-Butyl-2-(2,4-difluoro-phenyl)-8-hydroxy-3H-benzo[4,5]thieno[2,3-d]pyrimidin-4-one or a physiologically acceptable salt thereof.

Pharmaceutically acceptable salts of the compounds of the invention as well as commonly used pro-drugs and active metabolites of these compounds are also within the scope of the invention.

The invention also relates to pharmaceutical compositions comprising one or more of the compounds of the invention for which no use in therapy has been disclosed earlier, or their salts or pro-drugs, as active agent and at lease one pharmaceutically acceptable carrier.

Furthermore, the invention relates to the use of an effective amount of a novel compound as defined herein for the treatment or prevention of a steroid hormone dependent disease or disorder in a mammal, in particular a human. Preferably the steroid hormone dependent disease or disorder is an estradiol or testosterone dependent disease or disorder.

In a preferred embodiment, the invention relates to the use of an effective amount of a novel compound as defined within the present invention for the treatment or prevention of a steroid hormone dependent disease or disorder in a mammal, whereby the steroid hormone dependent disease or disorder requires the inhibition of a 17β-hydroxysteroid dehydrogenase (HSD) enzyme, preferably the human 17β-hydroxysteroid dehydrogenase (HSD) enzyme type 1, type 2 or type 3.

In a further preferred embodiment of the invention the steroid hormone dependent disease or disorder to be treated and/or prevented requires the lowering of the endogenous 17β-estradiol or testosterone concentration in a generalized and/or tissue specific manner.

The invention also relates to a method of treating a mammal such as a human having a condition related to 17β-hydroxysteroid dehydrogenase (HSD) type 1, type 2 or type 3 activity, comprising administering to the mammal an amount of a compound of this invention, or a salt or a prodrug thereof, which amount is effective to treat the condition. Administration of compounds of this invention in combination with other pharmaceuticals used in treatment of the listed conditions is contemplated.

The conditions to be treated and/or prevented in the context of the present invention include but are not limited to breast cancer, prostate carcinoma, ovarian cancer, uterine cancer, endometrial cancer, endometrial hyperplasia, endometriosis, uterine fibroids, uterine leiomyoma, adenomyosis, dysmenorrhea, menorrhagia, metrorrhagia, prostadynia, benign prostatic hyperplasia, prostatitis, acne, seborrhea, hirsutism, androgenic alopecia, precocious puberty, adrenal hyperplasia, polycystic ovarian syndrome, and urinary dysfunction. A further condition to be treated and/or prevented in the context of the present invention includes osteoporosis.

Further estrogen-dependent diseases which may be treated and/or prevented with an effective amount of a compound of the invention are multiple sclerosis, rheumatoid arthritis, Alzheimer's disease, colon cancer, tissue wounds, skin wrinkles and cataracts.

In a preferred embodiment the invention relates to use of an effective amount of a compound of the invention for the treatment or prevention of one of the aforementioned disease or disorders in a mammal whereby the mammal is a human, preferably a female and most preferably a pre- or peri-menopausal female in the case of gynaecological disorders.

Furthermore, compounds of formula (I) may be useful for blocking spermatogenesis and as an anti-fertility agent for males.

The disclosed compounds are also useful as diagnostic agents (e.g. in diagnostic kits or for use in clinical laboratories) for screening for the presence or absence of 17β-hydroxysteroid dehydrogenase (HSD) type 1, type 2 and/or type 3 activity.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

Administration Forms

The method of the invention is primarily intended for treatment in a mammal, preferably in humans and other primates, of steroid hormone dependent diseases or disorders, in particular estradiol dependent diseases or disorders, wherein the steroid hormone dependent disease or disorder preferably requires the inhibition of a 17β-hydroxysteroid dehydrogenase (HSD) enzyme, preferably the type 1 17β-hydroxysteroid dehydrogenase (HSD) enzyme [EC 1.1.1.62].

The compounds may be administered orally, dermally, parenterally, by injection, by pulmonal or nasal delivery, or sublingually, rectally or vaginally in dosage unit formulations. The term "administered by injection" includes intravenous, intraarticular, intramuscular (e.g. by depot injection where the active compounds are released slowly into the blood from the depot and carried from there to the target organs), intraperitoneal, intradermal, subcutaneous, and intrathecal injections, as well as use of infusion techniques. Dermal administration may include topical application or transdermal administration. One or more compounds may be present in association with one or more non-toxic pharmaceutically acceptable auxiliaries such as excipients, adjuvants (e.g. buffers), carriers, inert solid diluents, suspensing agents, preservatives, fillers, stabilizers, anti-oxidants, food additives, bioavailability enhancers, coating materials, granulating and disintegrating agents, binding agents etc., and, if desired, other active ingredients.

The pharmaceutical composition may be formulated for example as immediate release, sustained release, pulsatile release, two or more step release, depot or other kind of release formulations.

The manufacture of the pharmaceutical compositions according to the invention may be performed according to methods known in the art and will be explained in further detail below. Commonly known and used pharmaceutically acceptable auxiliaries as well as further suitable diluents, flavorings, sweetening agents, coloring agents etc. may be used, depending on the intended mode of administration as well as particular characteristics of the active compound to be used, such as solubility, bioavailability etc. Suitable auxiliaries and further ingredients may be such as recommended for pharmacy, cosmetics and related fields and which preferably are listed in the European Pharmacopoeia, FDA approved or cited in the "GRAS" list (FDA List of food additives that are 'generally recognized as safe' (GRAS)).

One mode of application of the compounds of general formula (I) or of pharmaceutical compositions comprising one or more of said compounds is oral application, e. g., by tablets, pills, dragees, hard and soft gel capsules, granules, pellets, aqueous, lipid, oily or other solutions, emulsions such as oil-in-water emulsions, liposomes, aqueous or oily suspensions, syrups, elixiers, solid emulsions, solid dispersions or dispersible powders. For the preparation of pharmaceutical compositions for oral administration, the compounds suitable for the purposes of the present invention as defined above can be admixed with commonly known and used adjuvants and excipients such as for example, gum arabic, talcum, starch, sugars (such as, e. g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e. g., ethereal oils), solubility enhancers (e. g., benzyl benzoate or benzyl alcohol) or bioavailability enhancers (e.g. Gelucire™). In the pharmaceutical composition, the active ingredients may also be dispersed in a microparticle, e. g. a nanoparticulate, composition.

For parenteral administration, the active agents can be dissolved or suspended in a physiologically acceptable diluent, such as, e. g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration the active agent can be in the form of an aqueous, lipid, oily or other kind of solution or suspension or even administered in the form of liposomes or nano-suspensions.

Transdermal application can be accomplished by suitable patches, as generally known in the art, specifically designed for the transdermal delivery of active agents, optionally in the presence of specific permeability enhancers. Furthermore, also emulsions, ointments, pastes, creams or gels may be used for transdermal delivery.

Another suitable mode of administration is via intravaginal devices (e. g. vaginal rings) or intrauterine systems (IUS) containing reservoirs for controlled release of active agents over extended periods of time. For rectal or vaginal administration of the drug the compounds may also be administered in the form of suppositories. These compositions can be prepared by mixing the drug with a suitable non-irritating excipient which is solid at ordinary temperatures but liquid at the rectal or vaginal temperature and will therefore melt in the rectum or vagina to release the drug.

Another mode of application is by implantation of a depot implant comprising an inert carrier material, such as biologically degradable polymers or synthetic silicones such as e. g. silicone rubber. Such implants are designed to release the active agent in a controlled manner over an extended period of time (e. g., 3 to 5 years).

It will be appreciated by those skilled in the art that the particular method of administration will depend on a variety of factors, all of which are considered routinely when administering therapeutics.

The actually required dosages of the agents of this invention for any given patient will depend upon a variety of factors, including, but not limited to the activity of the specific compound employed, the particular HSD type 1, type 2 or type 3 related condition being treated, the particular composition formulated, the mode of administration, time and duration of administration, route of administration and the particular site being treated, and furthermore the age of the patient, the body weight of the patient, the general health of the patient, the gender of the patient, the diet of the patient, rate of excretion, drug combinations, and the severity of the condition undergoing therapy.

It will be further appreciated by one skilled in the art that the optimal course of treatment, i.e., the mode of treatment and the daily number of doses of a compound of Formula I or a pharmaceutically acceptable salt thereof given for a defined number of days, can be ascertained by those skilled in the art using conventional treatment tests. Optimal dosages for a given set of conditions may be ascertained by those skilled in the art using conventional dosage-determination tests in view of the experimental data for a given compound. For oral administration, an exemplary daily dose generally employed will be from about 0.01 µg/kg to about 100 mg/kg of total body weight, whereby courses of treatment may be repeated at appropriate time intervals. Administration of pro-drugs may be dosed at weight levels that are chemically equivalent to the weight levels of the fully active compounds. The daily dosage for parenteral administration will generally be from about 0.01 μg/kg to about 100 mg/kg of total body weight. A daily rectal dosage regimen will generally be from about 0.01 μg/kg to about 200 mg/kg of total body weight. A daily vaginal dosage regimen will generally be from about 0.01 μg/kg to about 100 mg/kg of total body weight. The daily topical dosage regimen will generally be from about 0.1 μg to about 100 mg administered between one to four times daily. The transdermal concentration will generally be that required to maintain a daily dose of from 0.61 μg/kg to 100 mg/kg of total body weight.

Abbreviations and Acronyms

As employed herein, the following terms have the indicated meanings.

| | |
|---|---|
| 20βP | 20β-hydroxyprogesterone |
| A | 4-androstene-3,17-one |
| Ac | Acetyl |
| AcOH | acetic acid |
| HSD | hydroxysteroid dehydrogenase |
| DHT | dehydrotestosterone |
| DMF | N,N-dimethylformamide |
| E1 | estron |
| E2 | estradiol |
| ER | estrogen receptor |
| EtOAc | ethyl acetate |
| GnRH | Gonadotropin Releasing Hormone |
| GRAS | generally recognized as safe |
| MS | mass spectrometry |
| NAD(P)[H] | nicotinamide-adenine-dinucleotide (phosphate) [reduced NAD(P)] |
| NMR | nuclear magnetic resonance |
| P | progesterone |
| PCC | pyridinium chlorochromate |
| T | testosterone |
| TBAB | Tetrabutylammonium Bromide |
| THF | tetrahydrofuran |
| TOF | 'Time-of-flight' |

General Preparative Methods

The compounds of the present invention may be prepared by use of known chemical reactions and procedures. Nevertheless, the following general preparative methods are presented to aid the reader in synthesizing the 17-β-Hydroxysteroid Dehydrogenase inhibitors with specific details provided below in the experimental section to illustrate working examples.

All variable groups of these methods are as described in the generic description if they are not specifically defined below.

It is recognized that compounds of the invention with each claimed optional functional group may not be prepared by each of the below-listed methods. Within the scope of each method, optional substituents may appear on reagents or intermediates which may act as protecting or otherwise non-participating groups. Utilizing methods well known to those skilled in the art, these groups are introduced and/or removed during the course of the synthetic schemes which provide the compounds of the present invention.

Flow Diagrams

The compounds according to this invention can be prepared as shown in Schemes 1 to 4.

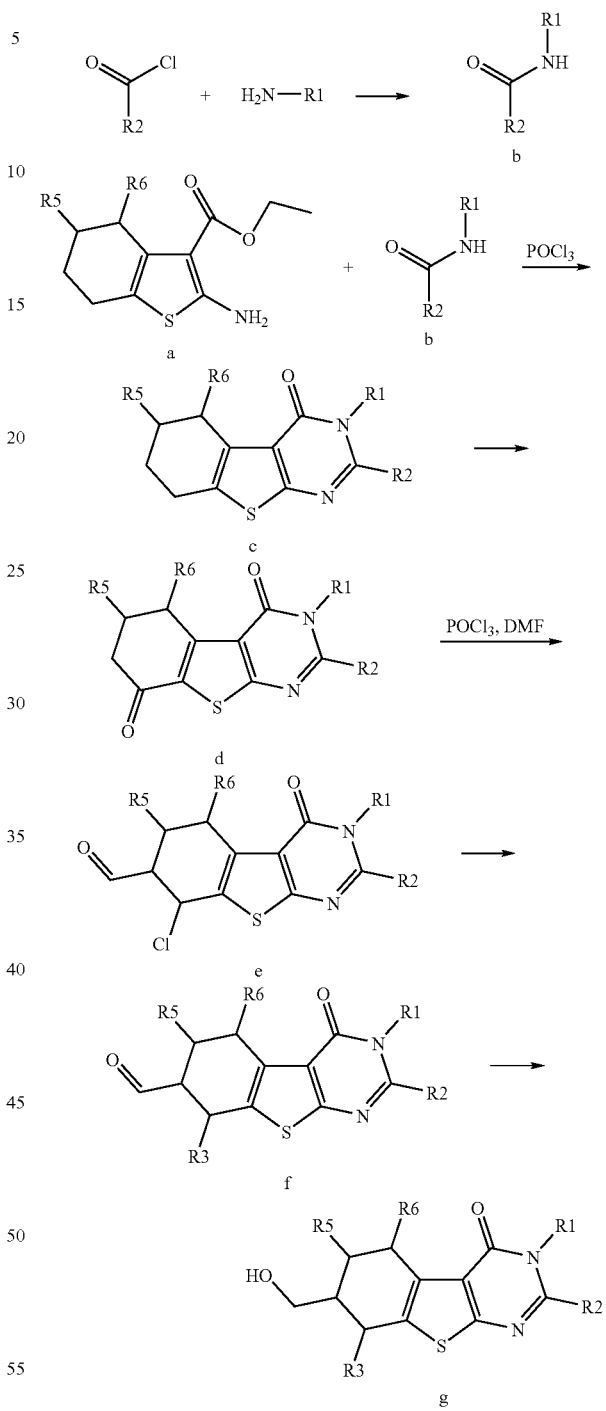

Synthesis of thienopyrimidinones is presented in Scheme 1. Thienopyrimidinones of the formula c can be synthesized starting from commercially available ethyl 2-amino4,5,6,7-tetrahydrobenzo[b]thiophene-3-carboxylate a in a reaction with suitable amides b in the presence of phosphorous oxychloride to give compound of the formula c. (Ref. Kapustina, M. V., Kharizomenova, I. A., Shvedov, V. I., *Chem. Heterocycl. Compd. (Engl. Trans.)* 1991, 425.). The appropriate N-substituted amides b can be prepared by variety of synthetic methods. The treatment of acyl halides with primary amines is a general procedure for the preparation of amides. Oxidation of compound c was performed by using oxidant like PCC (pyridinium chlorochromate) affording 4,8-dione of the formula d. Carbonyl compound d was formylated in the Vilsmeier reaction using phosphorous oxychloride in DMF affording chloroaldehydes of the formula e (Ref. Koeller, S., Lellouche, J.-P., *Tetrahedron Lett.* 1999, 40, 7043. and Kapustina, M. V, Nikolaeva, I. S., Kharizomenova, I. A., Shvedov, V. I., Pushkina, T. V., Fomina, A. N., *Pharm. Chem. J.* 1992, 789.) Chloroaldehyde e was treated with alkyl and aryl alcohols or thiols in the presence of base to form compound of the formula f. Aldehydes can be reduced to primary alcohols, i.e. compound of the formula g, by a number of reducing agents (e.g. LiAlH$_4$ and NaBH$_4$).

According to the reaction route of the Scheme 2 aromatic compounds of the formula j and k can be prepared by dehydrobromination of bromide derivatives of the formula h and i. The bromination of carbonyl compound of the formula c by using bromine and a catalyst e.g. benzoylperoxide afforded several different bromides which were isolated and identified. Generally 3,4,5-trimethoxyphenyl group in the R2-position was monobrominated as well as α-bromo- and α,α-dibromo carbonyl derivatives were produced.

The aromatization was achieved by the use of microwaves. In microwave dielectric heating the temperature increase is uniform throughout the sample (Ref. Lidstroem, P. et al. *Tetrahedron* 2001, 57, 9225). In addition, the temperature increase considerably above the conventional boiling point of the solvent used is rapidly achieved. Microwave chemistry is generally suitable for various chemical reactions having several benefits like decrease of the reaction time, increase of yield and purity. A bromide of the formula h or i in the presence of sodium acetate in acetic acid was heated by the use of microwaves at 180° C. Both the phenol of the formula j as well as the acetylated compound of the formula k could be obtained.

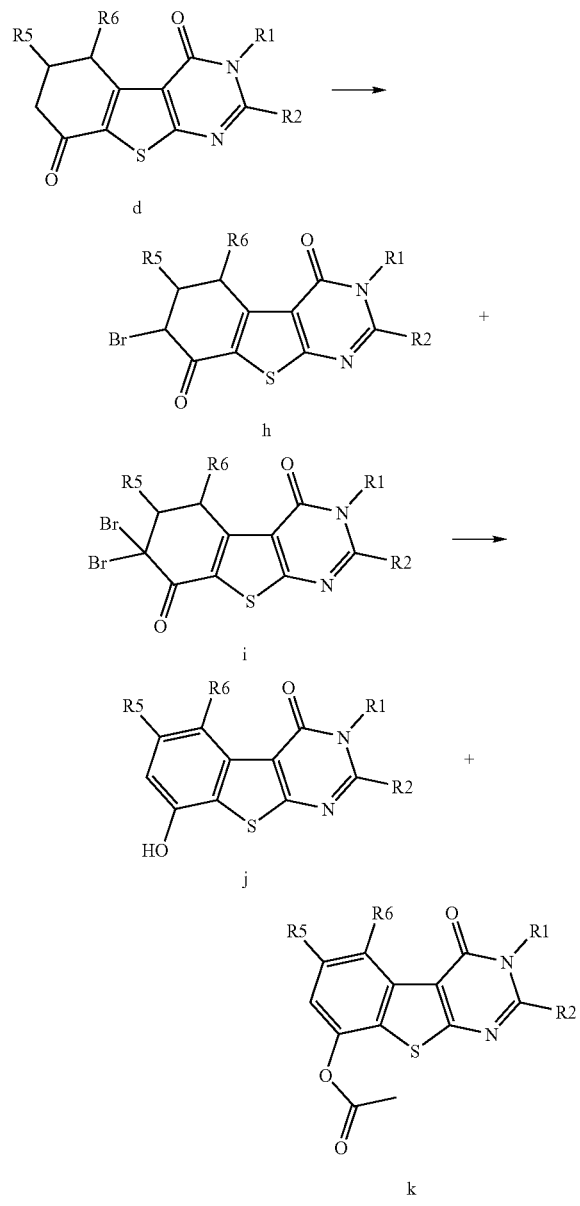

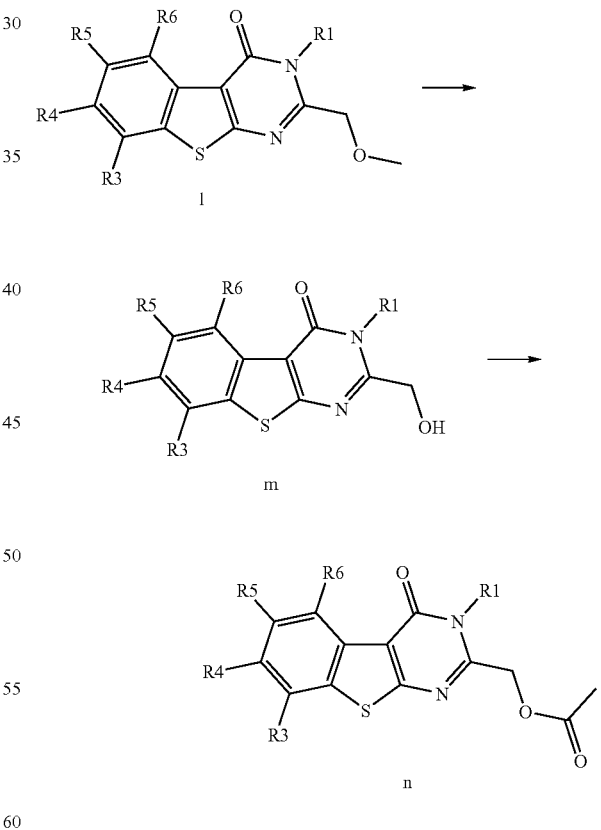

The cleavage of ethers can be achieved by numerous reagents e.g. different acidic reagents or Lewis acids. Methoxymethyl derivative l was easily demethylated by using boron tribromide according to the Scheme 3. Alcohol m was acetylated to compound n by using a general procedure (AcOH, pyridine).

Scheme 4.

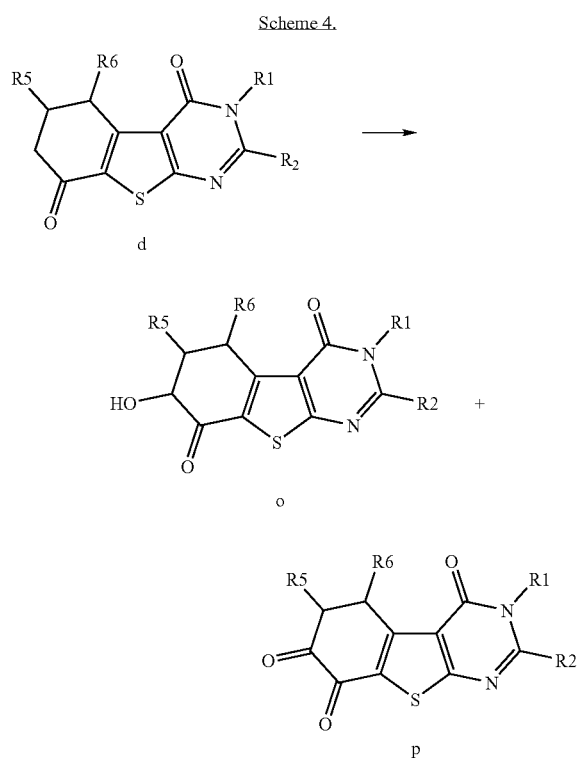

A number of methods are available to prepare α-hydroxy carbonyls and α-diketones. Carbonyl compounds of the formula c can be α-hydroxylated or α-carbonylated according to the reaction route of Scheme 4. Alternative route is, for example, the alkaline hydrolysis of α-bromo carbonyl compound affords α-hydroxy ketones of the formula o and α-diketones of the formula p.

Further compounds of general formula q falling under the scope of general formula I can prepared by parallel chemistry using a reaction as shown in the following scheme 5 (according to the first step of general flow scheme 1), thereby using different separately synthesized starting materials of formula I:

Scheme 5: General route to substituted Benzothienopyrimidinones.

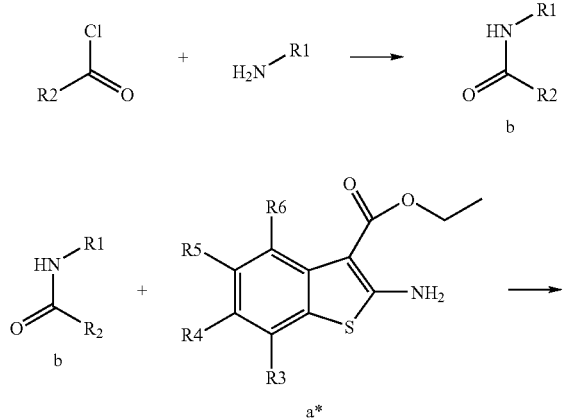

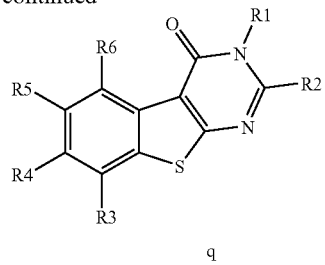

Synthesis of substituted benzothienopyrimidinones is presented in Scheme 5. Substituted Benzothienopyrimidinones of the general formula q can be synthesized starting from a substituted 2-amino-benzo[b]thiophene-3-carboxylic acid ethyl ester a* in a reaction with suitable amides b in the presence of phosphorous oxychloride to give compound of the formula q. (Ref. Kapustina, M. V., Kharizomenova, I. A., Shvedov, V. I., *Chem. Heterocycl. Compd.* (*Engl. Trans.*) 1991, 425.). The appropriate N-substituted amides b can be prepared by variety of synthetic methods. The treatment of acyl halides with primary amines is a general procedure for the preparation of amides.

The invention will be illuminated by the following non-restrictive Experimental Section.

EXPERIMENTAL SECTION

The general procedure for preparation of amides (yields 60-99% depending on the amide).

Reference Example

Preparation of N-benzyl-3,4,5-trimethoxybenzamide 3,4,5-Trimethoxybenzoyl chloride (5.0 g, 21.7 mmol) was dissolved in dichloromethane (50 ml). The reaction mixture was cooled with an ice-bath and benzylamine (4.74 ml, 43.4 mmol) was added slowly. The solid material was removed by filteration. The filtrate was poured into 30 ml of water. The organic phase was washed several times with water. The crude product was recrystallized from i-propanol.

EXAMPLES

In order to more fully illustrate the nature of the invention and the manner of practicing the same, the following examples are presented, but they should not be taken as limiting.

Compound No. 1

Preparation of 3-benzyl-2-(3,4,5-trimethoxyphenyl)-5,6,7,8-tetrahydro-3H-benzo[4,5]thieno[2,3-d]pyrimidin-4-one

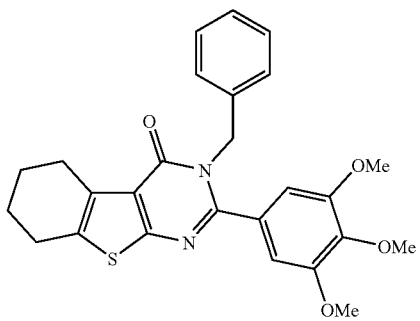

Commercially available ethyl 2-amino-4,5,6,7-tetrahydrobenzo(b)-thiophene-3-carboxylate (6.0 g, 26.6 mmol, 100 mol-%) and N-benzyl-3,4,5-trimethoxybenzamide (10.4 g, 34.6 mmol, 130 mol-%) were dissolved in dry 1,2-dichloroethane. The reaction mixture was cooled with an ice-salt-bath and POCl₃ (1.7 ml, 24.6 mmol, 130 mol-%) was added. The reaction mixture was refluxed for 24 hours. During refluxing POCl₃ (340 µl) was added twice. The reaction mixture was poured into ice-water and after neutralization with sodium acetate the product was extracted into dichloromethane. The organic phases combined were washed with sodium bicarbonate sat. (3×50 ml) and dried with MgSO₄. The yield after recrystallization from i-propanol was 8.3 g (yield 68%).

NMR: 1.89 (br s, 4H), 2.82 (br s, 2H), 3.09 (br s, 2H), 3.59 (s, 6H), 3.84 (s, 3H), 5.23 (s, 2H), 6.48 (s, 2H), 7.02 (m, 2H), 7.22-7.31 (m, 3H). MS (TOF, ES+) m/z 463 (M+1)

Compound No. 2

3-Benzyl-2-(3,4,5-trimethoxyphenyl)-6,7-dihydro-3H,5H-benzo[4,5]thieno[2,3-d]pyrimidine-4,8-dione

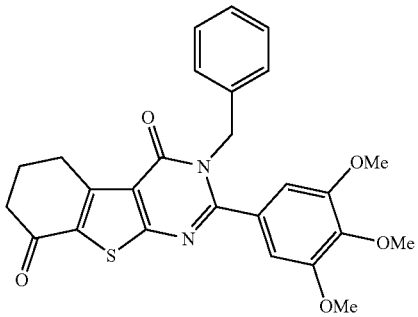

3-Benzyl-2-(3,4,5-trimethoxyphenyl)-5,6,7,8-tetrahydro-3H-benzo[4,5]thieno[2,3-d]pyrimidin-4-one (Compound No. 1) (8.2 g, 17.7 mmol) dissolved in dry dichloromethane (30 ml) was added quickly to a mixture of PCC (19.2 g, 89.0 mmol, 500 mol-%) in dichloromethane (200 ml). During refluxing PCC was added several times until the reaction was completed. The reaction mixture was filtered through Celite with dichloromethane. The crude product was purified by flash chromatography. The yield of the compound No. 2 was 4.1 g (48%).

NMR: 2.28 (m, 2H), 2.72 (m, 2H), 3.36 (m, 2H), 3.60 (s, 6H), 3.88 (s, 3H), 5.25 (s, 2H), 6.53 (s, 2H), 7.04 (m, 2H), 7.25-7.32 (m, 3H). MS (TOF, ES+) m/z 499 (M+Na)

Compound No. 3

3-Benzyl-8-chloro-4-oxo-2-(3,4,5-trimethoxyphenyl)-3,4,5,6-tetrahydro-benzo[4,5]thieno[2,3-d]pyrimidine-7-carbaldehyde

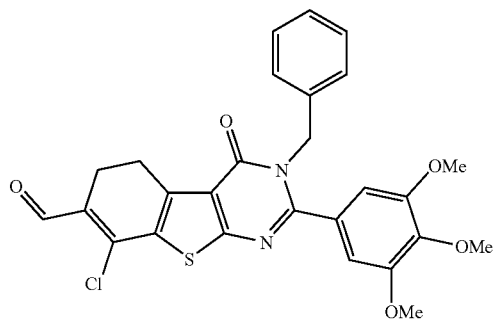

POCl₃ (3.5 ml) was added slowly to a cold, dry DMF (2.3 ml). 3-Benzyl-2-(3,4,5-trimethoxyphenyl)-6,7-dihydro-3H,5H-benzo[4,5]thieno[2,3-d]pyrimidine-4,8-dione (compound No. 2) (0.5 g, 1.1 mmol) in 1,2-dichloroethane was added slowly to the Vilsmeier reagent and stirred at room temperature for three hours after which the reaction mixture was refluxed for 15 minutes. After stirring overnight at room temperature the reaction mixture was diluted with dichloromethane and neutralized with NaOAc-solution (12 g/100 ml). The product was extracted with dichloromethane (3×30 ml). Organic phase was washed with water and dried. The crude product was purified by flash chromatography. The yield was 0.45 g (82%).

NMR: 2.85 (dd, 2H), 3.36 (dd, 2H), 3.60 (s, 6H), 3.86 (s, 3H), 5.25 (s, 2H), 6.52 (s, 2H), 7.28 (m, 5H), 10.24 (s, 1H). MS (TOF, ES+) m/z 523/525 (M⁺)

Compound No. 4

3-Benzyl-4-oxo-8-phenoxy-2-(3,4,5-trimethoxyphenyl)-3,4,5,6-tetrahydro-benzo[4,5]thieno[2,3-d]pyrimidine-7-carbaldehyde

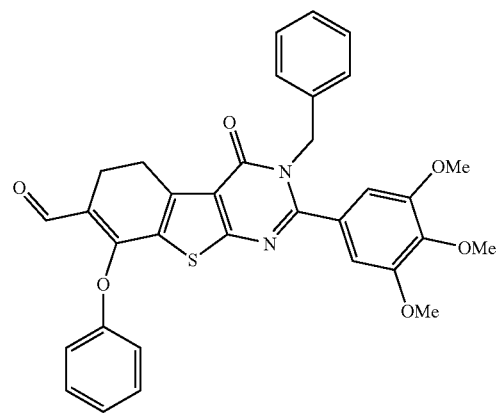

3-Benzyl-8-chloro-4-oxo-2-(3,4,5-trimethoxyphenyl)-3,4,5,6-tetrahydro-benzo[4,5]thieno[2,3-d]pyrimidine-7-carbaldehyde (Compound No. 3) (50 mg, 96 µmol), phenol (13.5 mg, 143.4 µmol), KOH powder (8.0 mg, 143.4 µmol) and TBAB (1.0 mg) were heated at 85° C. for five hours and at 60° C. for 4.5 hours. The reaction mixture was filtered through cotton wool and evaporated. The crude product was purified by flash-chromatography. The compound No. 5 was isolated as a by-product.

NMR (CDCl₃): 2.88 (dd, 2H), 3.60 (s, 6H), 3.86 (s, 3H), 4.31 (dd, 2H), 5.23 (s, 2H), 6.46 (s, 2H), 7.04-7.34 (m, 1OH), 10.14 (s, 1H). MS (TOF, ES+) m/z 581 (M+1).

Compound No. 5

3-Benzyl-4-oxo-8-phenoxy-2-(3,4,5-trimethoxyphenyl)-3,4-dihyrdo-benzo[4,5]thieno[2,3-d]pyrimidine-7-carbaldehyde

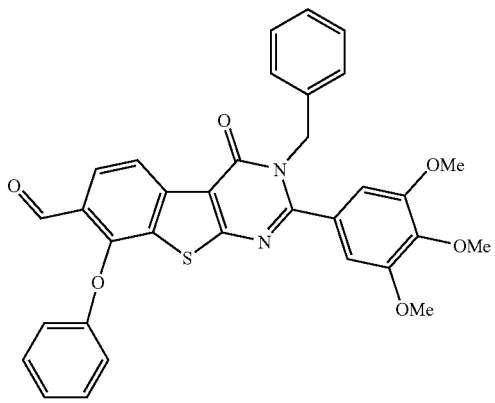

NMR (CDCl₃): 3.59 (s, 6H), 3.87 (s, 3H), 5.56 (s, 2H), 6.53 (s, 2H), 6.98-7.34 (m, 10H), 8.62 (d, 1H), 8.66 (1 H), 10.44 (s, 1H). MS (TOF, ES+) m/z 579 (M+1).

Compound No. 6

3-Benzyl-8-ethylsulfanyl-4-oxo-2-(3,4,5-trimethoxyphenyl)-3,4,5,6-tetrahydro-benzo[4,5]thieno[2,3-d]pyrimidine-7-carbaldehyde

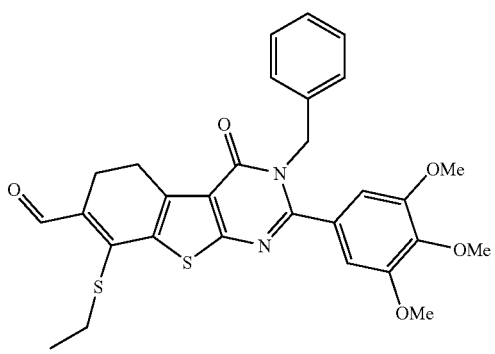

According to the method described for the compound No. 4 using ethanethiol instead of phenol.

NMR: 1.30 (t, 3H), 2.76-2.99 (m, 4H), 3.31 (m, 2H), 3.60 (s, 6H), 3.86 (s, 3H), 5.23 (s, 2H), 6.51 (s, 2H), 7.02-7.34 (m, 5H), 10.52 (s, 1H). MS (TOF, ES+) m/z 549 (M+1).

Compound No. 7

3-Benzyl-8-ethoxy-4-oxo-2-(3,4,5-trimethoxyphenyl)-3,4,5,6-tetrahydro-benzo[4,5]thieno[2,3-d]pyrimidine-7-carbaldehyde

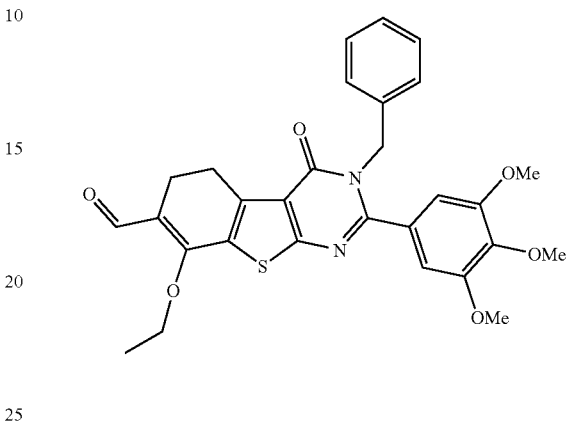

According to the method described for the compound 4 using ethanol instead of phenol.

NMR: 1.57 (t, 3H), 2.76 (m, 2H), 3.29 (m, 2H), 3.60 (s, 6H), 3.86 (s, 3H), 5.25 (s, 2H), 6.51 (s, 2H), 7.02-7.55 (m, 5H), 10.19 (s, 1H). MS (TOF, ES+) m/z 533 (M+1).

Compound No. 8

3-Benzyl-4-oxo-8-phenylsulfanyl-2-(3,4,5-trimethoxyphenyl )-3,4,5,6-tetrahydrobenzo[4,5]thieno[2,3-d]pyrimidine-7-carbaldehyde

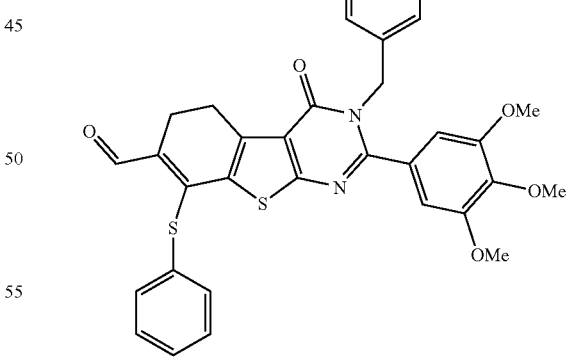

According to the method described for the compound No. 4 using benzenethiol instead of phenol. The compound No. 9 was isolated as a by-product.

NMR (CDCl₃): 2.90 (m, 2H), 3.32 (m, 2H), 3.56 (s, 6H), 4.30 (s, 3H), 5.21 (s, 2H), 6.46 (s, 2H), 7.04-7.26 (m, 10H), 10.54 (s, 1H). MS (TOF, ES+) m/z 597 (M+1).

Compound No. 9

3-Benzyl-4-oxo-8-phenylsulfanyl-2-(3,4,5-trimethoxyphenyl)-3,4-dihydro-benzo[4,5]thieno[2,3-d]pyrimidine-7-carbaldehyde

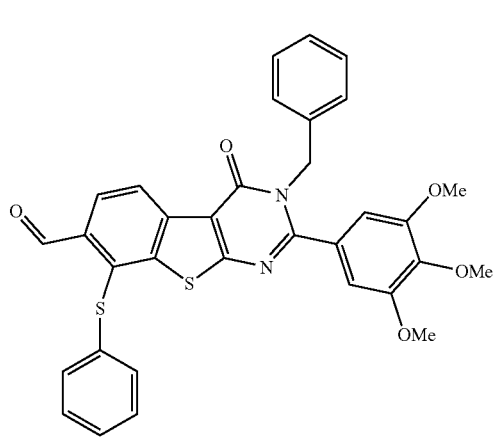

NMR (CDCl$_3$): 3.60 (s, 6H), 3.86 (s, 3H), 5.36 (s, 2H), 6.53 (s, 2H), 7.04-7.52 (m, 10H), 8.20 (d, 1H), 8.84 (d, 1H), 10.81 (s, 1H). MS (TOF, ES+) m/z 595 (M+1).

Compound No. 10

3-Phenyl-2-(3,4,5-trimethoxyphenyl)-5,6,7,8-tetrahydro-3H-benzo[4,5]thieno[2,3-d]pyrimidin-4-one

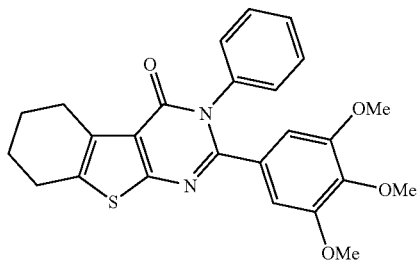

According to the method described for the compound No. 1 using N-phenyl-3,4,5-trimethoxylbenzamide as an amide.

NMR: 1.88 (m, 4H), 2.83 (m, 2H), 3.03 (m, 2H), 3.66 (s, 6H), 3.77 (s, 3H), 6.54 (s, 2H), 7.15-7.40 (m, 5H). MS (TOF ES+) m/z 449 (M+1).

Compound No. 11

3-Phenyl-2-(3,4,5-trimethoxyphenyl)-6,7-dihydro-3H,5H-benzo[4,5]thieno[2,3-d]pyrimidine-4,8-dione

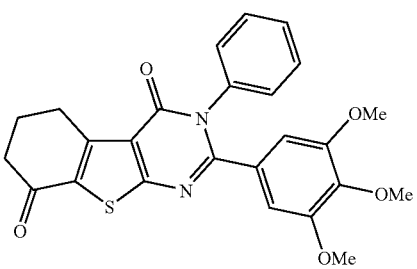

According to the method described for the compound No. 2 using the compound No. 10 as a starting material.

NMR: 2.28 (m, 2H), 2.72 (m, 2H), 3.36 (m, 2H), 3.60 (s, 6H), 3.88 (s, 3H), 6.53 (s, 2H), 7.04 (m, 2H), 7.25-7.32 (m, 3H). MS (TOF, ES+) m/z 463 (M+1)

Compound No. 12

3-Benzyl-2-(p-methoxyphenyl)-5,6,7,8-tetrahydro-3H-benzo[4,5]thieno[2,3-d]pyrimidin-4-one

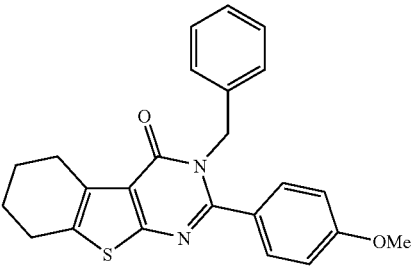

According to the method described for the compound No. 1 using N-benzyl-p-methoxybenzamide as an amide.

NMR: 1.88 (m, 4H), 2.80 (m, 2H), 3.06 (m, 2H), 3.83 (s, 3H), 5.27 (s, 2H), 6.84-6.99 (m, 4H), 7.17-7.30 (m, 5H). MS (TOF ES+) m/z 403 (M+1).

Compound No. 13

3-Benzyl-2-(p-methoxyphenyl)-6,7-dihydro-3H,5H-benzo[4,5]thieno[2,3-d]pyrimidine-4,8-dione

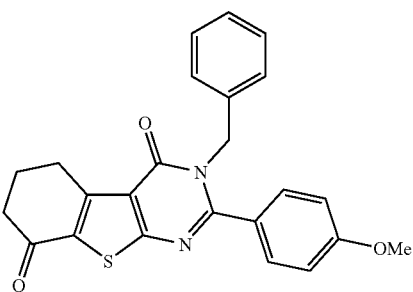

According to the method described for the compound No. 2 using the compound No. 12 as a starting material.

NMR: 2.25 (m, 2H), 2.69 (m, 2H), 3.33 (m, 2H), 3.85 (s, 3H), 5.30 (s, 2H), 6.89-7.00 (m, 4H), 7.25-7.36 (m, 5H). MS (TOF, ES+) m/z 417 (M+1)

Compound No. 14

8-Chloro-2-(p-methoxyphenyl)-4-oxo-3-phenyl-3,4,5,6-tetrahydro-benzo[4,5]thieno[2,3-d]pyrimidine-7-carbaldehyde

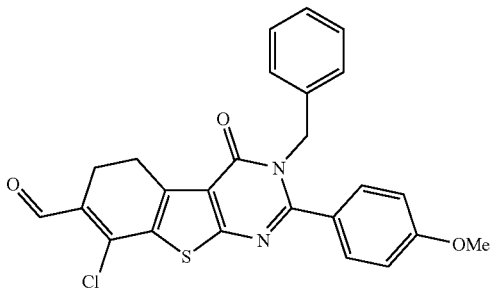

According to the method described for the compound No. 3 using the compound No. 13 as a starting material. The compound No. 15 was isolated as a by-product.

NMR (CDCl$_3$): 2.82 (m, 2H), 3.33 (m, 2H), 3.85 (s, 3H), 5.30 (s, 2H), 6.90-7.01 (m, 4H), 7.19-7.36 (m, 5H) 10.22 (s, 1H). MS (TOF, ES+) m/z 463/465 (M$^+$)

Compound No. 15

3-Benzyl-2-(p-methoxyphenyl)-4-oxo-3,4,5,6-tetrahydro-benzo[4,5]thieno[2,3-d]pyrimidine-7-carboxylic acid ethyl ester

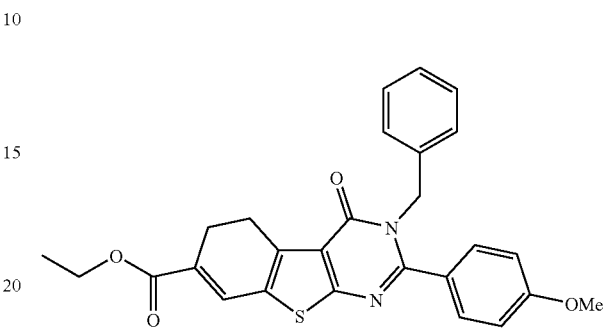

NMR (CDCl$_3$): 1.41 (t, 3H), 2.88 (m, 2H), 3.34 (m, 2H), 3.84 (s, 3H), 4.15 (q, 2H), 5.30 (s, 2H), 6.89-6.98 (m, 5H), 7.04-7.55 (m, 5H). MS (TOF, ES+) m/z 473 (M+1)

Compound No. 16

3-Benzyl-8-ethylsulfanyl-2-(p-methoxyphenyl)-4-oxo-3,4,5,6-tetrahydro-benzo[4,5]thieno[2,3-d]pyrimidine-7-carbaldehyde

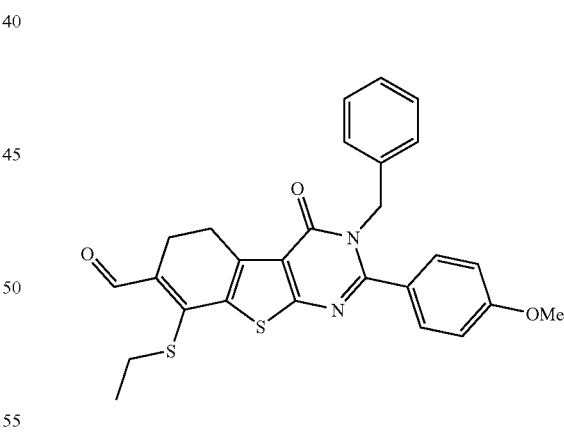

According to the method described for the compound No. 4 using the compound No. 14 as a starting material and ethanethiol instead of phenol. The compounds No. 17 and 18 were isolated as a by-product.

NMR (CDCl$_3$): 1.29 (t, 3H), 2.75-2.98 (m, 4H), 3.28 (m, 2H), 3.85 (s, 3H), 5.30 (s, 2H), 6.89-7.02 (m, 4H), 7.24-7.35 (m, 5H), 10.51 (s, 1H). MS (TOF, ES+) m/z 489 (M+1).

Compound No. 17

3-Benzyl-2-(p-methoxyphenyl)-4-oxo-3,4-dihydro-benzo[4,5]thieno[2,3-d]pyrimidine-7-carbaldehyde

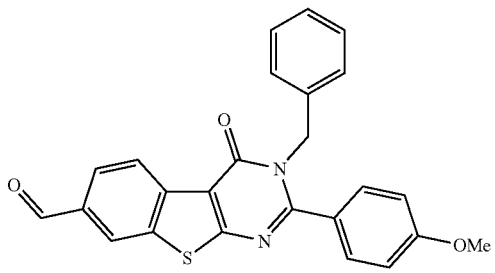

NMR (CDCl$_3$): 3.87 (s, 3H), 5.43 (s, 2H), 6.92-7.06 (m, 4H), 7.26-7.41 (m, 5H), 8.03 (d, 1H), 8.39 (s, 1H), 8.83 (d, 1H), 10.13 (s, 1H). MS (TOF, ES+) m/z 426 (M+1).

Compound No. 18

3-Benzyl-8-ethylsulfanyl-2-(p-methoxyphenyl)-4-oxo-3,4-dihydro-benzo[4,5]thieno[2,3-d]pyrimidine-7-carbaldehyde

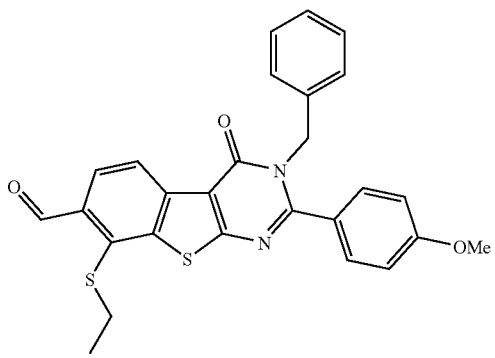

NMR (CDCl$_3$): 1.25 (t, 3H), 3.00 (q, 2H), 3.87 (s, 3H), 5.42 (s, 2H), 6.92-7.05 (m, 5H), 7.25-7.43 (m, 4H), 8.11 (d, 1H), 8.74 (d, 1H), 10.86 (s, 1H). MS (TOF, ES+) m/z 487 (M+1).

Compound No. 19

3-Benzyl-8-ethylsulfanyl-7-hydroxymethyl-2-(p-methoxyphenyl)-3,4-dihydro-3H-benzo[4,5]thieno[2,3-d]pyrimidin-4-one

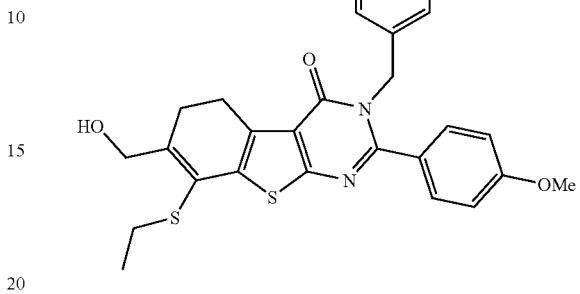

NaBH$_4$ (26.2 mg, 0.05 μmol) was dissolved in ethyl acetate (2 ml). The compound No. 16 was dissolved in ethyl acetate (3 ml) and added to the reaction mixture. The reaction was completed in 2.5 hours and 20 ml of EtOAc was added. The reaction mixture was poured into water (10 ml) and saturated NH$_4$Cl-solution (10 ml) was added. The phases were separated and the water phase was extracted with EtOAc (3×10 ml). Organic phase was washed with brine and evaporated.

NMR (CDCl$_3$): 1.23 (t, 3H), 2.00 (br s, 1H), 2.64-2.79 (m, 4H), 3.25 (m, 2H), 3.83 (s, 3H), 4.60 (s, 2H), 5.28 (s, 2H), 6.86-7.01 (m, 4H), 7.15-7.35 (m, 5H). MS (TOF, ES+) m/z 491 (M+1).

Compound No. 20

3-Benzyl-7-hydroxymethyl-2-(p-methoxyphenyl)-8-phenoxy-3H-benzo[4,5]thieno[2,3-d]pyrimidin-4-one

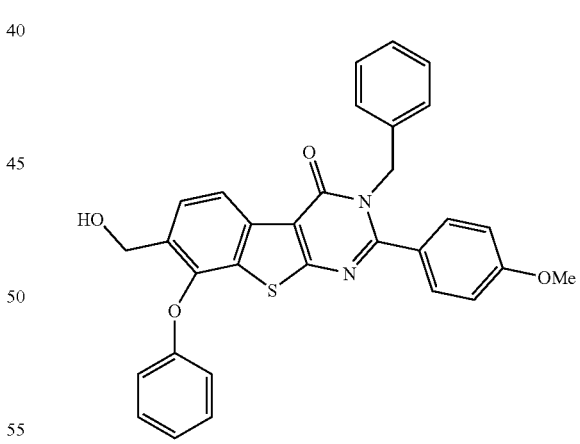

The compound No. 14 (49.9 mg, 108 μmol), phenol (21.1 mg, 216 μmol), KOH powder (13.0 mg, 216 μmol) and TBAB (2.3 mg) in THF (2 ml) were refluxed for 2.5 hours. The solvent was evaporated and the precipitate was dissolved in dichloromethane. The reaction mixture was filtered through cotton wool and evaporated. The crude product was purified by flash-chromatography. The compound No. 21 was isolated as a by-product.

NMR (CDCl$_3$): 3.84-3.89 (m, 4H), 4.80 (d, 2H), 5.41 (s, 2H), 6.88-7.42 (14H), 7.69 (d, 1H), 8.56 (d, 1H). MS (TOF, ES+) m/z 521 (M+1)

Compound No. 21

3-Benzyl-7-methyl-2-(p-methoxyphenyl)-8-phenoxy-3H-benzo[4,5]thieno[2,3-d]pyrimidin-4-one

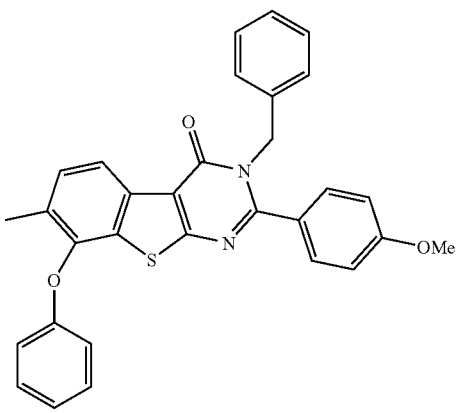

NMR (CDCl$_3$): 2.56 (s, 3H), 3.86 (s, 3H), 5.41 (s, 2H), 6.85-7.40 (m, 15H), 8.5 (d, 1H), MS (TOF, ES+) m/z 505 (M+1)

Compound No. 22

3-Phenyl-2-(p-methoxyphenyl)-5,6,7,8-tetrahydro-3H-benzo[4,5]thieno[2,3-d]pyrimidin-4-one

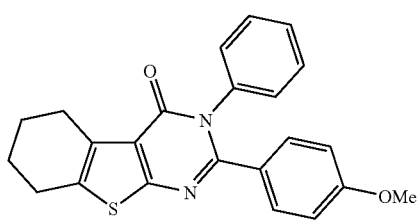

According to the method described for the compound No. 1 using N-phenyl-p-methoxybenzamide as an amide.

NMR: 1.88 (m, 4H), 2.81 (m, 2H), 3.05 (m, 2H), 3.74 (s, 3H), 6.69 (m, 2H), 7.12-7.40 (m, 7H). MS (TOF ES+) m/z 389 (M+1).

Compound No. 23

3-Phenyl-2-(p-methoxyphenyl)-6,7-dihydro-3H,5H-benzo[4,5]thieno[2,3-d]pyrimidin-4,8-dione

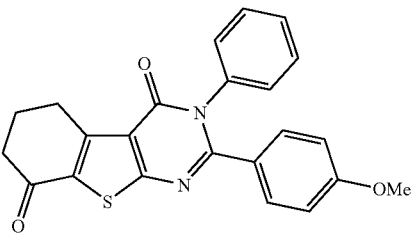

According to the method described for the compound 2 using the compound No. 22 as a starting material.

NMR: 2.25 (m, 2H), 2.70 (m, 2H), 3.30 (m, 2H), 3.76 (s, 3H), 6.71 (d, 2H), 7.14-7.36 (m, 7H). MS (TOF, ES+) m/z 403 (M+1)

Compound No. 24

2-Methyl-3-phenyl-5,6,7,8-tetrahydro-3H-benzo[4,5]thieno[2,3-d]pyrimidin-4-one

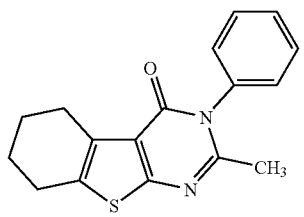

According to the method described for the compound No. 1 using N-phenyl-acetamide as an amide.

NMR: 1.84 (m, 4H), 2.20 (s, 3H), 2.76 (m, 2H), 2.97 (m, 2H), 7.20-7.26 (m, 2H), 7.45-7.6 (m, 3H). MS (TOF ES+) m/z 297 (M+1).

Compound No. 25

2-Methyl-3-phenyl-6,7-dihydro-3H,5H-benzo[4,5]thieno[2,3-d]pyrimidine-4,8-dione

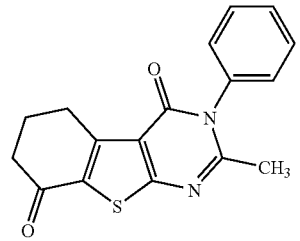

According to the method described for the compound No. 2 using the compound No. 24 as a starting material.

NMR: 2.19 (m, 2H), 2.27 (s, 3H), 2.68 (m, 2H), 3.24 (m, 2H), 7.22-7.27 (m, 2H), 7.53-7.56 (m, 3H). MS (TOF ES+) m/z 311 (M+1).

Compound No. 26

2-(acetic acid methyl ester)-3-benzyl-5,6,7,8-tetrahydro-3H-benzo[4,5]thieno[2,3-d]pyrimidin-4-one

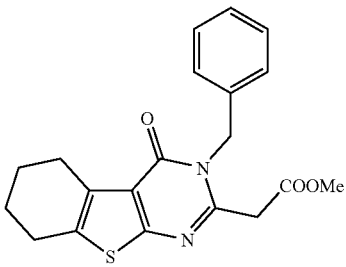

According to the method described for the compound No. 1 using N-benzyl-malonamic acid methyl ester as an amide.

NMR: 1.87 (m, 4H), 2.79 (m, 2H), 3.05 (m, 2H), 3.68 (s, 3H), 3.80 (s, 2H), 5.36 (s, 2H), 7.13-7.32 (m, 5H). MS (TOF ES+) m/z 369 (M+1)

Compound No. 27

3-Benzyl-2-methoxymethyl-5,6,7,8-tetrahydro-3H-benzo[4,5]thieno[2,3-d]pyrimidin-4-one

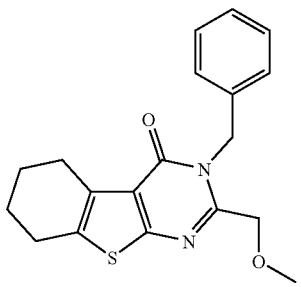

According to the method described for the compound No. 1 using N-benzyl-2-methoxy-acetamide as an amide.

NMR (CDCl$_3$): 1.86 (m, 4H), 2.79 (m, 2H), 3.05 (m, 2H), 3.41 (s, 3H), 4.39 (s, 2H), 5.51 (s, 2H), 7.15-7.36 (m, 5H). MS (TOF ES+) m/z 341 (M+1).

Compound No. 28

3-Benzyl-2-hydroxymethyl-5,6,7,8-tetrahydro-3H-benzo[4,5]thieno[2,3-d]pyrimidin-4-one

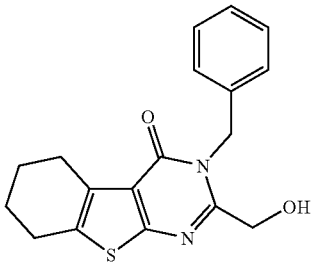

The compound No. 27 (1.0 g, 2.94 mmol) was dissolved in dichloromethane (30 ml), cooled with ice-bath and BBr$_3$ (2.9 ml, 2.94 mmol) was added. Stirring was continued at room temperature for five hours. Water (1 ml) was added and the solvent was evaporated. 10% NaOH-solution (10 ml) was added and stirred well for 10 min. The solution was acidified by HCl-addition. The product was extracted with EtOAc and organic phase was washed with brine. The crude product was recrystallized from ethanol.

NMR (CDCl$_3$): 1.25 (s, 1H), 1.88 (m, 4H), 2.80 (m, 2H), 3.05 (m, 2H), 4.55 (s, 2H), 5.21 (s, 2H), 7.15-7.40 (m, 5H). MS (TOF ES+) m/z 327 (M+1).

Compound No. 29

Acetic acid 3-benzyl-4-oxo-3,4,5,6,7,8-hexahydro-benzo[4,5]thieno[2,3-d]pyrimidin-2-ylmethyl ester

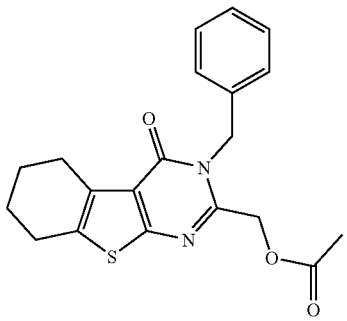

The compound No. 28 (200 mg, 0.61 mmol) was dissolved in a solution of acetic acid anhydride (2 ml) and pyridine (1 ml) and stirred for an hour at room temperature. Water (5 ml) was added and the solid precipitate was isolated. The yield of the acetylated product was 213 mg (95%).

NMR (CDCl$_3$): 1.88 (m, 4H), 1.99 (s, 3H), 2.80 (m, 2H), 3.07 (m, 2H), 5.04 (s, 2H), 5.36 (s, 2H), 7.12-7.36 (m, 5H). MS (TOF ES+) m/z 391 (M+Na).

Compound No. 30

Acetic acid 3-benzyl-4,8-dioxo-3,4,5,6,7,8-hexahydro-benzo[4,5]thieno[2,3-d]pyrimidin-2-ylmethyl ester

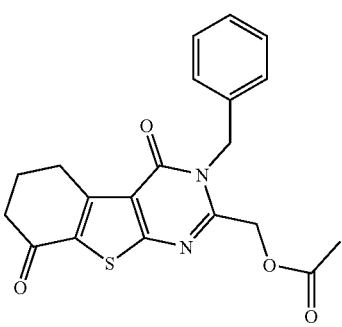

According to the method described for the compound No. 2 using the compound No. 29 as a starting material.

NMR (CDCl$_3$): 2.07 (s, 3H), 2.26 (m, 2H), 2.70 (m, 4H), 5.08 (s, 2H), 5.37 (s, 2H), 7.15-7.37 (m, 5H). MS (TOF ES+) m/z 383 (M+1).

Compound No. 31

3-Benzyl-2-methoxymethyl-6,7-dihydro-3H,5H-benzo[4,5]thieno[2,3-d]pyrimidine-4,8-dione

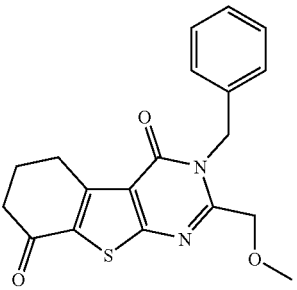

According to the method described for the compound No. 2 using the compound No. 27 as a starting material. The compound No. 32 was isolated as a by-product in the oxidation.

NMR: 2.25 (m, 2H), 2.69 (m, 2H), 3.33 (m, 2H), 3.45 (s, 3H), 4.44 (s, 2H), 5.52 (s, 2H), 7.17-7.54 (m, 5H). MS (TOF ES+) m/z 355 (M+1)

Compound No. 32

3-Benzyl-4,8-dioxo-3,4,5,6,7,8-hexahydro-benzo[4,5]thieno[2,3-d]pyrimidine-2-carboxylic acid methyl ester

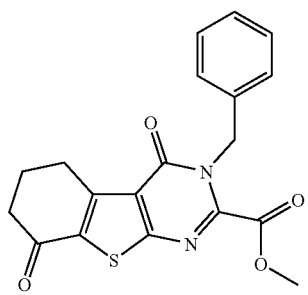

NMR (CDCl$_3$): 2.27 (m, 2H), 2.70 (m, 2H), 3.33 (m, 2H), 3.35 (s, 3H), 5.51 (s, 2H), 7.18-7.33 (m, 5H). MS (TOF ES+) m/z 368 (M+Na)

Compound No. 33

3-Benzyl-4,9,9-trioxo4,5,6,7,8,9-hexahydro-3H-9lambda*6*-benzo[4,5]thieno[2,3-d]pyrimidine-2-carbaldehyde

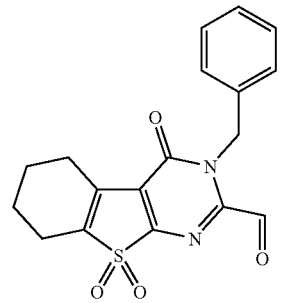

SeO$_2$ in a dioxane-water solution was heated in 50-55° C. until all the solid material was dissolved. The compound No. 27 was added and the reaction mixture was heated in a microwave reactor for 15 minutes at 160° C. The reaction mixture was filtered and the filterate was evaporated. The crude product was purified by chromatography.

NMR (CDCl$_3$): 1.89 (m, 4H), 2.8 (m, 2H), 3.09 (m, 2H), 5.84 (s, 2H), 7.26 (m, 5H), 9.60 (s, 1H). MS (TOF ES+) m/z 357 (M+1)

Compound No. 34

3-Benzyl-8-chloro-2-methoxymethyl-4-oxo-3,4,5,6-tetrahydro-benzo[4,5]thieno[2,3-d]pyrimidine-7-carbaldehyde

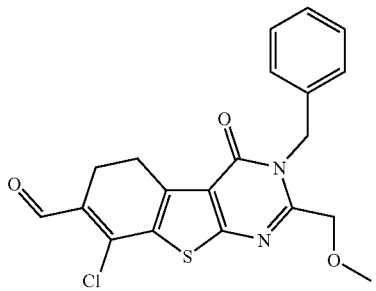

According to the method described for the compound No. 3 using the compound No. 31 as a starting material. Compound No. 35 was isolated as a by-product.

NMR (CDCl$_3$): 2.82 (m, 2H), 3.32 (m, 2H), 3.50 (s, 3H), 4.43 (s, 2H), 5.52 (s, 2), 7.17-7.78 (m, 5H), 10.23 (s, 1H). MS (TOF ES+) m/z 401 (M+1)

Compound No. 35

3-Benzyl-8-chloro-7-formyl-5-hydroxyl-2-methoxymethyl-4-oxo-benzo[4,5]thieno[2,3-d]pyrimidine-6-carboxylic acid

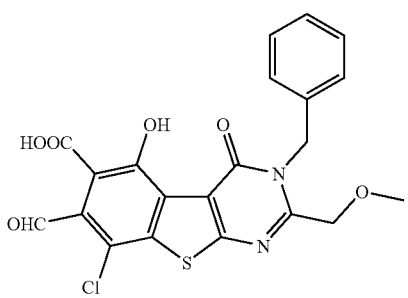

NMR (CDCl$_3$): 3.51 (s, 3H), 4.54 (s, 2H), 5.62 (s, 2H), 7.19-7.39 (m, 5H), 8.57 (s, 1H), 10.57 (s, 1H), 11.35 (s, 1H). MS (TOF ES+) m/z 481/483 (M+Na)

Compound No. 36

2-Methoxymethyl-3-phenyl-5,6,7,8-tetrahydro-3H-benzo[4,5]thieno[2,3-d]pyrimidin-4-one

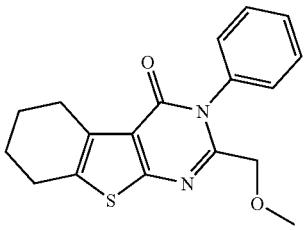

According to the method described for the compound No. 1 using N-phenyl-2-methoxy-acetamide as an amide.

NMR: 1.87 (m, 4H), 2.79 (m, 2H), 2.99 (m, 2H), 3.28 (s, 3H), 4.09 (s, 2H), 7.24-7.32 (m, 2H), 7.46-7.60 (m, 3H). MS (TOF ES+) m/z 327 (M+1)

Compound No. 37

2-Methoxymethyl-3-phenyl-6,7-dihydro-3H,5H-benzo[4,5]thieno[2,3-d]pyrimidin-4,8-dione

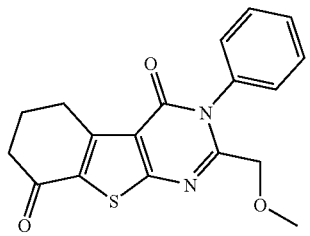

According to the method described for the compound No. 2 using the compound No. 36 as a starting material.

NMR (CDCl$_3$): 2.33 (m, 2H), 2.69 (m, 2H), 3.26 (m, 2H), 3.32 (s, 3H), 4.12 (s, 2H), 7.19-7.29 (m, 2H), 7.52-7.56 (m, 3H). MS (TOF ES+) m/z 341 (M+1)

Compound No. 38

2-Hydroxymethyl-3-phenyl-5,6,7,8-tetrahydro-3H-benzo[4,5]thieno[2,3-d]pyrimidin-4-one

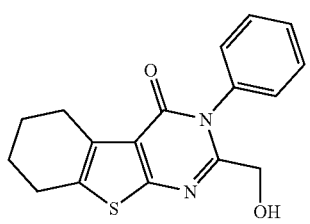

According to the method described for the compound No. 28 using the compound No. 36 as a starting material.

NMR (CDCl$_3$): 1.85 (m, 4H), 2.81 (m, 2H), 2.98 (m, 2H), 3.82 (br s, 1H), 4.13 (s, 2H), 7.20-7.57 (m, 5H). MS (TOF ES+) m/z 313 (M+1)

Compound No. 39

Acetic acid 4-oxo-3-phenyl-3,4,5,6,7,8-hexahydro-benzo[4,5]thieno[2,3-d]pyrimidin-2-ylmethyl ester

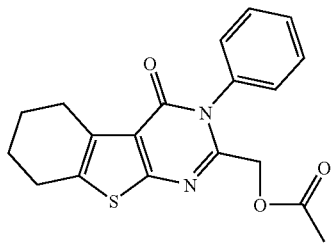

According to the method described for the compound No. 29 using the compound No. 38 as a starting material.

NMR (CDCl$_3$): 1.80-1.90 (m, 4H), 2.06 (s, 3H), 2.80 (m, 2H), 2.97 (m, 2H), 4.72 (s, 2H), 7.15-7.60 (m, 5H). MS (TOF ES+) m/z 377 (M+Na)

Compound No. 40

4-Oxo-3-phenyl-3,4,5,6,7,8-hexahydro-benzo[4,5]thieno[2,3-d]pyrimidine-2-carboxylic acid ethyl ester

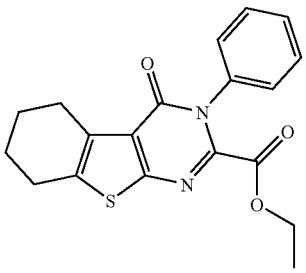

According to the method described for the compound No. 1 using ethyl oxanilate as an amide.

NMR: 1.00 (t, 3H), 1.87 (m, 4H), 2.83 (m, 2H), 3.01 (m, 2H), 4.06 (q, 2H), 7.26-7.51 (m, 5H). MS (TOF ES+) m/z 355 (M+1)

Compound No. 41

3-Benzyl-2-(3,4,5-trihydroxyphenyl)-5,6,7,8-tetrahydro-3H-benzo[4,5]thieno[2,3-d]pyrimidin-4-one

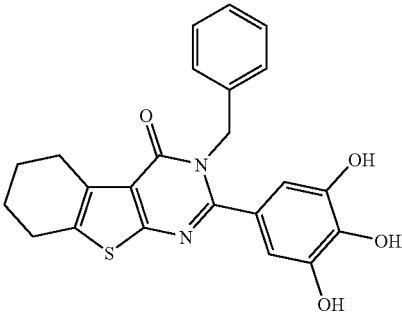

The compound No. 1 (100 mg, 0.22 mmol) was dissolved in dichloromethane. BBr$_3$ (1M-solution, 220 μl, 0.22 mmol) was added. The reaction mixture was stirred at room temperature and boron tribromide was added several times (portionwise 100 μl) until the reaction was completed. The reaction mixture was washed with water. Water phase was extracted with ethyl acetate and organic phase was washed with brine. The crude product was purified by crystallization from CH$_2$Cl$_2$.

NMR (DMSO-d6): 1.79 (m, 4H), 2.76 (m, 2H), 2.87 (m, 2H) 5.22 (s, 2H), 6.37 (s, 2H), 6.93-6.97 (m, 2H), 7.13-7.31 (m, 3H). MS (TOF, ES+) m/z 421 (M+1).

Compound No. 42

3-Phenyl-2-(3,5-dihydroxy-4-methoxyphenyl)-5,6,7,8-tetrahydro-3H-benzo[4,5]thieno[2,3-d]pyrimidin-4-one

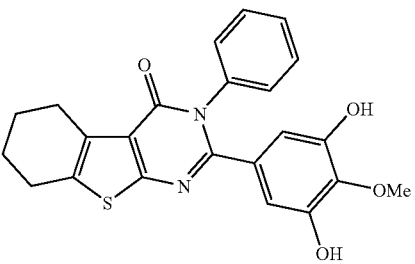

According to the method described for the compound No. 41 using ice-bath during the reagent addition. The compound No. 43 was isolated as a by-product.

NMR (CDCl$_3$): 1.85-1.88 (m, 4H), 2.78-2.81 (m, 2H), 3.03 (m, 2H), 3.62 (s, 3H), 5.61 (br s, 2H), 6.33 (d, 1 H), 6.63 (d, 1 H), 7.12-7.35 (m, 5H). MS (TOF, ES+) m/z 421 (M+1).

Compound No. 43

3-Phenyl-2-(3,4,5-trihydroxyphenyl)-5,6,7,8-tetrahydro-3H-benzo[4,5]thieno[2,3-d]pyrimidin-4-one

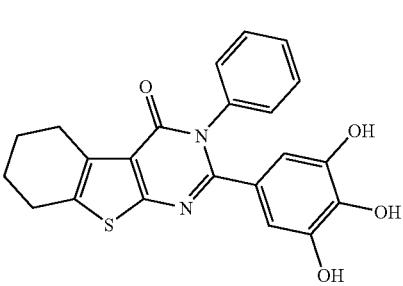

NMR (DMSO-d6): 1.78 (m, 4H), 2.77-2.85 (m, 4H), 3.39 (br m, 3H), 6.25 (s, 2H), 7.19-7.34 (m, 5H). MS (TOF, ES+) m/z 407 (M+1).

Compound No. 44

7-Bromo-2-methyl-3-phenyl-6,7-dihydro-3H,5H-benzo[4,5]thieno[2,3-d]pyrimidine-4,8-dione

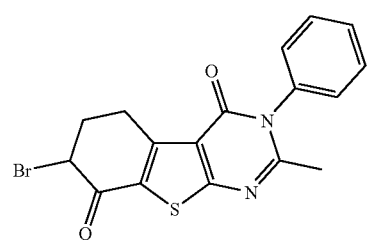

The compound No. 25 (250 mg, 0.81 mmol) was dissolved in dichloromethane (10 ml) and benzoyl peroxide (1-2 mg) was added. The reaction mixture was refluxed and bromine (85 μl, 1.61 mmol, 200 mol-%) was added. Refluxing was continued until the reaction was compleated. The reaction mixture was washed with water (10 ml). The organic phase was evaporated and the precipitate was purified by flash chromatography. The compound No. 45 was isolated as a by-product.

NMR (CDCl$_3$): 2.28 (s, 3H), 2.57-2.78 (m, 2H), 3.08-3.17 (m, 2H), 4.70 (m, 1H), 7.20-7.30 (5H). MS (TOF, ES+) m/z 411/413 (M+Na).

Compound No. 45

7,7-Dibromo-2-methyl-3-phenyl-6,7-dihydro-3H, 5H-benzo[4,5]thieno[2,3-d]pyrimidine-4,8-dione

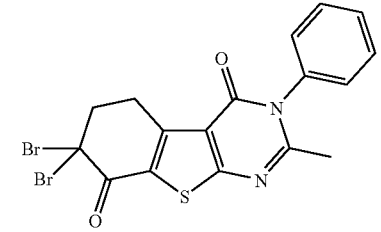

NMR (CDCl$_3$): 2.28 (s, 3H), 2.50-2.70 (m, 1H), 3.12-3.36 (m, 3H), 7.21-7.27 (m, 5H). MS (TOF, ES+) m/z 487/489/591 (M+Na).

Compound No. 46

3-benzyl-7-bromo-2-(3,4,5-trimethoxyphenyl)-6,7-dihydro-3H,5H-benzo[4,5]thieno[2,3-d]pyrimidine4,8-dione

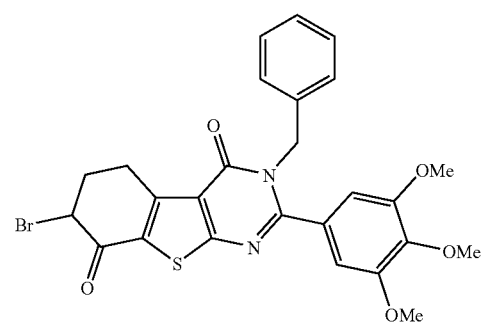

The compound No. 2 (2.0 g, 4. mmol, 100 mol-%) and benzoylperoxide (99 mg, 0.4 mmol, 10 mmol %) were dissolved in dichloromethane (40 ml). While the reaction mixture was refluxing bromine (440 μl, 8.4 mmol, 200 mol-%) in dichloromethane (16 ml) was added. The reaction was completed in 3.5 hours. The cooled reaction mixture was washed with water (40 ml). The organic phase was evaporated. The crude product was purified by chromatography using di-chloromethane-EtOAc as an eluent. The compounds No. 47, 48 and 49 were isolated as by-products.

NMR (CDCl$_3$): 2.62-2.66 (m, 2H), 3.23-3.69 (m, 8H), 3.96 (s, 3H), 4.74 (m,1H), 5.26 (s, 2H), 6.53 (s, 2H), 7.03-7.35 (m, 5H). MS (TOF, ES+) m/z 555/557 (M+).

Compound No. 47

3-benzyl-7-bromo-2-(2-bromo-3,4,5-trimethoxyphenyl)-6,7-dihydro-3H,5H-benzo[4,5]thieno[2,3-d]pyrimidine-4,8-dione

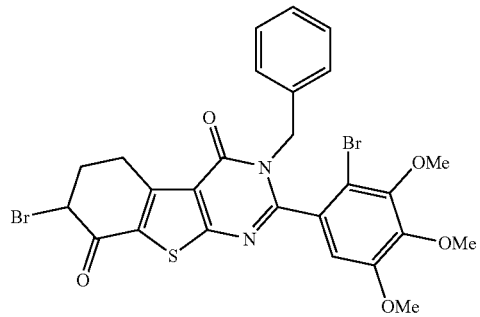

NMR (CDCl$_3$): 2.59-2.67 (m, 2H), 3.29-3.46 (m, 4H), 3.56-3.73 (m, 1H), 3.92 (s, 3H), 3.96 (s, 3H), 4.46 (dd, 1H), 4.75 (m, 1H), 5.91 (dd, 1H), 6.14 (d, 1H), 6.89 (m, 2H), 7.21-7.27 (m, 3H). MS (TOF, ES+) m/z 633/635/637 (M$^{30}$).

Compound No. 48

3-benzyl-7,7-dibromo-2-(2-bromo-3,4,5-trimethoxyphenyl)-6,7-dihydro-3H,5H-benzo[4,5]thieno[2,3-d]pyrimidine-4,8-dione

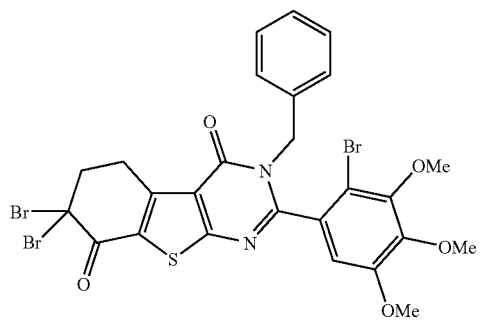

NMR (CDCl$_3$): 3.21 (m, 2H), 3.46-3.54 (m, 5H), 3.92 (s, 3H), 3.96 (s, 3H), 4.46 (d, 1H), 5.90 (d, 1H), 6.14 (s, 1H), 6.87 (m, 2H), 7.17-7.20 (m, 3H). MS (TOF, ES+) m/z 711/713/715/717 (M$^+$).

Compound No. 49

3-Benzyl-2-(2-bromo-3,4,5-trimethoxyphenyl)-8-hydroxy-3H-benzo[4,5]thieno[2,3-d]pyrimidin-4-one

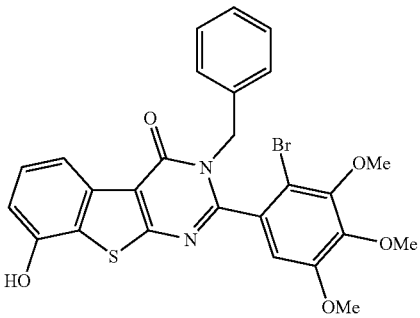

The compound No. 47 (0.6 g, 1.0 mmol), NaOAc (1.66 g, 20.2 mmol) was dissolved in acetic acid (4 ml) in a microwave vial. The reaction mixture was heated with microwaves at 180° C. for an hour. Water (20 ml) was added to the reaction mixture and the product was extracted with EtOAc (5×30 ml). The crude product was purified by flash chromatography. The compounds No. 50, 51 and 52 were isolated as by-products.

NMR (CDCl$_3$): 3.44 (s, 3H), 3.92 (s, 3H), 3.95 (s, 3H), 4.53 (d, 1H), 6.06 (d, 1H), 6.17 (s, 1H), 6.31 (br s, 1H), 6.88-6.92 (m, 3H), 7.18-7.24 (m, 3H), 7.41 (dd, 1H), 8.34 (d, 1H). MS (TOF, ES+) m/z 553/555 (M$^+$).

Compound No. 50

Acetic acid 3-benzyl-2-(2-bromo-3,4,5-trimethoxyphenyl)-4-oxo-3,4-dihydro-benzo[4,5]thieno[2,3-d]pyrimidin-8-yl ester

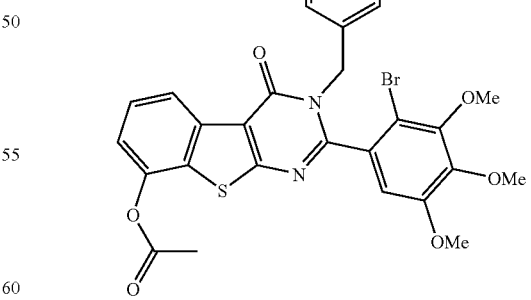

NMR (CDCl$_3$): 2.44 (s, 3H), 3.45 (s, 3H), 3.90 (s, 3H), 3.97 (s, 3H), 4.84 (d, 1H), 6.06 (d, 1H), 6.17 (s, 1H), 6.87-6.93 (m, 2H), 7.18-7.32 (m, 3H), 7.36 (d, 1H), 7.60 (d, 1H), 8.61 (d, 1H). MS (TOF, ES+) m/z 595/597 (M$^+$).

Compound No. 51

3-benzyl-2-(2-bromo-3,4,5-trimethoxyphenyl)-3H-benzo[4,5]thieno[2,3-d]pyrimidin-4-one

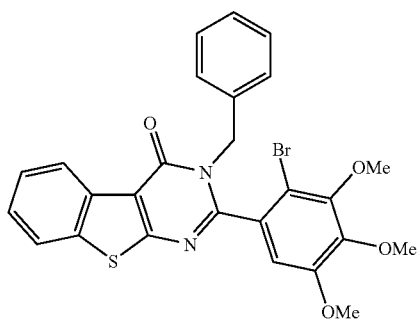

NMR (CDCl$_3$): 3.45 (s, 3H), 3.90 (s, 3H), 3.96 (s, 3H), 4.52 (d, 1H), 6.04 (d, 1H), 6.12 (s, 1H), 6.87-6.92 (m, 2H), 7.20-7.60 (m, 5H), 7.79 (d, 1H), 8.50 (d, 1H). MS (TOF, ES+) m/z 537/539 (M$^+$).

Compound No. 52

3-benzyl-7-bromo-2-(2-bromo-3,4,5-trimethoxyphenyl)-8-hydroxy-3H-benzo[4,5]thieno[2,3-d]pyrimidin-4-one

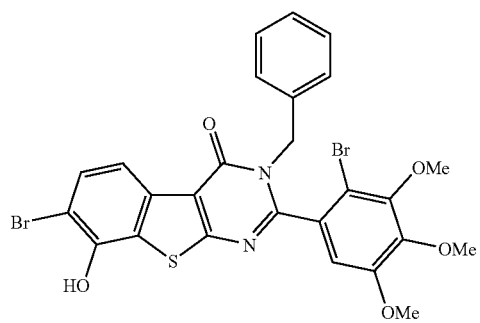

NMR (CDCl$_3$): 3.46 (s, 3H), 3.89 (s, 3H), 3.93 (s, 3H), 4.55 (d, 1H), 6.05 (m, 2H), 6.19 (s, 1H), 6.92 (m, 2H), 7.21-7.29 (m, 3H), 7.65 (d, 1H), 8.23 (d, 1H). MS (TOF, ES+) m/z 631/633/635 (M+1).

Compound No. 53

3-Benzyl-8-hydroxy-2-(3,4,5-trimethoxyphenyl)-3H-benzo[4,5]thieno[2,3-d]pyrimidin-4-one

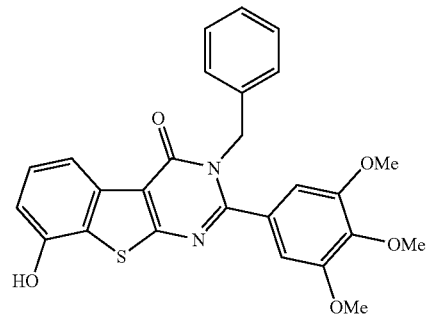

According to the method described for the compound No. 49 using the compound No. 46 as a starting material. The compound No. 54 was isolated as a by-product.

NMR (CDCl$_3$): 3.60 (s, 6H), 3.93 (s, 3H), 5.53 (d, 2H), 6.58 (d, 2H), 6.93 (d, 1H), 7.08 (m, 2H), 7.22-7.43 (m, 4H), 8.19 (d, 1H). MS (TOF, ES+) m/z 475 (M+1).

Compound No. 54

Acetic acid 3-benzyl-2-(3,4,5-trimethoxyphenyl)-4-oxo-3,4-dihydro-benzo[4,5]thieno[2,3-d]pyrimidin-8-yl ester

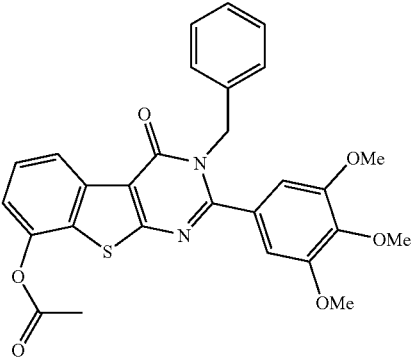

NMR (CDCl$_3$): 2.44 (s, 3H), 3.61 (s, 6H), 3.93 (s, 3H), 5.53 (d, 2H), 6.55 (d, 2H), 7.05 (m, 2H), 7.24-7.32 (m, 4H), 7.57 (m, 1H), 8.58 (d, 1H). MS (TOF, ES+) m/z 517 (M+1).

Compound No. 55

3-benzyl-7-bromo-9-oxo-2-(3,4,5-trimethoxyphenyl)-5,6,7,9-tetrahydro-3H-9lambda*4*-benzo[4,5]thieno[2,3-d]pyrimidine-4,8-dione

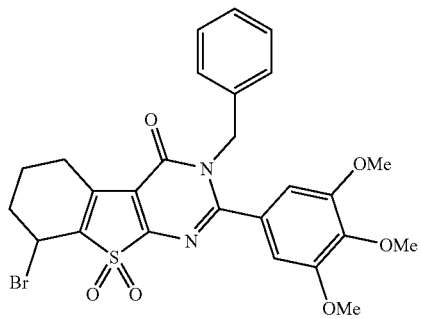

The compound No. 46 (157 mg, 0.28 mmol) was dissolved in pyridine (4 ml). Powdered NaOH (23 mg, 0.56 mmol) dissolved in water (1 ml) was added to the reaction mixture. Stirring was continued at room temperature for 1.5 hours and the reaction mixture was poured into 1% HCl (10 ml) and the product was extracted with EtOAc (3×10 ml). The organic phase was washed with 5% NaHCO3-solution (3×10 ml), water (3×10 ml) and brine (3×10 ml). The crude product was purified by flash chromatography.

NMR (CDCl$_3$): 2.18-2.28 (m, 2H), 2.58 (m, 2H), 2.95 (m, 2H), 3.89 (s, 3H), 3.92 (s, 3H), 3.94 (s, 3H), 4.64 (d, 2H), 6.20 (m, 1H), 7.05-7.36 (m, 7H). MS (TOF, ES+) m/z 595/597 (M+1).

Compound No. 56

3-Benzyl-2-phenyl-5,6,7,8-tetrahydro-3H-benzo[4,5]thieno[2,3-d]pyrimidin-4-one

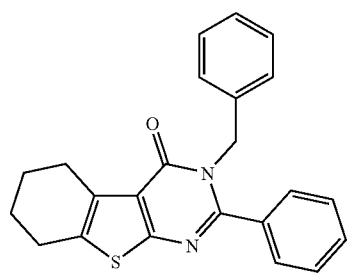

According to the method described for the compound No. 1 using N-benzylbenzamide as a starting material.

NMR (CDCl$_3$): 1.87 (m, 4H), 2.80 (m, 2H), 3.09 (m, 2H), 5.23 (s, 2H), 6.89-6.96 (m, 2H), 7.14-7.30 (8H). MS (TOF, ES+) m/z 373 (M+1)

Compound No. 57

3-Benzyl-2-phenyl-6,7-dihydro-3H,5H-benzo[4,5]thieno[2,3-d]pyrimidine-4,8-dione

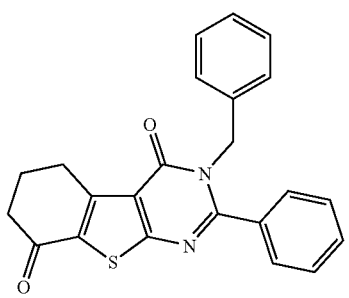

According to the method described for the compound No. 2 using the compound No. 56 as a starting material.

NMR (CDCl$_3$): 2.23 (m, 2H), 2.70 (m, 2H), 3.34 (m, 2H), 5.27 (s, 2H), 6.93 (m, 2H), 7.21-7.38 (m, 8H). MS (TOF, ES+) m/z 439 (M+Na)

Compound No. 58

3-Benzyl-7-bromo-2-phenyl-6,7-dihydro-3H,5H-benzo[4,5]thieno[2,3-d]pyrimidine-4,8-dione

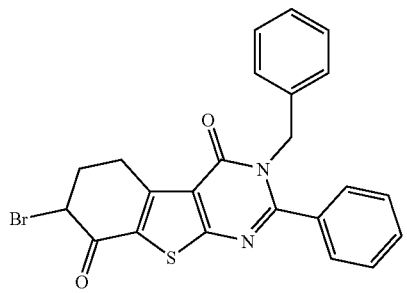

According to the method described for the compound No. 46 using the compound No. 57 as a starting material. The compound No. 59 was isolated as a by-product.

NMR (CDCl$_3$): 2.60 (m, 2H), 3.15-3.74 (m, 2H), 4.73 (t, 1H), 5.28 (s, 2H), 6.94 (m, 2H), 7.12-7.60 (m, 8H). MS (TOF, ES+) m/z 487/489 (M+Na).

Compound No. 59

3-Benzyl-7,7-dibromo-2-phenyl-6,7-dihydro-3H,5H-benzo[4,5]thieno[2,3-d]pyrimidine-4,8-dione

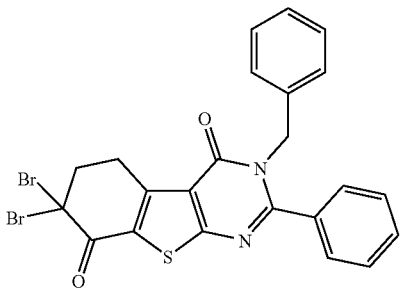

NMR (CDCl₃): 3.16 (dd, 2H), 3.47 (dd, 2H), 5.30 (s, 2H), 6.95 (m, 2H), 7.12-7.60 (m, 8H). MS (TOF, ES+) m/z 565/567/569 (M+Na).

Compound No. 60

3-Benzyl-8-hydroxy-2-phenyl-3H-benzo[4,5]thieno[2,3-d]pyrimidine-4-one

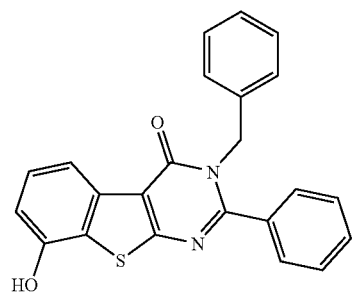

According to the method described for the compound No. 49 using the compound No. 58 as a starting material.

NMR (CDCl₃): 5.38 (s, 2H), 6.95 (m, 3H), 7.24 (m, 3H), 7.33-7.58 (m, 6H), 8.18 (dd, 1H). MS (TOF, ES+) m/z 407 (M+1).

Compound No. 61

3-Benzyl-2-thiophen-2-yl-5,6,7,8-tetrahydro-3H-benzo[4,5]thieno[2,3-d]pyrimidin-4-one

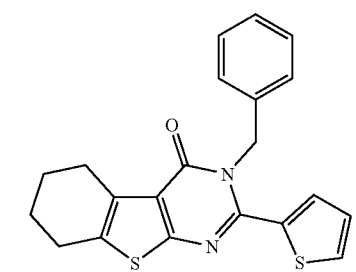

According to the method described for the compound No. 1 using thiophene-2-carboxylic acid benzylamide as a starting material.

NMR (CDCl₃): 1.86-1.91 (m, 4H), 2.80 (m, 2H), 3.04 (m, 2H), 5.47 (s, 2H), 6.96 (dd, 1H), 7.08 (m, 2H), 7.20-7.35 (m, 4H), 7.45 (d, 1H). MS (TOF, ES+) m/z 379.

Compound No. 62

3-Benzyl-2-thiophen-2-yl-6,7-dihydro-3H,5H-benzo[4,5]thieno[2,3-d]pyrimidine-4,8-dione

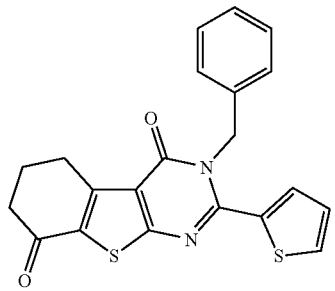

According to the method described for the compound No. 2 using the compound No. 61 as a starting material.

NMR (CDCl₃): 2.24 (m, 2H), 2.68 (m, 2H), 3.30 (m, 2H), 5.52 (s, 2H), 7.00 (dd, 1H), 7.10 (m, 2H), 7.25-7.40 (m, 4H), 7.54 (d, 1H). MS (TOF, ES+) m/z 415 (M+Na).

Compound No. 63

3-Benzyl-2-thiophen-2-yl-6,7-dihydro-3H,5H-benzo[4,5]thieno[2,3-d]pyrimidine-4,8-dione

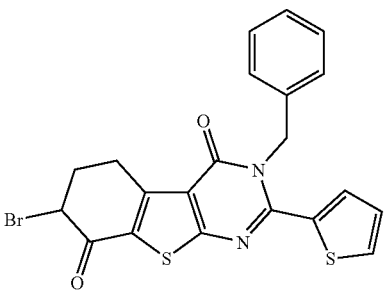

According to the method described for the compound No. 46 using the compound No. 62 as a starting material. The compounds No. 64, No. 65 and No. 66 were isolated as by-products.

NMR (CDCl$_3$): 2.57-2.63 (m, 2H), 3.22-3.61 (m, 2H), 4.72 (t, 1H), 5.54 (s, 2H), 6.95-7.17 (s, 1H), 7.22 (m, 2H), 7.30 (m, 4H), 7.60 (d,1H). MS (TOF, ES+) m/z 493/495 (M+Na).

Compound No. 64

3-Benzyl-2-(5-bromothiophen-2-yl)-6,7-dihydro-3H,5H-benzo[4,5]thieno[2,3-d]pyrimidine-4,8-dione

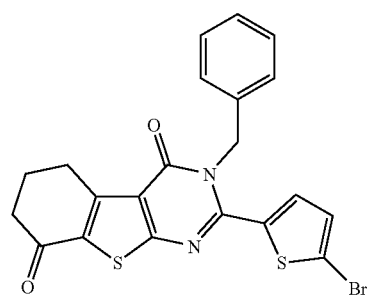

NMR (CDCl$_3$): 2.23 (m, 2H), 2.68 (m, 2H), 3.29 (m, 2H), 5.52 (s, 2H), 6.94-7.01 (m, 2H), 7.10-7.17 (m, 2H), 7.30-7.44 (m, 3H). MS (TOF, ES+) m/z 472 (M+1).

Compound No. 65

3-Benzyl-7-bromo-2-(5-bromothiophen-2-yl)-6,7-dihydro-3H,5H-benzo[4,5]thieno[2,3-d]pyrimidine-4,8-dione

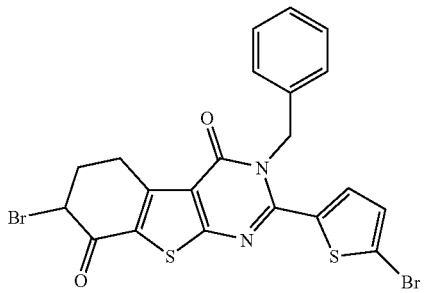

NMR (CDCl$_3$): 2.56 (m, 2H), 3.30-3.52 (m, 2H), 4.71 (t, 1H), 5.53 (s, 2H), 6.95-7.03 (m, 2H), 7.13-7.17 (m, 2H), 7.32-7.36 (m, 3H). MS (TOF, ES+) m/z 571/573/575 (M+Na).

Compound No. 66

3-Benzyl-7,7-dibromo-2-(5-bromothiophen-2-yl)-6,7-dihydro-3H,5H-benzo[4,5]thieno[2,3-d]pyrimidine-4,8-dione

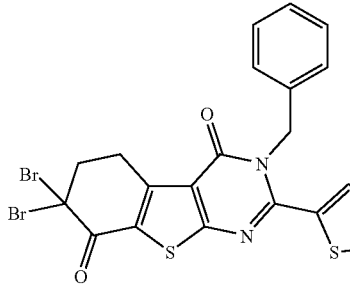

NMR (CDCl$_3$): 3.16 (m, 2H), 3.41 (m, 2H), 5.53 (s, 2H), 6.96-7.05 (m, 2H), 7.13-7.17 (m, 2H), 7.28-7.45 (m, 3H). MS (TOF, ES+) m/z 623/625/627/629

Compound No. 67

3-Benzyl-8-hydroxy-2-thiophen-2-yl-3H-benzo[4,5]thieno[2,3-d]pyrimidine-4-one

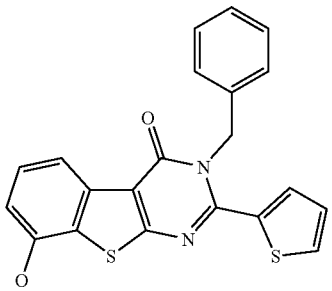

According to the method described for the compound No. 49 using the compound No. 63 as a starting material.

NMR (CDCl$_3$): 5.62 (s, 2H), 6.90 (dd, 1H), 7.01 (dd, 1H), 7.15 (m, 2H), 7.24-7.42 (m, 6H), 7.55 (dd, 1H), 8.18 (dd, 1H). MS (TOF, ES+) m/z 391 (M+1)

Compound No. 68

3-Benzyl-2-(5-bromothiophen-2-yl)-8-hydroxy-3H-benzo[4,5]thieno[2,3-d]pyrimidin-4-one

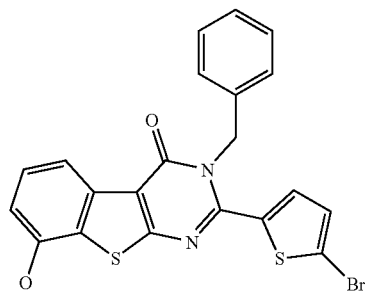

According to the method described for the compound No. 49 using the compound No. 65 as a starting material.

NMR (CDCl$_3$+MeOH-d$_4$): 5.62 (s, 2H), 6.90-7.01 (m, 3H), 7.15-7.42 (m, 6H), 8.13 (dd, 1H). MS (TOF, ES−) m/z 467/469

Compound No. 69

Thiophene-2-carboxylic acid 2-(4-oxo-2-thiohen-2-yl-5,6,7,8-tetrahydro-4H-benzo[4,5]thieno[2,3-d]pyrimidin-3-yl)-ethyl ester

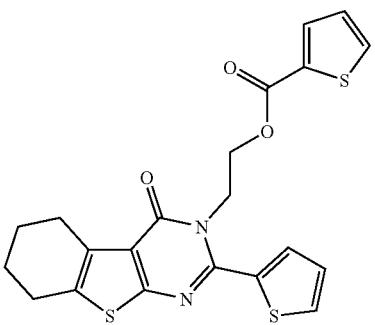

According to the method described for the compound No. 1 using amide thiophene-2-carboxylic acid 2-[(thiophene-2-carbonyl)-amino]-ethyl ester as one starting material. The amide thiophene-2-carboxylic acid 2-[(thiophene-2-carbonyl)-amino]-ethyl ester was prepared as usually using thiophene carbonyl chloride and ethanolamine as starting materials.

NMR (CDCl$_3$): 1.85-1.96 (m, 4H), 2.76-2.80 (m, 2H), 3.01-3.06 (m, 2H), 4.50-4.71 (m, 4H), 7.01 (m, 2H), 7.40-7.55 (m, 3H), 7.65 (d, 1H). MS (TOF, ES+) m/z 465 (M+Na)

Compound No. 70

Thiophene-2-carboxylic acid 2-(4,8-dioxo-2-thiohen-2-yl-5,6,7,8-tetrahydro-4H-benzo[4,5]thieno[2,3-d]pyrimidin-3-yl)-ethyl ester

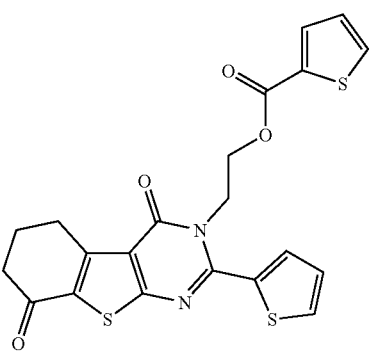

According to the method described for the compound No. 2 using the compound No. 69 as a starting material.

NMR (CDCl$_3$): 2.20-2.32 (m, 2H), 2.69 (dd, 2H), 3.27 (dd, 2H), 4.63-4.80 (m, 4H), 7.05-7.16 (m, 2H), 7.54-7.58 (m, 2H), 7.64-7.71 (m, 2H). MS (TOF, ES+) m/z 457 (M+1)

Compound No. 71

Thiophene-2-carboxylic acid 2-(7-bromo-4,8-dioxo-2-thiohen-2-yl-5,6,7,8-tetrahydro-4H-benzo[4,5]thieno[2,3-d]pyrimidin-3-yl)-ethyl ester

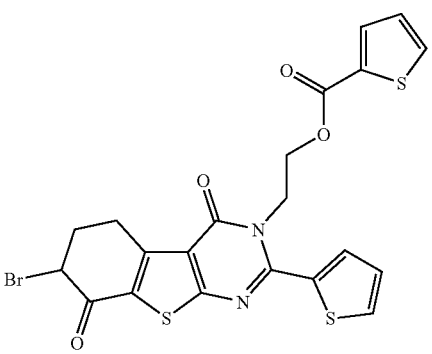

According to the method described for the compound No. 46 using the compound No. 70 as a starting material. The compound No. 72 was isolated as a by-product.

NMR (CDCl$_3$): 3.17 (dd, 2H), 3.39-3.44 (m, 2H), 4.63-4.86 (m, 5H), 7.04-7.15 (m, 2H), 7.54-7.62 (m, 2H), 7.67-7.72 (m, 2H).

Compound No. 72

Thiophene-2-carboxylic acid 2-(7,7-dibromo-4,8-dioxo-2-thiohen-2-yl)-5,6,7,8-tetrahydro-4H-benzo[4,5]thieno[2,3-d]pyrimidin-3-yl)-ethyl ester

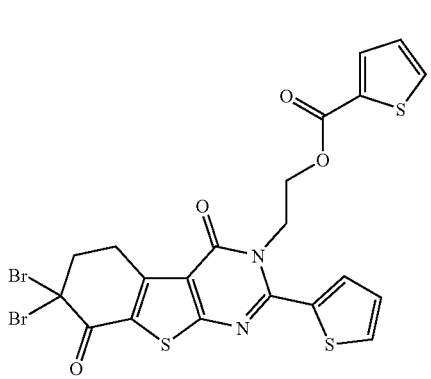

NMR (CDCl$_3$): 2.55-2.64 (m, 2H), 3.22-3.50 (m, 2H), 4.62-4.85 (m, 4H), 7.04-7.19 (m, 2H), 7.54-7.59 (m, 2H), 7.66-7.70 (m, 2H).

Compound No. 73

Thiophene-2-carboxylic acid 2-(8-hydroxy-4-oxo-2-thiohen-2-yl)-4H-benzo[4,5]thieno[2,3-d]pyrimidin-3-yl)-ethyl ester

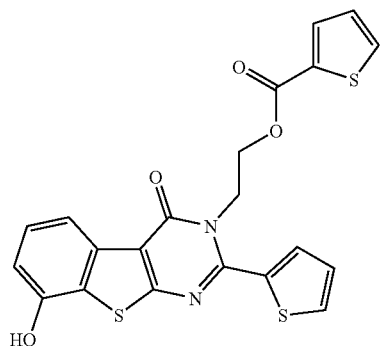

According to the method described for the compound No. 49 using the compound No. 71 as a starting material.

NMR (CDCl$_3$+MeOH-d$_4$): 4.56-4.88 (m, 4H), 6.91 (dd, 1H), 7.10 (2×dd, 2H), 7.37 (dd, 1H), 7.54-7.80 (m, 4H), 8.15 (dd, 1H). MS (TOF, ES−) m/z 477 (M+Na).

Compound No. 74

3-(2-Methoxyethyl)-2-thiophen-2-yl-5,6,7,8-tetrahydro-3H-benzo[4,5]thieno[2,3-d]pyrimidin-4-one

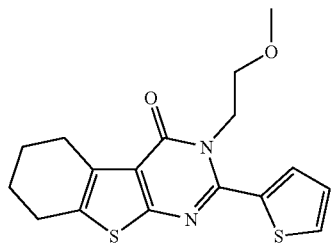

According to the method described for the compound No. 1 using amide thiophene-2-carboxylic acid 2-(2-methoxyethyl)-amide as one starting material. The amide thiophene-2-carboxylic acid 2-(2-methoxy-ethyl)-amide was prepared as usually using thiophene carbonyl chloride and 2-methoxyethylamine as starting materials.

NMR (CDCl$_3$): 1.87 (m, 4H), 2.79 (m, 2H), 3.04 (m, 2H), 3.30 (s, 3H), 3.77 (dd, 2H), 4.44 (dd, 2H), 7.12 (m, 1H), 7.52 (dd, 1H), 7.66 (dd, 1H). MS (TOF, ES+) m/z 369 (M+Na)

Compound No. 75

3-(2-Methoxyethyl)-2-thiophen-2-yl-6,7-dihydro-3H,5H-benzo[4,5]thieno[2,3-d]pyrimidine-4,8-dione

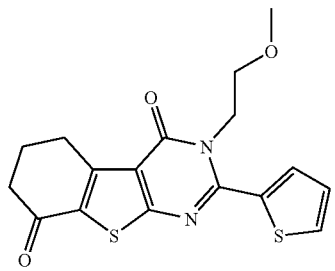

According to the method described for the compound No. 2 using the compound No. 74 as a starting material. The product was used directly to bromination.

Compound No. 76

7-Bromo-3-(2-methoxyethyl)-2-thiophen-2-yl-6,7-dihydro-3H,5H-benzo[4,5]thieno[2,3-d]pyrimidine-4,8-dione

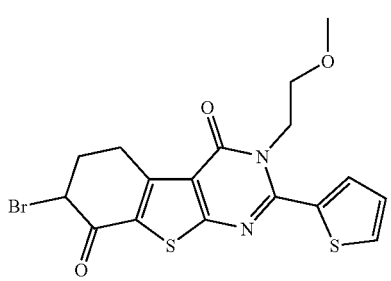

According to the method described for the compound No. 46 using the compound No. 75 as a starting material.

NMR (CDCl₃): 2.57-2.59 (m, 2H), 3.26-3.61 (m, 5H), 3.81 (dd, 2H), 2.52 (dd, 2H), 4.72 (t, 1H), 7.11-7.30 (m, 2H), 7.71 (d, 1H). MS (TOF, ES+) m/z 439/441

Compound No. 77

3-Benzyl-2-thiophen-2-yl-5,6,7,8-tetrahydro-3H-benzo[4,5]thieno[2,3-d]pyrimidin-4-one

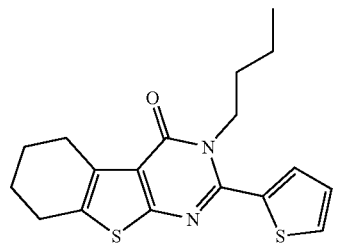

According to the method described for the compound No. 1 using the amide thiophene-2-carboxylic acid butylamide as a starting material.

NMR (CDCl₃): 0.90 (t, 3H), 1.20-1.54 (m, 2H), 1.71-1.89 (m, 6H), 2.78 (m, 2H), 3.05 (m, 2H), 4.16 (m, 2H), 7.12 (dd, 1H), 7.41 (dd, 1H), 7.55 (dd, 1H). MS (TOF, ES+) m/z 345 (M+1)

Compound No. 78

3-Benzyl-2-(m-methoxyphenyl)-5,6,7,8-tetrahydro-3H-benzo[4,5]thieno[2,3-d]pyrimidin-4-one

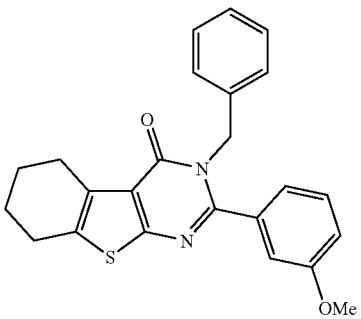

According to the method described for the compound No. 1 using N-benzyl-3-methoxybenzamide as a starting material.

NMR (CDCl₃): 1.89 (m, 4H), 2.81 (m, 2H), 3.08 (m, 2H), 3.59 (s, 3H), 5.23 (s, 2H), 6.73 (m, 1H), 6.90-6.99 (m, 3H), 7.19-7.34 (m, 5H) MS (TOF, ES+) m/z 403 (M+1)

Compound No. 79

3-Benzyl-2-(m-methoxyphenyl)-6,7-dihydro-3H,5H-benzo[4,5]thieno[2,3-d]pyrimidine-4,8-dione

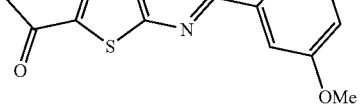

According to the method described for the compound No. 2 using the compound No 78 as a starting material.

NMR (CDCl₃): 2.23 (m, 2H), 2.69 (dd, 2H), 3.34 (dd, 2H), 3.61 (s, 3H), 5.26 (s, 2H), 6.68 (s, 1H), 6.94-6.98 (m, 3H), 7.03-7.36 (m, 5H). MS (TOF, ES+) m/z 439 (M+Na)

Compound No. 80

3-Benzyl-7-bromo-2-(m-methoxyphenyl)-6,7-dihydro-3H,5H-benzo[4,5]thieno[2,3-d]pyrimidine-4,8-dione

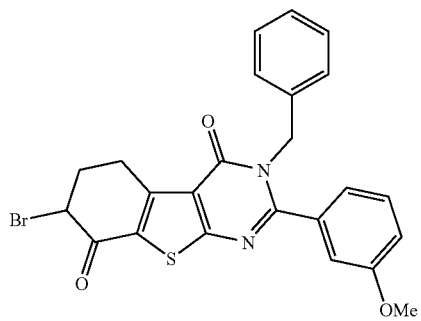

According to the method described for the compound No. 46 using the compound No. 79 as a starting material. The bromides No. 81 and 82 were isolated as by-products. MS (TOF, ES+) m/z 495/497 Rf (toluene-ethyl acetate, 9:1)=0.38

Compound No. 81

3-Benzyl-7,7-dibromo-2-(m-methoxyphenyl)-6,7-dihydro-3H,5H-benzo[4,5]thieno[2,3-d]pyrimidine-4,8-dione

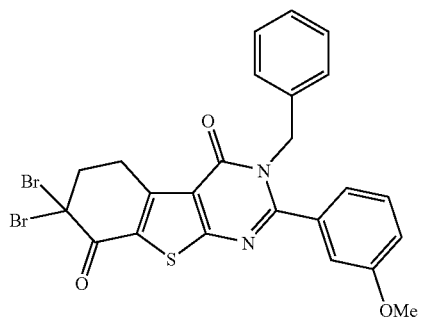

MS (TOF, ES+) m/z 573/575/577 Rf (toluene-ethyl acetate, 9:1)=0.52

Compound No. 82

3-Benzyl-7,7-dibromo-2-(5-bromo-3-methoxyphenyl)-6,7-dihydro-3H,5H-benzo[4,5]thieno[2,3-d]pyrimidine-4,8-dione

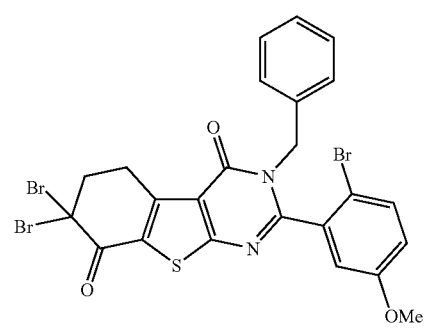

MS (TOF, ES+) m/z 651/653/655/657 Rf (toluene-ethyl acetate, 9:1)=0.62

Compound No. 83

3-Benzyl-8-hydroxy-2-(m-methoxyphenyl)-3H-benzo[4,5]thieno[2,3-d]pyrimidin-4-one

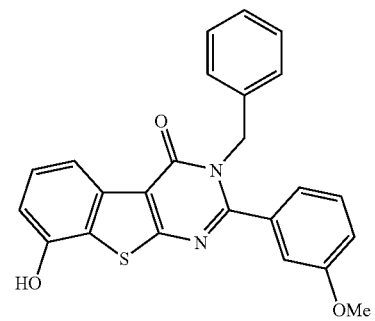

According to the method described for the compound No. 49 using the compound No. 80 as a starting material. The compound No. 84 was isolated as a by-product.

NMR (CDCl$_3$): 3.61 (s, 3H), 5.36 (s, 2H), 6.79 (m, 1H), 6.80-7.05 (m, 4H), 7.24-7.40 (m, 6H), 8.10 (d, 1H). Rf (toluene-methanol, 9.5:0.5)=0.32 MS (TOF, ES+) m/z 415 (M+1)

Compound No. 84

Acetic acid 3-benzyl-4-oxo-2-(m-methoxyphenyl)-3,4-dihydro-benzo[4,5]thieno[2,3-d]pyrimidin-8-yl ester

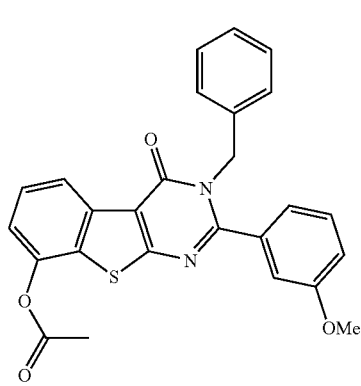

Rf (toluene-methanol, 9.5:0.5)=0.61 MS (TOF, ES+) m/z 457 (M+1)

Compound No. 85

3-Butyl-2-(3,4,5-trimethoxyphenyl)-5,6,7,8-tetrahydro-3H-benzo[4,5]thieno[2,3-d]pyrimidin-4-one

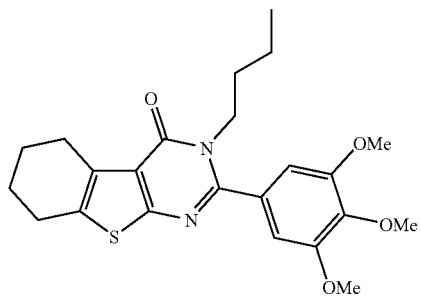

According to the method described for the compound No. 1 using N-butyl-3,4,5-trimethoxybenzamide as a starting material.

NMR (CDCl$_3$): 0.82 (t, 3H), 1.18-1.39 (m, 2H), 1.43-1.89 (m, 2H), 1.88 (m, 4H), 2.79 (m, 2H), 3.07 (m, 2H), 3.89 (s, 9H), 3.90-3.99 (m, 2H), 6.69 (s, 2H). Rf (toluene-MeOH, 9.5:0.5)=0.57 MS (TOF, ES+) m/z 429 (M+1)

Compound No. 86

3-Butyl-2-(3,4,5-trimethoxyphenyl)-6,7-dihydro-3H,5H-benzo[4,5]thieno[2,3-d]pyrimidine-4,8-dione

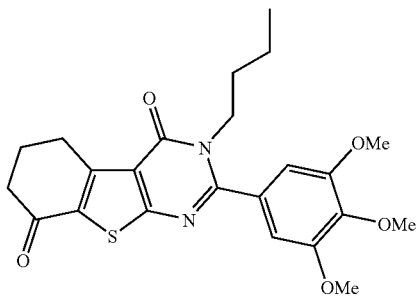

According to the method described for the compound No. 2 using the compound No. 85 as a starting material.

R$_f$(toluene-MeOH, 9.5:0.5)=0.46 MS (TOF, ES+) m/z 443 (M+1)

Compound No. 87

7-Bromo-3-butyl-2-(3,4,5-trimethoxyphenyl)-6,7-dihydro-3H,5H-benzo[4,5]thieno[2,3-d]pyrimidine-4,8-dione

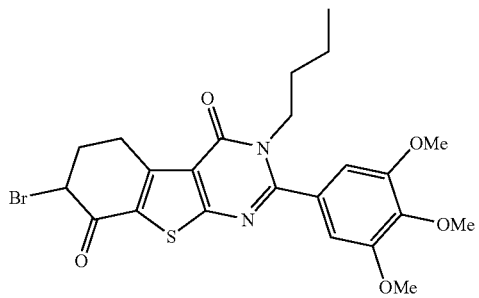

According to the method described for the compound No. 46 using the compound No. 86 as a starting material. The bromide No. 88 was isolated as a by-product.

MS (TOF, ES+) m/z 521/523. Rf (toluene-ethyl acetate, 9:1)=0.29

Compound No. 88

3-Butyl-7,7-dibromo-2-(3,4,5-trimethoxyphenyl)-6,7-dihydro-3H,5H-benzo[4,5]thieno[2,3-d]pyrimidine-4,8-dione

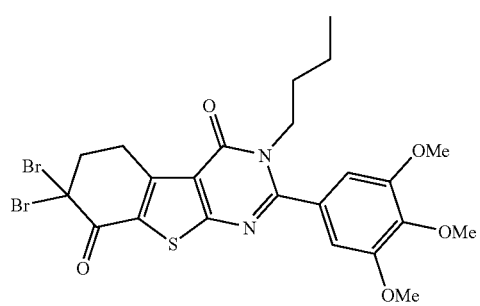

MS (TOF, ES+) m/z 597/599/601. Rf(toluene-ethyl acetate, 9:1)=0.67

Compound No. 89

3-Butyl-8-hydroxy-2-(3,4,5-trimethoxyphenyl)-3H-benzo[4,5]thieno[2,3-d]pyrimidin-4-one

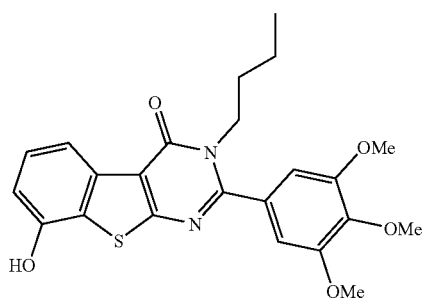

According to the method described for the compound No. 49 using the compound No 87 as a starting material.

NMR (CDCl$_3$): 0.84 (t, 3H), 1.30 (m, 2H), 1.78 (m, 2H), 3.91 (s, 9H), 4.10 (m, 2H), 6.77 (s, 2H), 6.90 (d, 1H), 7.43 (dd, 1H), 8.28 (d, 1H). Rf (toluene-methanol, 9.5:0.5)=0.26 MS (TOF, ES+) m/z 441 (M+1)

Compound No. 90

7-Bromo-3-butyl-8-hydroxy-2-(3,4,5-trimethoxyphenyl)-3H-benzo[4,5]thieno[2,3-d]pyrimidin-4-one

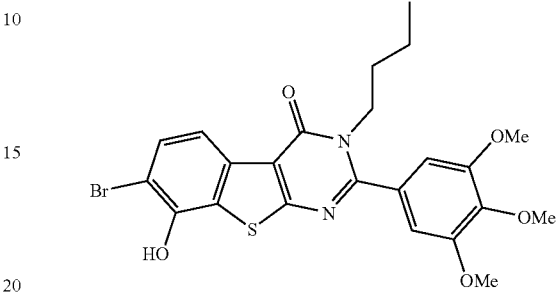

According to the method described for the compound No. 49 using the compound No 88 as a starting material.

NMR (CDCl$_3$): 0.81 (t, 3H), 1.28 (m, 2H), 1.74 (m, 2H), 3.91 (s, 9H), 4.10 (m, 2H), 6.12 (s, 2H), 7.62 (d, 1H), 8.15 (d, 1H). Rf (toluene-methanol, 9.5:0.5)=0.44 MS (TOF, ES−) m/z 517/519

Compound No. 91

3-Benzyl-8-methoxy-2-(2-bromo-3,4,5-trimethoxyphenyl)-3H-benzo[4,5]thieno[2,3-d]pyrimidin-4-one

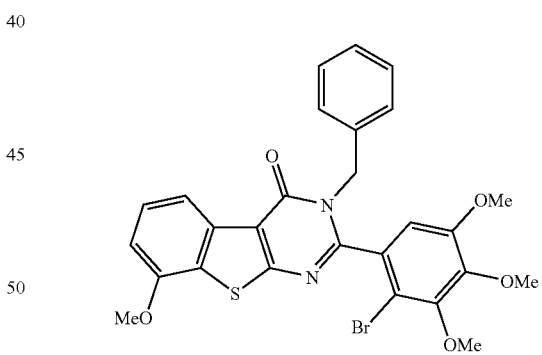

The compound No. 49 (50 mg, 0.09 mmol), dimethylsulphate (11 mg, 0.09 mmol) and anhydrous K$_2$CO$_3$ (25 mg, 018 mmol) were dissolved in acetone (1.5 ml) and refluxed for two hours. The solid material was filtered and washed with cold acetone. The crude product was purified by chromatography using toluene-EtOAc (99:1) as an eluent.

NMR (CDCl$_3$): 3.45 (s, 3H), 3.92 (s, 3H), 3.96 (s, 3H), 4.04 (s, 3H), 4.51 (d, 1H), 6.07 (d, 1H), 6.18 (s, 1H), 6.89-7.00 (m, 3H), 7.20 (m, 3H), 7.54 (t, 1H), 8.35 (d, 1H). Rf (toluene-EtOAc, 9:1)=0.50 MS (TOF, ES+) m/z 567/569

Compound No. 92

3-Benzyl-7-bromo-8-hydroxy-2-phenyl-3H-benzo[4,5]thieno[2,3-d]pyrimidin-4-one

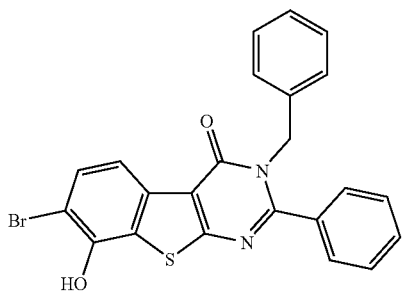

The compound No. 59 (100 mg, 0.18 mmol) and Li$_2$CO$_3$ (10 mg, 0.14 mmol) were dissolved in DMF (2.5 ml) and warmed at 100° C. for three hours. After stirring overnight at room temperature water (0.3 ml) and acetic acid (0.4 ml) were added. The product precipitated and it was washed with water-ethanol (v/v1:1).

NMR (DMSO-d6): 5.26 (s, 2H), 6.97 (m, 2H), 7.23 (m, 3H), 7.50 (m, 5H), 7.72 (m, 1H), 7.96 (d, 1H). Rf (toluene-EtOAc, 9:1)=0.50 MS (TOF, ES+) m/z 485/487 (M+Na)

Compound No. 93

Acetic acid 3-benzyl-7-bromo-4-oxo-2-phenyl-3,4-dihydro-benzo[4,5]thieno[2,3-d]pyrimidin-8-yl ester

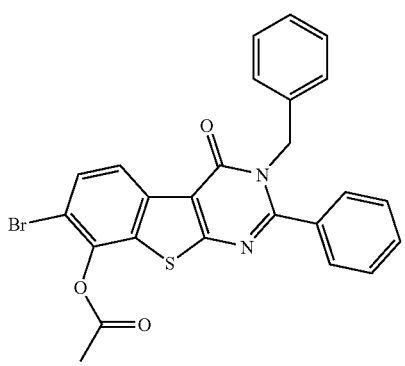

According to the method described for the compound No. 49 using the compound No. 59 as a starting material.

NMR (CDCl$_3$): 2.48 (s, 3H), 5.37 (s, 2H), 6.96 (m, 2H), 7.34 (m, 3H), 7.35-7.60 (m, 5H), 7.74 (d, 1H), 8.50 (d, 1H). Rf (toluene-methanol, 9.5:0.5)=0.74 MS (TOF, ES+) m/z 527/529 (M+Na)

Compound No. 94

3-(2-Methoxybenzyl)-2-propyl-5,6,7,8-tetrahydro-3H-benzo[4,5]thieno[2,3-d]pyrimidin-4-one

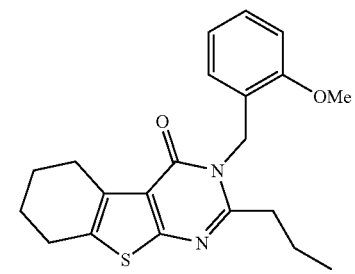

According to the method described for the compound No. 1 using 2-methoxy-N-benzylbutyramide as a starting material.

NMR (CDCl$_3$): 0.95 (t, 3H), 1.68-1.89 (m, 6H), 2.62 (dd, 2H), 2.77 (m, 2H), 3.02 (m, 2H), 3.90 (s, 3H), 5.34 (s, 2H), 6.73-6.87 (m, 3H), 7.22 (m, 1H). Rf (toluene-methanol, 9.5:0.5)=0.74 MS (TOF, ES+) m/z 391 (M+Na)

Compound No. 95

3-(2-Methoxybenzyl)-2-propyl-6,7-dihydro-3H,5H-benzo[4,5]thieno[2,3-d]pyrimidine-4,8-dione

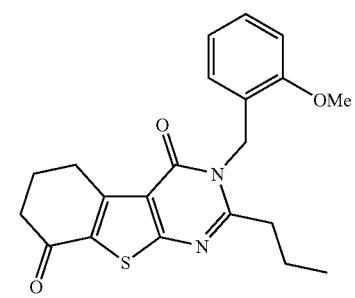

According to the method described for the compound No. 2 using the compound No. 94 as a starting material.

NMR (CDCl$_3$): 0.96 (t, 3H), 1.68-1.87 (m, 2H), 2.17-2.29 (m, 2H), 2.67 (m, 4H), 3.29 (m, 2H), 3.91 (s, 3H), 5.36 (s, 2H), 6.75-6.94 (m, 3H), 7.27 (m, 1H). Rf (toluene-methanol, 9.5:0.5)=0.57 MS (TOF, ES+) m/z 383 (M+1)

Compound No. 96

7-Bromo-3-(2-methoxybenzyl)-2-propyl-6,7-dihydro-3H,5H-benzo[4,5]thieno[2,3-d]pyrimidine-4,8-dione

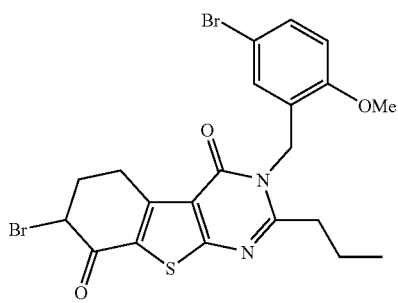

According to the method described for the compound No. 46 using the compound No. 95 as a starting material. The bromide No. 97 was isolated as a by-product.

NMR (CDCl₃): 0.97 (t, 3H), 1.70-1.85 (m, 2H), 2.54-2.72 (m, 4H), 3.23-3.49 (m, 1H), 3.51-3.90 (m, 1H), 3.90 (s, 3H), 4.72 (t, 1H), 5.30 (s, 2H), 6.83 (dd, 2H), 7.39 (dd, 1H). Rf (toluene-EtOAc, 9:1)=0.41 MS (TOF, ES+) m/z 561/563/565 (M+Na)

Compound No. 97

7,7-Dibromo-3-(5-bromo-2-methoxybenzyl)-2-propyl-6,7-dihydro-3H,5H-benzo[4,5]thieno[2,3-d]pyrimidine-4,8-dione

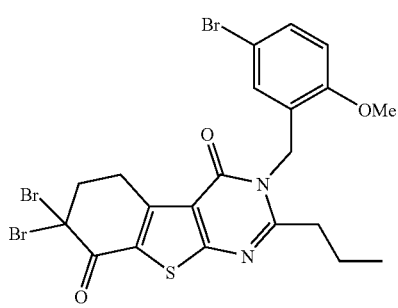

NMR (CDCl₃): 0.96 (t, 3H), 1.70-1.85 (m, 2H), 2.68 (m, 2H), 3.17 (dd, 2H), 3.43 (dd, 2H), 3.90 (s, 3H), 5.30 (s, 2H), 6.83 (dd, 2H), 7.39 (dd, 1H). Rf (toluene-EtOAc, 9:1)=0.59 MS (TOF, ES+) m/z 639/641/643/645 (M+Na)

Compound No. 98

3-Benzyl-3-(5-bromo-2-methoxybenzyl)-8-hydroxy-2-propyl-3H-benzo[4,5]thieno[2,3-d]pyrimidin-4-one

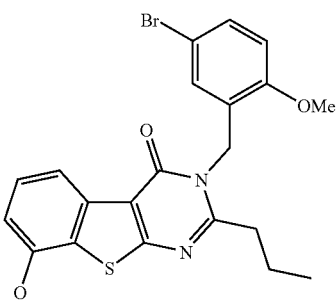

According to the method described for the compound No. 49 using the compound No. 96 as a starting material. The compound No. 99 was isolated as a by-product.

NMR (CDCl₃): 1.00 (t, 3H), 1.77-1.93 (dd, 2H), 2.68-2.76 (dd, 2H), 3.90 (s, 3H), 5.42 (s, 2H), 6.78-6.90 (m, 3H), 7.33-7.40 (m, 3H), 8.14 (d, 1H). Rf (toluene-methanol, 9.5:0.5)=0.24 MS (TOF, ES+) m/z 459/461

Compound No. 99

Acetic acid 3-benzyl-3-(5-bromo-2-methoxybenzyl)-4-oxo-2-propyl-3,4-dihydrobenzo[4,5]thieno[2,3-d]pyrimidin-8-yl ester

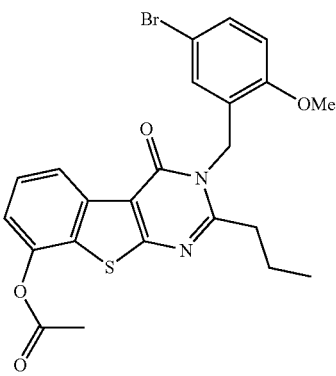

Rf (toluene-methanol, 9.5:0.5)=0.59 MS (TOF, ES+) m/z 523/525

Compound No. 100

3-(5-Bromo-2-hydroxybenzyl)-8-hydroxy-2-propyl-3H-benzo[4,5]thieno[2,3-d]pyrimidin-4-one

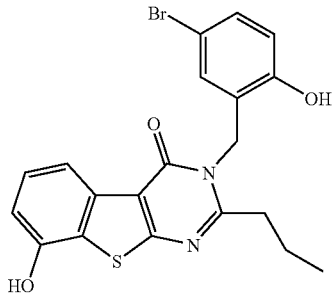

The compound No. 98 (50 mg, 0.11 mmol) was dissolved in dry dichloromethane (2 ml). Boron tribromide (100 μl, 1M in $CH_2Cl_2$) was added to cooled solution. After 30 minutes stirring was continued at room temperature for four hours. NaOH-solution (5 ml, 10%-solution) was added and stirred well for 10 minutes. The solution was acidified with dilute HCl-solution. The product was extracted into EtOAc and washed with brine. The crude product was purified by chromatography using toluene:EtOAc 4:1 as an eluent.

NMR ($CDCl_3$+MeOH-d4): 1.03 (t, 3H), 1.81 (m, 2H), 2.84 (dd, 2H), 5.41 (s, 2H), 6.75 (d, 1H), 6.95 (m, 1H), 7.22 (m, 2H), 7.38 (m, 1H), 8.12 (d, 1H). Rf (toluene-methanol, 9:1)= 0.31 MS (TOF, ES+) m/z 467/469 (M+Na)

Compound No. 101

3-(Furan-2-ylmethyl)-2-propyl-5,6,7,8-tetrahydro-3H-benzo[4,5]thieno[2,3-d]pyrimidin-4-one

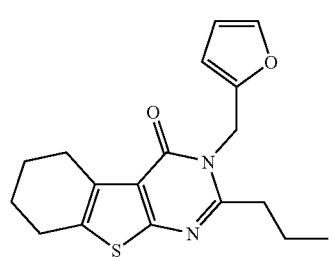

According to the method described for the compound No. 1 using N-furan-2-ylmethyl-butyramide as a starting material.

NMR ($CDCl_3$): 1.06 (t, 3H), 1.78-1.92 (m, 6H), 2.75 (m, 2H), 2.90-3.03 (m, 4H), 5.29 (s, 2H), 6.31-6.37 (m, 2H), 7.34 (d, 1H). Rf (toluene-methanol, 9.5:0.5)=0.71 MS (TOF, ES+) m/z 351 (M+Na)

Compound No. 102

3-(Furan-2-ylmethyl)-2-propyl-6,7-dihydro-3H,5H-benzo[4,5]thieno[2,3-d]pyrimidine-4,8-dione

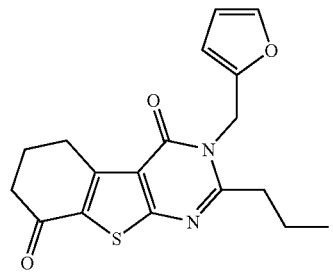

According to the method described for the compound No. 2 using the compound No. 101 as a starting material.

NMR ($CDCl_3$): 1.08 (t, 3H), 1.85 (m, 2H), 2.22 (m, 2H), 2.66 (m, 2H), 3.00 (m, 2H), 3.28 (m, 2H), 5.29 (s, 2H), 6.33-6.42 (m, 2H), 7.36 (d, 1H). Rf (toluene-methanol, 9.5: 0.5)=0.5 MS (TOF, ES+) m/z 365 (M+Na)

Compound No. 103

7-Bromo-3-(5-bromofuran-2-ylmethyl)-2-propyl-6,7-dihydro-3H,5H-benzo[4,5]thieno[2,3-d]pyrimidine-4,8-dione

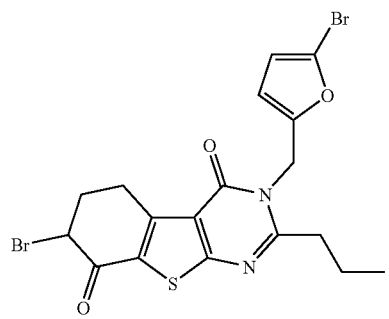

According to the method described for the compound No. 46 using the compound No. 102 as a starting material. The bromide No. 104 was isolated as a by-product.

NMR ($CDCl_3$): 1.08 (t, 3H), 1.90 (m, 2H), 2.55 (m, 2H), 3.00 (m, 2H), 3.19-3.51 (m, 1H), 3.54-3.58 (m, 1H), 4.69 (t, 1H), 5.25 (s, 2H), 6.27 (d, 1H), 7.41 (d, 1H). Rf (toluene-EtOAc, 9:1)=0.44 MS (TOF, ES+) m/z 521/523/525 (M+Na)

Compound No. 104

7,7-Dibromo-3-(5-bromofuran-2-ylmethyl)-2-propyl-6,7-dihydro-3H,5H-benzo[4,5]thieno[2,3-d]pyrimidine-4,8-dione

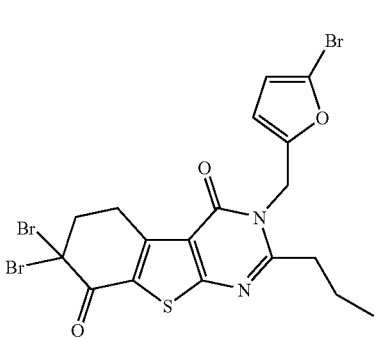

Rf (toluene-EtOAc, 9:1)=0.59 MS (TOF, ES+) m/z 601/603/605/607 (M+Na)

Compound No. 105

3-(5-Bromofuran-2-ylmethyl)-8-hydroxy-2-propyl-3H-benzo[4,5]thieno[2,3-d]pyrimidin-4-one

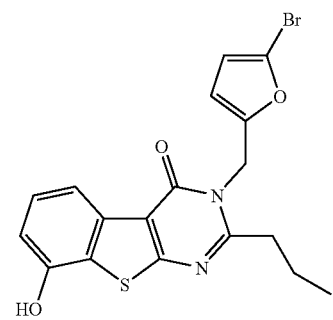

According to the method described for the compound No. 49 using the compound No. 103 as a starting material. The compound No. 106 was isolated as a by-product.

NMR (CDCl₃+MeOH-d₄): 1.08 (t, 3H), 1.92 (m, 2H), 3.04 (m, 2H), 5.36 (s, 2H), 6.27 (d, 1H), 6.35 (d, 1H), 6.87 (d, 1H), 7.31-7.44 (m, 1H), 8.10 (d, 1H). Rf (toluene-methanol, 9.5:0.5)=0.24 MS (TOF, ES+) m/z 441/443 (M+Na)

Compound No. 106

Acetic acid 3-(5-bromofuran-2-ylmethyl)-4-oxo-2-propyl-3,4-dihydro-benzo[4,5]thieno[2,3-d]pyrimidin-8-yl ester

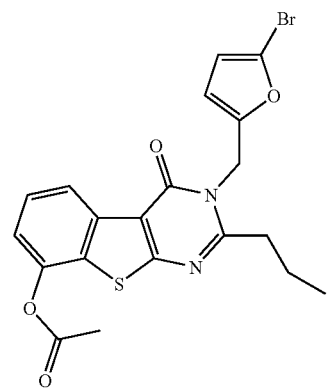

NMR (CDCl₃): 1.11 (t, 3H), 1.91 (m, 2H), 2.42 (s, 3H), 3.03 (m, 2H), 5.35 (s, 2H), 6.25 (d, 1H), 6.43 (d, 1H), 7.22 (d, 1H), 7.55 (dd, 1H), 8.45 (d, 1H). Rf (toluene-methanol, 9.5:0.5)=0.44 MS (TOF, ES+) m/z 483/485 (M+Na)

Compound No. 107

7-Bromo-3-(5-bromofuran-2-ylmethyl)-8-hydroxy-2-propyl-3H-benzo[4,5]thieno[2,3-d]pyrimidin-4-one

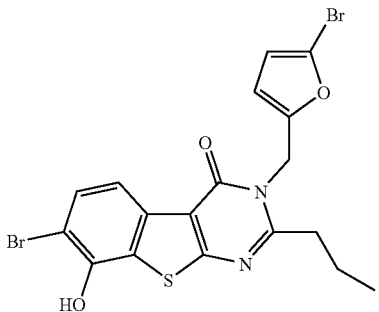

According to the method described for the compound No. 92 using the compound No. 104 as a starting.

NMR (CDCl₃+MeOH-d4): 1.10 (t, 3H), 1.91 (m, 2H), 3.04 (m, 2H), 5.32 (s, 2H), 6.28 (d, 1H), 6.45 (d, 1H), 7.57 (d, 1H), 7.98 (dd, 1H). Rf (toluene-EtOAc, 9:1)=0.53 MS (TOF, ES−) m/z 497/499

Compound No. 108

3-(2-Methoxyethyl)-2-(3,4,5-trimethoxyphenyl)-5,6,7,8-tetrahydro-3H-benzo[4,5]thieno[2,3-d]pyrimidin-4-one

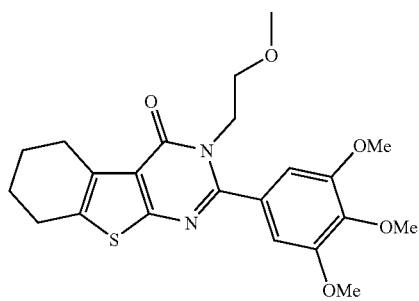

According to the method described for the compound No. 1 using N-(2-methoxyethyl)-3,4,5-trimethoxybenzamide as a starting material.

NMR (CDCl$_3$): 1.88 (m, 4H), 2.88 (m, 2H), 3.06 (m, 2H), 3.24 (s, 3H), 3.52-3.75 (m, 2H), 3.89 (s, 9H), 4.23 (m, 2H), 6.83 (s, 2H). Rf (toluene-methanol, 9.5:0.5)=0.53 MS (TOF, ES+) m/z 431 (M+1)

Compound No. 109

3-(2-Methoxyethyl)-2-(3,4,5-trimethoxyphenyl)-6,7-dihydro-3H,5H-benzo[4,5]thieno[2,3-d]pyrimidine-4,8-dione

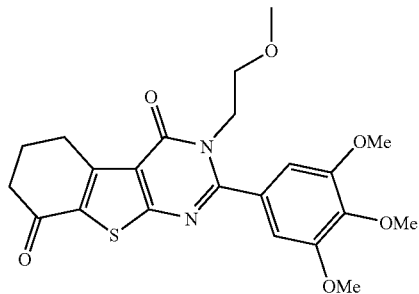

According to the method described for the compound No. 2 using the compound No. 108 as a starting material.

NMR (CDCl$_3$): 2.27 (m, 2H), 2.70 (m, 2H), 3.26 (s, 3H), 3.34 (m, 2H), 3.72 (m, 2H), 3.90 (s, 9H), 4.28 (m, 2H), 6.87 (s, 2H). Rf (toluene-methanol, 9.5:0.5)=0.47 MS (TOF, ES+) m/z 467 (M+Na)

Compound No. 110

7,7-Dibromo-2-(2-bromo-3,4,5-trimethoxyphenyl)-3-(2-methoxy-ethyl)-6,7-dihydro-3H,5H-benzo[4,5]thieno[2,3-d]pyrimidine-4,8-dione

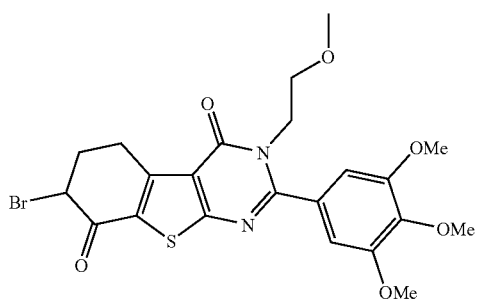

According to the method described for the compound No. 46 using the compound No. 109 as a starting material. The bromide No. 111 was isolated as a by-product.

Rf (toluene-methanol, 9.5:0.5)=0.41 MS (TOF, ES+) m/z 523/525

Compound No. 111

7-Bromo-2-(2-bromo-3,4,5-trimethoxyphenyl)-3-(2-methoxyethyl)-6,7-dihydro-3H,5H-benzo[4,5]thieno[2,3-d]pyrimidine-4,8-dione NMR (CDCl$_3$): 2.61 (m, 2H), 3.19 (s, 3H), 3.38-3.76 (m, 5H), 3.89 (s, 3H), 3.94 (s, 6H), 4.42-4.51 (m, 1H), 4.73 (t, 1H), 6.88 (s, 1H). Rf (toluene-methanol, 9.5:0.5)=0.56 MS (TOF, ES+) m/z 623/625/627 (M+Na)

Compound No. 112

2-(2-Bromo-3,4,5-trimethoxyphenyl)-8-hydroxy-3-(2-methoxyethyl)-3H-benzo[4,5]thieno[2,3-d]pyrimidin-4-one

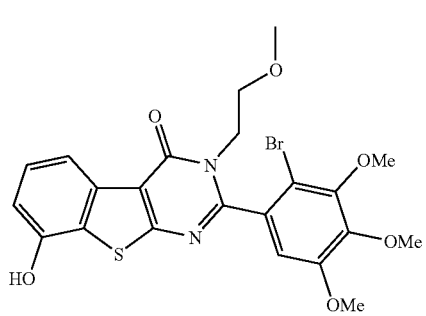

According to the method described for the compound No. 49 using the compound No. 111 as a starting material.

NMR (CDCl$_3$): 3.21 (s, 3H), 3.50-3.77 (m, 1H), 3.81-3.94 (m, 11H), 4.52-4.63 (m, 1H), 6.87 (d, 1H), 6.98 (s, 1H), 7.36 (dd, 1H), 8.18 (d, 1H). Rf (toluene-methanol, 9.5:0.5)=0.29 MS (TOF, ES+) m/z 543/545 (M+Na)

Compound No. 113

3-Isobutyl-2-(3,4,5-trimethoxyphenyl)-5,6,7,8-tetrahydro-3H-benzo[4,5]thieno[2,3-d]pyrimidin-4-one

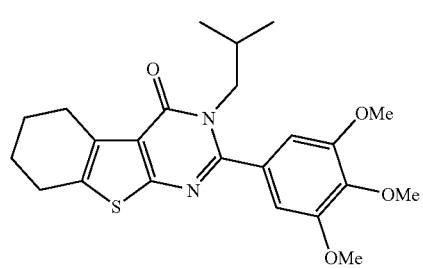

According to the method described for the compound No. 1 using N-isobutyl-3,4,5-trimethoxy-benzamide as a starting material.

NMR (CDCl$_3$): 0.74 (s, 3H), 0.77 (s, 3H), 1.88 (m, 4H), 2.03 (m, 1H), 2.79 (m, 2H), 3.06 (m, 2H), 3.86-3.98 (m, 11H), 6.67 (s, 2H). Rf (toluene-methanol, 9.5:0.5)=0.44 MS (TOF, ES+) m/z 429 (M+1)

Compound No. 114

3-Isobutyl-2-(3,4,5-trimethoxyphenyl)-6,7-dihydro-3H,5H-benzo[4,5]thieno[2,3-d]pyrimidine-4,8-dione

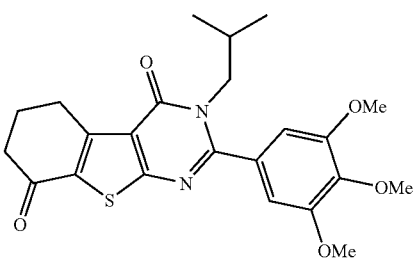

According to the method described for the compound No. 2 using the compound No. 113 as a starting material.

NMR (CDCl$_3$): 0.76 (s, 3H), 0.79 (s, 3H), 2.03 (m, 1H), 2.28 (m, 2H), 2.70 (m, 2H), 3.34 (m, 2H), 3.91 (s, 9H), 4.00 (m, 2H), 6.71 (s, 2H). Rf (toluene-methanol, 9.5:0.5)=0.38 MS (TOF, ES+) m/z 443 (M+1)

Compound No. 115

7-Bromo-3-isobutyl-2-(3,4,5-trimethoxyphenyl)-6,7-dihydro-3H,5H-benzo[4,5]thieno[2,3-d]pyrimidine-4,8-dione

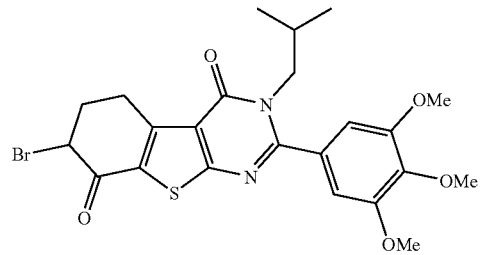

According to the method described for the compound No. 46 using the compound No. 114 as a starting material. The compound No. 116 was isolated as a by-product.

NMR (CDCl$_3$): 0.77 (s, 3H), 0.80 (s, 3H), 2.03 (m, 1H), 2.60 (m, 2H), 3.29-3.63 (m, 2H), 3.91 (s, 9H), 4.03 (m, 2H), 4.73 (t, 1H), 6.70 (s, 2H). Rf (toluene-EtOAc, 9:1)=0.12 MS (TOF, ES+) m/z 543/545 (M+Na)

Compound No. 116

7-Bromo-2-(2-bromo-3,4,5-trimethoxyphenyl)-3-isobutyl-6,7-dihydro-3H,5H-benzo[4,5]thieno[2,3-d]pyrimidine-4,8-dione

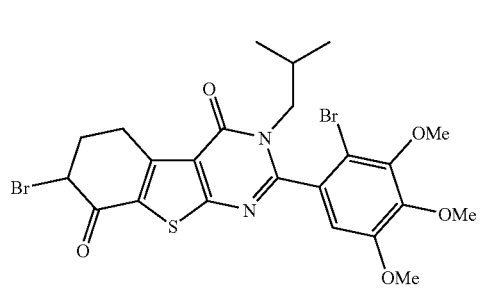

Rf (toluene-EtOAc, 9:1)=0.23 MS (TOF, ES+) m/z 599/601/603

Compound No. 117

8-Hydroxy-3-isobutyl-2-(2-bromo-3,4,5-trimethoxyphenyl)-3H-benzo[4,5]thieno[2,3-d]pyrimidin-4-one

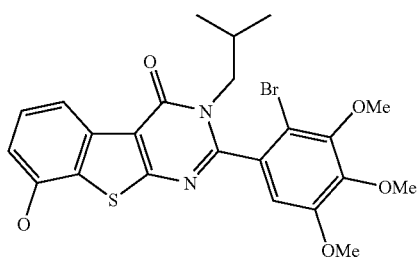

According to the method described for the compound No. 49 using the compound No. 116 as a starting material. The compound No. 118 was isolated as a by-product.

NMR (CDCl$_3$): 0.73 (d, 3H), 0.90 (d, 3H), 2.15 (m, 1H), 3.42 (m, 1H), 3.89 (s, 3H), 3.96 (s, 6H), 4.38 (m, 1H), 6.88 (m, 2H), 7.45 (dd, 1H), 8.35 (d, 1H). Rf (toluene-methanol, 9.5:0.5)=0.23 MS (TOF, ES+) m/z 519/521

Compound No. 118

Acetic acid 2-(2-bromo-3,4,5-trimethoxyphenyl)-3-isobutyl-4-oxo-3,4-dihydro-benzo[4,5]-thieno[2,3-d]pyrimidin-8-yl ester

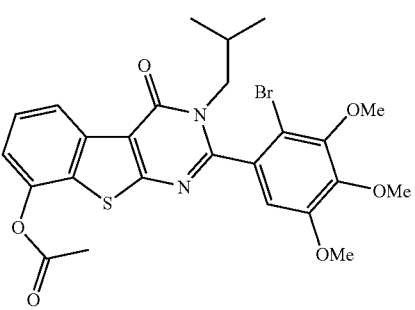

NMR (CDCl$_3$): 0.75 (d, 3H), 0.90 (d, 3H), 2.18 (m, 1H), 2.47 (s, 3H), 3.42 (m, 1H), 3.90 (s, 3H), 3.97 (s, 6H), 4.34 (m, 1H), 6.86 (m, 1H), 7.19 (m, 1H), 7.65 (dd, 1H), 8.40 (d, 1H). Rf (toluene-methanol, 9.5:0.5)=0.43 MS (TOF, ES+) m/z 561/563 (M+Na)

Compound No. 119

3-(Furan-2-ylmethyl)-2-(3,4,5-trimethoxylphenyl)-5,6,7,8-tetrahydro-3H-benzo[4,5]thieno[2,3-d]pyrimidin-4-one

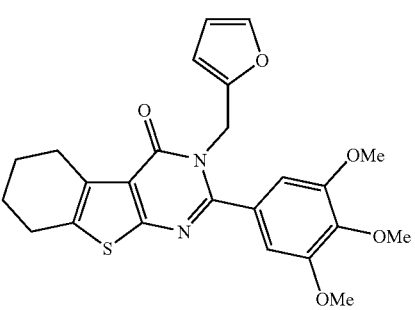

According to the method described for the compound No. 1 using N-furan-2-ylmethyl-3,4,5-trimethoxy-benzamide as a starting material.

NMR (CDCl$_3$): 1.87 (m, 4H), 2.80 (m, 2H), 3.06 (m, 2H), 3.81 (s, 6H), 3.88 (s, 3H), 5.16 (s, 2H), 6.20 (dd, 1H), 6.32 (dd, 1H), 6.73 (s, 2H), 7.30 (m, 1H). Rf (toluene-methanol, 9.5:0.5)=0.56 MS (TOF, ES+) m/z 475 (M+Na)

Compound No. 120

3-(Furan-2-ylmethyl)-2-(3,4,5-trimethoxylphenyl)-6,7-dihydro-3H,5H-benzo[4,5]thieno[2,3-d]pyrimidine-4,8-dione

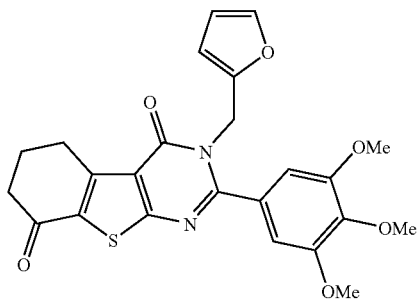

According to the method described for the compound No. 2 using the compound No. 119 as a starting material.

NMR (CDCl$_3$): 2.25 (m, 2H), 2.66 (m, 2H), 3.34 (m, 2H), 3.83 (s, 6H), 3.88 (s, 3H), 5.20 (s, 2H), 6.24 (dd, 1H), 6.35 (dd, 1H), 6.77 (s, 2H), 7.33 (m, 1H). Rf (toluene-methanol, 9.5:0.5)=0.38 MS (TOF, ES+) m/z 467 (M+1)

Compound No. 121

7-Bromo-3-(5-bromofuran-2-ylmethyl)-2-(2-bromo-3,4,5-trimethoxylphenyl)-6,7-dihydro-3H,5H-benzo[4,5]thieno[2,3-d]pyrimidine-4,8-dione

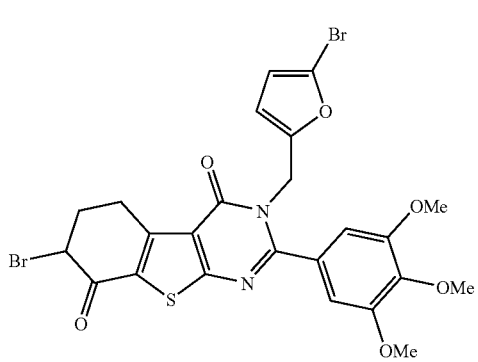

According to the method described for the compound No. 46 using the compound No. 120 as a starting material. Rf (toluene-methanol, 9.5:0.5)=0.59 MS (TOF, ES+) m/z 623/625/627

Compound No. 122

3-(5-Bromofuran-2-ylmethyl)-8-hydroxy-2-(3,4,5-trimethoxyphenyl)-3H-benzo[4,5]thieno[2,3-d]pyrimidin-4-one

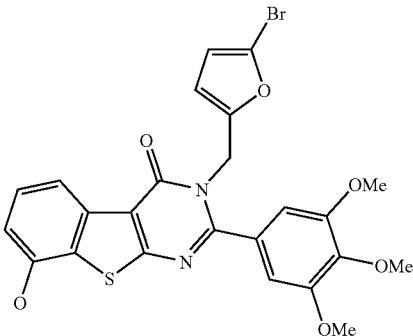

According to the method described for the compound No. 49 using the compound No. 121 as a starting material.

NMR (CDCl$_3$): 3.91 (s, 6H), 3.92 (s, 3H), 5.25 (s, 2H), 6.26 (d, 1H), 6.42 (d, 1H), 6.81-6.93 (m, 3H), 7.40 (dd, 1H), 8.24 (d, 1H). Rf (toluene-methanol, 9.5:0.5)=0.17 MS (TOF, ES−) m/z 541/543

Compound No. 123

3-Benzyl-7-chloro-2-(2-chloro-3,4,5-trimethoxyphenyl)-6,7-dihydro-3H,5H-benzo[4,5]thieno[2,3-d]pyrimidine-4,8-dione

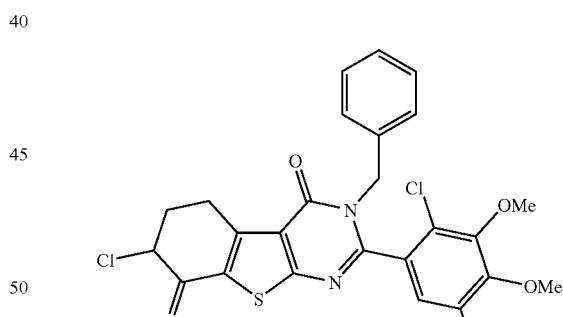

The compound No. 2 (500 mg, 1.05 mmol) was dissolved in CCl$_4$ (5 ml). Freshly distilled sulfuryl chloride (94 μl, 116 mmol) was added under nitrogen. The reaction mixture was warmed 45-55° C. Additional portion of sulfuryl chloride (94 μl) was added after two hours. The crude product was purified by chromatography using toluene-EtOAc (9.8:0.2) as an eluent.

NMR (CDCl$_3$): 2.65 (m, 2H), 3.48 (s, 3H), 3.56 (m, 2H), 3.93 (s, 3H), 3.96 (s, 3H), 4.49 (dd, 1H), 4.66 (t, 1H), 5.89 (dd, 1H), 6.15 (d, 1H), 7.22 (m, 5H). Rf (toluene-methanol, 9.5:0.5)=0.65 MS (TOF, ES+) m/z 545/547/549

Compound No. 124

3-Benzyl-2-(2-chloro-3,4,5-trimethoxyphenyl)-8-hydroxy-3H-benzo[4,5]thieno[2,3-d]pyrimidin-4-one

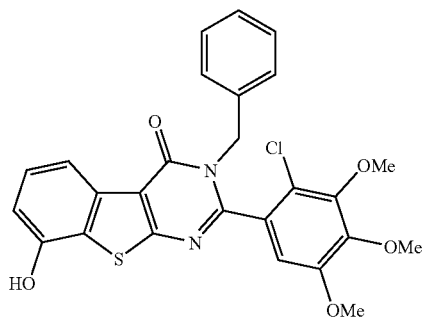

According to the method described for the compound No. 92 using the compound No. 123 as a starting material.

NMR (CDCl$_3$): 3.47 (s, 3H), 3.92 (s, 3H), 4.01 (s, 3H), 4.56 (d, 1H), 6.05 (d, 1H), 6.20 (s, 1H), 6.92 (m, 3H), 7.20 (m, 3H), 7.40 (dd, 1H), 8.32 (d, 1H). Rf (toluene-methanol, 9.5:0.5)= 0.16 MS (TOF, ES+) m/z 509/511

Compound No. 125

3-(2-Methylbutyl)-2-(3,4,5-trimethoxyphenyl)-5,6,7,8-tetrahydro-3H-benzo[4,5]thieno[2,3-d]pyrimidin-4-one

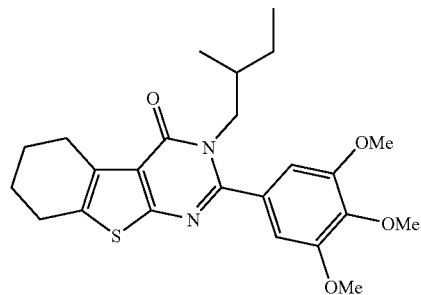

According to the method described for the compound No. 1 using 3,4,5-trimethoxy-N-(2-methylbutyl)-benzamide as a starting material.

NMR (CDCl$_3$): 0.70 (d, 3H), 0.74 (t, 3H), 1.22 (m, 2H), 1.85 (m, 5H), 2.79 (m, 2H), 3.07 (m, 2H), 3.86 (s, 9H), 3.98 (m, 2H), 6.67 (s, 2H). Rf (toluene-EtOAc, 9:1)=0.25 MS (TOF, ES+) m/z 443 (M+1)

Compound No. 126

3-(2-Methylbutyl)-2-(3,4,5-trimethoxyphenyl)-6,7-dihydro-3H,5H-benzo[4,5]thieno[2,3-d]pyrimidine-4,8-dione

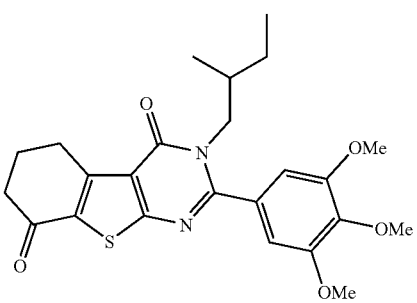

According to the method described for the compound No. 2 using the compound No. 125 as a starting material.

NMR (CDCl$_3$): 0.74 (m, 6H), 1.12 (m, 2H), 1.80 (m, 1H), 2.30 (m, 2H), 2.70 (m, 2H), 3.34 (m, 2H), 3.90 (s, 9H), 4.01 (m, 2H), 6.70 (s, 2H). Rf (toluene-methanol, 9.5:0.5)=0.51 MS (TOF, ES+) m/z 457 (M+1)

Compound No. 127

7-Bromo-3-(2-methylbutyl)-2-(3,4,5-trimethoxyphenyl)-6,7-dihydro-3H,5H-benzo[4,5]thieno[2,3-d]pyrimidine-4,8-dione

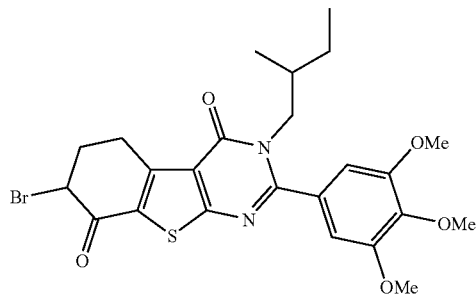

According to the method described for the compound No. 46 using the compound No. 126 as a starting material. The compound No. 128 was isolated as a by-product.

NMR (CDCl$_3$): 0.72 (m, 6H), 0.88-1.31 (m, 2H), 1.79 (m, 1H), 2.60 (m, 2H), 3.34-3.63 (m, 2H), 3.91 (s, 9H), 4.06 (m, 2H), 4.73 (t, 1H), 6.71 (s, 2H). Rf (toluene-EtOAc, 9:1)=0.15 MS (TOF, ES+) m/z 535/537

Compound No. 128

7,7-Dibromo-2-(2-bromo-3,4,5-trimethoxyphenyl)-3-(2-methylbutyl)-6,7-dihydro-3H,5H-benzo[4,5]thieno[2,3-d]pyrimidine-4,8-dione

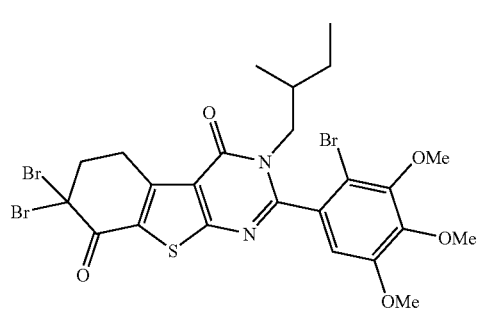

Rf (toluene-EtOAc, 9:1)=0.56 MS (TOF, ES+) m/z 691/693/695

Compound No. 129

8-Hydroxy-3-(2-methylbutyl)-2-(3,4,5-trimethoxyphenyl)-3H-benzo[4,5]thieno[2,3-d]pyrimidin-4-one

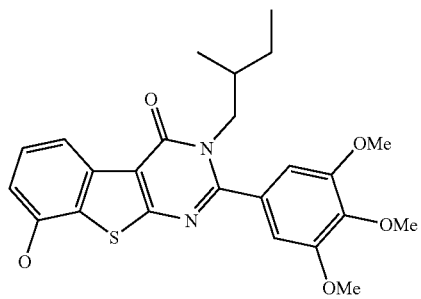

According to the method described for the compound No. 92 using the compound No. 127 as a starting material.

NMR (CDCl$_3$): 0.76 (m, 6H), 1.08 (m, 2H), 1.88 (m, 1H), 3.92 (s, 9H), 4.14 (m, 2H), 6.76 (s, 2H), 6.91 (dd, 1H), 7.41 (dd, 1H), 8.22 (dd, 1H). Rf (toluene-methanol, 9.5:0.5)=0.13 MS (TOF, ES+) m/z 455 (M+1)

Compound No. 130

3-(Tetrahydrofuran-2-ylmethyl)-2-(3,4,5-trimethoxyphenyl)-5,6,7,8-tetrahydro-3H-benzo[4,5]thieno[2,3-d]pyrimidin-4-one

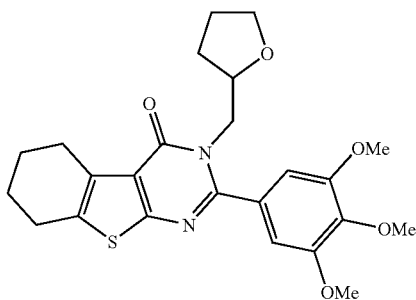

According to the method described for the compound No. 1 using 3,4,5-trimethoxy-N-(tetrahydrofuran-2-ylmethyl)-benzamide as a starting material. Rf (toluene-MeOH, 9:1)=0.40 MS (TOF, ES+) m/z 457 (M+1)

Compound No. 131

3-(Tetrahydrofuran-2-ylmethyl)-2-(3,4,5-trimethoxyphenyl)-6,7-dihydro-3H,5H-benzo[4,5]thieno[2,3-d]pyrimidine-4,8-dione

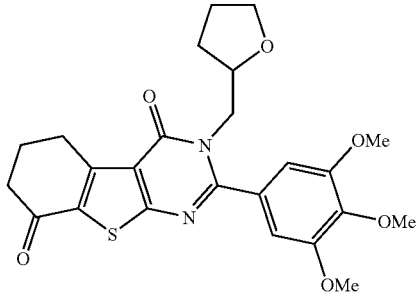

According to the method described for the compound No. 2 using the compound No. 130 as a starting material.

NMR (CDCl$_3$): 1.44 (m, 1H), 1.74 (m, 2H), 2.02 (m, 1H), 2.28 (m, 2H), 2.70 (m, 2H), 3.33 (m, 2H), 3.57 (m, 2H), 3.89 (s, 9H), 3.99 (m, 1H), 4.22 (m, 2H), 6.81 (s, 2H). Rf (toluene-methanol, 9:1)=0.44 MS (TOF, ES+) m/z 471 (M+1)

Compound No. 132

7-Bromo-2-(2-bromo-3,4,5-trimethoxyphenyl)-3-(tetrahydrofuran-2-ylmethyl)-6,7-dihydro-3H,5H-benzo[4,5]thieno[2,3-d]pyrimidine-4,8-dione

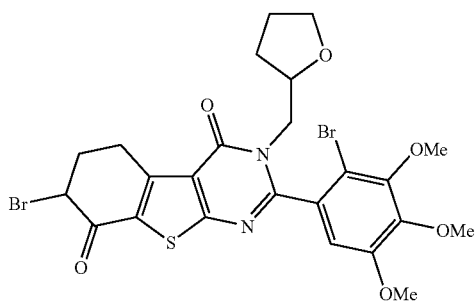

According to the method described for the compound No. 46 using the compound No. 131 as a starting material.

NMR (CDCl$_3$): 1.58 (m, 3H), 2.07 (m, 1H), 2.58 (m, 2H), 3.26-3.67 (m, 5H), 3.94 (s, 3H), 3.95 (s, 3H), 3.96 (s, 3H), 4.44 (m, 2H), 4.73 (t, 1H), 7.00 (s, 1H). Rf (toluene-MeOH, 9,5:0,5)=0.59 MS (TOF, ES+) m/z 649/651/653 (M+Na)

Compound No. 133

2-(2-Bromo-3,4,5-trimethoxyphenyl)-8-hydroxy-3-(tetrahydrofuran-2-ylmethyl)-3H-benzo[4,5]thieno[2,3-d]pyrimidin-4-one

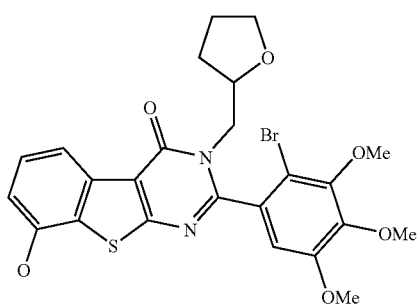

The compound No. 132 (50 mg, 0.08 mmol) was dissolved in methanol (1.5 ml). NaOH (13 mg, 0.32 mmol) was added. The reaction mixture was heated using microwaves (120° C., 2 min.). The solvent was evaporated and the precipitate was dissolved into ethylacetate, washed with 1N HCl and water. Purified by using chromatography (eluent: CH$_2$Cl$_2$-diethyl ether 9:1).

NMR (CDCl$_3$): 1.45-1.93 (m, 4H), 2.15 (m, 1H), 3.34-3.79 (m, 2H), 3.94 (s, 3H), 3.95 (s, 3H), 3.96 (s, 3H), 4.60 (m, 2H), 6.77 (d, 1H), 7.13 (s, 1H), 7.31 (dd, 1H), 8.03 (d, 1H). Rf (toluene-methanol, 9.5:0.5)=0.32 MS (TOF, ES+) m/z 547/549

Compound No. 134

3-Butyl-2-thiophen-2-yl-6,7-dihydro-3H,5H-benzo[4,5]thieno[2,3-d]pyrimidine-4,8-dione

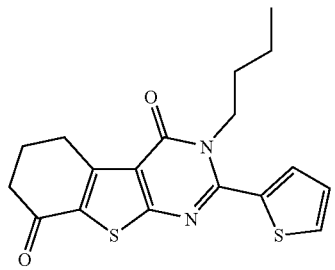

According to the method described for the compound No. 2 using the compound No. 77 as a starting material.

NMR (CDCl$_3$): 0.95 (t, 3H), 1.36 (m, 2H), 1.81 (m, 2H), 2.26 (m, 2H), 2.69 (m, 2H), 3.32 (m, 2H), 4.24 (m, 2H), 7.18 (dd, 1H), 7.58 (dd, 2H). Rf (toluene-methanol, 9:1)=0.49 MS (TOF, ES+) m/z 359 (M+1)

Compound No. 135

5-Bromo-3-isobutyl-2-(3,4,5-trimethoxyphenyl)-6,7-dihydro-3H,5H-benzo[4,5]thieno[2,3-d]pyrimidine-4,8-dione

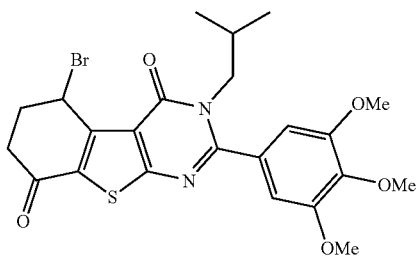

The compound No. 114 (200 mg, 0.45 mmol), NBS (40 mg, 0.23 mmol) and benzoylperoxide (27 mg, 0.11 mmol) were dissolved in carbon tetrachloride (4 ml) and refluxed for 1.5 hours. After 30 minutes a new portion of NBS (40 mg) was added. The reaction mixture was filtered and the solid was washed carefully with dichloromethane. The filtrate was washed with water and evaporated. The crude product was purified by chromatography using toluene-EtOAc (4:1) as an eluent.

NMR (CDCl$_3$): 0.79 (dd, 6H), 2.04 (m, 1H), 2.74 (m, 3H), 3.15 (m, 1H), 3.90 (s, 6H), 3.91 (s, 3H), 3.95 (1H), 4.17 (m, 1H), 6.20 (t, 1H), 6.71 (s, 2H). Rf (toluene-methanol, 9.5:0.5)=0.53 MS (TOF, ES+) m/z 521/523

Compound No. 136

3-Isobutyl-8-methoxy-2-(3,4,5-trimethoxyphenyl)-3H-benzo[4,5]thieno[2,3-d]pyrimidin-4-one

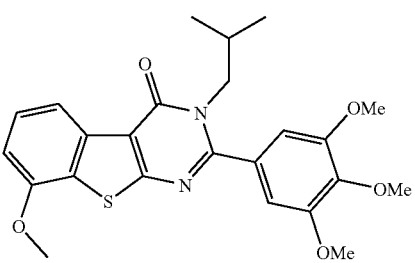

The compound No. 135 (50 mg) was dissolved in a mixture of dichloromethane and methanol (v/v 1:1, 2 ml) and warmed at 40° C. for two days. The solvent was evaporated. The crude product was purified by chromatography using toluene-EtOAc (9:1) as an eluent.

NMR (CDCl$_3$): 0.78 (s, 3H), 0.81 (s, 3H), 2.13 (m, 1H), 3.92 (s, 9H), 4.03 (s, 3H), 4.10 (m, 2H), 6.75 (s, 2H), 6.95 (d, 1H), 7.51 (dd, 1H), 8.29 (d, 1H). Rf (toluene-methanol, 9.5:0.5)=0.35 MS (TOF, ES+) m/z 455 (M+1)

Compound No. 137

3-Benzyl-5-bromo-2-(3,4,5-trimethoxyphenyl)-6,7-dihydro-3H,5H-benzo[4,5]thieno[2,3-d]pyrimidine-4,8-dione

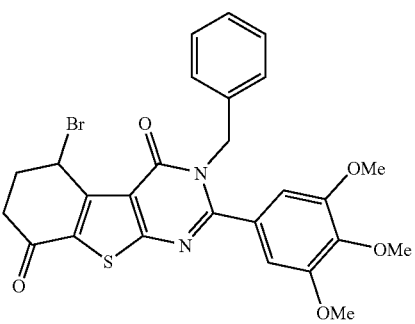

According to the method described for the compound No. 135 using the compound No. 2 as a starting material.

NMR (CDCl$_3$): 2.74 (m, 3H), 3.21 (m, 1H), 3.61 (s, 6H), 3.86 (s, 3H), 5.29 (dd, 2H), 6.20 (t, 1H), 6.53 (s, 2H), 7.06 (m, 2H), 7.30 (m, 3H). Rf (toluene-methanol, 9.5:0.5)=0.59 MS (TOF, ES+) m/z 555/557

Compound No. 138

3-Benzyl-8-methoxy-2-(3,4,5-trimethoxyphenyl)-3H-benzo[4,5]thieno[2,3-d]pyrimidin-4-one

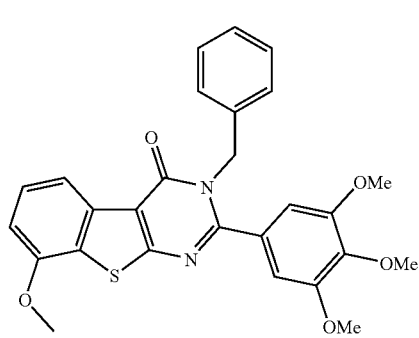

According to the method described for the compound No. 136 using the compound No. 137 as a starting material.

NMR (CDCl$_3$): 3.61 (s, 6H), 3.86 (s, 3H), 4.04 (s, 3H), 5.34 (s, 2H), 6.56 (s, 2H), 6.96 (d, 1H), 7.08 (m, 2H), 7.30 (m, 3H), 7.51 (dd, 1H), 8.33 (d, 1H). Rf (toluene-methanol, 9.5:0.5)= 0.56 MS (TOF, ES+) m/z 489 (M+1)

Compound No. 139

7-Chloro-2-(2-chloro-3,4,5-trimethoxyphenyl)-3-(tetrahydrofuran-2-ylmethyl)-6,7-dihydro-3H,5H-benzo[4,5]thieno[2,3-d]pyrimidine-4,8-dione

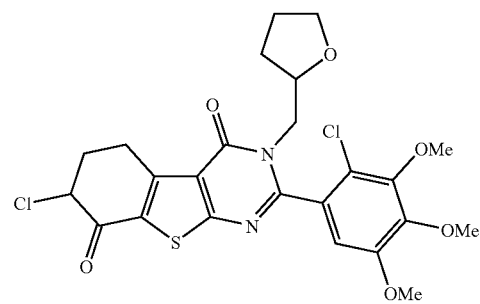

According to the method described for the compound No. 123 using the compound No. 131 as a starting material.

Rf (toluene-methanol, 9.5:0.5)=0.53

Compound No. 140

2-(2-Chloro-3,4,5-trimethoxyphenyl)-8-hydroxy-3-(tetrahydrofuran-2-ylmethyl)-3H-benzo[4,5]thieno[2,3-d]pyrimidin-4-one

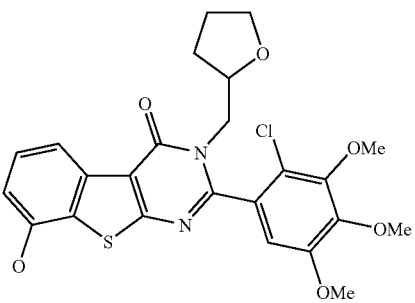

According to the method described for the compound No. 92 using the compound No. 139 as a starting material.

NMR (CDCl$_3$): 1.46-1.94 (m, 3H), 2.16 (m, 1H), 3.33-3.81 (m, 2H), 3.95 (m, 1H), 3.96 (s, 9H), 4.64 (m, 2H), 6.73 (d, 1H), 7.12 (s, 1H), 7.54 (m, 1H), 7.86 (d, 1H). Rf (toluene-methanol, 9:1)=0.29 MS (TOF, ES+) m/z 503/505

Compound No. 141

7-Chloro-2-(2-chloro-3,4,5-trimethoxyphenyl)-3-(2-methylbutyl)-6,7-dihydro-3H,5H-benzo[4,5]thieno[2,3-d]pyrimidine-4,8-dione

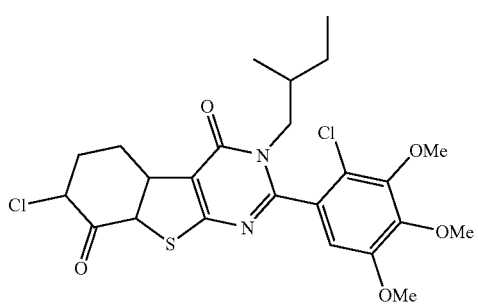

According to the method described for the compound No. 123 using the compound No. 126 as a starting material. The compound No. 142 was isolated as a by-product.

NMR (CDCl$_3$): 0.65 (m, 3H), 0.75 (m, 4H), 0.82-1.30 (m, 2H), 2.62 (m, 2H), 3.41-3.55 (m, 3H), 3.90 (s, 3H), 3.95 (s, 6H), 4.27 (m, 1H), 4.65 (m, 1H), 6.79 (s, 1H). Rf (toluene-methanol, 9.5:0.5)=0.37 MS (TOF, ES+) m/z 525/527

Compound No. 142

7,7-Dichloro-2-(2-chloro-3,4,5-trimethoxyphenyl)-3-(2-methylbutyl)-6,7-dihydro-3H,5H-benzo[4,5]thieno[2,3-d]pyrimidine-4,8-dione

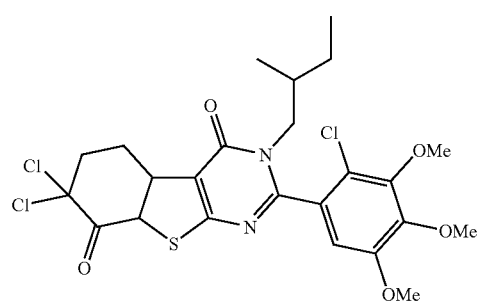

NMR (CDCl$_3$): 0.68 (t, 3H), 0.86 (m, 4H), 1.00-1.30 (m, 2H), 2.62 (dd, 2H), 3.34-3.61 (m, 3H), 3.89 (s, 3H), 3.90 (s, 6H), 4.26 (m, 1H), 6.78 (s, 1H). Rf (toluene-methanol, 9.5:0.5)=0.53 MS (TOF, ES+) m/z 559/561/563

Compound No. 143

2-(2-Chloro-3,4,5-trimethoxyphenyl)-8-hydroxy-3-(2-methylbutyl)-3H-benzo[4,5]thieno[2,3-d]pyrimidin-4-one

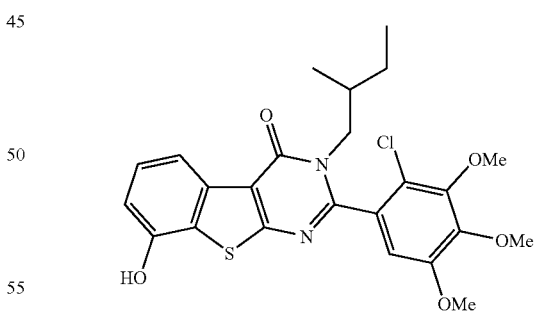

According to the method described for the compound No. 133 using the compound No. 141 as a starting material.

NMR (CDCl$_3$): 0.61-0.88 (m, 6H), 1.20 (m, 3H), 3.54 (m, 1H), 3.88 (s, 3H), 3.95 (s, 6H), 4.41 (m, 1H), 6.87 (d, 1H), 6.92 (dd, 1H), 7.40 (dd, 1H), 8.28 (d, 1H). Rf (toluene-methanol, 9.5:0.5)=0.12 MS (TOF, ES+) m/z 489/491

Compound No. 144

3-Pyridin-3-ylmethyl-2-(3,4,5-trimethyl-phenyl)-5,6,7,8-tetrahydro-3H-benzo[4,5]thieno[2,3-d]pyrimidin-4-one

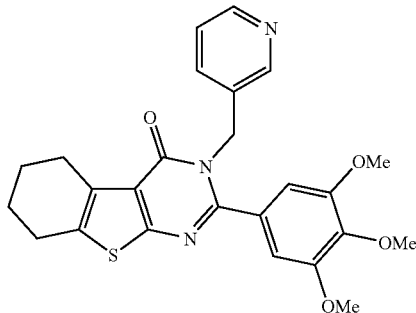

According to the method described for the compound No. 1 using 3,4,5-trimethoxy-N-pyridin-3-ylmethyl-benzamide as a starting material.

NMR (CDCl$_3$): 1.90 (m, 4H), 2.82 (m, 2H), 3.07 (m, 2H), 3.81 (s, 3H), 3.86 (s, 3H), 3.91 (s, 3H), 5.26 (s, 2H), 6.49 (s, 2H), 7.44 (dd, 1H), 7.68 (dd, 1H), 8.55 (m, 2H). MS (TOF, ES+) m/z 464 (M+1)

Compound No. 145

3-Benzyl-8-hydroxy-2-(3,4,5-trimethoxyphenyl)-5,6,7,8-tetrahydro-3H-benzo[4,5]thieno[2,3-d]pyrimidin-4-one

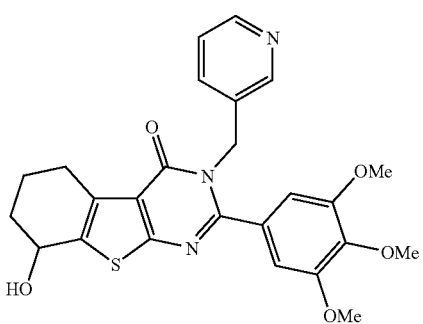

The compound No. 2 (200 mg, 0.42 mmol) was dissolved in EtOAc (10 ml) and added to mixture of NaBH$_4$ (32 mg, 0.84 mmol) in EtOAc (5 ml) and stirred overnight at room temperature. The reaction mixture was diluted with EtOAc, washed with saturated ammonium chloride and brine. After evaporation of solvent, the crude product was purified by chromatography.

NMR (CDCl$_3$): 1.91 (m, 1H), 1.97-2.23 (m, 4H), 3.09 (m, 2H), 3.58 (s, 6H), 3.84 (s, 3H), 4.89 (br s,1H), 5.22 (d, 2H), 6.51 (s, 2H), 7.01 (m, 2H), 7.20 (m, 3H). Rf (toluene-methanol, 9:1)=0.38 MS (TOF, ES+) m/z 501 (M+Na)

Compound No. 146

3-Benzyl-7-bromo-2-p-methoxyphenyl-6,7-dihydro-3H,5H-benzo[4,5]thieno[2,3-d]pyrimidine-4,8-dione

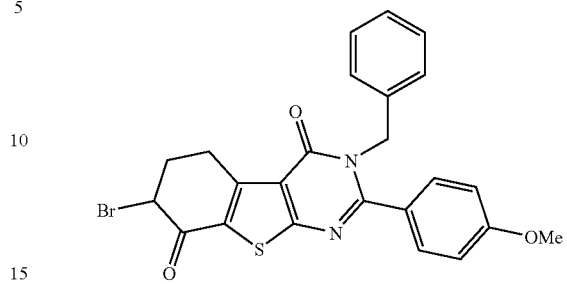

According to the method described for the compound No. 46 using the compound No. 13 as a starting material. The compound No. 147 was isolated as a by-product.

NMR (CDCl$_3$): 2.58 (m, 2H), 3.25-3.64 (m, 2H), 3.85 (s, 3H), 4.72 (t, 1H), 5.32 (s, 2H), 7.0 (m, 4H), 7.30 (m, 5H). MS (TOF, ES+) m/z 495/497

Compound No. 147

3-Benzyl-7,7-dibromo-2-p-methoxyphenyl-6,7-dihydro-3H,5H-benzo[4,5]thieno[2,3-d]pyrimidine-4,8-dione

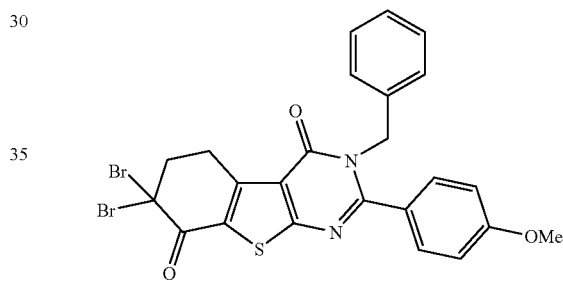

NMR (CDCl$_3$): 3.17 (dd, 2H), 3.45 (dd, 2H), 3.85 (s, 3H), 5.29 (s, 2H), 6.98 (m, 4H), 7.30 (m, 5H). MS (TOF, ES+) m/z 595/597/599 (M+Na)

Compound No. 148

7-Bromo-8-hydroxy-3-(2-methoxyethyl)-2-thiophen-2-yl-3H-benzo[4,5]thieno[2,3-d]pyrimidin-4-one

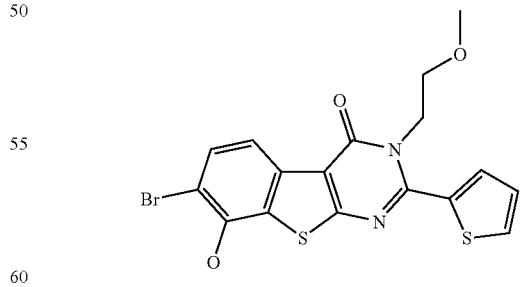

According to the method described for the compound No. 133 using the compound No. 76 as a starting material.

NMR (CDCl$_3$+MeOH-d4): 3.56 (s, 3H), 3.85 (m, 2H), 4.58 (m, 2H), 6.91 (d, 1H), 7.13 (d, 1H), 7.39 (m, 1H), 7.64 (m, 1H), 8.12 (d, 1H). Rf (toluene-methanol, 9:1)=0.47 MS (TOF, ES−) m/z 435/437

Compound No. 149

7-Bromo-8-hydroxy-3-(2-hydroxyethyl)-2-thiophen-2-yl-3H-benzo[4,5]thieno[2,3-d]pyrimidin-4-one

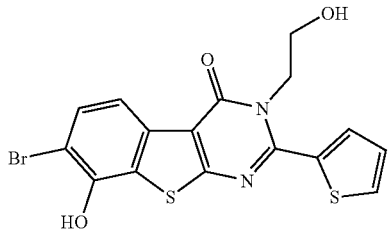

According to the method described for the compound No. 100 using the compound No. 76 as a starting material.

NMR (DMSO-d6): 3.80 (m, 2H), 4.39 (m, 2H), 5.16 (dd, 1H), 6.95 (d, 1H), 7.40 (m, 2H), 7.90 (m, 2H), 10.69 (s, 1H). Rf (toluene-methanol, 9:1)=0.31 MS (TOF, ES−) m/z 421/423

Compound No. 150

3-Benzyl-8-chloro-2-(2-chloro-3,4,5-trimethoxyphenyl)-4-oxo-3,4-dihydro-benzo[4,5]thieno[2,3-d]pyrimidine-7-carbaldehyde

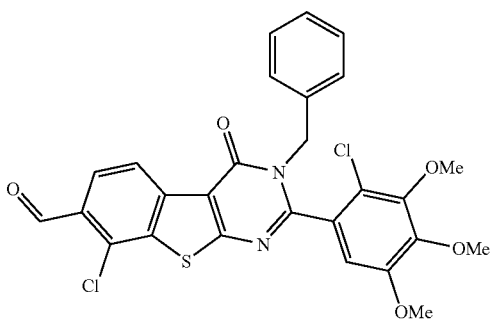

The compound No. 3 (200 mg, 0.38 mmol), sulfurylchloride (46 µl, 0.57 mmol) in chloroform (s 2 ml) were refluxed under nitrogen atmosphere for 45 minutes. The reaction mixture was diluted with dichloromethane and washed with water. After evaporation the crude product was purified with chromatography using toluene-EtOAc (9.9:0.1) as an eluent.

NMR (CDCl3): 3.50 (s, 3H), 3.95 (s, 3H), 3.98 (s, 3H), 4.58 (d, 1H), 6.03 (d, 1H), 6.20 (s, 1H), 6.93 (m, 2H), 7.20 (m, 3H), 8.13 (d, 1H), 8.74 (d, 1H), 10.61 (s, 1H). Rf (toluene-EtOAc, 9:1)=0.44 MS (TOF, ES+) m/z 555/557/559

Compound No. 151

8-Hydroxy-3-isobutyl-2-(3,4,5-trimethoxyphenyl)-3H-benzo[4,5]thieno[2,3-d]pyrimidin-4-one

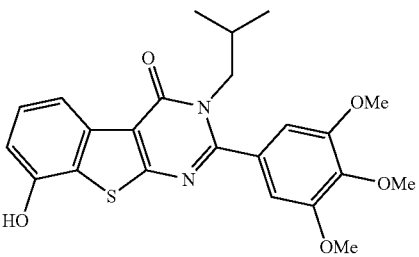

The compound No. 135 (50 mg, 0.1 mmol) and K2CO3 (25 mg) were stirred in ethanol for two hours. The solvent was evaporated. The precipitate was dissolved in dichloromethane and washed with water.

NMR (CDCl3): 0.77 (s, 3H), 0.81 (s, 3H), 2.13 (m, 1H), 3.91 (s, 9H), 4.11 (d, 2H), 6.75 (s, 2H), 6.90 (d, 1H), 7.42 (d, 1H), 8.28 (d, 1H). Rf (toluene-methanol, 9:1)=0.31 MS (TOF, ES+) m/z 441 (M+1)

Further compounds of general formula q-0 falling under the scope of general formula I can prepared by parallel chemistry using a reaction as shown already in the following scheme 6 (according to general flow scheme 5):

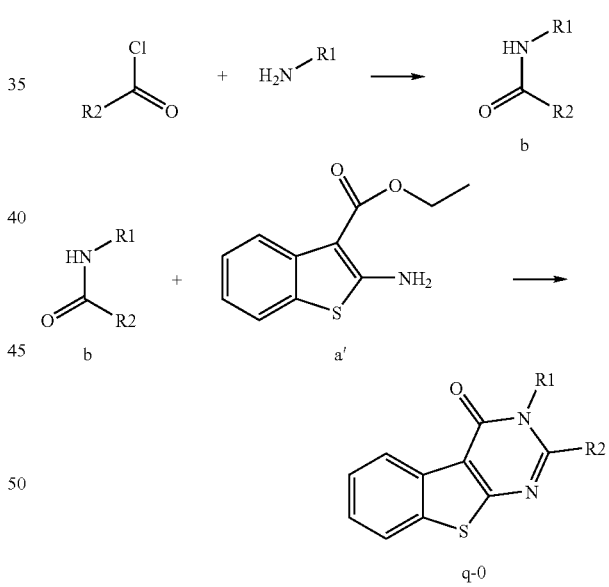

In a reaction vessel at room temperature are put together sequentially 0.25 M primary amine R1-NH$_2$, 1 M diisopropylethylamine and 0.25 M acid chloride R2-CO—Cl. To this mixture is added 0.25 M 2-amino-benzo[b]thiophene-3-carboxylic acid ethyl ester a' followed by 0.25 M POCl$_3$. Of all reactants one equivalent is used as solution or suspension in chlorobenzene. After shaking for 80 hours at 100° C., the mixtures are cooled to room temperature, washed with 5% NaOAc and extracted with EtOAc. The organic layers are collected and concentrated to yield the desired compound. The obtained material of the formula q-0 was thereafter analyzed by LC-MS.

The LC-MS system consists of 2 Perkin Elmer series 200 micro-pumps. The pumps are connected to each other by a 50 µ tee mixer. The mixer is connected to the Gilson 215 autosampler. The LC methode consists of the following steps:

| Step | total time | flow (ul/min) | A(%) | B(%) |
|---|---|---|---|---|
| 0 | 0 | 2300 | 95 | 5 |
| 1 | 1.8 | 2300 | 0 | 100 |
| 2 | 2.5 | 2300 | 0 | 100 |
| 3 | 2.7 | 2300 | 95 | 5 |
| 4 | 3.0 | 2300 | 95 | 5 |

Solution A=100% Water with 0.025% HCOOH and 10 mmol NH$_4$HCOO pH=+/−3
Solution B=100% MeOH with 0.025% HCOOH The auto sampler has a 2 µl injection loop. The auto sampler is connected to a Varian Polaris C18 A 30*4.6 mm column with 3 µm particles. The column is thermo stated in a Perkin Elmer series 200 column oven at 40° C. The column is connected to an Applied Biosystems ABI 785 UV meter with a 2.7 µl flowcel. The wavelength is set to 254 nm. The UVmeter is connected to a Sciex API 150EX mass spectrometer having the following parameters (Scanrange:150-900 Amu, Polarity: positive, Scan mode: profile, Resolution Q1: UNIT, Step size: 0.10 amu, Time per scan: 0.500 sec, NEB: 10, CUR: 10, IS: 5200, TEM: 325, DF: 30, FP: 225, EP: 10). The light scattering detector is connected to the Sciex API 150. The light scattering detector is a Sedere Sedex 55 operating at 50° C. and 3 bar N$_2$ pressure. The complete systems is controlled by a Dell optiplex GX400 computer operating under Windows NT.

The following table 1 lists compounds No. 152 to 616 of the general formula q-0, which were prepared according to Scheme 6 starting with the primary amines R1-NH$_2$ and the acide chlorides R2-CO—Cl. In addition, the Molecular Weight and the Retention Time of the synthesized compounds determined by the LC-MS analysis are shown.

TABLE 1

Compounds No. 152 to 616 of the general formula q:

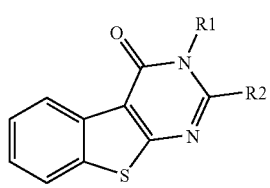

q-0

| No. | R2—CO—Cl (name) | R1—NH$_2$ (name) | MH+ | RT |
|---|---|---|---|---|
| 152 | HYDROCINNAMOYL CHLORIDE | ANILINE | 382,11 | 2,060 |
| 153 | 2-NAPHTHOYL CHLORIDE | ANILINE | 404,10 | 2,028 |
| 154 | HYDROCINNAMOYL CHLORIDE | 6-AMINOPHTHALIDE | 438,10 | 1,919 |
| 155 | DIPHENYLACETYL CHLORIDE | CYCLOHEXYLAMINE | 450,18 | 2,229 |
| 156 | HYDROCINNAMOYL CHLORIDE | 4-(2-AMINOETHYL)MORPHOLINE | 419,17 | 1,771 |
| 157 | 2-NAPHTHOYL CHLORIDE | 4-(2-AMINOETHYL)MORPHOLINE | 441,15 | 1,721 |
| 158 | PHENYLACETYL CHLORIDE | ANILINE | 368,10 | 1,990 |
| 159 | 2-METHOXYBENZOYL CHLORIDE | ANILINE | 384,09 | 1,838 |
| 160 | PHENYLACETYL CHLORIDE | 6-AMINOPHTHALIDE | 424,09 | 1,845 |
| 161 | 4-CYANOBENZOYL CHLORIDE | CYCLOHEXYLAMINE | 385,12 | 1,448 |
| 162 | PHENYLACETYL CHLORIDE | 4-(2-AMINOETHYL)MORPHOLINE | 405,15 | 1,661 |
| 163 | 2-METHOXYBENZOYL CHLORIDE | 4-(2-AMINOETHYL)MORPHOLINE | 421,15 | 1,521 |
| 164 | CYCLOPROPANECARBONYL CHLORIDE | ANILINE | 318,08 | 2,007 |
| 165 | 3-CYCLOPENTYLPROPIONYL CHLORIDE | ANILINE | 374,15 | 2,183 |
| 166 | 3-FLUOROBENZOYL CHLORIDE | ANILINE | 372,07 | 1,964 |
| 167 | 3-CYCLOPENTYLPROPIONYL CHLORIDE | 6-AMINOPHTHALIDE | 430,14 | 2,070 |
| 168 | CYCLOPROPANECARBONYL CHLORIDE | CYCLOHEXYLAMINE | 324,13 | 1,491 |
| 169 | 3,5-BIS(TRIFLUOROMETHYL)BENZOYL CHLORIDE | CYCLOHEXYLAMINE | 496,10 | 2,242 |
| 170 | 3-FLUOROBENZOYL CHLORIDE | CYCLOHEXYLAMINE | 378,12 | 2,140 |
| 171 | CYCLOPROPANECARBONYL CHLORIDE | 4-(2-AMINOETHYL)MORPHOLINE | 355,14 | 1,599 |
| 172 | 3-CYCLOPENTYLPROPIONYL CHLORIDE | 4-(2-AMINOETHYL)MORPHOLINE | 411,20 | 1,997 |
| 173 | 3-FLUOROBENZOYL CHLORIDE | 4-(2-AMINOETHYL)MORPHOLINE | 409,13 | 1,675 |
| 174 | 2,6-DIFLUOROBENZOYL CHLORIDE | ANILINE | 390,06 | 1,953 |
| 175 | 2-ETHYLHEXANOYL CHLORIDE | ANILINE | 376,16 | 2,167 |
| 176 | METHOXYACETYL CHLORIDE | ANILINE | 322,08 | 1,757 |
| 177 | 2,4-DICHLOROBENZOYL CHLORIDE | ANILINE | 422,00 | 2,053 |
| 178 | 2-ETHYLHEXANOYL CHLORIDE | 6-AMINOPHTHALIDE | 432,15 | 2,096 |
| 179 | 2-ETHYLHEXANOYL CHLORIDE | 4-(2-AMINOETHYL)MORPHOLINE | 413,21 | 2,086 |
| 180 | METHOXYACETYL CHLORIDE | 4-(2-AMINOETHYL)MORPHOLINE | 359,13 | 1,403 |
| 181 | 2,4-DICHLOROBENZOYL CHLORIDE | 4-(2-AMINOETHYL)MORPHOLINE | 459,06 | 1,895 |
| 182 | 3,4-DIMETHOXYPHENYLACETYL CHLORIDE | ANILINE | 428,12 | 1,909 |
| 183 | 2,4-DIFLOUROBENZOYL CHLORIDE | ANILINE | 390,06 | 1,951 |
| 184 | 3,3-DIMETHYLACRYLOYL CHLORIDE | ANILINE | 332,10 | 2,005 |
| 185 | ETHYL SUCCINYL CHLORIDE | ANILINE | 378,10 | 1,897 |
| 186 | METHYL MALONYL CHLORIDE | ANILINE | 350,07 | 1,743 |
| 187 | 3,3-DIMETHYLACRYLOYL CHLORIDE | 6-AMINOPHTHALIDE | 388,09 | 1,853 |

TABLE 1-continued

Compounds No. 152 to 616 of the general formula q:

q-0

| No. | R2—CO—Cl (name) | R1—NH₂ (name) | MH+ | RT |
|---|---|---|---|---|
| 188 | 2,4-DIFLOUROBENZOYL CHLORIDE | CYCLOHEXYLAMINE | 396,11 | 2,129 |
| 189 | 3,3-DIMETHYLACRYLOYL CHLORIDE | CYCLOHEXYLAMINE | 338,15 | 2,110 |
| 190 | ETHYL SUCCINYL CHLORIDE | CYCLOHEXYLAMINE | 384,15 | 2,077 |
| 191 | 3,4-DIMETHOXYPHENYLACETYL | 4-(2-AMINOETHYL)MORPHOLINE | 465,17 | 1,619 |
| 192 | 2,4-DIFLOUROBENZOYL CHLORIDE | 4-(2-AMINOETHYL)MORPHOLINE | 427,12 | 1,687 |
| 193 | 3,3-DIMETHYLACRYLOYL CHLORIDE | 4-(2-AMINOETHYL)MORPHOLINE | 369,15 | 1,548 |
| 194 | ETHYL SUCCINYL CHLORIDE | 4-(2-AMINOETHYL)MORPHOLINE | 415,16 | 1,491 |
| 195 | 1-PHENYL-5-(TRIFLUOROMETHYL)PYRAZOLE-4-CARBONYL CHLORIDE | ANILINE | 488,09 | 2,024 |
| 196 | 2-(4-CHLOROPHENOXY)PYRIDINE-3-CARBONYL CHLORIDE | 6-AMINOPHTHALIDE | 537,06 | 1,979 |
| 197 | 2-(4-CHLOROPHENOXY)PYRIDINE-3-CARBONYL CHLORIDE | CYCLOHEXYLAMINE | 487,11 | 2,206 |
| 198 | 2-(4-CHLOROPHENOXY)-2-METHYLPROPANOYL CHLORIDE | CYCLOHEXYLAMINE | 452,13 | 2,407 |
| 199 | METHYL OXALYL CHLORIDE | CYCLOHEXYLAMINE | 342,10 | 2,104 |
| 200 | 2-(4-CHLOROPHENOXY)PYRIDINE-3-CARBONYL CHLORIDE | 4-(2-AMINOETHYL)MORPHOLINE | 518,12 | 1,946 |
| 201 | 1-PHENYL-5-(TRIFLUOROMETHYL)PYRAZOLE-4-CARBONYL CHLORIDE | 4-(2-AMINOETHYL)MORPHOLINE | 525,14 | 1,859 |
| 202 | 4-[(DIPROPYLAMINO)SULFONYL]BENZENE-1-CARBONYL CHLORIDE | 4-(2-AMINOETHYL)MORPHOLINE | 554,20 | 1,845 |
| 203 | HYDROCINNAMOYL CHLORIDE | PIPERONYLAMINE | 440,12 | 2,148 |
| 204 | 2-NAPHTHOYL CHLORIDE | PIPERONYLAMINE | 462,10 | 2,120 |
| 205 | DIPHENYLACETYL CHLORIDE | PIPERONYLAMINE | 502,14 | 2,173 |
| 206 | 2-FUROYL CHLORIDE | PIPERONYLAMINE | 402,07 | 2,020 |
| 207 | ISONICOTINOYL CHLORIDE HYDROCHLORIDE | PIPERONYLAMINE | 413,08 | 2,308 |
| 208 | HYDROCINNAMOYL CHLORIDE | CYCLOPROPYLAMINE | 346,11 | 2,038 |
| 209 | 2-NAPHTHOYL CHLORIDE | CYCLOPROPYLAMINE | 368,10 | 2,065 |
| 210 | 2-FUROYL CHLORIDE | CYCLOPROPYLAMINE | 308,06 | 1,849 |
| 211 | HYDROCINNAMOYL CHLORIDE | 3-(AMINOMETHYL)PYRIDINE | 397,12 | 1,973 |
| 212 | 2-NAPHTHOYL CHLORIDE | 3-(AMINOMETHYL)PYRIDINE | 419,11 | 1,904 |
| 213 | 2-FUROYL CHLORIDE | 3-(AMINOMETHYL)PYRIDINE | 359,07 | 1,793 |
| 214 | HYDROCINNAMOYL CHLORIDE | PHENETHYLAMINE | 410,15 | 2,170 |
| 215 | 2-NAPHTHOYL CHLORIDE | PHENETHYLAMINE | 432,13 | 2,149 |
| 216 | DIPHENYLACETYL CHLORIDE | PHENETHYLAMINE | 472,16 | 2,195 |
| 217 | 2-FUROYL CHLORIDE | PHENETHYLAMINE | 372,09 | 2,120 |
| 218 | PHENYLACETYL CHLORIDE | PIPERONYLAMINE | 426,10 | 2,110 |
| 219 | 2-METHOXYBENZOYL CHLORIDE | PIPERONYLAMINE | 442,10 | 1,994 |
| 220 | 3,4-DICHLOROBENZOYL CHLORIDE | PIPERONYLAMINE | 480,01 | 2,158 |
| 221 | PHENYLACETYL CHLORIDE | CYCLOPROPYLAMINE | 332,10 | 1,959 |
| 222 | 2-METHOXYBENZOYL CHLORIDE | CYCLOPROPYLAMINE | 348,09 | 1,884 |
| 223 | BENZO[B]THIOPHENE-2-CARBONYL Chloride | CYCLOPROPYLAMINE | 374,05 | 2,132 |
| 224 | 3,4-DICHLOROBENZOYL CHLORIDE | CYCLOPROPYLAMINE | 386,00 | 2,101 |
| 225 | PHENYLACETYL CHLORIDE | 3-(AMINOMETHYL)PYRIDINE | 383,11 | 1,862 |
| 226 | 2-METHOXYBENZOYL CHLORIDE | 3-(AMINOMETHYL)PYRIDINE | 399,10 | 1,772 |
| 227 | PHENYLACETYL CHLORIDE | PHENETHYLAMINE | 396,13 | 2,127 |
| 228 | 2-METHOXYBENZOYL CHLORIDE | PHENETHYLAMINE | 412,12 | 2,028 |
| 229 | 4-CYANOBENZOYL CHLORIDE | PHENETHYLAMINE | 407,11 | 1,977 |
| 230 | BENZO[B]THIOPHENE-2-CARBONYL Chloride | PHENETHYLAMINE | 438,09 | 2,258 |
| 231 | 3,4-DICHLOROBENZOYL CHLORIDE | PHENETHYLAMINE | 450,04 | 2,188 |
| 232 | 3-CYCLOPENTYLPROPIONYL CHLORIDE | PIPERONYLAMINE | 432,15 | 2,259 |
| 233 | 3-FLUOROBENZOYL CHLORIDE | PIPERONYLAMINE | 430,08 | 2,054 |
| 234 | 3-CYCLOPENTYLPROPIONYL CHLORIDE | CYCLOPROPYLAMINE | 338,15 | 2,173 |
| 235 | 3-FLUOROBENZOYL CHLORIDE | CYCLOPROPYLAMINE | 336,07 | 1,962 |
| 236 | CYCLOPROPANECARBONYL CHLORIDE | 3-(AMINOMETHYL)PYRIDINE | 333,09 | 1,863 |
| 237 | 3-CYCLOPENTYLPROPIONYL CHLORIDE | 3-(AMINOMETHYL)PYRIDINE | 389,16 | 2,105 |

TABLE 1-continued

Compounds No. 152 to 616 of the general formula q:

$$\text{q-0}$$

[Structure: benzothieno-pyrimidinone core with R1 on N and R2 on C adjacent to N]

| No. | R2—CO—Cl (name) | R1—NH$_2$ (name) | MH+ | RT |
|---|---|---|---|---|
| 238 | CYCLOPROPANECARBONYL CHLORIDE | PHENETHYLAMINE | 346,11 | 2,130 |
| 239 | 3-CYCLOPENTYLPROPIONYL CHLORIDE | PHENETHYLAMINE | 402,18 | 2,311 |
| 240 | 3,5-BIS(TRIFLUOROMETHYL)BENZOYL CHLORIDE | PHENETHYLAMINE | 518,09 | 2,199 |
| 241 | 3-FLUOROBENZOYL CHLORIDE | PHENETHYLAMINE | 400,10 | 2,096 |
| 242 | 2,6-DIFLUOROBENZOYL CHLORIDE | PIPERONYLAMINE | 448,07 | 2,071 |
| 243 | 2-ETHYLHEXANOYL CHLORIDE | PIPERONYLAMINE | 434,17 | 2,242 |
| 244 | METHOXYACETYL CHLORIDE | PIPERONYLAMINE | 380,08 | 2,001 |
| 245 | 3-CYANOBENZOYL CHLORIDE | PIPERONYLAMINE | 437,08 | 1,975 |
| 246 | 2,4-DICHLOROBENZOYL CHLORIDE | PIPERONYLAMINE | 480,01 | 2,162 |
| 247 | 2-ETHYLHEXANOYL CHLORIDE | CYCLOPROPYLAMINE | 340,16 | 2,192 |
| 248 | METHOXYACETYL CHLORIDE | CYCLOPROPYLAMINE | 286,08 | 1,717 |
| 249 | 2,4-DICHLOROBENZOYL CHLORIDE | CYCLOPROPYLAMINE | 386,00 | 2,095 |
| 250 | 2-ETHYLHEXANOYL CHLORIDE | 3-(AMINOMETHYL)PYRIDINE | 391,17 | 2,091 |
| 251 | METHOXYACETYL CHLORIDE | 3-(AMINOMETHYL)PYRIDINE | 337,09 | 1,680 |
| 252 | 2,4-DICHLOROBENZOYL CHLORIDE | 3-(AMINOMETHYL)PYRIDINE | 437,02 | 1,995 |
| 253 | 2,6-DIFLUOROBENZOYL CHLORIDE | PHENETHYLAMINE | 418,10 | 2,138 |
| 254 | 2-ETHYLHEXANOYL CHLORIDE | PHENETHYLAMINE | 404,19 | 2,332 |
| 255 | METHOXYACETYL CHLORIDE | PHENETHYLAMINE | 350,11 | 2,029 |
| 256 | 3-CYANOBENZOYL CHLORIDE | PHENETHYLAMINE | 407,11 | 2,002 |
| 257 | 2,4-DICHLOROBENZOYL CHLORIDE | PHENETHYLAMINE | 450,04 | 2,203 |
| 258 | 3,4-DIMETHOXYPHENYLACETYL CHLORIDE | PIPERONYLAMINE | 486,12 | 2,024 |
| 259 | 2,4-DIFLOUROBENZOYL CHLORIDE | PIPERONYLAMINE | 448,07 | 2,070 |
| 260 | 3,3-DIMETHYLACRYLOYL CHLORIDE | PIPERONYLAMINE | 390,10 | 2,067 |
| 261 | ETHYL SUCCINYL CHLORIDE | PIPERONYLAMINE | 436,11 | 1,989 |
| 262 | METHYL MALONYL CHLORIDE | PIPERONYLAMINE | 408,08 | 1,904 |
| 263 | 3,4-DIMETHOXYPHENYLACETYL CHLORIDE | CYCLOPROPYLAMINE | 392,12 | 1,888 |
| 264 | 3,3-DIMETHYLACRYLOYL CHLORIDE | CYCLOPROPYLAMINE | 296,10 | 1,960 |
| 265 | 3,4-DIMETHOXYPHENYLACETYL CHLORIDE | 3-(AMINOMETHYL)PYRIDINE | 443,13 | 1,787 |
| 266 | 2,4-DIFLOUROBENZOYL CHLORIDE | 3-(AMINOMETHYL)PYRIDINE | 405,07 | 1,857 |
| 267 | 3,3-DIMETHYLACRYLOYL CHLORIDE | 3-(AMINOMETHYL)PYRIDINE | 347,11 | 1,835 |
| 268 | ETHYL SUCCINYL CHLORIDE | 3-(AMINOMETHYL)PYRIDINE | 393,11 | 1,742 |
| 269 | 3,4-DIMETHOXYPHENYLACETYL CHLORIDE | PHENETHYLAMINE | 456,15 | 2,054 |
| 270 | 2,4-DIFLOUROBENZOYL CHLORIDE | PHENETHYLAMINE | 418,10 | 2,112 |
| 271 | 3,3-DIMETHYLACRYLOYL CHLORIDE | PHENETHYLAMINE | 360,13 | 2,109 |
| 272 | ETHYL SUCCINYL CHLORIDE | PHENETHYLAMINE | 406,14 | 2,058 |
| 273 | METHYL MALONYL CHLORIDE | PHENETHYLAMINE | 378,10 | 1,943 |
| 274 | 2-(4-CHLOROPHENOXY)PYRIDINE-3-CARBONYL CHLORIDE | PIPERONYLAMINE | 539,07 | 2,133 |
| 275 | 1-PHENYL-5-(TRIFLUOROMETHYL)PYRAZOLE-4-CARBONYL CHLORIDE | PIPERONYLAMINE | 546,10 | 2,086 |
| 276 | 4-[(DIPROPYLAMINO)SULFONYL]BENZENE-1-CARBONYL CHLORIDE | PIPERONYLAMINE | 575,15 | 2,103 |
| 277 | 2-(4-CHLOROPHENOXY)PYRIDINE-3-CARBONYL CHLORIDE | CYCLOPROPYLAMINE | 445,07 | 2,038 |
| 278 | 4-[(DIPROPYLAMINO)SULFONYL]BENZENE-1-CARBONYL CHLORIDE | CYCLOPROPYLAMINE | 481,15 | 2,021 |
| 279 | 2-(4-CHLOROPHENOXY)PYRIDINE-3-CARBONYL CHLORIDE | 3-(AMINOMETHYL)PYRIDINE | 496,08 | 2,004 |
| 280 | 1-PHENYL-5-(TRIFLUOROMETHYL)PYRAZOLE-4-CARBONYL CHLORIDE | 3-(AMINOMETHYL)PYRIDINE | 503,10 | 1,938 |
| 281 | 2-(4-CHLOROPHENOXY)PYRIDINE-3-CARBONYL CHLORIDE | PHENETHYLAMINE | 509,10 | 2,173 |
| 282 | 1-PHENYL-5-(TRIFLUOROMETHYL)PYRAZOLE-4-CARBONYL CHLORIDE | PHENETHYLAMINE | 516,12 | 2,122 |

TABLE 1-continued

Compounds No. 152 to 616 of the general formula q:

q-0

| No. | R2—CO—Cl (name) | R1—NH$_2$ (name) | MH+ | RT |
|---|---|---|---|---|
| 283 | 4-((DIPROPYLAMINO)SULFONYL]BENZENE-1-CARBONYL CHLORIDE | PHENETHYLAMINE | 545,18 | 2,105 |
| 284 | 2-(4-CHLOROPHENOXY)-2-METHYLPROPANOYL CHLORIDE | PHENETHYLAMINE | 474,12 | 2,359 |
| 285 | METHYL OXALYL CHLORIDE | PHENETHYLAMINE | 364,09 | 2,079 |
| 286 | HYDROCINNAMOYL CHLORIDE | N-BUTYLAMINE | 362,15 | 2,141 |
| 287 | 2-NAPHTHOYL CHLORIDE | N-BUTYLAMINE | 384,13 | 2,226 |
| 288 | DIPHENYLACETYL CHLORIDE | N-BUTYLAMINE | 424,16 | 2,187 |
| 289 | 2-FUROYL CHLORIDE | N-BUTYLAMINE | 324,09 | 2,083 |
| 290 | HYDROCINNAMOYL CHLORIDE | 2-THIOPHENEETHYLAMINE | 416,10 | 2,160 |
| 291 | 2-NAPHTHOYL CHLORIDE | 2-THIOPHENEETHYLAMINE | 438,09 | 2,135 |
| 292 | DIPHENYLACETYL CHLORIDE | 2-THIOPHENEETHYLAMINE | 478,12 | 2,173 |
| 293 | 2-FUROYL CHLORIDE | 2-THIOPHENEETHYLAMINE | 378,05 | 2,119 |
| 294 | HYDROCINNAMOYL CHLORIDE | FURFURYLAMINE | 386,11 | 2,098 |
| 295 | 2-NAPHTHOYL CHLORIDE | FURFURYLAMINE | 408,09 | 2,064 |
| 296 | DIPHENYLACETYL CHLORIDE | FURFURYLAMINE | 448,12 | 2,129 |
| 297 | 2-FUROYL CHLORIDE | FURFURYLAMINE | 348,06 | 1,972 |
| 298 | HYDROCINNAMOYL CHLORIDE | BENZYLAMINE | 396,13 | 2,147 |
| 299 | 2-NAPHTHOYL CHLORIDE | BENZYLAMINE | 418,11 | 2,131 |
| 300 | DIPHENYLACETYL CHLORIDE | BENZYLAMINE | 458,15 | 2,213 |
| 301 | 2-FUROYL CHLORIDE | BENZYLAMINE | 358,08 | 2,036 |
| 302 | PHENYLACETYL CHLORIDE | N-BUTYLAMINE | 348,13 | 2,118 |
| 303 | 2-METHOXYBENZOYL CHLORIDE | N-BUTYLAMINE | 364,12 | 1,999 |
| 304 | BENZO[B]THIOPHENE-2-CARBONYL Chloride | N-BUTYLAMINE | 390,09 | 2,248 |
| 305 | 3,4-DICHLOROBENZOYL CHLORIDE | N-BUTYLAMINE | 402,04 | 2,181 |
| 306 | PHENYLACETYL CHLORIDE | 2-THIOPHENEETHYLAMINE | 402,09 | 2,113 |
| 307 | 2-METHOXYBENZOYL CHLORIDE | 2-THIOPHENEETHYLAMINE | 418,08 | 2,030 |
| 308 | BENZO[B]THIOPHENE-2-CARBONYL Chloride | 2-THIOPHENEETHYLAMINE | 444,04 | 2,254 |
| 309 | 3,4-DICHLOROBENZOYL CHLORIDE | 2-THIOPHENEETHYLAMINE | 455,99 | 2,156 |
| 310 | PHENYLACETYL CHLORIDE | FURFURYLAMINE | 372,09 | 2,079 |
| 311 | 2-METHOXYBENZOYL CHLORIDE | FURFURYLAMINE | 388,09 | 1,917 |
| 312 | BENZO[B]THIOPHENE-2-CARBONYL Chloride | FURFURYLAMINE | 414,05 | 2,150 |
| 313 | 3,4-DICHLOROBENZOYL CHLORIDE | FURFURYLAMINE | 426,00 | 2,130 |
| 314 | PHENYLACETYL CHLORIDE | BENZYLAMINE | 382,11 | 2,131 |
| 315 | 2-METHOXYBENZOYL CHLORIDE | BENZYLAMINE | 398,11 | 1,998 |
| 316 | BENZO[B]THIOPHENE-2-CARBONYL Chloride | BENZYLAMINE | 424,07 | 2,231 |
| 317 | 3,4-DICHLOROBENZOYL CHLORIDE | BENZYLAMINE | 436,02 | 2,191 |
| 318 | 3-CYCLOPENTYLPROPIONYL CHLORIDE | N-BUTYLAMINE | 354,18 | 2,280 |
| 319 | 3,5-BIS(TRIFLUOROMETHYL)BENZOYL CHLORIDE | N-BUTYLAMINE | 470,09 | 2,165 |
| 320 | 3-FLUOROBENZOYL CHLORIDE | N-BUTYLAMINE | 352,10 | 2,074 |
| 321 | CYCLOPROPANECARBONYL CHLORIDE | 2-THIOPHENEETHYLAMINE | 352,07 | 2,103 |
| 322 | 3-CYCLOPENTYLPROPIONYL CHLORIDE | 2-THIOPHENEETHYLAMINE | 408,13 | 2,257 |
| 323 | 3,5-BIS(TRIFLUOROMETHYL)BENZOYL CHLORIDE | 2-THIOPHENEETHYLAMINE | 524,05 | 2,179 |
| 324 | 3-FLUOROBENZOYL CHLORIDE | 2-THIOPHENEETHYLAMINE | 406,06 | 2,040 |
| 325 | 3-CYCLOPENTYLPROPIONYL CHLORIDE | FURFURYLAMINE | 378,14 | 2,206 |
| 326 | 3-FLUOROBENZOYL CHLORIDE | FURFURYLAMINE | 376,07 | 2,000 |
| 327 | CYCLOPROPANECARBONYL CHLORIDE | BENZYLAMINE | 332,10 | 1,413 |
| 328 | 3-CYCLOPENTYLPROPIONYL CHLORIDE | BENZYLAMINE | 388,16 | 2,274 |
| 329 | 3,5-BIS(TRIFLUOROMETHYL)BENZOYL CHLORIDE | BENZYLAMINE | 504,07 | 2,187 |
| 330 | 3-FLUOROBENZOYL CHLORIDE | BENZYLAMINE | 386,09 | 2,092 |
| 331 | 2,6-DIFLUOROBENZOYL CHLORIDE | N-BUTYLAMINE | 370,10 | 2,078 |
| 332 | 2-ETHYLHEXANOYL CHLORIDE | N-BUTYLAMINE | 356,19 | 2,267 |
| 333 | METHOXYACETYL CHLORIDE | N-BUTYLAMINE | 302,11 | 1,976 |
| 334 | 3-CYANOBENZOYL CHLORIDE | N-BUTYLAMINE | 359,11 | 1,978 |
| 335 | 2,4-DICHLOROBENZOYL CHLORIDE | N-BUTYLAMINE | 402,04 | 2,161 |
| 336 | 2,6-DIFLUOROBENZOYL CHLORIDE | 2-THIOPHENEETHYLAMINE | 424,05 | 2,113 |

TABLE 1-continued

Compounds No. 152 to 616 of the general formula q:

q-0

| No. | R2—CO—Cl (name) | R1—NH$_2$ (name) | MH+ | RT |
|---|---|---|---|---|
| 337 | 2-ETHYLHEXANOYL CHLORIDE | 2-THIOPHENEETHYLAMINE | 410,15 | 2,296 |
| 338 | METHOXYACETYL CHLORIDE | 2-THIOPHENEETHYLAMINE | 356,07 | 1,974 |
| 339 | 3-CYANOBENZOYL CHLORIDE | 2-THIOPHENEETHYLAMINE | 413,07 | 1,976 |
| 340 | 2,4-DICHLOROBENZOYL CHLORIDE | 2-THIOPHENEETHYLAMINE | 455,99 | 2,170 |
| 341 | 2-ETHYLHEXANOYL CHLORIDE | FURFURYLAMINE | 380,16 | 2,215 |
| 342 | METHOXYACETYL CHLORIDE | FURFURYLAMINE | 326,07 | 1,901 |
| 343 | 2,4-DICHLOROBENZOYL CHLORIDE | FURFURYLAMINE | 426,00 | 2,110 |
| 344 | 2,6-DIFLUOROBENZOYL CHLORIDE | BENZYLAMINE | 404,08 | 2,079 |
| 345 | 2-ETHYLHEXANOYL CHLORIDE | BENZYLAMINE | 390,18 | 2,259 |
| 346 | METHOXYACETYL CHLORIDE | BENZYLAMINE | 336,09 | 1,981 |
| 347 | 3-CYANOBENZOYL CHLORIDE | BENZYLAMINE | 393,09 | 1,988 |
| 348 | 2,4-DICHLOROBENZOYL CHLORIDE | BENZYLAMINE | 436,02 | 2,163 |
| 349 | 3,4-DIMETHOXYPHENYLACETYL CHLORIDE | N-BUTYLAMINE | 408,15 | 2,030 |
| 350 | 2,4-DIFLOUROBENZOYL CHLORIDE | N-BUTYLAMINE | 370,10 | 2,072 |
| 351 | 3,3-DIMETHYLACRYLOYL CHLORIDE | N-BUTYLAMINE | 312,13 | 2,092 |
| 352 | ETHYL SUCCINYL CHLORIDE | N-BUTYLAMINE | 358,14 | 2,004 |
| 353 | 3,4-DIMETHOXYPHENYLACETYL CHLORIDE | 2-THIOPHENEETHYLAMINE | 462,11 | 2,045 |
| 354 | 2,4-DIFLOUROBENZOYL CHLORIDE | 2-THIOPHENEETHYLAMINE | 424,05 | 2,078 |
| 355 | 3,3-DIMETHYLACRYLOYL CHLORIDE | 2-THIOPHENEETHYLAMINE | 366,09 | 2,069 |
| 356 | ETHYL SUCCINYL CHLORIDE | 2-THIOPHENEETHYLAMINE | 412,09 | 2,014 |
| 357 | METHYL MALONYL CHLORIDE | 2-THIOPHENEETHYLAMINE | 384,06 | 1,928 |
| 358 | 3,4-DIMETHOXYPHENYLACETYL CHLORIDE | FURFURYLAMINE | 432,11 | 1,970 |
| 359 | 3,3-DIMETHYLACRYLOYL CHLORIDE | FURFURYLAMINE | 336,09 | 1,996 |
| 360 | 3,4-DIMETHOXYPHENYLACETYL CHLORIDE | BENZYLAMINE | 442,14 | 2,052 |
| 361 | 2,4-DIFLOUROBENZOYL CHLORIDE | BENZYLAMINE | 404,08 | 2,071 |
| 362 | 3,3-DIMETHYLACRYLOYL CHLORIDE | BENZYLAMINE | 346,11 | 2,077 |
| 363 | ETHYL SUCCINYL CHLORIDE | BENZYLAMINE | 392,12 | 2,005 |
| 364 | METHYL MALONYL CHLORIDE | BENZYLAMINE | 364,09 | 1,915 |
| 365 | 2-(4-CHLOROPHENOXY)PYRIDINE-3-CARBONYL CHLORIDE | N-BUTYLAMINE | 461,10 | 2,156 |
| 366 | 1-PHENYL-5-(TRIFLUOROMETHYL)PYRAZOLE-4-CARBONYL CHLORIDE | N-BUTYLAMINE | 468,12 | 2,108 |
| 367 | 4-[(DIPROPYLAMINO)SULFONYL]BENZENE-1-CARBONYL CHLORIDE | N-BUTYLAMINE | 497,18 | 2,089 |
| 368 | 2-(4-CHLOROPHENOXY)PYRIDINE-3-CARBONYL CHLORIDE | 2-THIOPHENEETHYLAMINE | 515,05 | 2,160 |
| 369 | 1-PHENYL-5-(TRIFLUOROMETHYL)PYRAZOLE-4-CARBONYL CHLORIDE | 2-THIOPHENEETHYLAMINE | 522,08 | 2,129 |
| 370 | 4-[(DIPROPYLAMINO)SULFONYL]BENZENE-1-CARBONYL CHLORIDE | 2-THIOPHENEETHYLAMINE | 551,14 | 2,096 |
| 371 | 2-(4-CHLOROPHENOXY)PYRIDINE-3-CARBONYL CHLORIDE | FURFURYLAMINE | 485,06 | 2,103 |
| 372 | 1-PHENYL-5-(TRIFLUOROMETHYL)PYRAZOLE-4-CARBONYL CHLORIDE | FURFURYLAMINE | 492,09 | 2,030 |
| 373 | 4-[(DIPROPYLAMINO)SULFONYL]BENZENE-1-CARBONYL CHLORIDE | FURFURYLAMINE | 521,14 | 2,066 |
| 374 | 2-(4-CHLOROPHENOXY)-2-METHYLPROPANOYL CHLORIDE | FURFURYLAMINE | 450,08 | 2,215 |
| 375 | 2-(4-CHLOROPHENOXY)PYRIDINE-3-CARBONYL CHLORIDE | BENZYLAMINE | 495,08 | 2,155 |
| 376 | 1-PHENYL-5-(TRIFLUOROMETHYL)PYRAZOLE-4-CARBONYL CHLORIDE | BENZYLAMINE | 502,11 | 2,100 |
| 377 | 4-[(DIPROPYLAMINO)SULFONYL]BENZENE-1-CARBONYL CHLORIDE | BENZYLAMINE | 531,17 | 2,106 |

TABLE 1-continued

Compounds No. 152 to 616 of the general formula q:

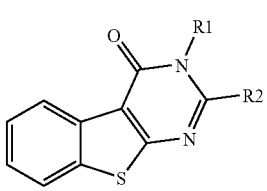

q-0

| No. | R2—CO—Cl (name) | R1—NH$_2$ (name) | MH+ | RT |
|---|---|---|---|---|
| 378 | 2-(4-CHLOROPHENOXY)-2-METHYLPROPANOYL CHLORIDE | BENZYLAMINE | 460,10 | 2,264 |
| 379 | HYDROCINNAMOYL CHLORIDE | TETRAHYDROFURFURYLAMINE | 390,14 | 2,065 |
| 380 | 2-NAPHTHOYL CHLORIDE | TETRAHYDROFURFURYLAMINE | 412,12 | 2,014 |
| 381 | 2-FUROYL CHLORIDE | TETRAHYDROFURFURYLAMINE | 352,09 | 1,901 |
| 382 | HYDROCINNAMOYL CHLORIDE | 2-(2-AMINOETHYL)PYRIDINE | 411,14 | 2,031 |
| 383 | 2-NAPHTHOYL CHLORIDE | 2-(2-AMINOETHYL)PYRIDINE | 433,12 | 1,958 |
| 384 | 2-FUROYL CHLORIDE | 2-(2-AMINOETHYL)PYRIDINE | 373,09 | 1,841 |
| 385 | HYDROCINNAMOYL CHLORIDE | 4-(AMINOMETHYL)PYRIDINE | 397,12 | 1,961 |
| 386 | PHENYLACETYL CHLORIDE | TETRAHYDROFURFURYLAMINE | 376,12 | 2,035 |
| 387 | 2-METHOXYBENZOYL CHLORIDE | TETRAHYDROFURFURYLAMINE | 392,12 | 1,862 |
| 388 | BENZO[B]THIOPHENE-2-CARBONYL Chloride | TETRAHYDROFURFURYLAMINE | 418,08 | 2,093 |
| 389 | 3,4-DICHLOROBENZOYL CHLORIDE | TETRAHYDROFURFURYLAMINE | 430,03 | 2,090 |
| 390 | PHENYLACETYL CHLORIDE | 2-(2-AMINOETHYL)PYRIDINE | 397,12 | 1,960 |
| 391 | 2-METHOXYBENZOYL CHLORIDE | 2-(2-AMINOETHYL)PYRIDINE | 413,12 | 1,783 |
| 392 | BENZO[B]THIOPHENE-2-CARBONYL Chloride | 2-(2-AMINOETHYL)PYRIDINE | 439,08 | 2,112 |
| 393 | 3,4-DICHLOROBENZOYL CHLORIDE | 2-(2-AMINOETHYL)PYRIDINE | 451,03 | 2,015 |
| 394 | PHENYLACETYL CHLORIDE | 4-(AMINOMETHYL)PYRIDINE | 383,11 | 1,825 |
| 395 | 2-METHOXYBENZOYL CHLORIDE | 4-(AMINOMETHYL)PYRIDINE | 399,10 | 1,713 |
| 396 | CYCLOPROPANECARBONYL CHLORIDE | TETRAHYDROFURFURYLAMINE | 326,11 | 1,970 |
| 397 | 3-FLUOROBENZOYL CHLORIDE | TETRAHYDROFURFURYLAMINE | 380,10 | 1,952 |
| 398 | 3-CYCLOPENTYLPROPIONYL CHLORIDE | 2-(2-AMINOETHYL)PYRIDINE | 403,17 | 2,145 |
| 399 | CYCLOPROPANECARBONYL CHLORIDE | 4-AMINO-1-BENZYLPIPERIDINE | 415,17 | 1,718 |
| 400 | 3-FLUOROBENZOYL CHLORIDE | 4-AMINO-1-BENZYLPIPERIDINE | 469,16 | 1,710 |
| 401 | 3-CYCLOPENTYLPROPIONYL CHLORIDE | 4-(AMINOMETHYL)PYRIDINE | 389,16 | 2,091 |
| 402 | 2,6-DIFLUOROBENZOYL CHLORIDE | TETRAHYDROFURFURYLAMINE | 398,09 | 1,943 |
| 403 | 2-ETHYLHEXANOYL CHLORIDE | TETRAHYDROFURFURYLAMINE | 384,19 | 2,196 |
| 404 | METHOXYACETYL CHLORIDE | TETRAHYDROFURFURYLAMINE | 330,10 | 1,855 |
| 405 | 2-ETHYLHEXANOYL CHLORIDE | 2-(2-AMINOETHYL)PYRIDINE | 405,19 | 2,188 |
| 406 | METHOXYACETYL CHLORIDE | 2-(2-AMINOETHYL)PYRIDINE | 351,10 | 1,752 |
| 407 | 2,4-DICHLOROBENZOYL CHLORIDE | 2-(2-AMINOETHYL)PYRIDINE | 451,03 | 2,018 |
| 408 | 2,6-DIFLUOROBENZOYL CHLORIDE | 4-AMINO-1-BENZYLPIPERIDINE | 487,15 | 1,787 |
| 409 | METHOXYACETYL CHLORIDE | 4-AMINO-1-BENZYLPIPERIDINE | 419,17 | 1,633 |
| 410 | 2,4-DICHLOROBENZOYL CHLORIDE | 4-AMINO-1-BENZYLPIPERIDINE | 519,09 | 1,873 |
| 411 | 2-ETHYLHEXANOYL CHLORIDE | 4-(AMINOMETHYL)PYRIDINE | 391,17 | 2,126 |
| 412 | 3,4-DIMETHOXYPHENYLACETYL-CHLORIDE | TETRAHYDROFURFURYLAMINE | 436,15 | 1,962 |
| 413 | 2,4-DIFLOUROBENZOYL CHLORIDE | TETRAHYDROFURFURYLAMINE | 398,09 | 1,961 |
| 414 | 3,3-DIMETHYLACRYLOYL CHLORIDE | TETRAHYDROFURFURYLAMINE | 340,12 | 1,955 |
| 415 | ETHYL SUCCINYL CHLORIDE | TETRAHYDROFURFURYLAMINE | 386,13 | 1,925 |
| 416 | METHYL MALONYL CHLORIDE | TETRAHYDROFURFURYLAMINE | 358,10 | 1,818 |
| 417 | 3,4-DIMETHOXYPHENYLACETYL ☐CHLORIDE | 2-(2-AMINOETHYL)PYRIDINE | 457,15 | 1,877 |
| 418 | 2,4-DIFLOUROBENZOYL CHLORIDE | 2-(2-AMINOETHYL)PYRIDINE | 419,09 | 1,909 |
| 419 | 3,3-DIMETHYLACRYLOYL CHLORIDE | 2-(2-AMINOETHYL)PYRIDINE | 361,12 | 1,895 |
| 420 | ETHYL SUCCINYL CHLORIDE | 2-(2-AMINOETHYL)PYRIDINE | 407,13 | 1,735 |
| 421 | 2,4-DIFLOUROBENZOYL CHLORIDE | 4-AMINO-1-BENZYLPIPERIDINE | 487,15 | 1,752 |
| 422 | 3,3-DIMETHYLACRYLOYL CHLORIDE | 4-AMINO-1-BENZYLPIPERIDINE | 429,19 | 1,693 |
| 423 | ETHYL SUCCINYL CHLORIDE | 4-AMINO-1-BENZYLPIPERIDINE | 475,19 | 1,648 |
| 424 | 3,4-DIMETHOXYPHENYLACETYL ☐CHLORIDE | 4-(AMINOMETHYL)PYRIDINE | 443,13 | 1,748 |
| 425 | 3,3-DIMETHYLACRYLOYL CHLORIDE | 4-(AMINOMETHYL)PYRIDINE | 347,11 | 1,801 |
| 426 | 2-(4-CHLOROPHENOXY)PYRIDINE-3-CARBONYL CHLORIDE | TETRAHYDROFURFURYLAMINE | 489,09 | 2,096 |
| 427 | 1-PHENYL-5-(TRIFLUOROMETHYL)PYRAZOLE-4-CARBONYL CHLORIDE | TETRAHYDROFURFURYLAMINE | 496,12 | 2,052 |
| 428 | 2-(4-CHLOROPHENOXY)-2-METHYLPROPANOYL CHLORIDE | TETRAHYDROFURFURYLAMINE | 454,11 | 2,231 |
| 429 | 2-(4-CHLOROPHENOXY)PYRIDINE-3-CARBONYL CHLORIDE | 2-(2-AMINOETHYL)PYRIDINE | 510,09 | 2,057 |

TABLE 1-continued

Compounds No. 152 to 616 of the general formula q:

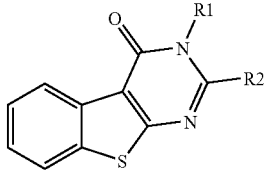

q-0

| No. | R2—CO—Cl (name) | R1—NH₂ (name) | MH+ | RT |
|---|---|---|---|---|
| 430 | 1-PHENYL-5-(TRIFLUOROMETHYL)PYRAZOLE-4-CARBONYL CHLORIDE | 2-(2-AMINOETHYL)PYRIDINE | 517,12 | 2,027 |
| 431 | 1-PHENYL-5-(TRIFLUOROMETHYL)PYRAZOLE-4-CARBONYL CHLORIDE | 4-AMINO-1-BENZYLPIPERIDINE | 585,18 | 1,867 |
| 432 | HYDROCINNAMOYL CHLORIDE | 2-PHENOXYETHYLAMINE | 426,14 | 2,211 |
| 433 | 2-NAPHTHOYL CHLORIDE | 2-PHENOXYETHYLAMINE | 448,12 | 2,155 |
| 434 | DIPHENYLACETYL CHLORIDE | 2-PHENOXYETHYLAMINE | 488,16 | 2,257 |
| 435 | 2-FUROYL CHLORIDE | 2-PHENOXYETHYLAMINE | 388,09 | 2,109 |
| 436 | PHENYLACEIYL CHLORIDE | 2-PHENOXYETHYLAMINE | 412,12 | 2,181 |
| 437 | 2-METHOXYBENZOYL CHLORIDE | 2-PHENOXYETHYLAMINE | 428,12 | 2,053 |
| 438 | BENZO[B]THIOPHENE-2-CARBONYL Chloride | 2-PHENOXYETHYLAMINE | 454,08 | 2,264 |
| 439 | 3,4-DICHLOROBENZOYL CHLORIDE | 2-PHENOXYETHYLAMINE | 466,03 | 2,222 |
| 440 | 4-CYANOBENZOYL CHLORIDE | METHYL 4-AMINOBUTYRATE HYDROCHLORIDE | 403,10 | 1,599 |
| 441 | 3-CYCLOPENTYLPROPIONYL CHLORIDE | 2-PHENOXYETHYLAMINE | 418,17 | 2,358 |
| 442 | 3-FLUOROBENZOYL CHLORIDE | 2-PHENOXYETHYLAMINE | 416,10 | 2,113 |
| 443 | 3-CYCLOPENTYLPROPIONYL CHLORIDE | METHYL 4-AMINOBUTYRATE HYDROCHLORIDE | 398,17 | 2,148 |
| 444 | 3-FLUOROBENZOYL CHLORIDEMETHYL | 4-AMINOBUTYRATE HYDROCHLORIDE | 396,09 | 1,927 |
| 445 | 2,4-DICHLOROBENZOYL CHLORIDE | ETHANOLAMINE | 390,00 | 2,332 |
| 446 | 2,6-DIFLUOROBENZOYL CHLORIDE | 2-PHENOXYETHYLAMINE | 434,09 | 2,118 |
| 447 | 2-ETHYLHEXANOYL CHLORIDE | 2-PHENOXYETHYLAMINE | 420,19 | 2,307 |
| 448 | METHOXYACETYL CHLORIDE | 2-PHENOXYETHYLAMINE | 366,10 | 2,045 |
| 449 | 3-CYANOBENZOYL CHLORIDE | 2-PHENOXYETHYLAMINE | 423,10 | 2,056 |
| 450 | 2,4-DICHLOROBENZOYL CHLORIDE | 2-PHENOXYETHYLAMINE | 466,03 | 2,201 |
| 451 | 3,4-DIMETHOXYPHENYLACETYL CHLORIDE | 2-PHENOXYETHYLAMINE | 472,15 | 2,103 |
| 452 | 2,4-DIFLOUROBENZOYL CHLORIDE | 2-PHENOXYETHYLAMINE | 434,09 | 2,118 |
| 453 | 3,3-DIMETHYLACRYLOYL CHLORIDE | 2-PHENOXYETHYLAMINE | 376,12 | 2,098 |
| 454 | ETHYL SUCCINYL CHLORIDE | 2-PHENOXYETHYLAMINE | 422,13 | 2,078 |
| 455 | METHYL MALONYL CHLORIDE | 2-PHENOXYETHYLAMINE | 394,10 | 1,990 |
| 456 | 3,4-DIMETHOXYPHENYLACETYL CHLORIDE | METHYL 4-AMINOBUTYRATE HYDROCHLORIDE | 452,14 | 1,947 |
| 457 | 3,3-DIMETHYLACRYLOYL CHLORIDE | METHYL 4-AMINOBUTYRATE HYDROCHLORIDE | 356,12 | 1,969 |
| 458 | 2-(4-CHLOROPHENOXY)PYRIDINE-3-CARBONYL CHLORIDE | 2-PHENOXYETHYLAMINE | 525,09 | 2,189 |
| 459 | 1-PHENYL-5-(TRIFLUOROMETHYL)PYRAZOLE-4-CARBONYL CHLORIDE | 2-PHENOXYETHYLAMINE | 532,12 | 2,139 |
| 460 | 4-[(DIPROPYLAMINO)SULFONYL]BENZENE-1-CARBONYL CHLORIDE | 2-PHENOXYETHYLAMINE | 561,18 | 2,133 |
| 461 | METHYL OXALYL CHLORIDE | 2-PHENOXYETHYLAMINE | 380,08 | 2,054 |
| 462 | 2-(4-CHLOROPHENOXY)PYRIDINE-3-CARBONYL CHLORIDE | METHYL 4-AMINOBUTYRATE HYDROCHLORIDE | 505,09 | 2,085 |
| 463 | HYDROCINNAMOYL CHLORIDE | 2-AMINO-1-PHENYLETHANOL | 426,14 | 2,071 |
| 464 | DIPHENYLACETYL CHLORIDE | 2-AMINO-1-PHENYLETHANOL | 488,16 | 2,079 |
| 465 | HYDROCINNAMOYL CHLORIDE | THIOPHENE-2-METHYLAMINE | 402,09 | 2,145 |
| 466 | 2-NAPHTHOYL CHLORIDE | THIOPHENE-2-METHYLAMINE | 424,07 | 2,143 |
| 467 | DIPHENYLACETYL CHLORIDE | THIOPHENE-2-METHYLAMINE | 464,10 | 2,183 |
| 468 | 2-FUROYL CHLORIDE | THIOPHENE-2-METHYLAMINE | 364,03 | 2,046 |
| 469 | HYDROCINNAMOYL CHLORIDE | NN-DIMETHYLETHYLENEDIAMINE | 377,16 | 1,682 |
| 470 | 2-NAPHTHOYL CHLORIDE | NN-DIMETHYLETHYLENEDIAMINE | 399,14 | 1,612 |
| 471 | 2-FUROYL CHLORIDE | NN-DIMETHYLETHYLENEDIAMINE | 339,10 | 1,454 |
| 472 | HYDROCINNAMOYL CHLORIDE | 2-AMINO-5-METHYLTHIAZOLE | 403,08 | 2,271 |
| 473 | 2-FUROYL CHLORIDE | 2-AMINO-5-METHYLTHIAZOLE | 365,03 | 2,144 |
| 474 | PHENYLACETYL CHLORIDE | 2-AMINO-1-PHENYLETHANOL | 412,12 | 2,041 |
| 475 | 4-CYANOBENZOYL CHLORIDE | 2-AMINO-1-PHENYLETHANOL | 423,10 | 2,008 |
| 476 | 3,4-DICHLOROBENZOYL CHLORIDE | 2-AMINO-1-PHENYLETHANOL | 466,03 | 2,156 |

TABLE 1-continued

Compounds No. 152 to 616 of the general formula q:

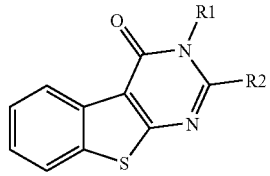

q-0

| No. | R2—CO—Cl (name) | R1—NH2 (name) | MH+ | RT |
|---|---|---|---|---|
| 477 | PHENYLACETYL CHLORIDE | THIOPHENE-2-METHYLAMINE | 388,07 | 2,110 |
| 478 | 2-METHOXYBENZOYL CHLORIDE | THIOPHENE-2-METHYLAMINE | 404,07 | 1,998 |
| 479 | BENZO[B]THIOPHENE-2-CARBONYL Chloride | THIOPHENE-2-METHYLAMINE | 430,03 | 2,180 |
| 480 | PHENYLACETYL CHLORIDE | NN-DIMETHYLETHYLENEDIAMINE | 363,14 | 1,566 |
| 481 | 2-METHOXYBENZOYL CHLORIDE | NN-DIMETHYLETHYLENEDIAMINE | 379,14 | 1,476 |
| 482 | 3,4-DICHLOROBENZOYL CHLORIDE | NN-DIMETHYLETHYLENEDIAMINE | 417,05 | 1,670 |
| 483 | 2-METHOXYBENZOYL CHLORIDE | 2-AMINO-5-METHYLTHIAZOLE | 405,06 | 2,079 |
| 484 | BENZO[8]THIOPHENE-2-CARBONYL Chloride | 2-AMINO-5-METHYLTHIAZOLE | 431,02 | 2,246 |
| 485 | 3-CYCLOPENTYLPROPIONYL CHLORIDE | 2-AMINO-1-PHENYLETHANOL | 418,17 | 2,140 |
| 486 | 3,5-BIS(TRIFLUOROMETHYL)BENZOYL CHLORIDE | 2-AMINO-1-PHENYLETHANOL | 534,08 | 2,198 |
| 487 | 3-FLUOROBENZOYL CHLORIDE | 2-AMINO-1-PHENYLETHANOL | 416,10 | 2,088 |
| 488 | 3-CYCLOPENTYLPROPIONYL CHLORIDE | THIOPHENE-2-METHYLAMINE | 394,12 | 2,248 |
| 489 | 3-FLUOROBENZOYL CHLORIDE | THIOPHENE-2-METHYLAMINE | 392,05 | 2,078 |
| 490 | 3-CYCLOPENTYLPROPIONYL CHLORIDE | NN-DIMETHYLETHYLENEDIAMINE | 369,19 | 1,855 |
| 491 | CYCLOPROPANECARBONYL CHLORIDE | 2-AMINO-5-METHYLTHIAZOLE | 339,05 | 2,080 |
| 492 | 3-FLUOROBENZOYL CHLORIDE | 2-AMINO-5-METHYLTHIAZOLE | 393,04 | 2,177 |
| 493 | METHOXYACETYL CHLORIDE | 2-AMINO-1-PHENYLETHANOL | 366,10 | 1,997 |
| 494 | 3-CYANOBENZOYL CHLORIDE | 2-AMINO-1-PHENYLETHANOL | 423,10 | 2,051 |
| 495 | 2-ETHYLHEXANOYL CHLORIDE | THIOPHENE-2-METHYLAMINE | 396,13 | 2,240 |
| 496 | METHOXYACETYL CHLORIDE | THIOPHENE-2-METHYLAMINE | 342,05 | 1,983 |
| 497 | 2,4-DICHLOROBENZOYL CHLORIDE | THIOPHENE-2-METHYLAMINE | 441,98 | 2,167 |
| 498 | 2-ETHYLHEXANOYL CHLORIDE | NN-DIMETHYLETHYLENEDIAMINE | 371,20 | 1,908 |
| 499 | METHOXYACETYL CHLORIDE | NN-DIMETHYLETHYLENEDIAMINE | 317,12 | 1,391 |
| 500 | 2,6-DIFLUOROBENZOYL CHLORIDE | 2-AMINO-5-METHYLTHIAZOLE | 411,03 | 2,147 |
| 501 | METHOXYACETYL CHLORIDE | 2-AMINO-5-METHYLTHIAZOLE | 343,04 | 2,234 |
| 502 | 3,4-DIMETHOXYPHENYLACETYL | 2-AMINO-1-PHENYLETHANOL | 472,15 | 1,997 |
| 503 | 3,4-DIMETHOXYPHENYLACETYL CHLORIDE | THIOPHENE-2-METHYLAMINE | 448,09 | 2,026 |
| 504 | 3,3-DIMETHYLACRYLOYL CHLORIDE | THIOPHENE-2-METHYLAMINE | 352,07 | 2,055 |
| 505 | ETHYL SUCCINYL CHLORIDE | THIOPHENE-2-METHYLAMINE | 398,08 | 1,980 |
| 506 | METHYL MALONYL CHLORIDE | THIOPHENE-2-METHYLAMINE | 370,04 | 1,883 |
| 507 | 3,4-DIMETHOXYPHENYLACETYL | NN-DIMETHYLETHYLENEDIAMINE | 423,16 | 1,558 |
| 508 | 3,3-DIMETHYLACRYLOYL CHLORIDE | NN-DIMETHYLETHYLENEDIAMINE | 327,14 | 1,500 |
| 509 | METHYL MALONYL CHLORIDE | NN-DIMETHYLETHYLENEDIAMINE | 345,11 | 1,568 |
| 510 | 3,4-DIMETHOXYPHENYLACETYL | 2-AMINO-5-METHYLTHIAZOLE | 449,09 | 2,130 |
| 511 | 1-PHENYL-5-(TRIFLUOROMETHYL)PYRAZOLE-4-CARBONYL CHLORIDE | THIOPHENE-2-METHYLAMINE | 508,06 | 2,080 |
| 512 | 4-[(DIPROPYLAMINO)SULFONYL]BENZENE-1-CARBONYL CHLORIDE | THIOPHENE-2-METHYLAMINE | 537,12 | 2,107 |
| 513 | 2-(4-CHLOROPHENOXY)-2-METHYLPROPANOYL CHLORIDE | THIOPHENE-2-METHYLAMINE | 466,06 | 2,267 |
| 514 | HYDROCINNAMOYL CHLORIDE | 3-AMINOQUINOLINE | 433,12 | 2,006 |
| 515 | HYDROCINNAMOYL CHLORIDE | 9-AMINOFLUORENE HYDROCHLORIDE | 470,15 | 2,405 |
| 516 | 2-FUROYL CHLORIDE | 9-AMINOFLUORENE HYDROCHLORIDE | 432,09 | 2,111 |
| 517 | PHENYLACETYL CHLORIDE | 3-AMINOQUINOLINE | 419,11 | 1,962 |
| 518 | 2-METHOXYBENZOYL CHLORIDE | AMINOETHYL)BENZENESULFONAMIDE MONOHYDROCHLORI | 491,10 | 1,787 |
| 519 | PHENYLACETYL CHLORIDE | 9-AMINOFLUORENE HYDROCHLORIDE | 456,13 | 2,113 |
| 520 | CYCLOPROPANECARBONYL CHLORIDE | 3-AMINOQUINOLINE | 369,09 | 1,976 |
| 521 | 3-CYCLOPENTYLPROPIONYL CHLORIDE | 3-AMINOQUINOLINE | 425,16 | 2,131 |
| 522 | 3-CYCLOPENTYLPROPIONYL CHLORIDE | 4-(2-AMINOETHYL)BENZENESULFONAMIDE MONOHYDROCHLORI | 481,15 | 2,081 |
| 523 | 3-FLUOROBENZOYL CHLORIDE | 4-(2-AMINOETHYL)BENZENESULFONAMIDE MONOHYDROCHLORI | 479,08 | 1,858 |
| 524 | CYCLOPROPANECAR8ONYL CHLORIDE | 9-AMINOFLUORENE HYDROCHLORIDE | 406,11 | 2,130 |
| 525 | 3-CYCLOPENTYLPROPIONYL CHLORIDE | 9-AMINOFLUORENE HYDROCHLORIDE | 462,18 | 2,333 |
| 526 | 3,5-BIS(TRIFLUOROMETHYL)BENZOYL CHLORIDE | 9-AMINOFLUORENE HYDROCHLORIDE | 578,09 | 2,373 |
| 527 | 2-ETHYLHEXANOYL CHLORIDE | 3-AMINOQUINOLINE | 427,17 | 2,164 |

TABLE 1-continued

Compounds No. 152 to 616 of the general formula q:

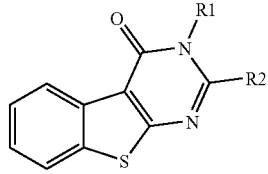

q-0

| No. | R2—CO—Cl (name) | R1—NH₂ (name) | MH+ | RT |
|---|---|---|---|---|
| 528 | METHOXYACETYL CHLORIDE | 3-AMINOQUINOLINE | 373,09 | 1,795 |
| 529 | 2,6-DIFLUOROBENZOYL CHLORIDE | 4-(2-AMINOETHYL)BENZENESULFONAMIDE MONOHYDROCHLORI | 497,07 | 1,927 |
| 530 | METHOXYACETYL CHLORIDE | 4-(2-AMINOETHYL)BENZENESULFONAMIDE MONOHYDROCHLORI | 429,08 | 1,781 |
| 531 | METHOXYACETYL CHLORIDE | 9-AMINOFLUORENE HYDROCHLORIDE | 410,11 | 2,064 |
| 532 | 2,4-DICHLOROBENZOYL CHLORIDE | 9-AMINOFLUORENE HYDROCHLORIDE | 510,04 | 2,283 |
| 533 | 3,3-DIMETHYLACRYLOYL CHLORIDE | 2-AMINOACETOPHENONE HYDROCHLORIDE | 374,11 | 1,953 |
| 534 | ETHYL SUCCINYL CHLORIDE | 3-AMINOQUINOLINE | 429,11 | 1,889 |
| 535 | 2,4-DIFLOUROBENZOYL CHLORIDE | 4-(2-AMINOETHYL)BENZENESULFONAMIDE MONOHYDROCHLORI | 497,07 | 1,886 |
| 536 | 3,4-DIMETHOXYPHENYLACETYL CHLORIDE | 9-AMINOFLUORENE HYDROCHLORIDE | 516,15 | 2,046 |
| 537 | 2-(4-CHLOROPHENOXY)PYRIDINE-3-CARBONYL CHLORIDE | 2-AMINOACETOPHENONE HYDROCHLORIDE | 523,08 | 2,271 |
| 538 | 2-(4-CHLOROPHENOXY)PYRIDINE-3-CARBONYL CHLORIDE | 3-AMINOQUINOLINE | 532,08 | 2,068 |
| 539 | 2-(4-CHLOROPHENOXY)PYRIDINE-3-CARBONYL CHLORIDE | 4-(2-AMINOETHYL)BENZENESULFONAMIDE MONOHYDROCHLORI | 588,07 | 2,029 |
| 540 | 1-PHENYL-5-(TRIFLUOROMETHYL)PYRAZOLE-4-CARBONYL CHLORIDE | 9-AMINOFLUORENE HYDROCHLORIDE | 576,12 | 2,252 |
| 541 | 4-[(DIPROPYLAMINO)SULFONYL]BENZENE-1-CARBONYL CHLORIDE | 9-AMINOFLUORENE HYDROCHLORIDE | 605,18 | 2,254 |
| 542 | HYDROCINNAMOYL CHLORIDE | 1-AMINOINDAN | 422,15 | 2,207 |
| 543 | HYDROCINNAMOYL CHLORIDE | 1-(3-AMINOPROPYL)-2-PYRROLIDINONE | 431,17 | 1,975 |
| 544 | 2-NAPHTHOYL CHLORIDE | 1-(3-AMINOPROPYL)-2-PYRROLIDINONE | 453,15 | 1,902 |
| 545 | HYDROCINNAMOYL CHLORIDE | 3,4-DICHLOROBENZYLAMINE | 464,05 | 2,338 |
| 546 | 2-NAPHTHOYL CHLORIDE | 3,4-DICHLOROBENZYLAMINE | 486,04 | 2,291 |
| 547 | 2-FUROYL CHLORIDE | 3,4-DICHLOROBENZYLAMINE | 426,00 | 2,190 |
| 548 | PHENYLACETYL CHLORIDE | 1-AMINOINDAN | 408,13 | 2,113 |
| 549 | PHENYLACETYL CHLORIDE | 1-(3-AMINOPROPYL)-2-PYRROLIDINONE | 417,15 | 1,927 |
| 550 | 2-METHOXYBENZOYL CHLORIDE | 1-(3-AMINOPROPYL)-2-PYRROLIDINONE | 433,15 | 1,769 |
| 551 | PHENYLACETYL CHLORIDE | 3,4-DICHLOROBENZYLAMINE | 450,04 | 2,220 |
| 552 | 2-METHOXYBENZOYL CHLORIDE | 3,4-DICHLOROBENZYLAMINE | 466,03 | 2,144 |
| 553 | 4-CYANOBENZOYL CHLORIDE | 3,4-DICHLOROBENZYLAMINE | 461,02 | 2,086 |
| 554 | 3,4-DICHLOROBENZOYL CHLORIDE | 3,4-DICHLOROBENZYLAMINE | 503,94 | 2,307 |
| 555 | 3-CYCLOPEN1YLPROPIONYL CHLORIDE | 1-AMINOINDAN | 414,18 | 2,358 |
| 556 | 3-FLUOROBENZOYL CHLORIDE | 1-AMINOINDAN | 412,10 | 2,341 |
| 557 | CYCLOPROPANECARBONYL CHLORIDE | 1-(3-AMINOPROPYL)-2-PYRROLIDINONE | 367,14 | 1,904 |
| 558 | 3-CYCLOPENTYLPROPIONYL CHLORIDE | 1-(3-AMINOPROPYL)-2-PYRROLIDINONE | 423,20 | 2,110 |
| 559 | CYCLOPROPANECARBONYL CHLORIDE | 3,4-DICHLOROBENZYLAMINE | 400,02 | 1,694 |
| 560 | 3-CYCLOPENTYLPROPIONYL CHLORIDE | 3,4-DICHLOROBENZYLAMINE | 456,08 | 2,478 |
| 561 | 3-FLUOROBENZOYL CHLORIDE | 3,4-DICHLOROBENZYLAMINE | 454,01 | 2,177 |
| 562 | 2,6-DIFLUOROBENZOYL CHLORIDE | 1-AMINOINDAN | 430,10 | 2,155 |
| 563 | METHOXYACETYL CHLORIDE | 1-AMINOINDAN | 362,11 | 2,024 |
| 564 | 2-ETHYLHEXANOYL CHLORIDE | 1-(3-AMINOPROPYL)-2-PYRROLIDINONE | 425,21 | 2,123 |
| 565 | METHOXYACETYL CHLORIDE | 1-(3-AMINOPROPYL)-2-PYRROLIDINONE | 371,13 | 1,734 |
| 566 | 2,6-DIFLUOROBENZOYL CHLORIDE | 3,4-DICHLOROBENZYLAMINE | 472,00 | 2,200 |
| 567 | 2-ETHYLHEXANOYL CHLORIDE | 3,4-DICHLOROBENZYLAMINE | 458,10 | 2,416 |
| 568 | METHOXYACETYL CHLORIDE | 3,4-DICHLOROBENZYLAMINE | 404,02 | 2,169 |
| 569 | 3-CYANOBENZOYL CHLORIDE | 3,4-DICHLOROBENZYLAMINE | 461,02 | 2,121 |
| 570 | 2,4-DICHLOROBENZOYL CHLORIDE | 3,4-DICHLOROBENZYLAMINE | 503,94 | 2,314 |
| 571 | 3,4-DIMETHOXYPHENYLACETYL CHLORIDE | 1-(3-AMINOPROPYL)-2-PYRROLIDINONE | 477,17 | 1,862 |
| 572 | 2,4-DIFLOUROBENZOYL CHLORIDE | 1-(3-AMINOPROPYL)-2-PYRROLIDINONE | 439,12 | 1,863 |
| 573 | 3,3-DIMETHYLACRYLOYL CHLORIDE | 1-(3-AMINOPROPYL)-2-PYRROLIDINONE | 381,15 | 1,879 |
| 574 | ETHYL SUCCINYL CHLORIDE | 1-(3-AMINOPROPYL)-2-PYRROLIDINONE | 427,16 | 1,649 |
| 575 | METHYL MALONYL CHLORIDE | 1-(3-AMINOPROPYL)-2-PYRROLIDINONE | 399,13 | 1,718 |
| 576 | 3,4-DIMETHOXYPHENYLACETYL CHLORIDE | 3,4-DICHLOROBENZYLAMINE | 510,06 | 2,164 |
| 577 | 2,4-DIFLOUROBENZOYL CHLORIDE | 3,4-DICHLOROBENZYLAMINE | 472,00 | 2,206 |

TABLE 1-continued

Compounds No. 152 to 616 of the general formula q:

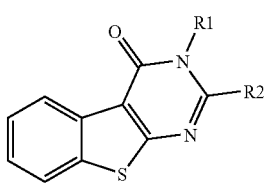

q-0

| No. | R2—CO—Cl (name) | R1—NH$_2$ (name) | MH+ | RT |
|---|---|---|---|---|
| 578 | 3,3-DIMETHYLACRYLOYL CHLORIDE | 3,4-DICHLOROBENZYLAMINE | 414,04 | 2,263 |
| 579 | ETHYL SUCCINYL CHLORIDE | 3,4-DICHLOROBENZYLAMINE | 460,04 | 2,179 |
| 580 | METHYL MALONYL CHLORIDE | 3,4-DICHLOROBENZYLAMINE | 432,01 | 2,120 |
| 581 | 1-PHENYL-5-(TRIFLUOROMETHYL)PYRAZOLE-4-CARBONYL CHLORIDE | 1-AMINOINDAN | 528,12 | 2,166 |
| 582 | 1-PHENYL-5-(TRIFLUOROMETHYL)PYRAZOLE-4-CARBONYL CHLORIDE | 1-(3-AMINOPROPYL)-2-PYRROLIDINONE | 537,14 | 1,979 |
| 583 | METHYL OXALYL CHLORIDE | 1-(3-AMINOPROPYL)-2-PYRROLIDINONE | 385,11 | 1,732 |
| 584 | 2-(4-CHLOROPHENOXY)PYRIDINE-3-CARBONYL CHLORIDE | 3-AMINOPYRAZINE-2-CARBOXYLIC ACID METHYL ESTER | 541,06 | 2,129 |
| 585 | 2-(4-CHLOROPHENOXY)PYRIDINE-3-CARBONYL CHLORIDE | 3,4-DICHLOROBENZYLAMINE | 563,00 | 2,238 |
| 586 | 1-PHENYL-5-(TRIFLUOROMETHYL)PYRAZOLE-4-CARBONYL CHLORIDE | 3,4-DICHLOROBENZYLAMINE | 570,03 | 2,180 |
| 587 | 4-[(DIPROPYLAMINO)SULFONYL]BENZENE-1-CARBONYL CHLORIDE | 3,4-DICHLOROBENZYLAMINE | 599,09 | 2,203 |
| 588 | METHYL OXALYL CHLORIDE | 3,4-DICHLOROBENZYLAMINE | 417,99 | 2,172 |
| 589 | HYDROCINNAMOYL CHLORIDE | 5-(AMINOMETHYL)-2,3-DIHYDROBENZO[B]FURAN | 438,14 | 2,165 |
| 590 | 2-NAPHTHOYL CHLORIDE | 5-(AMINOMETHYL)-2,3-DIHYDROBENZO[B]FURAN | 460,12 | 2,155 |
| 591 | DIPHENYLACETYL CHLORIDE | 5-(AMINOMETHYL)-2,3-DIHYDROBENZO[B]FURAN | 500,16 | 2,199 |
| 592 | 2-FUROYL CHLORIDE | 5-(AMINOMETHYL)-2,3-DIHYDROBENZO[B]FURAN | 400,09 | 2,053 |
| 593 | HYDROCINNAMOYL CHLORIDE | (S)-(+)-(2,2-DIMETHYL-[1,3]DIOXOLAN-4-YL)-METHYLA | 420,15 | 2,104 |
| 594 | PHENYLACETYL CHLORIDE | 5-(AMINOMETHYL)-2,3-DIHYDROBENZO[B]FURAN | 424,12 | 2,122 |
| 595 | PHENYLACETYL CHLORIDE | (S)-(+)-(2,2-DIMETHYL-[1,3]-DIOXOLAN-4-YL)-METHYLA | 406,14 | 2,071 |
| 596 | 2-METHOXYBENZOYL CHLORIDE | (S)-(+)-(2,2-DIMETHYL-[1,3]-DIOXOLAN-4-YL)-METHYLA | 422,13 | 1,933 |
| 597 | CYCLOPROPANECARBONYL CHLORIDE | 5-(AMINOMETHYL)-2,3-DIHYDROBENZO[B]FURAN | 374,11 | 2,117 |
| 598 | 3-CYCLOPENTYLPROPIONYL CHLORIDE | 5-(AMINOMETHYL)-2,3-DIHYDROBENZO[B]FURAN | 430,17 | 2,321 |
| 599 | 3-FLUOROBENZOYL CHLORIDE | 5-(AMINOMETHYL)-2,3-DIHYDROBENZO[B]FURAN | 428,10 | 2,120 |
| 600 | 3-FLUOROBENZOYL CHLORIDE | 3,4-DIHYDROXYBENZYLAMINE | 418,08 | 2,345 |
| 601 | 3-CYCLOPENTYLPROPIONYL CHLORIDE | (S)-(+)-(2,2-DIMETHYL-[1,3]-DIOXOLAN-4-YL)-METHYLA | 412,18 | 2,261 |
| 602 | 3-CYCLOPENTYLPROPIONYL CHLORIDE | 4-METHYLSULFONYLBENZYLAMINE HYDROCHLORIDE | 466,14 | 2,078 |
| 603 | 2-ETHYLHEXANOYL CHLORIDE | 5-(AMINOMETHYL)-2,3-DIHYDROBENZO[B]FURAN | 432,19 | 2,282 |
| 604 | METHOXYACETYL CHLORIDE | 5-(AMINOMETHYL)-2,3-DIHYDROBENZO[B]FURAN | 378,10 | 1,994 |
| 605 | 2,4-DICHLOROBENZOYL CHLORIDE | 5-(AMINOMETHYL)-2,3-DIHYDROBENZO[B]FURAN | 478,03 | 2,170 |
| 606 | METHOXYACETYL CHLORIDE | 3,4-DIHYDROXYBENZYLAMINE | 368,08 | 1,750 |
| 607 | 2-ETHYLHEXANOYL CHLORIDE | (S)-(+)-(2,2-DIMETHYL-[1,3]-DIOXOLAN-4-YL)-METHYLA | 414,20 | 2,262 |
| 608 | METHOXYACETYL CHLORIDE | (S)-(+)-(2,2-DIMETHYL-[1,3]-DIOXOLAN-4-YL)-METHYLAMIN | 360,11 | 1,926 |
| 609 | 2,4-DICHLOROBENZOYL CHLORIDE | (S)-(+)-(2,2-DIMETHYL-[1,3]-DIOXOLAN-4-YL)-METHYLA | 460,04 | 2,145 |
| 610 | 3,4-DIMETHOXYPHENYLACETYL CHLORIDE | 5-(AMINOMETHYL)-2,3-DIHYDROBENZO[B]FURAN | 484,15 | 2,059 |

TABLE 1-continued

Compounds No. 152 to 616 of the general formula q:

q-0

| No. | R2—CO—Cl (name) | R1—NH$_2$ (name) | MH+ | RT |
|---|---|---|---|---|
| 611 | 3,3-DIMETHYLACRYLOYL CHLORIDE | 5-(AMINOMETHYL)-2,3-DIHYDROBENZO[B]FURAN | 388,12 | 2,090 |
| 612 | METHYL MALONYL CHLORIDE | 5-(AMINOMETHYL)-2,3-DIHYDROBENZO[B]FURAN | 406,10 | 1,938 |
| 613 | 3,3-DIMETHYLACRYLOYL CHLORIDE | (S)-(+)-(2,2-DIMETHYL-[1,3]-DIOXOLAN-4-YL)-METHYLA | 370,14 | 2,028 |
| 614 | ETHYL SUCCINYL CHLORIDE | (S)-(+)-(2,2-DIMETHYL-[1,3]-DIOXOLAN-4-YL)-METHYLAMIN | 416,14 | 2,003 |
| 615 | 3,3-DIMETHYLACRYLOYL CHLORIDE | 4-METHYLSULFONYLBENZYLAMINE HYDROCHLORIDE | 424,09 | 1,868 |
| 616 | 1-PHENYL-5-(TRIFLUOROMETHYL)PYRAZOLE-4-CARBONYL CHLORIDE | 5-(AMINOMETHYL)-2,3-DIHYDROBENZO[B]FURAN | 544,12 | 2,119 |

Further compounds of general formula q-0-OH falling under the scope of general formula I can prepared by parallel chemistry using a reaction as shown in the following scheme 7 (according to general flow scheme 5):

Scheme 7: General route to 8-Hydroxy-benzothienopyrimidinones.

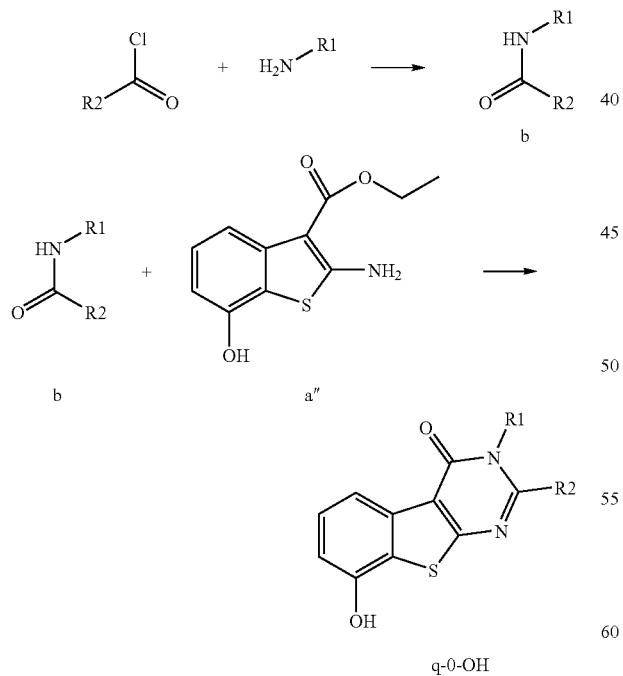

In a reaction vessel at room temperature are put together sequentially 0.25 M primary amine R1-NH$_2$, 1 M diisopropylethylamine and 0.25 M acid chloride R2-CO—Cl. To this mixture is added 0.25 M 2-amino-7-hydroxy-benzo[b]thiophene-3-carboxylic acid ethyl ester a″ followed by 0.25 M POCl$_3$. Of all reactants one equivalent is used as solution or suspension in chlorobenzene. After shaking for 80 hours at 100° C., the mixtures are cooled to room temperature, washed with 5% NaOAc and extracted with EtOAc. The organic layers are collected and concentrated to yield the desired compound. The obtained material of the formula q-0-OH was thereafter analyzed by LC-MS according to the procedure described in scheme 7.

Preparation of
2-amino-7-hydroxy-benzo[b]thiophene-3-carboxylic acid ethyl ester Scheme 8: Synthesis route to 2-amino-7-hydroxy-benzo[b]thiophene-3-carboxylic acid ethyl ester (compound of formula a″)

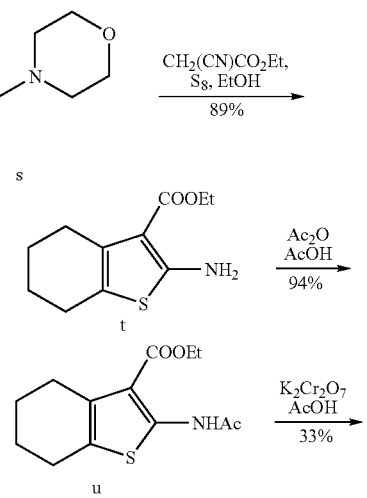

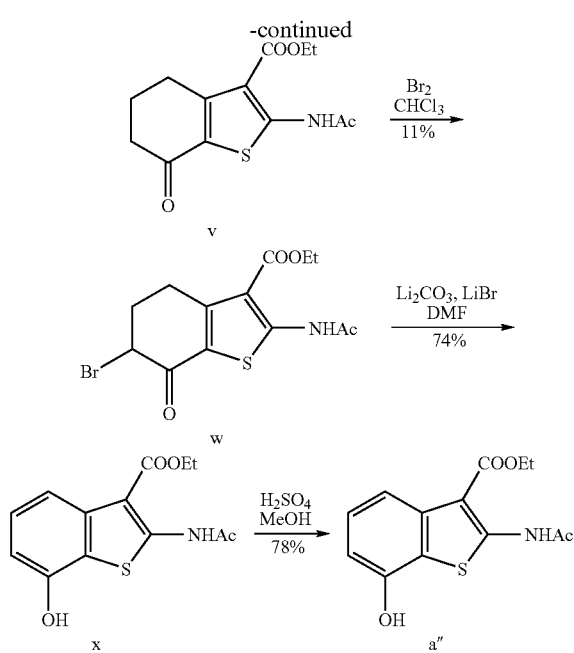

The thiophene t was prepared from 1-N-morpholino-cyclohexene s and equimolar amounts of cyanoethyl acetate and $S_8$ in ethanol. After acylation compound u was obtained [Perrissin M et al. (1980) Eur. J. Med. Chem. Chim. Ther. 15:413-418]. Oxidation of u with $K_2Cr_2O_7$ gave ketone v in a moderate yield, but starting material could also be recovered [Kharizomenova A et al. (1984) Chem. Heterocycl. Compd. (Engl. Transl.) 20:1339-1342] 1984, 20, 1339-1342]. α-Bromination of ketone v with $Br_2$ in $CHCl_3$ gave a mixture of starting material, monobrominated product w and dibrominated product [Kharizomenova A et al. (1984) Chem. Heterocycl. Compd. (Engl. Transl.) 20:1339-1342] 1984, 20, 1339-1342 and Kapustina M V et al. (1990) Chem. Heterocycl. Compd. (Engl. Transl.) 24:1269-271]. After column chromatography w was obtained in 11% yield. Elimination was achieved with $LiBr/Li_2CO_3$ and gave x in 74% yield [Samanta et al. (1997) J. Chem. Soc.; Perkin Trans. I, 3673-3677]. Compound a" was prepared in 78% yield from x with $H_2SO_4$ in MeOH.

Detailed Experimental Protocol:

2-Amino-4,5,6,7-tetrahydro-benzo[b]thiophene-3-carboxylic acid ethyl ester t

A solution of 4-cyclohex-1-enyl-morpholine (s) (1003 g, 6.0 mol) in abs. EtOH (1.51 L) was added dropwise to a mixture of sulfur (192.4 g, 6.0 mol) and ethylcyanoacetate (678.7 g, 6.0 mmol) in abs. EtOH (1.5 L) at 95° C. at such a rate that reflux was maintained. After complete addition the mixture was stirred for 2 h and then, without cooling, poured into a mixture of ice and $H_2O$ (~10 L). The resulting precipitate was filtered off and washed with $H_2O$ (2 L) and EtOH (3 L). The compound was dried in air to give 2 (1201 g, 5.33 mol, 89%) as a slight yellow solid.

2-Acetylamino-4,5,6,7-tetrahydro-benzo[b]thiophene-3-carboxylic acid ethyl ester u $Ac_2O$ (450 mL) was added dropwise to a solution of compound t (600 g, 2.66 mol) in acetic acid (3 L). The reaction was slightly exothermic. After complete addition the mixture was heated to 85° C. for 3 h. The hot mixture was poured on ice (10 L). The resulting precipitate was filtered, washed with $H_2O$ (2 L) and dried in air to give u (672 g, 2.51 mol, 94%) as a brown solid.

2-Acetylamino-7-oxo-4,5,6,7-tetrahydro-benzo[b]thiophene-3-carboxylic acid ethyl ester v A solution of compound u (660 g, 2.47 mol) in AcOH (3.5 L) was heated to 60° C. with mechical stirring. Then a solution of $K_2Cr_2O_7$ (1000 g, 5.15 mol) in $H_2O$ (1 L) was added dropwise keeping the internal temperature below 80° C. After complete addition the mixture was cooled to RT within 3 h. The mixture was poured into $H_2O$ (10 L) and left standing for crystallization during 2 h. The resulting precipitate was filtered off and washed with $H_2O$ (2×2 L). The solid was dissolved in $CH_2Cl_2$ (3 L) and some water was separated. The solution was concentrated in vacuo to a volume of 1 L and heptane was added (3 L). A part of $CH_2Cl_2$ (400 mL) was removed to induce precipitation. The resulting solid (350 g) was filtered giving a 5:1-mixture of product and starting material. The solid was recrystallized from a 1:1-mixture of $CHCl_3$ and heptane (700 ml) to give compound v (230 g, 0.82 mol, 33%) as a brown solid.

2-Acetylamino-6-bromo-7-oxo-4,5,6,7-tetrahydrobenzo[b]thiophene-3-carboxylic acid ethyl ester w A solution of compound v (230 g, 0.82 mol) in $CHCl_3$ (2 L) was heated to reflux and a solution of $Br_2$ (138 g, 0.86 mol) in $CHCl_3$ (2 L) was added dropwise. After complete addition the mixture was stirred for 2 h and then it was cooled to RT. The reaction mixture was washed acid free with $H_2O$ (5×250 mL). The solvent was removed in vacuo and the residue was stirred with EtOH (1 L). The resulting precipitate was filtered off and dried in air. The solid consisted of starting material, product and dibrominated ketone and was subjected to column chromatography on $SiO_2$ using $CH_2Cl_2$ as eluent to give compound w (34 g, 94 mmol, 11%). The dibrominated compound (80.1 g, 182 mmol, 22%) was isolated as well as was the starting compound v (29 g, 103 mmol, 12%).

2-Acetylamino-7-hydroxy-benzo[b]thiophene-3-carboxylic acid ethyl ester x.

A flame dried three-necked flask was purged with $N_2$ and charged with bromo ketone w (32.0 g, 91.4 mmol), LiBr (15.9 g, 183 mmol, 2.0 equiv.), $Li_2CO_3$ (13.7 g, 183 mmol, 2.0 equiv.) and DMF (1 L). The resulting suspension was refluxed overnight under $N_2$. The reaction mixture was concentrated to ~100 mL and neutralized by the addition of 1 N HCl until no gas evolved and $H_2O$ was added (300 mL). The crude product was isolated by extraction with EtOAc (3×400 mL). The combined organic layers were washed with $H_2O$ (400 mL), brine (400 mL) and dried over $Na_2SO_4$. Evaporation of the solvents gave the crude product which was purified by column chromatography ($CH_2Cl_2$/EtOAc=3/2) and crystallization from MeOH/$H_2O$ to give x as a pink solid (19.0 g, 68.0 mmol, 74%).

2-Amino-7-hydroxy-benzo[b]thiophene-3-carboxylic acid ethyl ester a"

Compound x (27.8 g, 100 mmol) was dissolved in MeOH, $H_2SO_4$ was added and the mixture was stirred for 7 days. The mixture was concentrated to half of the original volume. Water was added and the pH was cautiously adjusted to 6 with conc. $NH_3$. The resulting precipitate was filtered off, washed with MeOH/H$_2$O and dried to give a" (18.4 g, 78 mmol, 78%) as a grey solid.

The following table 2 lists compounds No. 617 to 682 of the general formula q0-OH, which were prepared according to Scheme 7 starting with the primary amines R1-NH$_2$ and the acide chlorides R2-CO—Cl. In addition, the determined Molecular Weight and the Retention Time from the LC-MS analysis of the synthesized compounds are shown.

TABLE 2

Compounds No. 617 to 682 of the general formula r:

q-0-OH

| No. | R2—CO—Cl (name) | R1—NH$_2$ (name) | MH+ | RT |
|---|---|---|---|---|
| 617 | PHENYLACETYL CHLORIDE | PIPERONYLAMINE | 442,10 | 2,011 |
| 618 | 2-METHOXYBENZOYL CHLORIDE | PIPERONYLAMINE | 458,09 | 1,887 |
| 619 | 3-CYCLOPENTYLPROPIONYL CHLORIDE | PIPERONYLAMINE | 448,15 | 2,096 |
| 620 | 2-ETHYLHEXANOYL CHLORIDE | PIPERONYLAMINE | 450,16 | 2,096 |
| 621 | METHOXYACETYL CHLORIDE | PIPERONYLAMINE | 396,08 | 1,827 |
| 622 | 3,3-DIMETHYLACRYLOYL CHLORIDE | PIPERONYLAMINE | 406,10 | 1,940 |
| 623 | HYDROCINNAMOYL CHLORIDE | PHENETHYLAMINE | 426,14 | 2,079 |
| 624 | 2-NAPHTHOYL CHLORIDE | PHENETHYLAMINE | 448,12 | 2,190 |
| 625 | PHENYLACETYL CHLORIDE | PHENETHYLAMINE | 412,12 | 2,037 |
| 626 | 2-METHOXYBENZOYL CHLORIDE | PHENETHYLAMINE | 428,12 | 1,953 |
| 627 | 3-CYCLOPENTYLPROPIONYL CHLORIDE | PHENETHYLAMINE | 418,17 | 2,148 |
| 628 | 2-ETHYLHEXANOYL CHLORIDE | PHENETHYLAMINE | 420,19 | 2,166 |
| 629 | METHOXYACETYL CHLORIDE | PHENETHYLAMINE | 366,10 | 1,888 |
| 630 | 2,4-DIFLOUROBENZOYL CHLORIDE | PHENETHYLAMINE | 434,09 | 2,011 |
| 631 | 2-NAPHTHOYL CHLORIDE | N-BUTYLAMINE | 400,12 | 2,087 |
| 632 | PHENYLACETYL CHLORIDE | N-BUTYLAMINE | 364,12 | 1,976 |
| 633 | 2-METHOXYBENZOYL CHLORIDE | N-BUTYLAMINE | 380,12 | 1,924 |
| 634 | 3-CYCLOPENTYLPROPIONYL CHLORIDE | N-BUTYLAMINE | 370,17 | 2,148 |
| 635 | 2-ETHYLHEXANOYL CHLORIDE | N-BUTYLAMINE | 372,19 | 2,140 |
| 636 | METHOXYACETYL CHLORIDE | N-BUTYLAMINE | 318,10 | 1,813 |
| 637 | 2,4-DIFLOUROBENZOYL CHLORIDE | N-BUTYLAMINE | 386,09 | 1,969 |
| 638 | 3,3-DIMETHYLACRYLOYL CHLORIDE | N-BU1YLAMINE | 328,12 | 1,931 |
| 639 | HYDROCINNAMOYL CHLORIDE | 2-THIOPHENEETHYLAMINE | 432,10 | 2,019 |
| 640 | 2-NAPHTHOYL CHLORIDE | 2-THIOPHENEETHYLAMINE | 454,08 | 2,031 |
| 641 | PHENYLACETYL CHLORIDE | 2-THIOPHENEETHYLAMINE | 418,08 | 1,996 |
| 642 | 2-METHOXYBENZOYL CHLORIDE | 2-THIOPHENEETHYLAMINE | 434,08 | 1,919 |
| 643 | 3-CYCLOPENTYLPROPIONYL CHLORIDE | 2-THIOPHENEETHYLAMINE | 424,13 | 2,141 |
| 644 | 2-ETHYLHEXANOYL CHLORIDE | 2-THIOPHENEETHYLAMINE | 426,14 | 2,165 |
| 645 | METHOXYACETYL CHLORIDE | 2-THIOPHENEETHYLAMINE | 372,06 | 1,841 |
| 646 | 3,4-DIMETHOXYPHENYLACETYL CHLORIDE | 2-THIOPHENEETHYLAMINE | 478,10 | 1,918 |
| 647 | 2,4-DIFLOUROBENZOYL CHLORIDE | 2-ThIOPHENEETHYLAMINE | 440,05 | 2,005 |
| 648 | 3,3-DIMETHYLACRYLOYL CHLORIDE | 2-THIOPHENEETHYLAMINE | 382,08 | 1,935 |
| 649 | HYDROCINNAMOYL CHLORIDE | 2-PHENOXYETHYLAMINE | 442,14 | 2,096 |
| 650 | 2-NAPHTHOYL CHLORIDE | 2-PHENOXYETHYLAMINE | 464,12 | 2,070 |
| 651 | PHENYLACETYL CHLORIDE | 2-PHENOXYETHYLAMINE | 428,12 | 2,039 |
| 652 | 2-METHOXYBENZOYL CHLORIDE | 2-PHENOXYETHYLAMINE | 444,11 | 1,942 |
| 653 | 3-CYCLOPENTYLPROPIONYL CHLORIDE | 2-PHENOXYETHYLAMINE | 434,17 | 2,149 |
| 654 | 2-ETHYLHEXANOYL CHLORIDE | 2-PHENOXYETHYLAMINE | 436,18 | 2,171 |
| 655 | METHOXYACETYL CHLORIDE | 2-PHENOXYETHYLAMINE | 382,10 | 1,877 |
| 656 | 3,4-DIMETHOXYPHENYLACETYL CHLORIDE | 2-PHENOXYETHYLAMINE | 488,14 | 1,954 |
| 657 | 2,4-DIFLOUROBENZOYL CHLORIDE | 2-PHENOXYETHYLAMINE | 450,08 | 2,013 |
| 658 | 3,3-DIMETHYLACRYLOYL CHLORIDE | 2-PHENOXYETHYLAMINE | 392,12 | 1,966 |
| 659 | HYDROCINNAMOYL CHLORIDE | BENZYLAMINE | 412,12 | 2,056 |
| 660 | PHENYLACETYL CHLORIDE | BENZYLAMINE | 398,11 | 1,995 |
| 661 | 2-METHOXYBENZOYL CHLORIDE | BENZYLAMINE | 414,10 | 1,894 |
| 662 | 3-CYCLOPENTYLPROPIONYL CHLORIDE | BENZYLAMINE | 404,16 | 2,114 |
| 663 | 2-ETHYLHEXANOYL CHLORIDE | BENZYLAMINE | 406,17 | 2,115 |
| 664 | METHOXYACETYL CHLORIDE | BENZYLAMINE | 352,09 | 1,820 |
| 665 | 3,4-DIMETHOXYPHENYLACETYL CHLORIDE | BENZYLAMINE | 458,13 | 1,905 |
| 666 | 2,4-DIFLOUROBENZOYL CHLORIDE | BENZYLAMINE | 420,07 | 1,945 |
| 667 | 3,3-DIMETHYLACRYLOYL CHLORIDE | BENZYLAMINE | 362,11 | 1,902 |
| 668 | HYDROCINNAMOYL CHLORIDE | 2-(2-AMINOETHYL)PYRIDINE | 427,14 | 1,895 |
| 669 | 2-NAPHTHOYL CHLORIDE | 2-(2-AMINOETHYL)PYRIDINE | 449,12 | 2,100 |

TABLE 2-continued

Compounds No. 617 to 682 of the general formula r:

q-0-OH

| No. | R2—CO—Cl (name) | R1—NH$_2$ (name) | MH+ | RT |
|---|---|---|---|---|
| 670 | PHENYLACETYL CHLORIDE | 2-(2-AMINOETHYL)PYRIDINE | 413,12 | 1,940 |
| 671 | 2-METHOXYBENZOYL CHLORIDE | 2-(2-AMINOETHYL)PYRIDINE | 429,11 | 1,649 |
| 672 | 3-CYCLOPENTYLPROPIONYL CHLORIDE | 2-(2-AMINOETHYL)PYRIDINE | 419,17 | 1,979 |
| 673 | 2-ETHYLHEXANOYL CHLORIDE | 2-(2-AMINOETHYL)PYRIDINE | 421,18 | 2,037 |
| 674 | 3,4-DIMETHOXYPHENYLACETYL CHLORIDE | 2-(2-AMINOETHYL)PYRIDINE | 473,14 | 1,724 |
| 675 | 3,3-DIMETHYLACRYLOYL CHLORIDE | 2-(2-AMINOETHYL)PYRIDINE | 377,12 | 1,696 |
| 676 | HYDROCINNAMOYL CHLORIDE | FURFURYLAMINE | 402,10 | 2,018 |
| 677 | 2-NAPHTHOYL CHLORIDE | FURFURYLAMINE | 424,09 | 2,120 |
| 678 | PHENYLACETYL CHLORIDE | FURFURYLAMINE | 388,09 | 1,928 |
| 679 | 2-ETHYLHEXANOYL CHLORIDE | FURFURYLAMINE | 396,15 | 2,078 |
| 680 | METHOXYACETYL CHLORIDE | FURFURYLAMINE | 342,07 | 1,727 |
| 681 | 3,4-DIMETHOXYPHENYLACETYL CHLORIDE | FURFURYLAMINE | 448,11 | 1,848 |
| 682 | 3,3-DIMETHYLACRYLOYL CHLORIDE | FURFURYLAMINE | 352,09 | 1,838 |

Further compounds No. 683 to No. 699 falling under the scope of general formula (I) were prepared:

Compound No. 683

3-Benzyl-5-methyl-2-(3,4,5-trimethoxyphenyl)-5,6,7,8-tetrahydro-3H-benzo[4,5]thieno[2,3-d]pyrimidin-4-one

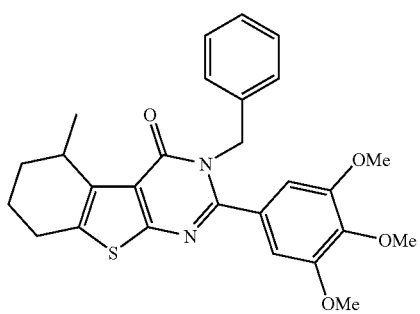

2-Amino-4-methyl-4,5,6,7-tetrahydro-benzo[b]-thiophene-3-carboxylic acid ethyl ester (26.6 mmol, 100 mol-%) and N-benzyl-3,4,5-trimethoxy-benzamide (34.6 mmol, 130 mol-%) were dissolved in dry 1,2-dichloroethane. The reaction mixture was cooled with an ice-salt-bath and POCl$_3$ (1.7 ml, 24.6 mmol, 130 mol-%) was added. The reaction mixture was refluxed for 24 hours. During refluxing POCl$_3$ (340 µl) was added twice. The reaction mixture was poured into ice-water and after neutralization with sodium acetate the product was extracted into dichloromethane. The organic phases combined were washed with sodium bicarbonate sat. (3×50 ml) and dried with MgSO$_4$.

The compound 2-amino-4-methyl-4,5,6,7-tetrahydro-benzo[b]thiophene-3-carboxylic acid ethyl ester was prepared starting from 2-methylcyclohexanone, cyanoacetic acid ethyl ester and sulphur using morpholino as a base (Gütschow M., et al. *J. Med. Chem.* 1999, 42, 5437).

Compound No. 683

NMR (CDCl$_3$): 1.35 (d, 3H), 1.78 (m, 1H), 1.91 (m, 4H), 2.79 (m, 2H), 3.59 (s, 6H), 3.92 (s, 3H), 5.24 (d, 2H), 6.48 (s, 2H), 7.01 (m, 2H), 7.30 (m, 3H). MS (TOF, ES+) m/z 477 (M+1)

Compound No. 684

3-Benzyl-5-methyl-2-(3,4,5-trimethoxyphenyl)-6,7-dihydro-3H,5H-benzo[4,5]thieno[2,3-d]pyrimidin-4,8-dione

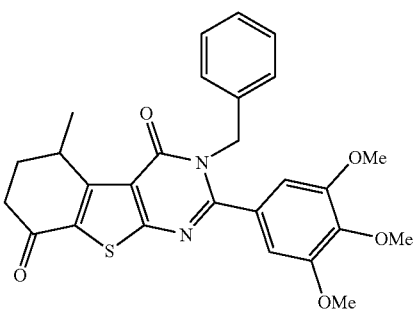

3-Benzyl-5-methyl-2-(3,4,5-trimethoxyphenyl)-5,6,7,8-tetrahydro-3H-benzo[4,5]thieno[2,3-d]pyrimidin-4-one (Compound No. 683) (17.7 mmol) dissolved in dry dichloromethane (30 ml) was added quickly to a mixture of PCC (19.2 g, 89.0 mmol, 500 mol-%) in dichloromethane (200 ml). During refluxing PCC was added several times until the reaction was completed. The reaction mixture was filtered through Celite with dichloromethane. The crude product was purified by flash chromatography.

NMR (CDCl$_3$): 1.46 (d, 3H), 2.08 (m, 1H), 2.50 (m, 2H), 2.67 (m, 1H), 2.91 (m, 1H), 3.59 (s, 6H), 3.86 (s, 3H), 5.27 (d, 2H), 6.53 (s, 2H), 7.05 (m, 2H), 7.28 (m, 3H). MS (TOF, ES+) m/z 491 (M+1)

Compound No. 685

3-Benzyl-7-bromo-2-(2-bromo-3,4,5-trimethoxyphenyl)-5-methyl-6,7-dihydro-3H,5H-benzo[4,5]thieno[2,3-d]pyrimidine-4,8-dione

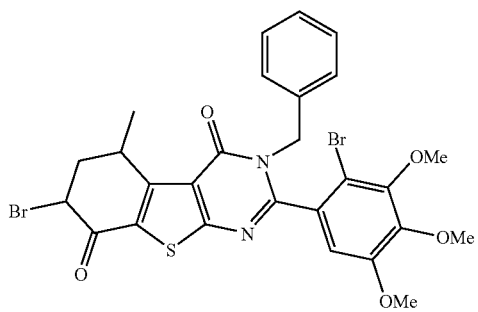

3-Benzyl-5-methyl-2-(3,4,5-trimethoxyphenyl)-6,7-dihydro-3H,5H-benzo[4,5]thieno[2,3-d]pyrimidin-4,8-dione (compound No. 684) (0.3 g, 100 mol-%) was diluted in methanol (20 ml). Bromine (31 µl, 100 mol-%) was added dropwise. The reaction mixture was heated at 50° C. for overnight. The reaction was cooled, and the solid material was filtered. The product was purified by chromatography using dichloromethane as an eluent.

NMR (CDCl$_3$): 1.60 (m, 1H), 1.84 (d, 3H), 2.62 (m, 1H), 3.01 (m, 1H), 3.46 (s, 3H), 3.92 (s, 3H), 3.99 (s, 3H), 4.46 (d, 1H), 4.78 (t, 1H), 5.91 (d, 1H), 6.15 (d, 1H), 6.87 (m, 2H), 7.21 (m, 3H). MS (TOF, ES+) m/z 647/649/651

Compound No. 686

3-Benzyl-2-(2-bromo-3,4,5-trimethoxyphenyl)-8-hydroxy-5-methyl-3H-benzo[4,5]thieno[2,3-d]pyrimidin-4-one

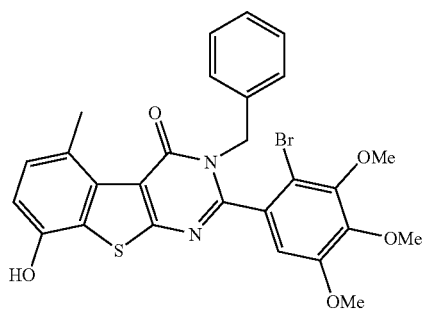

3-Benzyl-7-bromo-2-(2-bromo-3,4,5-trimethoxyphenyl)-5-methyl-6,7-dihydro-3H,5H-benzo[4,5]thieno[2,3-d]pyrimidine-4,8-dione (compound No. 685) (100 mg, 100 mol-%) and NaOH (20 mg, 400 mol-%) in 1.5 ml of ethanol was heated by using microwaves (100° C., 100 s). The solvent was evaporated. EtOAc was added and the reaction mixture was washed with 5% HCl-solution. The product was purified by chromatography using dichloromethane-EtOAc 9.5:0.5 as an eluent.

NMR (CDCl$_3$): 3.04 (s, 3H), 3.43 (s, 3H), 3.91 (s, 3H), 3.95 (s, 3H), 4.49 (d, 1H), 6.00 (dd, 2H), 6.19 (s, 1H), 6.76 (d, 1H), 6.90 (m, 2H), 7.13 (M, 3H). MS (TOF, ES+) m/z 567/569

Compound No. 687

3-Benzyl-6-methyl-2-(3,4,5-trimethoxyphenyl)-5,6,7,8-tetrahydro-3H-benzo[4,5]thieno[2,3-d]pyrimidin-4-one

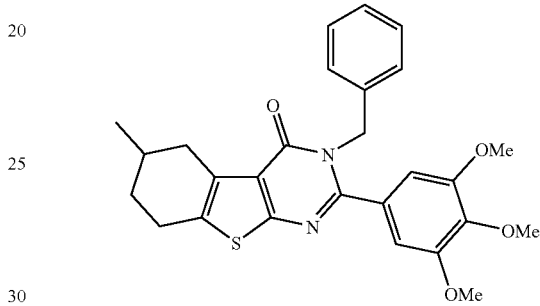

The compound No. 687 was prepared according to the method described for the compound No. 683 using N-benzyl-3,4,5-trimethoxy-benzamide and 2-amino-5-methyl-4,5,6,7-tetrahydro-benzo[b]-thiophene-3-carboxylic acid ethyl ester as starting materials. The starting material 2-amino-5-methyl-4,5,6,7-tetrahydro-benzo[b]thiophene-3-carboxylic acid ethyl ester was prepared starting from 3-methylcyclohexanone (Gütschow M., et al. *J. Med. Chem.* 1999, 42, 5437).

NMR (CDCl$_3$): 1.12 (d, 3H), 1.60 (m, 3H), 1.98 (m, 2H), 2.86 (m, 2H), 3.59 (s, 6H), 3.88 (s, 3H), 5.22 (d, 2H), 6.47 (s, 2H), 7.04 (m, 2H), 7.30 (m, 3H). MS (TOF, ES+) m/z 477 (M+1)

Compound No. 688

3-Benzyl-6-methyl-2-(3,4,5-trimethoxyphenyl)-6,7-dihydro-3H,5H-benzo[4,5]thieno[2,3-d]pyrimidin-4,8-dione

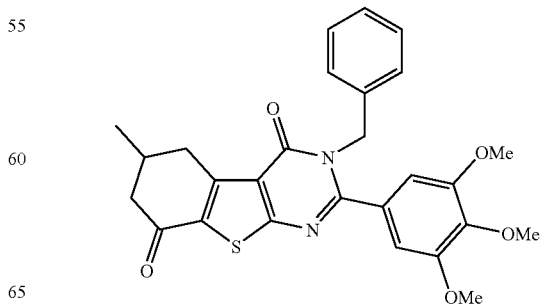

Compound No. 688 was prepared according to the method described for the compound No. 684 using the compound No. 5 as a starting material.

NMR (CDCl$_3$): 1.21 (d, 3H), 1.57 (m, 1H), 2.50 (m, 2H), 2.70 (m, 2H), 3.59 (s, 6H), 3.85 (s, 3H), 5.25 (d, 2H), 6.52 (s, 2H), 7.05 (m, 2H), 7.30 (m, 3H). MS (TOF, ES+) m/z 491 (M+1)

Compound No. 689

3-Benzyl-7-bromo-6-methyl-2-(2-bromo-3,4,5-trimethoxyphenyl)-6,7-dihydro-3H-benzo[4,5]thieno[2,3-d]pyrimidin-4,8-dione

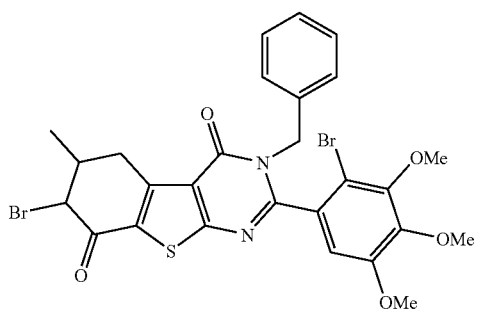

The compound No. 684 (4 mmol, 100 mol-%) and benzoylperoxide (99 mg, 0.4 mmol, 10 mmol %) were dissolved in dichloromethane (40 ml). While the reaction mixture was refluxing bromine (440 µl, 8.4 mmol, 200 mol-%) in dichloromethane (16 ml) was added. The reaction was completed in 3.5 hours. The cooled reaction mixture was washed with water (40 ml). The organic phase was evaporated. The crude product was purified by chromatography using di-chloromethane-EtOAc as an eluent.

NMR (CDCl$_3$): 1.31 (d, 3H), 2.44 (m, 1H), 2.95 (m, 1H), 3.42 (s, 3H), 3.64 (m, 1H), 3.92 (s, 3H), 3.96 (s, 3H), 4.43 (dd, 1H), 4.51 (t, 1H), 5.90 (dd, 1H), 6.16 (d, 1H), 6.89 (s, 2H), 7.27 (m, 3H). MS (TOF, ES+) m/z 647/649/651

Compound No. 690

3-Benzyl-2-(2-bromo-3,4,5-trimethoxyphenyl)-8-hydroxy-6-methyl-3H-benzo[4,5]thieno[2,3-d]pyrimidin-4-one

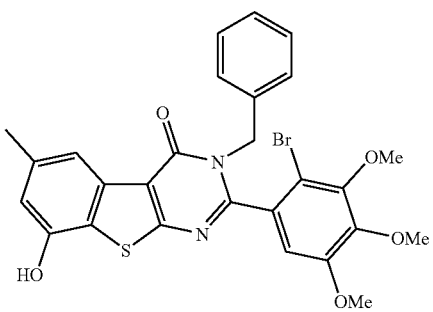

The compound No. 689 (0.08 mmol) was dissolved in methanol (1.5 ml). NaOH (13 mg, 0.32 mmol) was added. The reaction mixture was heated using microwaves (120° C., 2 min.). The solvent was evaporated and the precipitate was dissolved into ethylacetate, washed with 1N HCl and water. Purified by using chromatography (eluent: CH$_2$Cl$_2$-diethyl ether 9:1).

NMR (CDCl$_3$): 2.45 (s, 3H), 3.45 (s, 3H), 3.91 (s, 3H), 3.95 (s, 3H), 4.53 (d, 1H), 6.06 (d, 1H), 6.21 (s, 1H), 6.60 (s, 1H), 6.76 (s, 1H), 6.92 (m, 2H), 7.20 (m, 3H), 8.16 (s, 1H). MS (TOF, ES+) m/z 567/569

Compound No. 691

3-Butyl-6-methyl-2-(3,4,5-trimethoxyphenyl)-5,6,7,8-tetrahydro-3H-benzo[4,5]thieno[2,3-d]pyrimidin-4-one

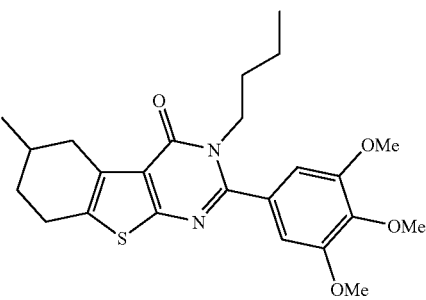

Compound No. 691 was prepared according to the method described for the compound No. 683 using N-butyl-3,4,5-trimethoxy-benzamide and 2-amino-5-methyl-4,5,6,7-tetrahydro-benzo[b]thiophene-3-carboxylic acid ethyl ester as starting materials.

NMR (CDCl3): 0.82 (t, 3H), 1.25 (m, 5H), 1.71 (m, 4H), 1.97 (m, 2H), 2.50 (m, 1H), 2.85 (m, 1H), 3.35 (m, 1H), 3.89 (s, 9H), 3.95 (m, 2H), 6.69 (s, 2H). MS (TOF, ES+) m/z 443 (M+1)

Compound No. 692

3-Butyl-6-methyl-2-(3,4,5-trimethoxyphenyl)-6,7-dihydro-3H,5H-benzo[4,5]thieno[2,3-d]pyrimidin-4,8-dione

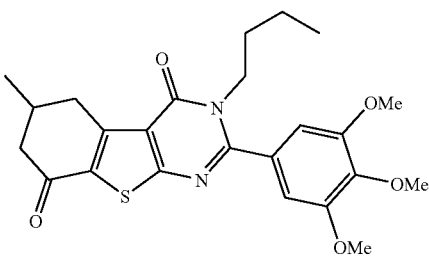

Compound No. 692 was prepared according to the method described for the compound No. 684 using the compound No. 691 as starting material.

NMR (CDCl3): 0.84 (t, 3H), 1.25 (m, 5H), 1.76 (m, 3H), 2.50 (m, 4H), 3.90 (s, 9H), 3.94 (m, 2H), 6.72 (s, 2H). MS (TOF, ES+) m/z 457 (M+1)

Compound No. 693

3-Butyl-7-bromo-6-methyl-2-(2-bromo-3,4,5-trimethoxyphenyl)-6,7-dihydro-3H-benzo[4,5]thieno[2,3-d]pyrimidin-4,8-dione

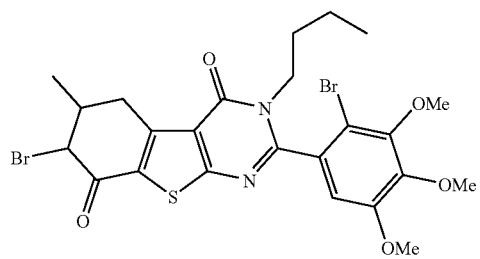

Compound No. 693 was prepared according to the method described for the compound No. 689 using the compound No. 692 as starting material. The compound 697 was isolated as a by-product.

R$_f$ (toluene-methanol 9:1) 0.55 NMR (CDCl$_3$): 0.77 (t, 3H), 1.40 (m, 7H), 2.90 (m, 1H), 3.53 (m, 2H), 3.90 (s, 9H), 3.94 (m, 2H), 4.48 (t, 1H), 6.76 (s, 1H). MS (TOF, ES+) m/z 613/615/617

Compound No. 694

3-Butyl-2-(2-bromo-3,4,5-trimethoxyphenyl)-8-hydroxy-6-methyl-3H-benzo[4,5]thieno[2,3-d]pyrimidin-4-one

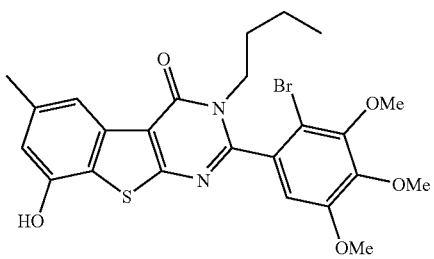

Compound No. 694 was prepared according to the method described for the compound No. 690 using the compound No. 693 as a starting material.

R$_f$ (toluene-methanol 9:1) 0.26

NMR (CDCl$_3$): 0.76 (t, 3H), 1.25 (m, 2H), 1.60 (m, 2H), 2.49 (s, 3H), 3.60 (m, 1H), 3.90 (s, 3H), 3.95 (s, 6H), 4.34 (m, 1H), 6.76 (s, 1H), 6.85 (s, 1H), 8.14 (s, 1H). MS (TOF, ES+) m/z 533/535

Compound No. 695

2-(2-Bromo-3-hydroxy-4,5-dimethoxyphenyl)-3-butyl-8-hydroxy-6-methyl-3H-benzo[4,5]thieno[2,3-d]pyrimidin-4-one

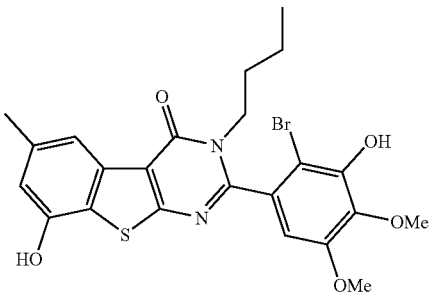

3-Butyl-2-(2-bromo-3,4,5-trimethoxyphenyl)-8-hydroxy-6-methyl-3H-benzo[4,5]thieno[2,3-d]pyrimidin-4-one (compound No. 694) (40 mg) was stirred with HBr in acetic acid (1 ml) for five days. Saturated sodium sulphate solution was added and the product was extracted into ethyl acetate. After washing with water and brine, the solvent was evaporated and the precipitate was purified by chromatography using dichloromethane-methanol 99:1 as an eluent. Compound No. 696 was isolated as a by-product.

Compound No. 695:

NMR (CDCl$_3$): 0.85 (t, 3H), 1.25 (m, 2H), 1.62 (m, 2H), 2.58 (s, 3H), 3.63 (m, 1H), 3.92 (s, 3H). 3.97 (s, 3H), 4.28 (m, 1H), 6.01 (br s, 1H), 6.12 (s, 1H), 6.66 (s, 1H), 8.20 (s, 1H). MS (TOF, ES+) m/z 519/521

Compound No. 696

2-(2-Bromo-3,4-dihydroxy-5-methoxyphenyl)-3-butyl-8-hydroxy-6-methyl-3H-benzo[4,5]thieno[2,3-d]pyrimidin-4-one

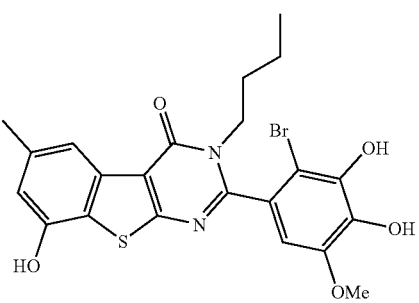

Compound No. 696 was isolated as a by-product in the demethylation of 3-Butyl-2-(2-bromo-3,4,5-trimethoxyphenyl)-8-hydroxy-6-methyl-3H-benzo[4,5]thieno[2,3-d]pyrimidin-4-one (Compound No. 694).

NMR (MeOH-d4): 0.62 (t, 3H), 1.10 (m, 2H), 1.50 (m, 2H), 2.29 (s, 3H), 3.71 (s, 3H), 3.90-4.35 (m, 2H), 6.41 (s, 1H), 6.66 (s, 1H), 7.8 (s, 1H). MS (TOF, ES+) m/z 505/507

Compound No. 697

7,7-Dibromo-3-butyl-6-methyl-2-(2-bromo-3,4,5-trimethoxyphenyl)-6,7-dihydro-3H-benzo[4,5]thieno[2,3-d]pyrimidine-4,8-dione

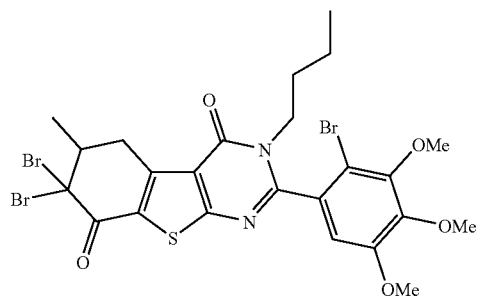

The compound 697 was isolated as a by-product in the bromination of the compound 692.

R$_f$(toluene-methanol 9:1) 0.68 MS (TOF, ES+) m/z 691/693/695/697

Compound No. 698: 7-Bromo-3-butyl-2-(2-bromo-3,4,5-trimethoxyphenyl)-8-hydroxy-6-methyl-3H-benzo[4,5]thieno[2,3-d]pyrimidin-4-one

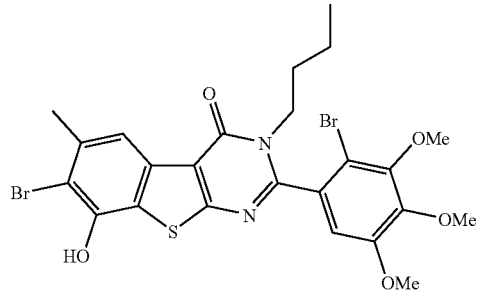

Compound No. 698 was prepared according to the method described for the compound No. 8, using the compound No. 697 as a starting material. The compound 698 was used directly in demethylation for the preparation of the compound 699.

R$_f$(toluene-methanol 9:1) 0.39 MS (TOF, ES+) m/z 611/613/615

Compound No. 699: 7-Bromo-2-(2-bromo-3-hydroxy4,5-dimethoxyphenyl)-3-butyl-8-hydroxy-6-methyl-3H-benzo[4,5]thieno[2,3-d]pyrimidin-4-one

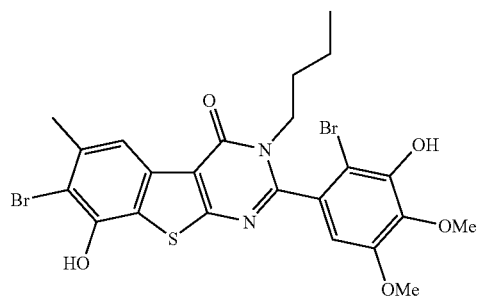

Compound No. 699 was prepared by demethylation of 7-bromo-3-butyl-2-(2-bromo-3,4,5-trimethoxyphenyl)-8-hydroxy-6-methyl-3H-benzo[4,5]thieno[2,3-d]pyrimidin-4-one (compound No. 698) according to the procedure described for the compound No. 695.

NMR (CDCl$_3$): 0.81 (t, 3H), 1.20 (m, 2H), 1.70 (m, 2H), 2.58 (s, 3H), 3.64 (m, 1H), 3.94 (d, 6H), 4.28 (m, 1H), 6.84 (s, 1H), 8.20 (s, 1H). MS (TOF, ES+) m/z 597/599/601

Further compounds of general formula (I) can prepared by parallel chemistry using a reaction as shown in the following scheme 9 (according to the first step of general flow scheme 1), thereby using different separately synthesized starting materials of formula (I):

Scheme 9: General route to substituted Benzothienopyrimidinoes

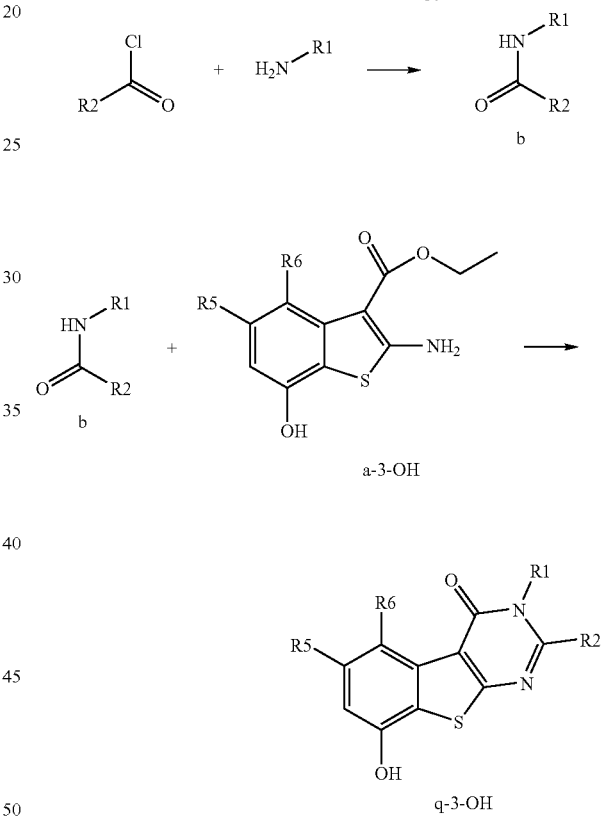

In a reaction vessel at room temperature are put together sequentially 0.25 M primary amine R1-NH$_2$, 1 M diisopropylethylamine and 0.25 M acid chloride R2-CO—Cl. To this mixture is added 0.25 M substituted and optionally protected 2-amino-benzo[b]thiophene-3-carboxylic acid ethyl ester a-3-OH followed by 0.25 M POCl$_3$. Of all reactants one equivalent is used as solution or suspension in chlorobenzene. After shaking for 80 hours at 100° C., the mixtures are cooled to room temperature, washed with 5% NaOAc and extracted with EtOAc. The organic layers are collected and concentrated to yield the desired compound. The obtained material of the formula q-3-OH was thereafter analyzed by LC-MS as described above.

Substituted 2-amino-benzo[b]thiophene-3-carboxylic acid ethyl esters a-3-OH

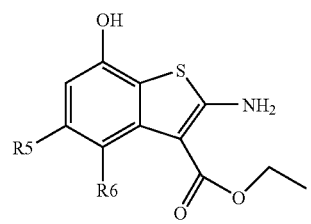

a-3-OH

Several substituted 2-amino-benzo[b]thiophene-3-carboxylic acid ethyl esters of the general formula a-3-OH which can be used in the synthesis scheme 6 are displayed in the following Scheme 10.

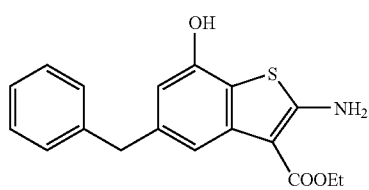

a-1

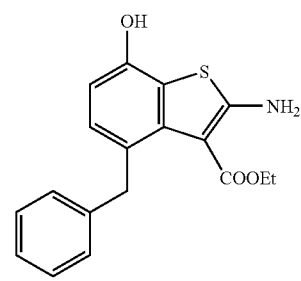

a-2

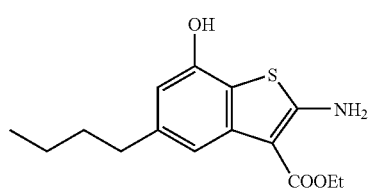

a-3

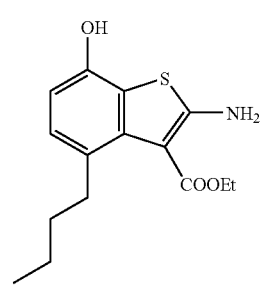

a-4

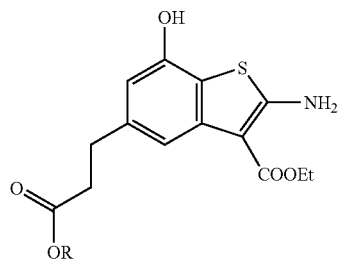

a-5

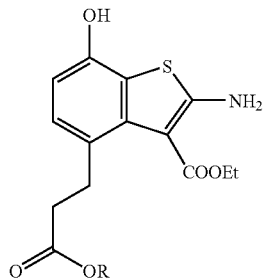

a-6

Synthesis of 2-Amino-5-benzyl-7-hydroxy-benzo[b]thiophene-3-carboxylic acid ethyl ester a-1

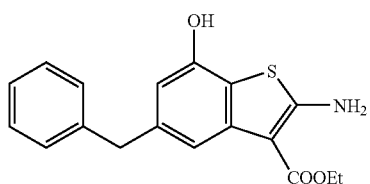

a-1

SCHEME 11: Synthesis of compound a-1

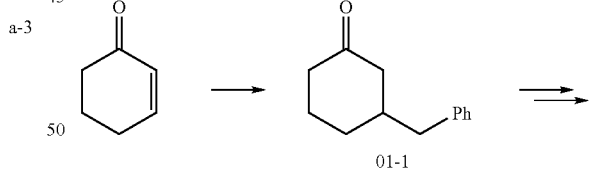

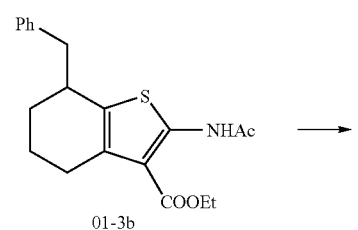

Synthesis of 2-Amino-5-butyl-7-hydroxy-benzo[b]thiophene-3-carboxylic acid ethyl ester a-3

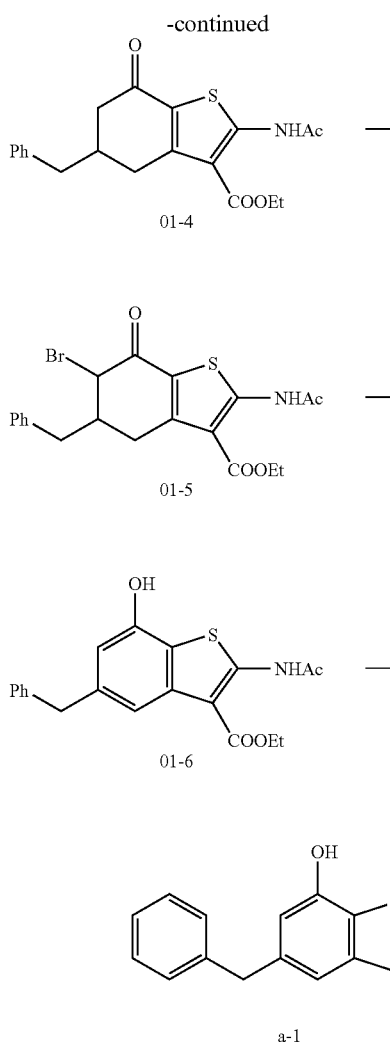

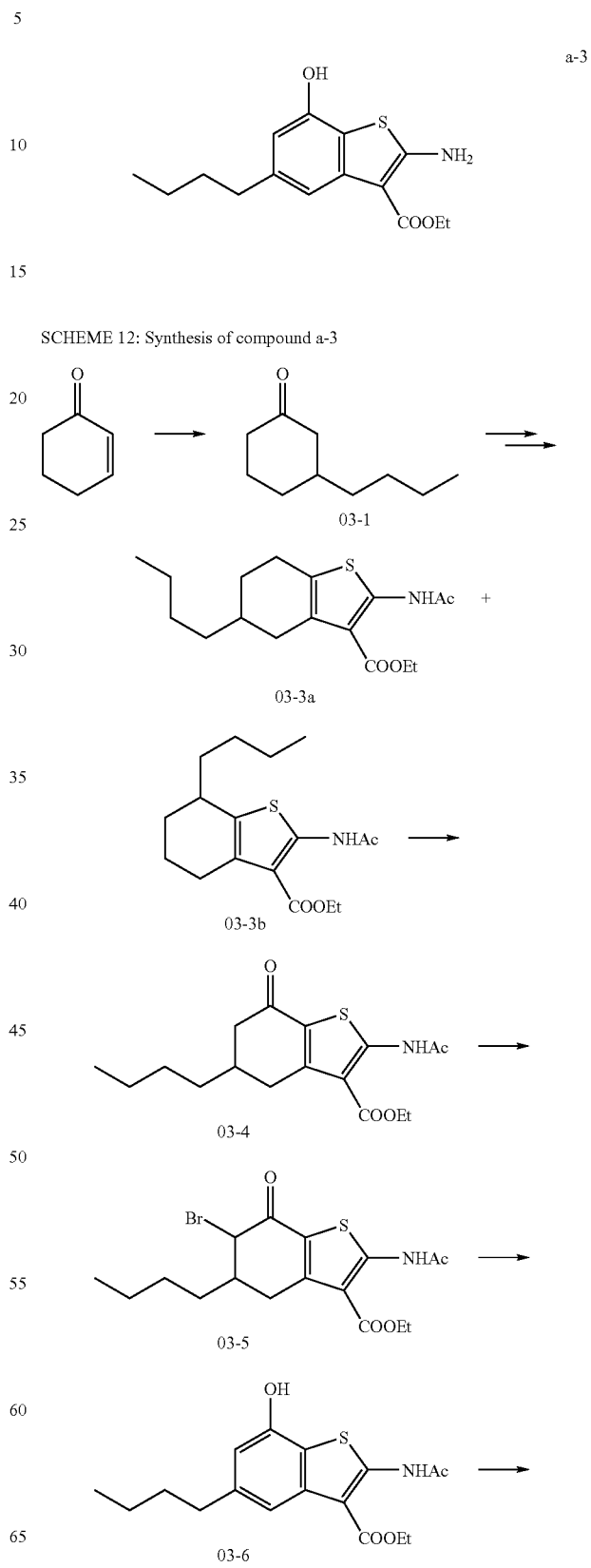

The synthesis of a-1 (Scheme 11) started from 3-benzyl-cyclohexanone (01-1), which was prepared according to literature [Mitra & Joshi (1988) Synth. Comm. 18:2259]. Compound 01-1 was converted to thiophene 01-3 over two steps using the literature procedure [Perrissin et al. (1980) Eur. J. Med. Chem. Chim. Ther. 15:413-418]. It was found that a mixture of two possible regio-isomers 01-3a and 01-3b in a ratio of 1:10 (according to NMR) was formed. Because it was not possible to separate the isomers by column chromatography, the crude mixture was treated with $Na_2Cr_2O_7$. It turned out that only the minor isomer, 01-3a, was converted to ketone 01-4 in 12% yield from 01-1. Monobromination of 014 with $CuBr_2$ in refluxing EtOAc gave 01-5 in 46% after crystallization [Tani et al. (1996) Chem. Pharm. Bull. 44:55-61]. The compound was isolated as mixture of the cis- and trans-isomers in a ratio of 1:23. One major side-product (~10%) was identified to be the O-ethylated elimination product. Final elimination was achieved according to Tani et al. with $LiBr/Li_2CO_3$ and gave 01-6 in 77% yield [Tani et al. (1996) Chem. Pharm. Bull. 44:55-61]. Conversion of 01-6 with $H_2SO_4$ in MeOH gave compound a-1 in 91%.

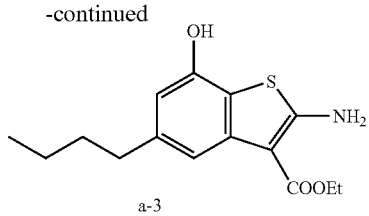
a-3

For the synthesis of a-3 the same strategy as for a-1 (Scheme 12) was used. 3-Butyl cyclohexanone 03-1 was prepared in 78% yield [Lipshutz et al. (1984) J. Org. Chem. 49:3938-3942]. The following thiophene formation and acylation gave a mixture of isomers 03-3a and 03-3b in a ratio 1:3. After oxidation with $Na_2Cr_2O_7$ ketone 03-4 was obtained in 18% yield from 03-1. Bromination with $CuBr_2$ in refluxing EtOAc gave bromide 5 in 61% yield. Elimination with LiBr/$Li_2CO_3$ afforded 03-6 in 68%. Conversion of 03-6 with $H_2SO_4$ in MeOH/MeCN gave compound a-3 in 82%.

Detailed Synthesis:

3-Benzyl-cyclohexanone (01-1)

To a solution of benzylmagnesiumchloride in THF (1.31 M, 393 mmol, 300 mL) CuCl (1.9 g) was added and the mixture was cooled to 0° C. The mixture was stirred for 6 min., and a solution of cyclohex-2-enone (193 mmol, 18.9 g) in THF (75 mL) was added dropwise at 0° C. over a period of 1 h. The reaction mixture was warmed to RT overnight. After cooling again to 0° C., saturated aqueous $NH_4Cl$ (450 mL) was added and the layers were separated. The aqueous layer was extracted with EtOAc (2×500 mL). The combined org. layers were washed with saturated aqueous $NH_4Cl$ (500 mL) and dried over $Na_2SO_4$. After evaporation, the crude product was subjected to column chromatography ($SiO_2$, EtOAc/Hept=1/19→1/9) to give two fractions of product 01-1. Fraction 1 (23.5 g, 125 mmol, 65%, yellow oil) was used in the next step.

3-Butyl-cyclohexanone (03-1)

A mixture of CuCN (49.3 mmol, 550 mmol, 1.1 equiv.) and $Et_2O$ (1 L) was cooled to −78° C. A 2.6 M-solution of n-BuLi in hexane (440 mL, 1.1 mol, 2.2 equiv.) was added dropwise keeping the temperature below −75° C. After complete addition, the mixture was slowly warmed up. After reaching 0° C., it was again cooled to −85° C. Cyclohex-2-enone (48.1 g, 500 mmol) was added dropwise keeping the internal temperature around −80° C. After complete addition the mixture was stirred for 2 h at −85° C. Then the reaction was quenched by adding a mixture of saturated aqueous $NH_4Cl$ (750 mL) and concentrated $NH_4OH$ (750 mL). A grey precipitate was formed. The layers were separated, and the aqueous layer was extracted with TBME (2×250 mL). The combined org. layers were washed with saturated aqueous $NH_4Cl$ (3×500 mL) and dried over $Na_2SO_4$. After evaporation of the solvents in vacuo the crude product was filtered over $SiO_2$ using heptane as eluent. After evaporation of the solvent product 03-1 (60.2 g, 391 mmol, 78%) was obtained as a yellow oil.

2-Amino-5-benzyl-4,5,6,7-tetrahydro-benzo[b]thiophene-3-carboxylic acid ethyl ester (01-2a)

Compound 01-1 (26 g, 138 mmol) was mixed with EtOH (70 mL), $H_2O$ (1 mL), ethyl cyanoacetate (14.7 mL, 15.6 g, 138 mmol) and sulfur (4.42 g, 138 mmol). To the resulting mixture morpholine (14 mL, 13.9 g, 159 mmol) was added and the mixture was heated for 4 at 45° C. It was concentrated to half of the original volume and poured into $H_2O$ (500 mL). The aqueous layer was extracted with EtOAc (3×200 mL). The combined organic layers were washed with brine, dried over $Na_2SO_4$ and the solvent was removed in vacuo to give the crude product as a red brown oil, which was used in the next step without further purification.

2-Amino-5-butyl-4,5,6,7-tetrahydro-benzo[b]thiophene-3-carboxylic acid ethyl ester (03-2a)

Crude mixture 03-2 was prepared from 03-1 (26 g, 168 mmol), ethyl cyanoacetate (18 mL, 19.1 g, 168 mmol) and sulfur (5.4 g, 168 mmol) and morpholine (17 mL) using the procedure for 01-2 and was used in the next step without further purification.

2-Acetylamino-5-benzyl-4,5,6,7-tetrahydro-benzo[b]thiophene-3-carboxylic acid ethyl ester (01-3a)

The crude product mixture of isomers 01-2a and 01-2b was dissolved in AcOH (40 mL). Acetic anhydride (40 mL) was added and the mixture was heated at 35° C. for 3 h. The mixture was cooled to RT and poured in $H_2O$ (250 mL). The aqueous layer was extracted with EtOAc (3×200 mL). The combined organic layers were washed with $H_2O$ (3×200 mL), brine (200 mL) and dried over $Na_2SO_4$. After removal of the solvent in vacuo the crude product was obtained as a red brown oil, which was used in the next step without further purification.

2-Acetylamino-5-butyl-4,5,6,7-tetrahydro-benzo[b]thiophene-3-carboxylic acid ethyl ester (03-3a)

Conversion of the crude mixture 03-2 according to the procedure for 01-3a with $Ac_2O$ (55 mL) in AcOH (55 mL) gave crude mixture 03-3, which was used in the next step without further purification.

2-Acetylamino-5-benzyl-7-oxo-4,5,6,7-tetrahydro-benzo[b]thiophene-3-carboxylic acid ethyl ester (01 4)

The crude product mixture of isomers 01-3a and 01-3b was dissolved in AcOH (450 mL). The mixture was heated to 50° C. and a solution of $Na_2Cr_2O_7.2H_2O$ (61.7 g, 207 mmol) in hot $H_2O$ (250 mL) was added dropwise. After complete addition the mixture was stirred for 1 h at 65° and then allowed to cool to RT within 5 h. The reaction mixture was quenched with saturated aqueous $Na_2SO_3$ (200 mL) and diluted with $H_2O$ (1.5 L). The resulting precipitate was filtered off and washed with $H_2O$. After drying, the solid was stirred in EtOAc (50 mL) and filtered to give product 01-4 (3.25 g, 8.7 mmol, 6% from 1). The aqueous filtrate was extracted with EtOAc (3×300 mL). The combined organic layers were washed with $H_2O$ (3×300 mL), brine (200 mL) and dried over $Na_2SO_4$. After removal of the solvent in vacuo the crude product was subjected to column chromatography ($SiO_2$, EtOAc/Hept=1/4) to give the product as a yellow solid. The solid was washed with EtOAc (20 mL), filtered off and washed with $Et_2O$ (2×25 mL) and dried to give 01-4 (3.25 g, 8.7 mmol) as an off-white solid. (Total yield of 01-4 from 01-1: 6.5 g, 17.4 mmol, 12%).

2-Acetylamino-5-butyl-7-oxo-4,5,6,7-tetrahydro-benzo[b]thiophene-3-carboxylic acid ethyl ester (03-4)

Crude mixture 03-3 was converted with $Na_2Cr_2O_7.2H_2O$ (75.1 g, 252 mmol) according to the procedure for 01-4. The crude product was subjected to column chromatography ($SiO_2$, EtOAc/Hept=1/4) giving product 03-4 as a yellow solid. The solid was washed with $Et_2O$ (25 mL), filtered and washed with a small amount of $Et_2O$ to give compound 03-4 (7.75 g, 23 mmol, 14% from 03-1) as a white solid. From the mother liquor a second crop of compound 03-4 (2.2 g, 6.5 mmol, 4% from 03-1) was obtained as a white solid. Total yield of 03-4: 9.95 g, 29.5 mmol, 18% from 03-1.

2-Acetylamino-5-benzyl-6-bromo-7-oxo-4,5,6,7-tetrahydro-benzo[b]thiophene-3-carboxylic acid ethyl ester (01-5)

A suspension of compound 01-4 (6.04 g, 16.3 mmol) in EtOAc (400 mL) was treated with $CuBr_2$ (7.3 g, 32.6 mmol, 2 equiv.). The resulting mixture was refluxed for 18 h under a $N_2$-atmosphere. After cooling to RT the mixture was filtered over Celite. The solvent was removed in vacuo to give a pink solid. After treatment with EtOAc the crude solid was filtered and washed with $Et_2O$ (3×20 mL) to give 01-5 as a pink solid (3.35 g, 7.4 mmol, 46%). The mother liquor was evaporated in vacuo and the residue was subjected to column chromatography ($SiO_2$, EtOAc/Hept=1/4) to give the product (950 mg) as off-white solid with a purity of 66% (HPLC-MS).

2-Acetylamino-5-butyl-6-bromo-7-oxo-4,5,6,7-tetrahydro-benzo[b]thiophene-3-carboxylic acid ethyl ester (03-5)

Compound 03-4 (3.24 g, 9.6 mmol) was converted with $CuBr_2$ (4.3 g, 19.2 mmol) using the procedure for 01-5. Two other batches (from a total of 4.44 g, 13.6 mmol of 03-4) were prepared and the crude products were combined and purified by column chromatography ($SiO_2$, EtOAc/Hept=1/4) to give two fractions of product. The first fraction (3.84 g, 9.2 mmol, 40%) was obtained as orange oil, the second fraction (2.02 g, 4.8 mmol, 21%) was obtained as a brown oily solid and contained some dibrominated ketone.

2-Acetylamino-5-benzyl-7-hydroxy-benzo[b]thiophene-3-carboxylic acid ethyl ester (01-6)

A flame dried three-necked flask was purged with $N_2$ and charged with bromide 01-5 (3.35 g, 7.4 mmol), LiBr (707 mg, 8.2 mmol, 1.1 equiv.), $Li_2CO_3$ (601 mg, 8.2 mmol, 1.1 equiv.) and DMF (85 mL). The resulting suspension was refluxed overnight under $N_2$-atmosphere. The reaction mixture was cooled to RT and poured into saturated aqueous $NH_4Cl$ (500 mL). The aqueous layer was extracted with EtOAc (3×100 mL). The combined organic layers were washed with $H_2O$ (3×200 mL), brine (200 mL) and dried over $Na_2SO_4$. The solvent was removed in vacuo to give the crude product as a brownish solid. The solid was washed with $Et_2O$ (25 mL) to give 01-6 (2.1 g, 5.7 mmol, 77%) as a slightly brown solid.

2-Acetylamino-5-butyl-7-hydroxy-benzo[b]thiophene-3-carboxylic acid ethyl ester (03-6)

Compound 03-5 (4.54 g, 10.9 mmol) was converted with LiBr (1.04 g, 12 mmol, 1.1 equiv.), $Li_2CO_3$ (886 mg, 12 mmol, 1.1 equiv.) to 03-6 using the procedure for 01-6. The crude product was washed with EtOAc (15 mL) and washed with $Et_2O$ (2×15 mL) to give 03-6 (1.8 g, 5.4 mmol 49%) as a brownish solid. The mother liquor was evaporated and treated with $Et_2O$ to give a second crop of 03-6 (0.67 g, 2.0 mmol, 18%) as a brownish solid. Total yield of 03-6: 2.47 9, 7.4 mmol, 68%.

2-Amino-5-benzyl-7-hydroxy-benzo[b]thiophene-3-carboxylic acid ethyl ester (a-1)

Compound 01-6 (2.1 g, 5.7 mmol) was dissolved in MeOH (250 mL), $H_2SO_4$ (1 mL) was added and the mixture was stirred for 3 days. Another batch of 01-6 (450 mg, 1.2 mmol) was added and the mixture was stirred further for 14 days while monitoring the reaction each third day by HPLC. After completion the mixture was concentrated to half of the original volume. Water was added and the pH was cautiously adjusted to 8 with conc. $NH_4OH$. The aqueous layer was extracted with EtOAc (3×100 mL). The combined organic layers were washed with $H_2O$ (100 mL), brine (100 mL) and dried over $Na_2SO_4$. The solvent was removed in vacuo to give product a-1 (2.05 g, 6.3 mmol, 91%) as a greenish brown foam.

2-Amino-5-butyl-7-hydroxy-benzo[b]thiophene-3-carboxylic acid ethyl ester (a-3)

Compound 03-6 (3.64 g, 10.9 mmol) was suspended in a mixture of MeOH (450 mL) and MeCN (100 mL). $H_2SO_4$ (1.5 mL) was added and the mixture was stirred under a $N_2$-atmosphere, while monitoring the reaction by HPLC. After 7 days the conversion was complete and the mixture was concentrated to half of the original volume. Water was added and the pH was cautiously adjusted to 8 with conc. $NH_4OH$. The aqueous layer was extracted with EtOAc (3×100 mL). The combined organic layers were washed with $H_2O$ (100 mL), brine (100 mL) and dried over $Na_2SO_4$. The solvent was removed in vacuo to give the crude product as a green sticky oil, which was purified by column chromatography ($SiO_2$, EtOAc/Hept=1/4+1% $Et_3N$). The product fractions were pooled and the solvent was removed in vacuo. The residue was dissolved in $Et_2O$ (50 mL) and the solution was washed with conc. aq. $NH_4Cl$ (2×50 mL) and brine (50 mL) to remove residual $NEt_3$. After drying over $Na_2SO_4$, the solvent was removed in vacuo to give a-3 (2.6 g, 8.9 mmol, 82%) as a greenish grey solid.

Synthesis of 2-Amino-4-benzyl-7-hydroxy-benzo[b]thiophene-3-carboxylic acid ethyl ester a-2 and of -Amino-5-butyl-7-hydroxy-benzo[b]thiophene-3-carboxylic acid ethyl ester a4

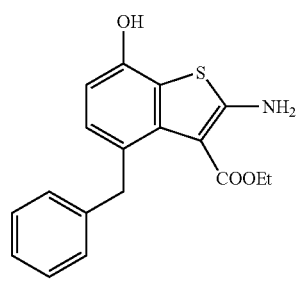

a-2

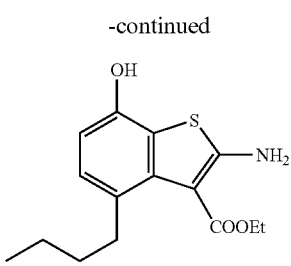

SCHEME 13: Synthesis of compounds a-2 (R = benzyl) and a-4 (R = butyl)

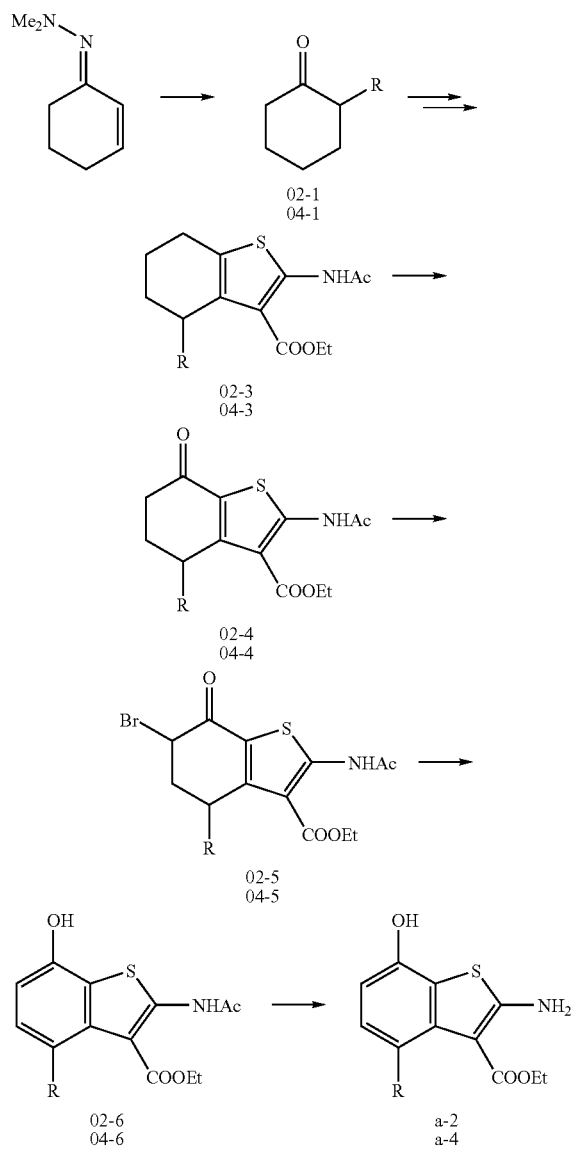

For the synthesis of compounds a-2 and a-4 a similar strategy as for compounds a-1 and a-3 was used (Scheme 13). Alkylation of cyclohexanone-N,N-dimethylhydrazone gave ketones 02-1 and 04-1. The ketones were converted to the corresponding 2-amino thiophenes using the standard procedure, followed by immediate protection to give acetamides 02-3 and 04-3 in rather moderate yields (28, 30%). The thiophenes 02-3 and 04-3 were oxidised to ketones 02-4 and 04-4 with $Na_2Cr_2O_7$ in yields of 51% resp. 41%. Bromination with $CuBr_2$ in refluxing EtOAc afforded bromides 02-5 and 04-5 in 82% resp. 38% yield. Subsequent elimination with $LiBr/Li_2CO_3$ gave phenols 02-6 and 04-6 in 67% resp. 62% yield. Deprotection of 02-6 and 04-6 to the requested compounds a-2 and a-4 with $H_2SO_4$ in MeOH proceeded in 55% resp. 51% yield.

Detailed Synthesis

2-Benzyl-cyclohexanone (02-1)

A mixture of cyclohexanone-N,N-dimethylhydrazone (30 g, 214 mmol) and THF (400 mL) mixture was cooled to 5° C. A 2.5 M-solution of n-BuLi (90 mL, 225 mmol, 1.05 equiv.) was added dropwise keeping the internal temperature below 0° C. After complete addition the mixture was stirred for 1 h at 5° C. Then benzylbromide was added slowly. After complete addition the reaction mixture was warmed to RT and stirred overnight. A solution of 3 N HCl (400 mL) was added and the mixture stirred for 2 h at RT. After dilution with $H_2O$ (400 mL), the layers were separated and the aqueous layer was extracted with EtOAc (2×200 mL). The combined organic layers were washed with $H_2O$ (2×400 mL), brine (400 mL) and dried over $Na_2SO_4$. The solvent was removed in vacuo to give crude 1a (41.5 g, >214 mmol) which was used in the next step without further purification.

3-Butyl-cyclohexanone (04-1)

Compound 04-1 was prepared analogeously to 02-1 from cyclohexanone-N,N-dimethyl-hydrazone (30 g, 214 mmol), n-BuLi (90 mL of 2.5 M, 225 mmol, 1.05 equiv.) and n-butylbromide (30.2 g, 220 mmol, 1.03 equiv) to give crude 04-1 (30.0 g, 194 mmol, 91%) as an orange oil, which was used in the next step without further purification.

2-Amino-6-benzyl-4,5,6,7-tetrahydro-benzo[b]
thiophene-3-carboxylic acid ethyl ester (02-2)

Compound 02-1 (crude, max. 214 mmol) was mixed with EtOH (110 mL), ethyl cyanoacetate (23 mL, 24.4 g, 214 mmol) and sulfur (6.85 g, 214 mmol). To the resulting mixture morpholine (21 mL) was added and the mixture was heated to reflux for 24 h. It was concentrated to half of the original volume and poured into $H_2O$ (600 mL). The aqueous layer was extracted with EtOAc (3×200 mL). The combined organic layers were washed with $H_2O$ (2×200 mL), brine (200 mL), dried over $Na_2SO_4$ and the solvent was removed in vacuo to give the crude product as a red brown oil, which was used in the next step without further purification.

2-Amino-6-butyl-4,5,6,7-tetrahydro-benzo[b]
thiophene-3-carboxylic acid ethyl ester (04-2)

Compound 04-2 was prepared from 04-1 (30 g, 194 mmol), ethyl cyanoacetate (20.7 mL, 21.9 g, 194 mmol), sulfur (6.2 g, 194 mmol) and morpholine (21 mL) using the procedure for 02-2 and was used in the next step without further purification.

2-Acetylamino-6-benzyl-4,5,6,7-tetrahydro-benzo[b]thiophene-3-carboxylic acid ethyl ester (02-3)

Crude 02-2 was dissolved in AcOH (65 mL). Acetic anhydride (65 mL) was added and the mixture was heated at 40° C. for 1.5 h. The mixture was cooled to RT and poured in $H_2O$ (600 mL), during which a solid precipitated. The solid was filtered off and washed with $H_2O$ and $Et_2O$ and dried in air to give 02-3 (4.9 g, 13.7 mmol, 6%) as an off-white solid. The filtrate was extracted with EtOAc (3×200 mL). The combined organic layers were washed with $H_2O$ (3×200 mL), brine (200 mL) and dried over $Na_2SO_4$. After removal of the solvent in vacuo the crude product was obtained as a semi-solid. After treatment with 100 mL of $Et_2O$, the solid was filtered off and washed with small portions of $Et_2O$ and dried in air to give 02-3 (17.2 g, 48 mmol, 22%) as a slightly yellow solid (total yield: 22.1 g, 62 mmol, 28%).

2-Acetylamino-6-butyl-4,5,6,7-tetrahydro-benzo[b]thiophene-3-carboxylic acid ethyl ester (04-3)

Conversion of crude 04-2 according to the procedure for 02-3 with $Ac_2O$ (60 mL) in AcOH (60 mL) gave crude product 04-3. Column chromatography ($SiO_2$, EtOAc/hept=1/9) afforded 04-3 (19.2 g, 59 mmol, 30%) as a yellow solid.

2-Acetylamino-6-benzyl-7-oxo-4,5,6,7-tetrahydro-benzo[b]thiophene-3-carboxylic acid ethyl ester (02-4)

Compound 02-3 (22.1 g, 62 mmol) was dissolved in AcOH (200 mL). The mixture was heated to 65° C. and a solution of $Na_2Cr_2O_7 \cdot 2H_2O$ (27.2 g, 93 mmol) in hot $H_2O$ (200 mL) was added over a period of 2 min. After complete addition the mixture was stirred for 3 h at 65-67° C. and 2 h at 75° C. The mixture was allowed to cool to RT and then quenched with saturated aqueous $Na_2SO_3$ (100 mL) and diluted with $H_2O$ (1.5 L). The aqueous mixture was extracted with EtOAc (3×300 mL). The combined organic layers were washed with $H_2O$ (3×400 mL), brine (400 mL) and dried over $Na_2SO_4$. After removal of the solvent in vacuo the crude product was treated with $Et_2O$ (50 mL) and filtered off to give 02-4 (9.5 g, 25 mmol, 41%) as yellow powder containing about 8% of starting material 02-3 (HPLC).

2-Acetylamino-6-butyl-7-oxo-4,5,6,7-tetrahydro-benzo[b]thiophene-3-carboxylic acid ethyl ester (04-4)

Compound 04-b (19.1 g, 59 mmol) was converted with $Na_2Cr_2O_7 \cdot 2H_2O$ (26.4 g, 88.5 mmol) according to the procedure for 02-4. The crude product was subjected to column chromatography ($SiO_2$, EtOAc/hept=1/4) giving product 04-4 (10.1 g, 30 mmol, 51%) as a yellow oil, that solidified upon standing to a yellow wax-like solid.

2-Acetylamino-6-benzyl-6-bromo-7-oxo-4,5,6,7-tetrahydro-benzo[b]thiophene-3-carboxylic acid ethyl ester (02-5)

A suspension of compound 02-4 (4.5 g, 11 mmol) in EtOAc (80 mL) was treated with $CuBr_2$ (5.4 g, 24 mmol, 2.2 equiv.). The resulting mixture was refluxed for 6 h under a $N_2$-atmosphere. After cooling to RT the mixture was filtered over Celite. The solvent was removed in vacuo to give a pink solid, which was treated with EtOAc (25 mL). The solid was filtered off and washed with $Et_2O$ (3×20 mL) to give 02-5 as a slightly brown solid (4.1 g, 9.0 mmol, 82%).

2-Acetylamino-6-butyl-6-bromo-7-oxo-4,5,6,7-tetrahydro-benzo[b]thiophene-3-carboxylic acid ethyl ester (04-5)

Compound 04-4 (10.2 g, 39.1 mmol) was converted with $CuBr_2$ (13.4 g, 60.2 mmol) using the procedure for 02-5 giving 04-5 (4.7 g, 11.4 mmol, 38%) as a grey powder.

2-Acetylamino-5-benzyl-7-hydroxy-benzo[b]thiophene-3-carboxylic acid ethyl ester (02-6)

A suspension of the bromide 02-5 (8.5 g, 18.9 mmol), LiBr (1.8 g, 20.8 mmol, 1.1 equiv.), $Li_2CO_3$ (1.5 g, 20.8 mmol, 1.1 equiv.) and DMF (200 mL) was heated to 150° C. for 4 h under a $N_2$-atmosphere. The reaction mixture was cooled to RT and poured into saturated aqueous $NH_4Cl$ (750 mL). The aqueous layer was extracted with EtOAc (3×200 mL). The combined organic layers were washed with $H_2O$ (3×200 mL), sat. aq. $NH_4Cl$ (200 mL) and dried over $Na_2SO_4$. The solvent was removed in vacuo to give the crude product. The solid was washed with $Et_2O$ (25 mL) to give 02-6 (1.52 g, 4.1 mmol, 22%). The filtrate was evaporated and the residue was purified by column chromatography ($SiO_2$, EtOAc/hept=1/1) to give another fraction of 02-6 (2.5 g, 6.8 mmol, 36%) as a yellow solid (total yield: 4.3 g, 11.7 mmol, 62%).

2-Acetylamino-6-butyl-7-hydroxy-benzo[b]thiophene-3-carboxylic acid ethyl ester (04-6)

Compound 04-5 (4.74 g, 10.9 mmol) was converted with LiBr (1.1 g, 12.5 mmol, 1.1 equiv.), $Li_2CO_3$ (0.9 g, 12.5 mmol, 1.1 equiv.) to 04-6 using the procedure for 02-6. The crude product was filtered off after aqueous workup, washed with $H_2O$ and $Et_2O$ (25 mL) to give 04-6 (1.9 g, 5.7 mmol, 50%) as a grey solid. The mother liquor was evaporated and treated with $Et_2O$ to give a second crop of 04-6 (0.6 g, 1.9 mmol, 17%) as a brownish solid (total yield of 04-6: 2.6 g, 7.6 mmol, 67%).

2-Amino-6-benzyl-7-hydroxy-benzo[b]thiophene-3-carboxylic acid ethyl ester (a-2)

Compound 02-6 (4.3 g, 11.7 mmol) was dissolved in MeOH (350 mL), conc. $H_2SO_4$ (2 mL) was added and the mixture was stirred for 8 days. The mixture was concentrated to half of the original volume. $H_2O$ was added and the pH was cautiously adjusted to 8 with conc. $NH_4OH$. The aqueous layer was extracted with EtOAc (3×100 mL). The combined organic layers were washed with $H_2O$ (100 mL), brine (100 mL) and dried over $Na_2SO_4$. The solvent was removed in vacuo to give the crude product, which was purified by column chromatography ($SiO_2$, EtOAc/hept=1/4+1% $Et_3N$ to 1/1). The product was obtained in only 80% purity according to HPLC and therefore subjected to automated column chromatography to give a-2 (2.1 g, 6.4 mmol, 55%) as a brown-yellow solid.

2-Amino-6-butyl-7-hydroxy-benzo[b]thiophene-3-carboxylic acid ethyl ester (a-4)

Compound 04-b (2.6 g, 7.6 mmol) was mixed with MeOH (200 mL) and treated with conc. $H_2SO_4$ (1 mL) for 9 d using the procedure as described for a-2. The crude product was purifed by automated column chromatography to give a-4 (1.1 g, 3.7 mmol, 50%) as orange oil.

Compounds No. 701 to 803 of the general formula q-3-OH

The following tables 3, 4, 5 and 6 list compounds No. 701 to 803 of the general formula q, which were prepared according to Scheme 9 starting with the primary amines R1-NH$_2$ and the acid chlorides R2-CO—Cl as given in the third and fourth column of each table. The compounds were synthesized using different starting compounds a-3OH (a-1, a-2, a-3 and a-4) giving rise to products of general formula q-3-OH, i.e. q-1 (table 3), q-2 (table 4), q-3 (table 5) and q4 (table 6), respectively.

Synthesis Protocol:

In a reaction vessel at room temperature are put together sequentially 200 pi of 0.25 M primary amine R1-NH$_2$, 200 µl of 1 M diisopropylethylamine and 50 µl of 0.25 M acid chloride R2-CO—Cl. To this mixture is added 200 µl of 0.25 M substituted and optionally protected 2-amino-benzo[b]thiophene-3-carboxylic acid ethyl ester a-3-OH followed by 200 µl of 0.25 M POCl$_3$. Of all reactants a solution or suspension in chlorobenzene is used. After shaking for 80 hours at 100° C., the mixtures are cooled to room temperature, washed with 5% NaOAc and extracted with EtOAc. The organic layers are collected and concentrated to yield the desired compound. The obtained material of the general formula q-3-OH was thereafter analyzed by LC-MS.

In addition, the Molecular Weight and the Retention Time of the synthesized compounds determined by the LC-MS analysis are shown in each table.

TABLE 3

Compounds No, 701 to 721 of the general formula q-1:

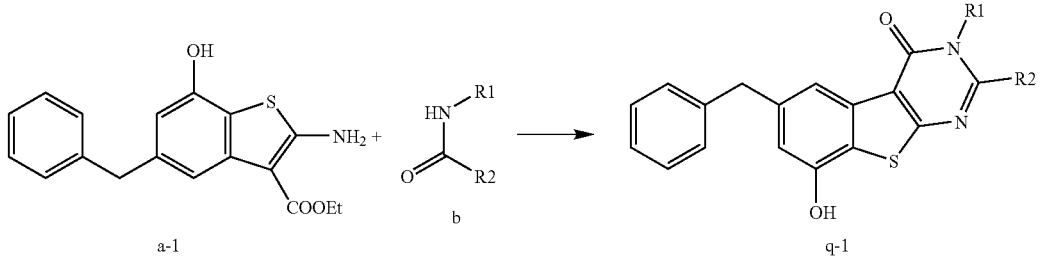

| No. | Formula | R1—NH$_2$ (name) | R2—CO—Cl (name) | MH+ | RT [min] |
|---|---|---|---|---|---|
| 701 | | 3,4-METHYLENE-DIOXYBENZYL-AMINE | 3-PHENYL-PROPIONYL CHLORIDE | 546.16 | 2.21 |
| 702 | | THIOPHENE-2-ETHYLAMINE | 3-PHENYL-PROPIONYL CHLORIDE | 522.14 | 2.23 |

TABLE 3-continued
Compounds No, 701 to 721 of the general formula q-1:
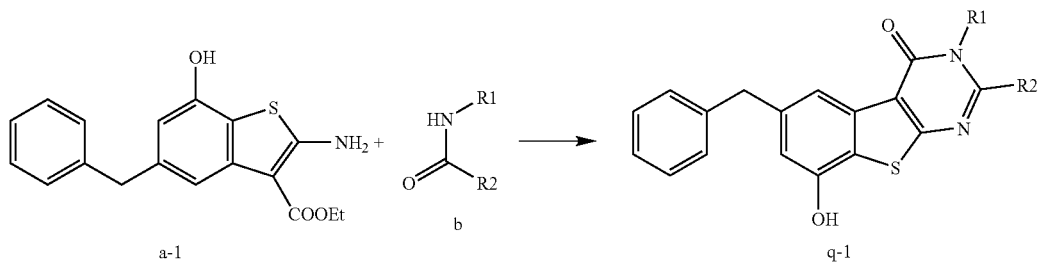
| No. | Formula | R1—NH$_2$ (name) | R2—CO—Cl (name) | MH+ | RT [min] |
|---|---|---|---|---|---|
| 703 | | BENZYLAMINE | 3-PHENYL-PROPIONYL CHLORIDE | 502.17 | 2.23 |
| 704 | | THIOPHENE-2-ETHYLAMINE | 2-FUROYL CHLORIDE | 484.09 | 2.20 |
| 705 | | THIOPHENE-2-ETHYLAMINE | PHENYLACETYL CHLORIDE | 508.13 | 2.21 |

TABLE 3-continued
Compounds No, 701 to 721 of the general formula q-1:
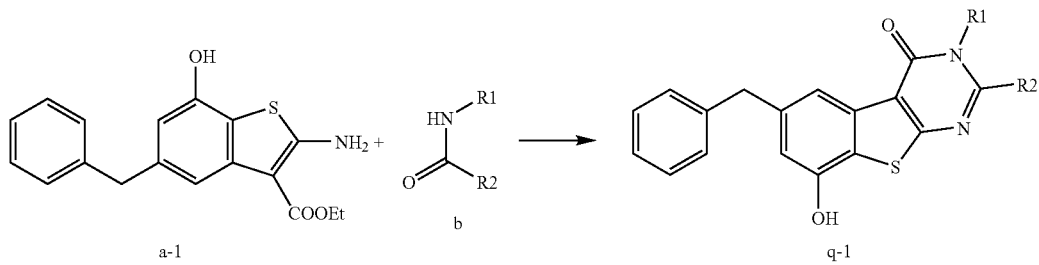
| No. | Formula | R1—NH₂ (name) | R2—CO—Cl (name) | MH+ | RT [min] |
|---|---|---|---|---|---|
| 706 | | FURFURYL-AMINE | PHENYLACETYL CHLORIDE | 478.14 | 2.15 |
| 707 | | THIOPHENE-2-ETHYLAMINE | 2-METHOXY-BENZOYL CHLORIDE | 524.12 | 2.12 |
| 708 | | 2-(4-METHOXY-PHENYL)-ETHYLAMINE | 3-PHENYL-PROPIONYL CHLORIDE | 546.20 | 2.25 |

TABLE 3-continued
Compounds No, 701 to 721 of the general formula q-1:
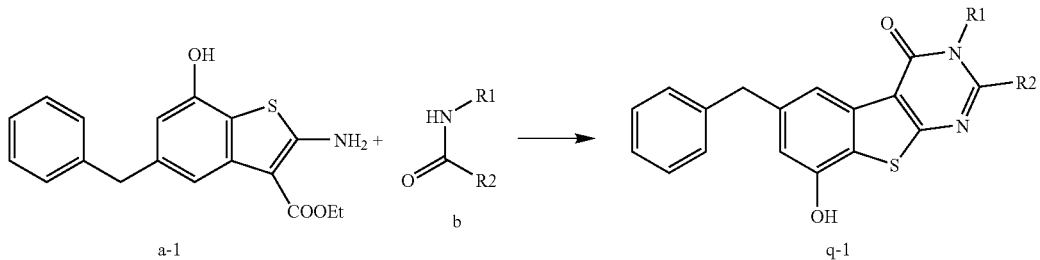
| No. | Formula | R1—NH₂ (name) | R2—CO—Cl (name) | MH+ | RT [min] |
|---|---|---|---|---|---|
| 709 | | THIOPHENE-2-METHYLAMINE | 3-PHENYL-PROPIONYL CHLORIDE | 508.13 | 2.20 |
| 710 | | 2-AMINO-5-METHYL-THIAZOLE | 3-PHENYL-PROPIONYL CHLORIDE | 509.12 | 2.19 |
| 711 | | TETRAHYDRO-FURFURYL-AMINE | PHENYLACETYL CHLORIDE | 482.17 | 2.14 |
| 712 | | THIOPHENE-2-METHYLAMINE | PHENYLACETYL CHLORIDE | 494.11 | 2.18 |

TABLE 3-continued
Compounds No, 701 to 721 of the general formula q-1:
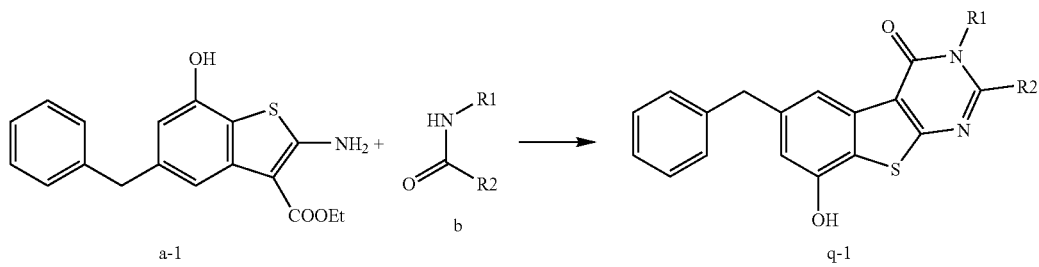
| No. | Formula | R1—NH₂ (name) | R2—CO—Cl (name) | MH+ | RT [min] |
|---|---|---|---|---|---|
| 713 | | FURFURYL-AMINE | 3-CYCLOPENTYL-PROPIONYL CHLORIDE | 484.18 | 2.29 |
| 714 | | 3,4-METHYLENE-DIOXY-BENZYLAMINE | 2-ETHYL-HEXANOYL CHLORIDE | 540.21 | 2.32 |
| 715 | | THIOPHENE-2-ETHYLAMINE | 2-ETHYL-HEXANOYL CHLORIDE | 516.19 | 2.45 |

TABLE 3-continued
Compounds No, 701 to 721 of the general formula q-1:
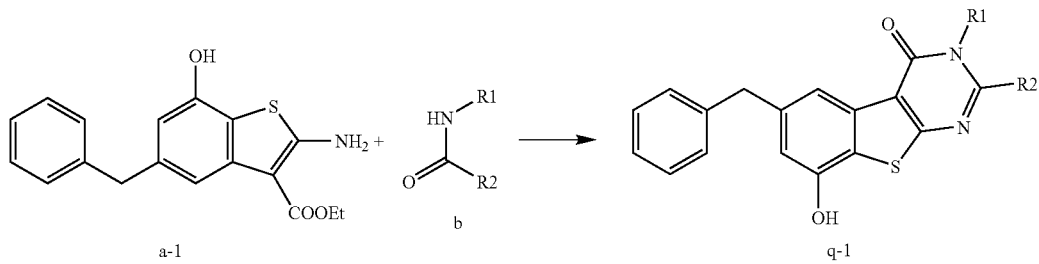
| No. | Formula | R1—NH$_2$ (name) | R2—CO—Cl (name) | MH+ | RT [min] |
|---|---|---|---|---|---|
| 716 | | 3,4-METHYLENE-DIOXY-BENZYLAMINE | METHOXY-ACETYL CHLORIDE | 486.12 | 2.08 |
| 717 | | THIOPHENE-2-ETHYLAMINE | METHOXY-ACETYL CHLORIDE | 462.11 | 2.10 |
| 718 | | 3,4-METHYLENE-DIOXY-BENZYLAMINE | (3,4-DIMETHYOXY-PHENYL)-ACETYL CHLORIDE | 592.17 | 2.12 |

TABLE 3-continued
Compounds No, 701 to 721 of the general formula q-1:
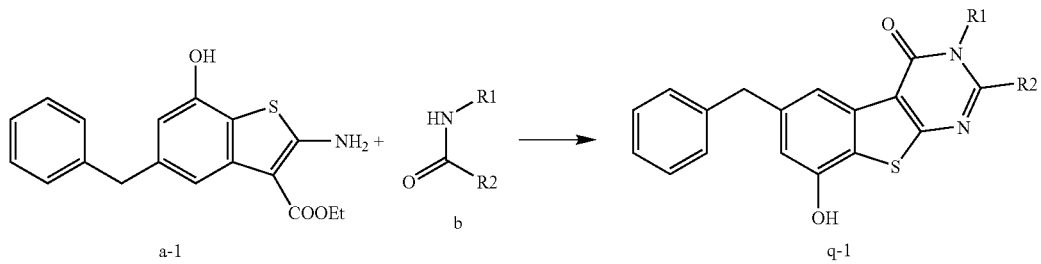
| No. | Formula | R1—NH₂ (name) | R2—CO—Cl (name) | MH+ | RT [min] |
|---|---|---|---|---|---|
| 719 | | FURFURYL-AMINE | (3,4-DIMETHOXY-PHENYL)-ACETYL CHLORIDE | 538.16 | 2.09 |
| 720 | | TETRAHYDRO-FURFURYL-AMINE | 2-ETHYL-HEXANOYL CHLORIDE | 490.23 | 2.31 |
| 721 | | THIOPHENE-2-METHYLAMINE | METHOXY-ACETYL CHLORIDE | 448.09 | 2.08 |

TABLE 4
Compounds No. 722 to 735 of the general formula q-2:
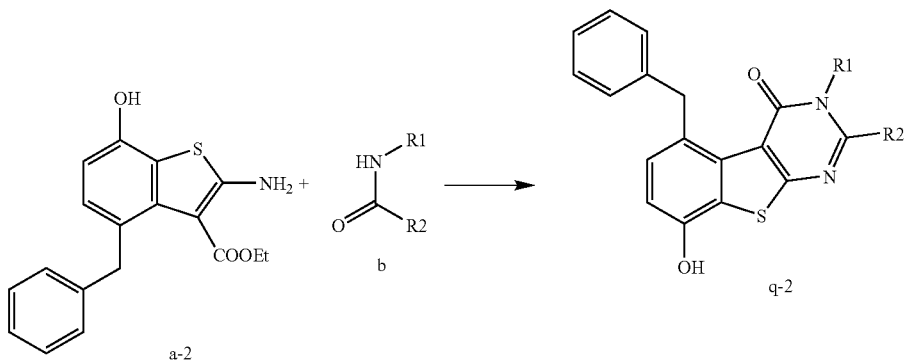
| No | Formula | R1—NH₂ (name) | R2—CO—Cl (name) | MH+ | RT [min] |
|---|---|---|---|---|---|
| 722 | | THIOPHENE-2-ETHYLAMINE | 3-PHENYL-PROPIONYL CHLORIDE | 522.14 | 2.24 |
| 723 | | FURFURYLAMINE | 3-PHENYL-PROPIONYL CHLORIDE | 492.15 | 2.18 |
| 724 | | FURFURYLAMINE | PHENYLACETYL CHLORIDE | 478.14 | 2.16 |

TABLE 4-continued
Compounds No. 722 to 735 of the general formula q-2:
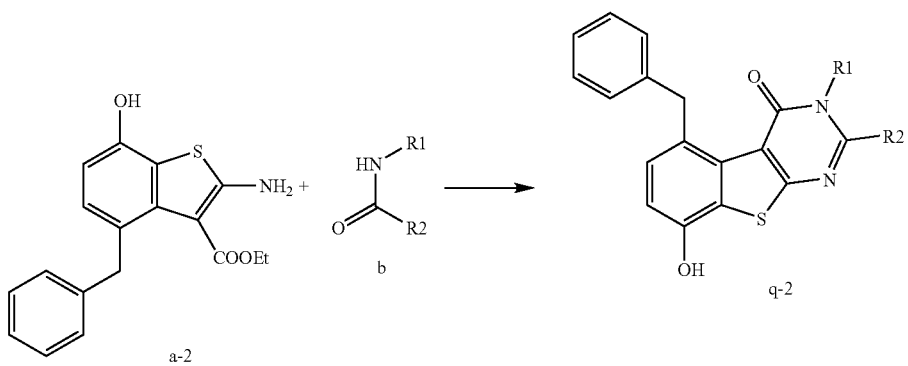
| No | Formula | R1—NH₂ (name) | R2—CO—Cl (name) | MH+ | RT [min] |
|---|---|---|---|---|---|
| 725 | | THIOPHENE-2-METHYLAMINE | 3-PHENYL-PROPIONYL CHLORIDE | 508.13 | 2.20 |
| 726 | | FURFURYLAMINE | 3-CYCLO-PENTYL-PROPIONYL CHLORIDE | 484.18 | 2.30 |
| 727 | | TETRAHYDRO-FURFURYLAMINE | 3-CYCLO-PENTYL-PROPIONYL CHLORIDE | 488.21 | 2.27 |

TABLE 4-continued
Compounds No. 722 to 735 of the general formula q-2:
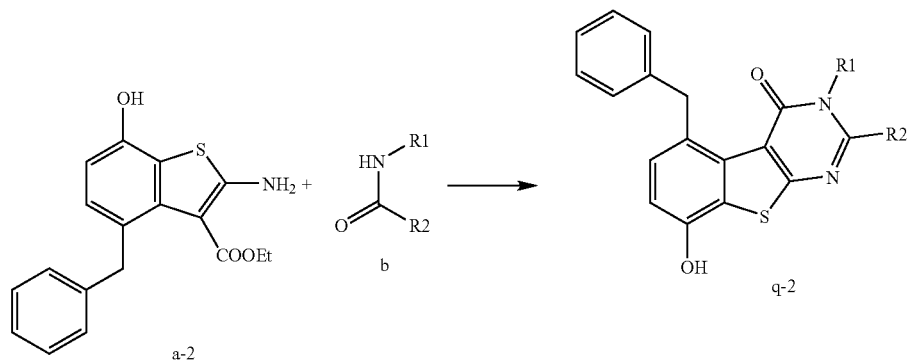
| No | Formula | R1—NH₂ (name) | R2—CO—Cl (name) | MH+ | RT [min] |
|---|---|---|---|---|---|
| 728 | | THIOPHENE-2-ETHYLAMINE | METHOXY-ACETYL CHLORIDE | 462.11 | 2.10 |
| 729 | | BENZYLAMINE | METHOXY-ACETYL CHLORIDE | 442.14 | 2.10 |
| 730 | | THIOPHENE-2-ETHYLAMINE | (3,4-DIMETHOXY-PHENYL) ACETYL CHLORIDE | 568.15 | 2.14 |

TABLE 4-continued
Compounds No. 722 to 735 of the general formula q-2:
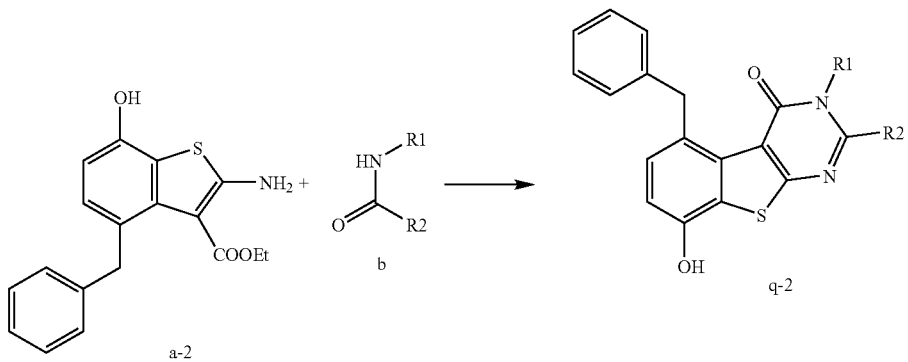
| No | Formula | R1—NH$_2$ (name) | R2—CO—Cl (name) | MH+ | RT [min] |
|---|---|---|---|---|---|
| 731 | | FURFURYLAMINE | (3,4-DIMETHOXY-PHENYL) ACETYL CHLORIDE | 538.16 | 2.09 |
| 732 | | THIOPHENE-2-METHYLAMINE | 2-ETHYL-HEXANOYL CHLORIDE | 502.17 | 2.31 |
| 733 | | TETRAHYDRO-FURFURYLAMINE | METHOXY-ACETYL CHLORIDE | 436.15 | 2.01 |

TABLE 4-continued
Compounds No. 722 to 735 of the general formula q-2:
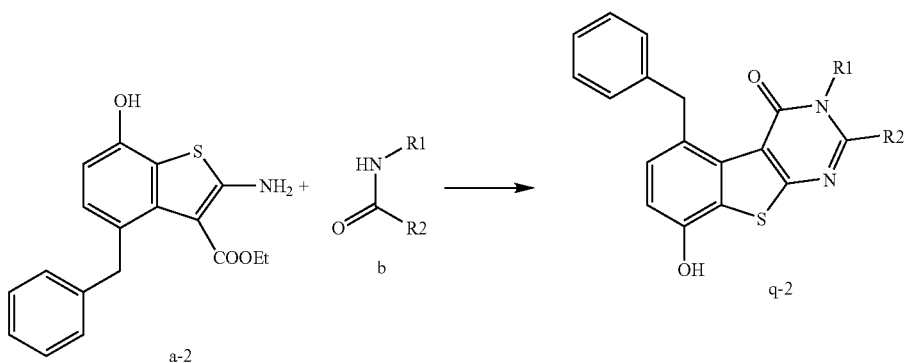
a-2
| No | Formula | R1—NH₂ (name) | R2—CO—Cl (name) | MH+ | RT [min] |
|---|---|---|---|---|---|
| 734 | 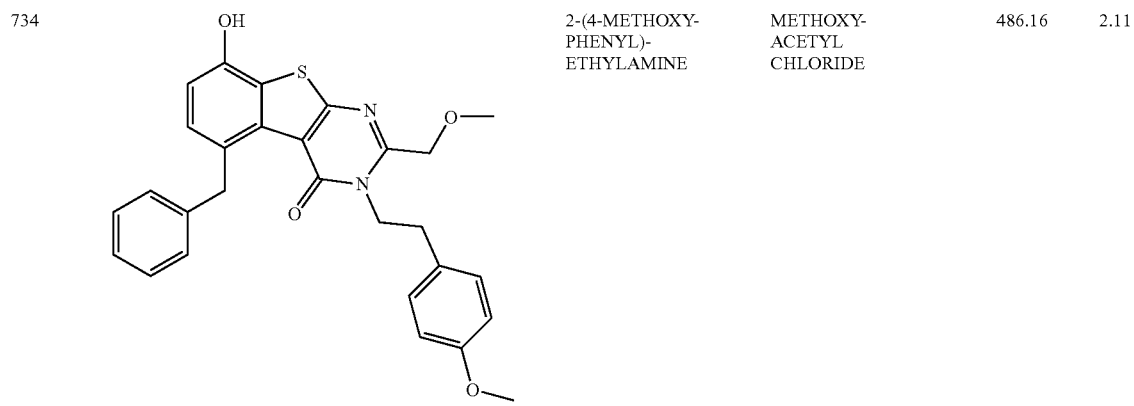 | 2-(4-METHOXY-PHENYL)-ETHYLAMINE | METHOXY-ACETYL CHLORIDE | 486.16 | 2.11 |
| 735 | 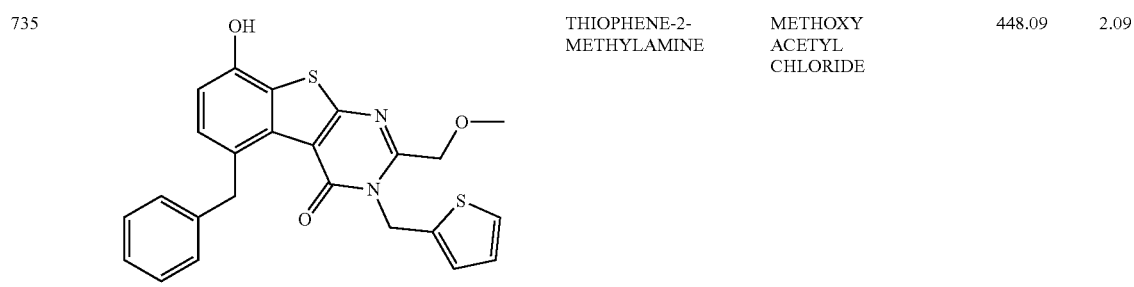 | THIOPHENE-2-METHYLAMINE | METHOXY ACETYL CHLORIDE | 448.09 | 2.09 |

TABLE 5
Compounds No. 736 to 776 of the general formula q-3:
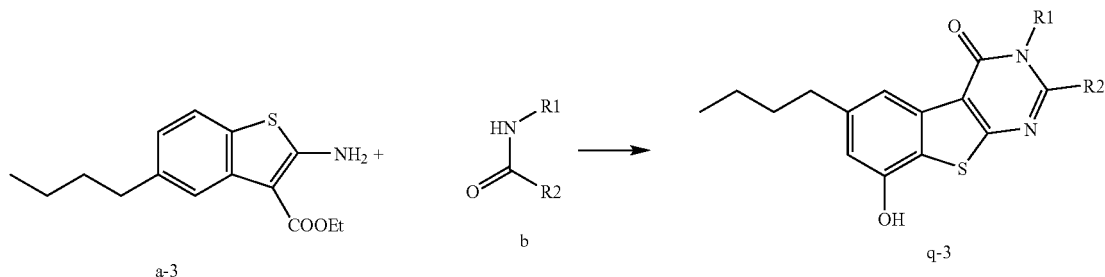
| No | Formula | R1—NH$_2$ (name) | R2—CO—Cl (name) | MH+ | RT [min] |
|---|---|---|---|---|---|
| 736 | | 3,4-METHYLENE-DIOXYBENZYL-AMINE | 3-PHENYL-PROPIONYL CHLORIDE | 512.18 | 2.22 |
| 737 | | THIOPHENE-2-ETHYLAMINE | 3-PHENYL-PROPIONYL CHLORIDE | 488.16 | 2.25 |
| 738 | | FURFURYLAMINE | 3-PHENYL-PROPIONYL CHLORIDE | 458.17 | 2.18 |
| 739 | | BENZYLAMINE | 3-PHENYL-PROPIONYL CHLORIDE | 468.19 | 2.25 |

TABLE 5-continued
Compounds No. 736 to 776 of the general formula q-3:
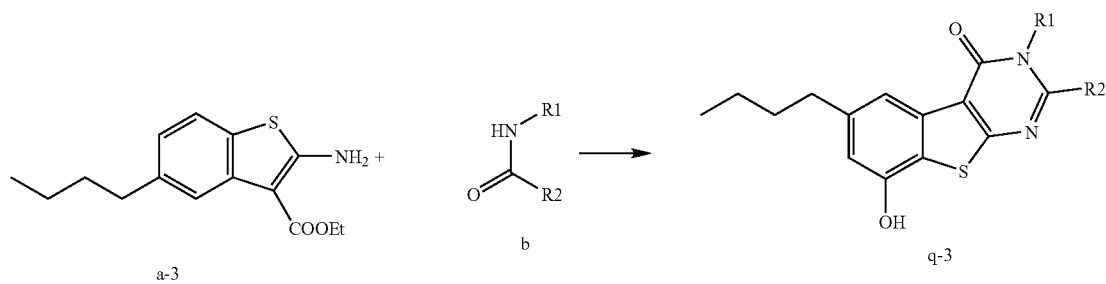
| No | Formula | R1—NH₂ (name) | R2—CO—Cl (name) | MH+ | RT [min] |
|---|---|---|---|---|---|
| 740 | | THIOPHENE-2-ETHYLAMINE | 2-FUROYL CHLORIDE | 450.11 | 2.22 |
| 741 | | BENZYLAMINE | 2-FUROYL CHLORIDE | 430.14 | 2.15 |
| 742 | | THIOPHENE-2-ETHYLAMINE | PHENYLACETYL CHLORIDE | 474.14 | 2.24 |

TABLE 5-continued

Compounds No. 736 to 776 of the general formula q-3:

| No | Formula | R1—NH$_2$ (name) | R2—CO—Cl (name) | MH+ | RT [min] |
|---|---|---|---|---|---|
| 743 | | FURFURYLAMINE | PHENYLACETYL CHLORIDE | 444.15 | 2.18 |
| 744 | | BENZYLAMINE | PHENYLACETYL CHLORIDE | 454.17 | 2.22 |
| 745 | | THIOPHENE-2-ETHYLAMINE | 2-METHOXY-BENZOYL-CHLORIDE | 490.14 | 2.15 |
| 746 | | BENZYLAMINE | 2-METHOXY-BENZOYL CHLORIDE | 470.17 | 2.15 |

TABLE 5-continued
Compounds No. 736 to 776 of the general formula q-3:
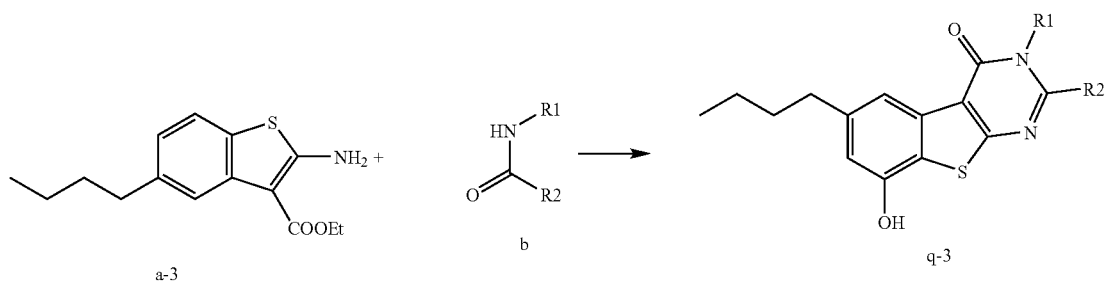
| No | Formula | R1—NH₂ (name) | R2—CO—Cl (name) | MH+ | RT [min] |
|---|---|---|---|---|---|
| 747 | | TETRAHYDRO-FURFURYLAMINE | 3-PHENYL-PROPIONYL CHLORIDE | 462.20 | 2.18 |
| 748 | | 2-(4-METHOXY-PHENYL)-ETHYLAMINE | 3-PHENYL-PROPIONYL CHLORIDE | 512.21 | 2.28 |
| 749 | | THIOPHENE-2-METHYLAMINE | 3-PHENYL-PROPIONYL CHLORIDE | 474.14 | 2.22 |

TABLE 5-continued
Compounds No. 736 to 776 of the general formula q-3:
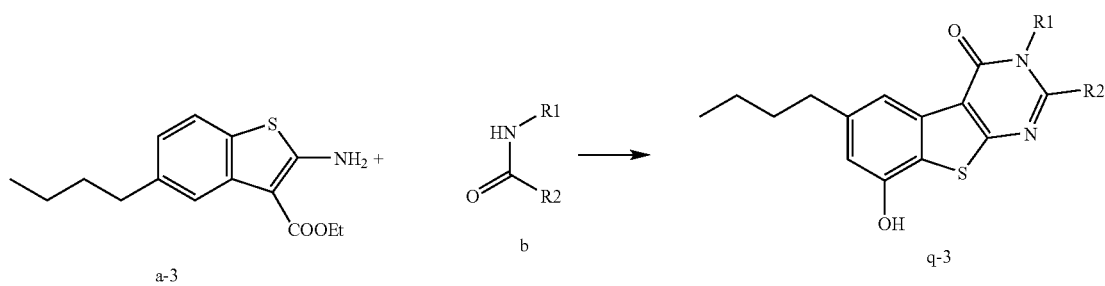
| No | Formula | R1—NH$_2$ (name) | R2—CO—Cl (name) | MH+ | RT [min] |
|---|---|---|---|---|---|
| 750 | | TETRAHYDRO-FURFURYLAMINE | 2-FUROYL CHLORIDE | 424.15 | 2.08 |
| 751 | | TETRAHYDRO-FURFURYLAMINE | PHENYLACETYL CHLORIDE | 448.18 | 2.18 |
| 752 | | 2-(4-METHOXY-PHENYL)-ETHYLAMINE | PHENYLACETYL CHLORIDE | 498.20 | 2.26 |

TABLE 5-continued
Compounds No. 736 to 776 of the general formula q-3:
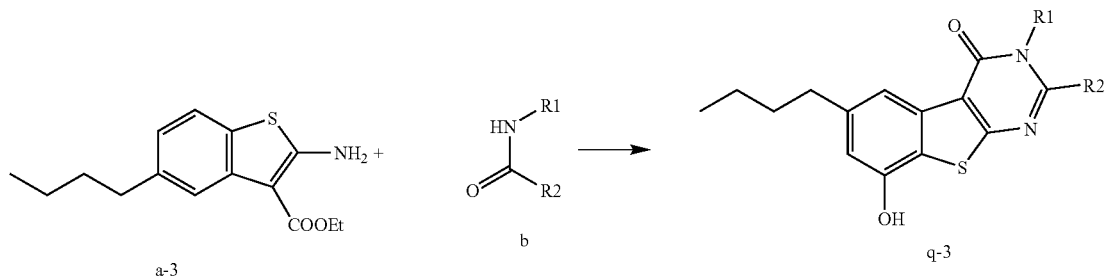
| No | Formula | R1—NH₂ (name) | R2—CO—Cl (name) | MH+ | RT [min] |
|----|---------|---------------|-----------------|-----|----------|
| 753 | | THIOPHENE-2-METHYLAMINE | PHENYLACETYL CHLORIDE | 460.13 | 2.20 |
| 754 | | 3,4-METHYLENE-DIOXY-BENZYLAMINE | 3-CYCLOPENTYL-PROPIONYL CHLORIDE | 504.21 | 2.39 |
| 755 | | THIOPHENE-2-ETHYLAMINE | 3-CYCLOPENTYL-PROPIONYL CHLORIDE | 480.19 | 2.44 |
| 756 | | FURFURYLAMINE | 3-CYCLOPENTYL-PROPIONYL CHLORIDE | 450.20 | 2.31 |

TABLE 5-continued
Compounds No. 736 to 776 of the general formula q-3:
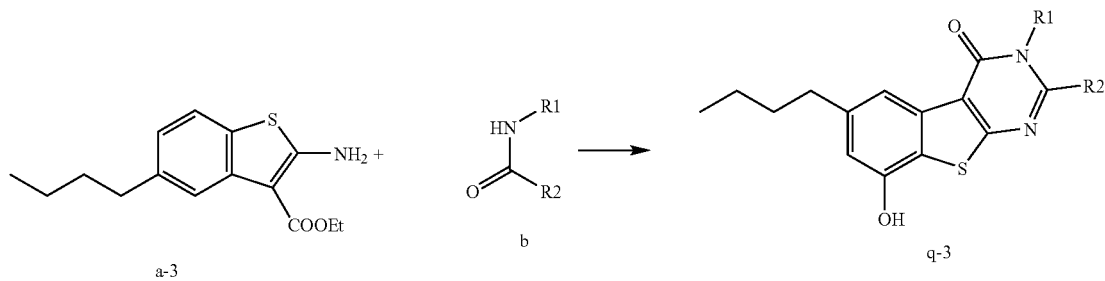
| No | Formula | R1—NH$_2$ (name) | R2—CO—Cl (name) | MH+ | RT [min] |
|---|---|---|---|---|---|
| 757 | | BENZYLAMINE | 3-CYCLOPENTYL-PROPIONYL CHLORIDE | 460.22 | 2.44 |
| 758 | | TETRAHYDRO-FURFURYLAMINE | 3-CYCLOPENTYL-PROPIONYL CHLORIDE | 454.23 | 2.33 |
| 759 | | 2-(4-METHOXY-PHENYL)-ETHYLAMINE | 3-CYCLOPENTYL-PROPIONYL CHLORIDE | 504.24 | 2.45 |
| 760 | | 3-(AMINO-METHYL)-PYRIDINE | 2-ETHYL-HEXANOYL CHLORIDE | 463.23 | 2.18 |

TABLE 5-continued
Compounds No. 736 to 776 of the general formula q-3:
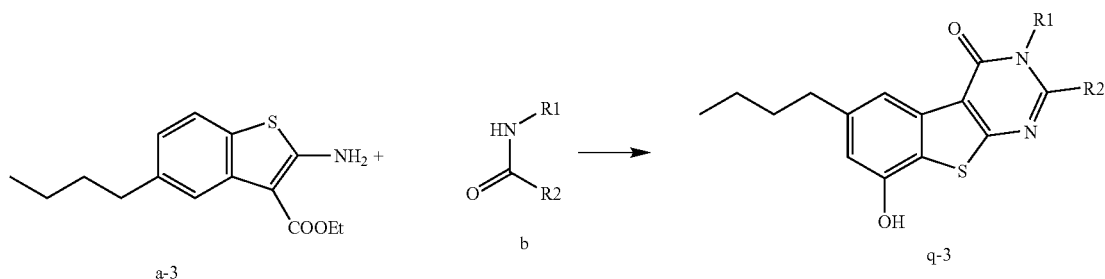
| No | Formula | R1—NH₂ (name) | R2—CO—Cl (name) | MH+ | RT [min] |
|---|---|---|---|---|---|
| 761 | | THIOPHENE-2-ETHYLAMINE | 2-ETHYL-HEXANOYL CHLORIDE | 428.21 | 2.46 |
| 762 | | BENZYLAMINE | 2-ETHYL-HEXANOYL CHLORIDE | 462.23 | 2.45 |
| 763 | | 3,4-METHYLENE-DIOXYBEN-ZYLAMINE | METHOXY-ACETYL CHLORIDE | 452.14 | 2.11 |

TABLE 5-continued
Compounds No. 736 to 776 of the general formula q-3:
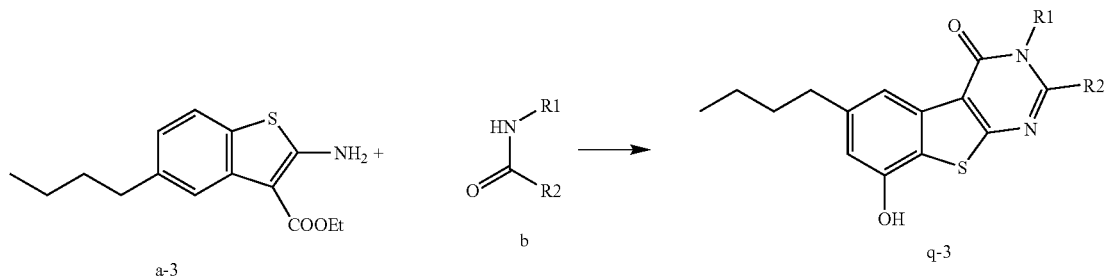
| No | Formula | R1—NH₂ (name) | R2—CO—Cl (name) | MH+ | RT [min] |
|---|---|---|---|---|---|
| 764 | | THIOPHENE-2-ETHYLAMINE | METHOXY-ACETYL CHLORIDE | 428.12 | 2.12 |
| 765 | | FURFURYLAMINE | METHOXY-ACETYL CHLORIDE | 398.13 | 2.07 |
| 766 | | BENZYLAMINE | METHOXY-ACETYL CHLORIDE | 408.15 | 2.11 |
| 767 | | 3,4-METHYLENE-DIMETHOXY-DIOXY-BENZYLAMINE | (3,4-DIMETHOXY-PHENYL)-ACETYL CHLORIDE | 558.18 | 2.14 |

TABLE 5-continued
Compounds No. 736 to 776 of the general formula q-3:
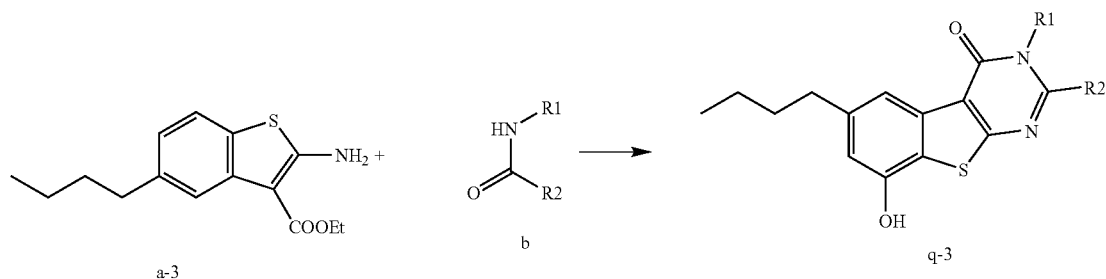
| No | Formula | R1—NH$_2$ (name) | R2—CO—Cl (name) | MH+ | RT [min] |
|---|---|---|---|---|---|
| 768 | | FURFURYLAMINE | (3,4-DIMETHOXY-PHENYL)-ACETYL CHLORIDE | 504.17 | 2.11 |
| 769 | | BENZYLAMINE | (3,4-DIMETHOXY-PHENYL)-ACETYL CHLORIDE | 514.19 | 2.15 |
| 770 | | TETRAHYDRO-FURFURYLAMINE | 2-ETHYL-HEXANOYL CHLORIDE | 456.24 | 2.36 |

TABLE 5-continued
Compounds No. 736 to 776 of the general formula q-3:
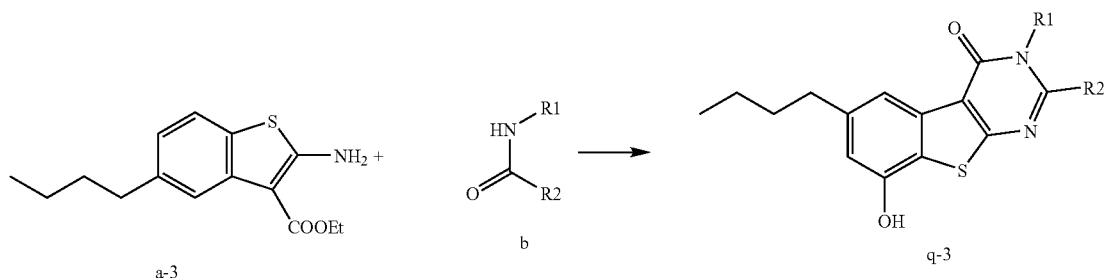
| No | Formula | R1—NH₂ (name) | R2—CO—Cl (name) | MH+ | RT [min] |
|---|---|---|---|---|---|
| 771 | | 2-(4-METHOXY-PHENYL)-ETHYLAMINE | 2-ETHYL-HEXANOYL CHLORIDE | 506.26 | 2.50 |
| 772 | | TETRAHYDRO-FURFURYLAMINE | METHOXY-ACETYL CHLORIDE | 402.16 | 2.05 |
| 773 | | 2-(4-METHOXY-PHENYL)-ETHYLAMINE | METHOXY-ACETYL CHLORIDE | 452.18 | 2.15 |

TABLE 5-continued
Compounds No. 736 to 776 of the general formula q-3:
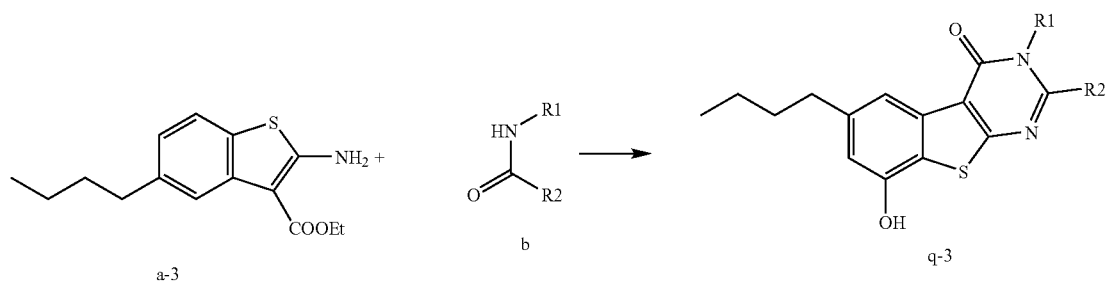
| No | Formula | R1—NH₂ (name) | R2—CO—Cl (name) | MH+ | RT [min] |
|---|---|---|---|---|---|
| 774 | | THIOPHENE-2-METHYLAMINE | METHOXY-ACETYL CHLORIDE | 414.11 | 2.10 |
| 775 | | TETRAHYDRO-FURFURYLAMINE | (3,4-DIMETHOXY-PHENYL)-ACETYL CHLORIDE | 508.20 | 2.09 |
| 776 | | THIOPHENE-2-METHYLAMINE | (3,4-DIMETHOXY-PHENYL)-ACETYL CHLORIDE | 520.15 | 2.14 |

TABLE 6
Compounds No. 777 to 803 of the general formula q-4:
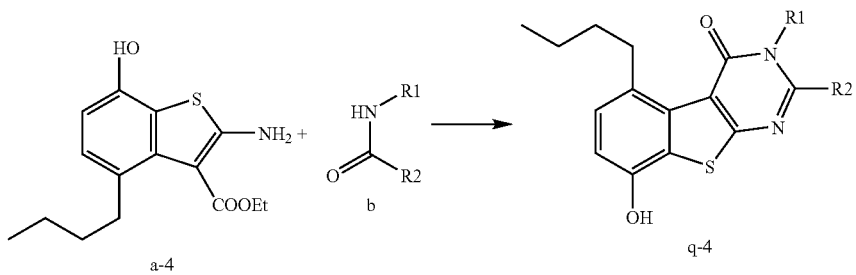
| No | Formula | R1-NH₂ (name) | R2-CO—Cl (name) | MH+ | RT [min] |
|---|---|---|---|---|---|
| 777 | | 3-(AMINOMETHYL)-PYRIDINE | 3-PHENYL-PROPIONYL CHLORIDE | 469.18 | 2.13 |
| 778 | | THIOPHENE-2-ETHYLAMINE | 3-PHENYL-PROPIONYL CHLORIDE | 488.16 | 2.28 |
| 779 | | FURFURYLAMINE | 3-PHENYL-PROPIONYL CHLORIDE | 458.17 | 2.23 |
| 780 | | BENZYLAMINE | 3-PHENYL-PROPIONYL CHLORIDE | 468.19 | 2.29 |

TABLE 6-continued
Compounds No. 777 to 803 of the general formula q-4:
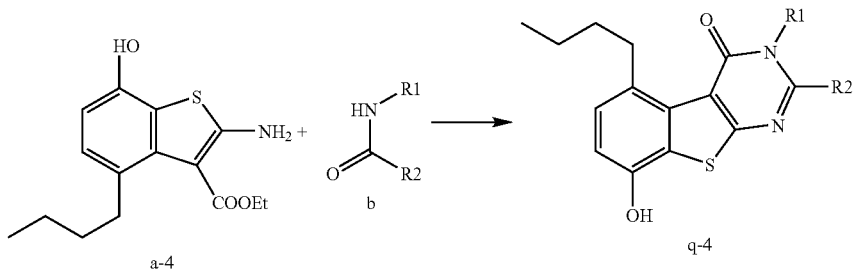
| No | Formula | R1-NH₂ (name) | R2-CO—Cl (name) | MH+ | RT [min] |
|---|---|---|---|---|---|
| 781 | | 3-(AMINO-METHYL)-PYRIDINE | PHENYL-ACETYL-CHLORIDE | 455.17 | 2.07 |
| 782 | | THIOPHENE-2-ETHYLAMINE | PHENYLACETYL CHLORIDE | 474.14 | 2.26 |
| 783 | | FURFURYLAMINE | PHENYLACETYL CHLORIDE | 444.15 | 2.21 |
| 784 | | BENZYLAMINE | PHENYLACETYL CHLORIDE | 454.17 | 2.26 |

TABLE 6-continued
Compounds No. 777 to 803 of the general formula q-4:
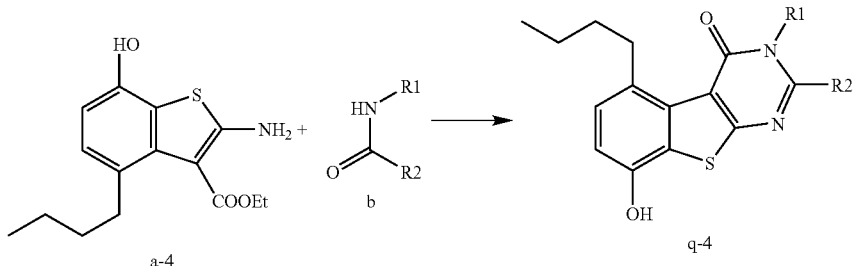
| No | Formula | R1-NH₂ (name) | R2-CO—Cl (name) | MH+ | RT [min] |
|---|---|---|---|---|---|
| 785 | | 2-(4-METHOXY-PHENYL)-ETHYLAMINE | 3-PHENYL-PROPIONYL CHLORIDE | 512.21 | 2.32 |
| 786 | | TETRAHYDRO-FURFURYLAMINE | PHENYLACETYL CHLORIDE | 448.18 | 2.21 |
| 787 | | ETHANOLAMINE | PHENYLACETYL CHLORIDE | 408.15 | 2.03 |

TABLE 6-continued

Compounds No. 777 to 803 of the general formula q-4:

| No | Formula | R1-NH₂ (name) | R2-CO—Cl (name) | MH+ | RT [min] |
|---|---|---|---|---|---|
| 788 | | THIOPHENE-2-ETHYLAMINE | 3-CYCLOPENTYL-PROPIONYL CHLORIDE | 480.19 | 2.47 |
| 789 | | FURFURYLAMINE | 3-CYCLOPENYL-PROPIONYL CHLORIDE | 450.20 | 2.38 |
| 790 | | BENZYLAMINE | 3-CYCLOPENTYL-PROPIONYL CHLORIDE | 460.22 | 2.45 |
| 791 | | TETRAHYDRO-FURFURYLAMINE | 3-CYCLOPENTYL-PROPIONYL CHLORIDE | 454.23 | 2.36 |

TABLE 6-continued
Compounds No. 777 to 803 of the general formula q-4:
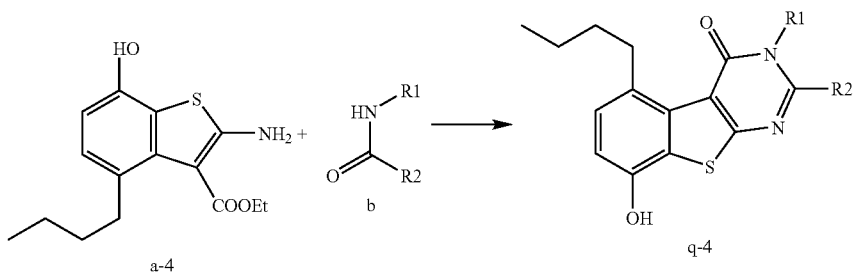
| No | Formula | R1-NH₂ (name) | R2-CO—Cl (name) | MH+ | RT [min] |
|---|---|---|---|---|---|
| 792 | | 2-(4-METHOXY-PHENYL)-ETHYLAMINE | 3-CYCLOPENTYL-PROPIONYL CHLORIDE | 504.24 | 2.49 |
| 793 | | THIOPHENE-2-METHYLAMINE | 3-CYCLOPENTYL-PROPIONYL CHLORIDE | 466.17 | 2.43 |
| 794 | | TETRAHYDRO-FURFURYLAMINE | 3-FLUORO-BENZOYL CHLORIDE | 452.55 | |

TABLE 6-continued
Compounds No. 777 to 803 of the general formula q-4:
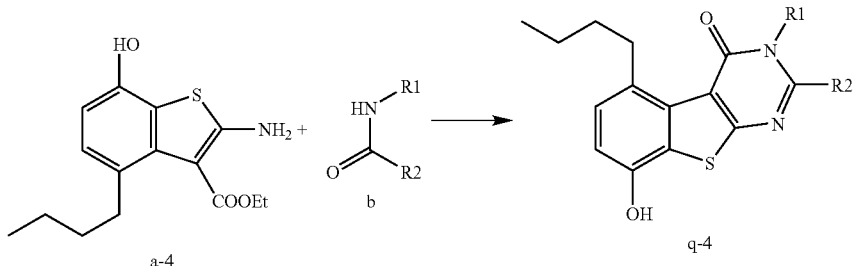
| No | Formula | R1-NH₂ (name) | R2-CO—Cl (name) | MH+ | RT [min] |
|---|---|---|---|---|---|
| 795 | | 2-AMINO-5-METHYL-THIAZOLE | 3-FLUORO-BENZOYL CHLORIDE | 465.10 | 2.27 |
| 796 | | THIOPHENE-2-ETHYLAMINE | 2-ETHYL-HEXANOYL CHLORIDE | 482.21 | 2.50 |
| 797 | | BENZYLAMINE | 2-ETHYL-HEXANOYL CHLORIDE | 462.23 | 2.44 |

TABLE 6-continued
Compounds No. 777 to 803 of the general formula q-4:
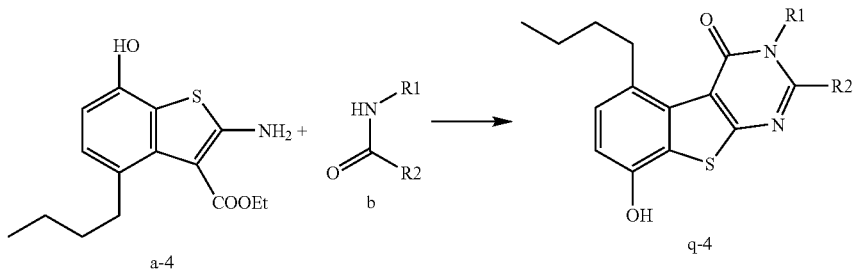
| No | Formula | R1-NH₂ (name) | R2-CO—Cl (name) | MH+ | RT [min] |
|---|---|---|---|---|---|
| 798 | | 3,4-METHYLENE-DIOXYBENZYL-AMINE | METHOXY-ACETYL CHLORIDE | 452.14 | 2.12 |
| 799 | | BENZYLAMINE | METHOXY-ACETYL CHLORIDE | 408.15 | 2.13 |
| 800 | | 3,4-METHYLENE-DIOXYBENZYL | (3,4-DIMETHOXY-PHENYL)ACETYL CHLORIDE | 558.18 | 2.15 |
| 801 | | FURFURYLAMINE | (3,4-DIMETHOXY-PHENYL)ACETYL CHLORIDE | 504.17 | 2.13 |

TABLE 6-continued

Compounds No. 777 to 803 of the general formula q-4:

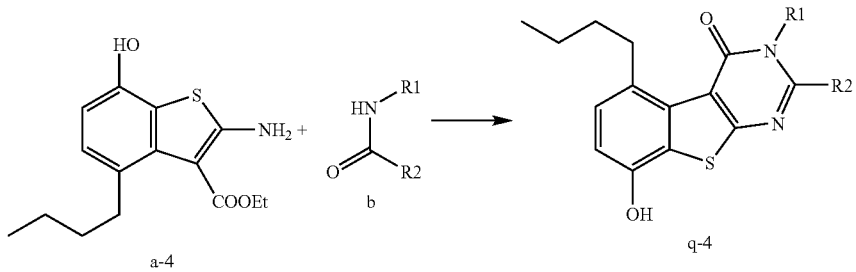

| No | Formula | R1-NH$_2$ (name) | R2-CO—Cl (name) | MH+ | RT [min] |
|---|---|---|---|---|---|
| 802 | (structure shown) | TETRAHYDRO-FURFURYLAMINE | 2-ETHYL-HEXANOYL CHLORIDE | 456.24 | 2.36 |
| 803 | (structure shown) | 2-(4-METHOXY-PHENYL)-ETHYLAMINE | METHOXY-ACETYL CHLORIDE | 452.18 | 2.15 |

Further compounds falling under the scope of general formula (I) can be prepared by a reaction as shown in Scheme 6 using a primary amine R1-NH$_2$ selected from the following table 5 and an acid chloride R2-CO—Cl selected from the following table 6 as starting materials. This mixture is reacted with a particular 2-amino-benzo[b]thiophene-3-carboxylic acid ethyl ester of general formula a-3-OH (e.g. selected from the compounds as displayed in Scheme 7).

TABLE 7

Different primary amines R1—NH$_2$ which can be used as starting materials

R1—NH$_2$ (name)

(S)-(+)-(2,2-DIMETHYL-[1,3]-DIOXOLAN-4-YL)-METHYLAMINE
1-(3-AMINOPROPYL)-2-PYRROLIDINONE
1-AMINOINDAN
2-(2-AMINOETHYL)PYRIDINE
2-AMINO-1-PHENYLETHANOL

TABLE 7-continued

Different primary amines R1—NH$_2$ which can be used as starting materials

R1—NH$_2$ (name)

2-AMINO-5-METHYLTHIAZOLE
2-AMINOACETOPHENONE HYDROCHLORIDE
2-PHENOXYETHYLAMINE
2-THIOPHENEETHYLAMINE
3-(AMINOMETHYL)PYRIDINE
3,4-DICHLOROBENZYLAMINE
3,4-DIHYDROXYBENZYLAMINE
3-AMINOPYRAZINE-2-CARBOXYLIC ACID METHYL ESTER
3-AMINOQUINOLINE
4-(2-AMINOETHYL)BENZENESULFONAMIDE MONOHYDROCHLORIDE
4-(2-AMINOETHYL)MORPHOLINE
4-(AMINOMETHYL)PYRIDINE
4-AMINO-1-BENZYLPIPERIDINE
4-METHYLSULFONYLBENZYLAMINE HYDROCHLORIDE

TABLE 7-continued

Different primary amines R1—NH$_2$ which
can be used as starting materials

R1—NH$_2$ (name)

5-(AMINOMETHYL)-2,3-DIHYDROBENZO[B]FURAN
6-AMINOPHTHALIDE
9-AMINOFLUORENE HYDROCHLORIDE
ANILINE
BENZYLAMINE
CYCLOHEXYLAMINE
CYCLOPROPYLAMINE
ETHANOLAMINE
FURFURYLAMINE
METHYL 4-AMINOBUTYRATE HYDROCHLORIDE
N-BUTYLAMINE
NN-DIMETHYLETHYLENEDIAMINE
PHENETHYLAMINE
PIPERONYLAMINE
TETRAHYDROFURFURYLAMINE
THIOPHENE-2-METHYLAMINE

TABLE 8

Different acid chloride R2—CO—Cl which
can be used as starting materials

R2—CO—Cl (name)

1-PHENYL-5-(TRIFLUOROMETHYL)PYRAZOLE-4-CARBONYL CHLORIDE
2-(4-CHLOROPHENOXY)-2-METHYLPROPANOYL CHLORIDE
2-(4-CHLOROPHENOXY)PYRIDINE-3-CARBONYL CHLORIDE
2,4-DICHLOROBENZOYL CHLORIDE
2,4-DIFLOUROBENZOYL CHLORIDE
2,6-DIFLUOROBENZOYL CHLORIDE
2-ETHYLHEXANOYL CHLORIDE
2-FUROYL CHLORIDE
2-METHOXYBENZOYL CHLORIDE
2-NAPHTHOYL CHLORIDE
3,3-DIMETHYLACRYLOYL CHLORIDE
3,4-DICHLOROBENZOYL CHLORIDE
3,4-DIMETHOXYPHENYLACETYL CHLORIDE
3,5-BIS(TRIFLUOROMETHYL)BENZOYL CHLORIDE
3-CYANOBENZOYL CHLORIDE
3-CYCLOPENTYLPROPIONYL CHLORIDE
3-FLUOROBENZOYL CHLORIDE
4-[(DIPROPYLAMINO)SULFONYL]BENZENE-1-CARBONYL CHLORIDE
4-CYANOBENZOYL CHLORIDE
BENZO[B]THIOPHENE-2-CARBONYL Chloride
CYCLOPROPANECARBONYL CHLORIDE
DIPHENYLACETYL CHLORIDE
ETHYL SUCCINYL CHLORIDE
HYDROCINNAMOYL CHLORIDE
ISONICOTINOYL CHLORIDE HYDROCHLORIDE
METHOXYACETYL CHLORIDE
METHYL MALONYL CHLORIDE
METHYL OXALYL CHLORIDE
PHENYLACETYL CHLORIDE Biological Testing Materials and Methods 1. Inhibition of the 17β-hydroxysteroid dehydrocienase type 1, type 2 and type 3 enzyme The compounds were screened in respect of 17β-HSD enzyme activity in vitro on established MCF-7 cell lines, each stably expressing one of the respective 17β-HSD isoenzymes. The interconversion of substrate by each isoenzyme and the 17β-HSD inhibiting activity of chemical compounds in these cell lines were detected by HPLC system.

Varying amounts of the test compounds were incubated in the growth medium of the 17β-HSD expressing cells together tritium labeled substrate (2 nM estrone for 17β-HSD type 1; 2 nM estradiol for 17β-HSD type 2; and 2 nM androstenedione for 17β-HSD type 3). The medium samples were removed after exact incubation time and the reaction is stopped by trichloroacetic acid (TCA). The samples were analyzed by HPLC-coupled flow scintillation analysis.

For each enzyme type, the HSD-inhibiting activity of an individual test compound was calculated by comparing the conversion of a control sample without any test compound (referred to as "Negative Control") to the (reduced) conversion of the test sample containing the particular compound to be tested (referred to as "Test Sample").

$$\% \text{ inhibition} = 100 \times \frac{\text{Conversion in Negative Control} - \text{Conversion in Test Sample}}{\text{Conversion Negative Control}}$$

The obtained results are shown in Table 3 below. Two concentrations of each compound were used. The number of the compound refers to the numbers indicated in the Experimental Section.

TABLE 9

% Inhibition of the 17(β-HSD enzymes type 1, type 2 and type 3 by the compounds of the invention

| Compound | HSD1 1 μM | HSD1 10 μM | HSD2 1 μM | HSD2 10 μM | HSD3 1 μM | HSD3 10 μM |
|---|---|---|---|---|---|---|
| No. 1 | 0.8 | 21.1 | 7.3 | 17.4 | −8.8 | 6.3 |
| No. 2 | 17.3 | 58.7 | 1.5 | 33.2 | 11.7 | 40.5 |
| No. 3 | 3.2 | 38.4 | −3.2 | 7.8 | −19.4 | 29.1 |
| No. 4 | 20.1 | 30.7 | −4.3 | 20.1 | −7.2 | 6.5 |
| No. 5 | −1.0 | 26.1 | −0.9 | 17.0 | 9.4 | 9.1 |
| No. 6 | 31.8 | 44.2 | 3.8 | 29.7 | 2.1 | 47.1 |
| No. 7 | 12.5 | 38.4 | 8.2 | 27.0 | −17.6 | 5.7 |
| No. 8 | 30.8 | 27.4 | 4.9 | 17.1 | 2.5 | 4.8 |
| No. 9 | 31.9 | 29.9 | −2.6 | −8.9 | 2.7 | 1.4 |
| No. 10 | 12.7 | 35.1 | 18.1 | 23.7 | −4.4 | 10.9 |
| No. 11 | 14.2 | 27.7 | −5.3 | 12.3 | −5.6 | 12.8 |
| No. 12 | 6.3 | 34.5 | 4.2 | 12.3 | 3.1 | 55.5 |
| No. 13 | 28.0 | 43.6 | 19.5 | 19.9 | 3.0 | 59.1 |
| No. 14 | 8.6 | 29.7 | 0.5 | 18.8 | 22.7 | 80.8 |
| No. 15 | −9.9 | −6.5 | −5.5 | 7.3 | 18.5 | 61.2 |
| No. 16 | 1.7 | 33.5 | 5.0 | 20.1 | 75.7 | 100.0 |
| No. 17 | 18.1 | 48.3 | −5.4 | 20.9 | 43.5 | 100.0 |
| No. 18 | 12.1 | 25.9 | 0.0 | 15.1 | 66.1 | 100.0 |
| No. 19 | 10.2 | 32.0 | 4.9 | 21.1 | 32.7 | 100.0 |
| No. 20 | 26.0 | 37.5 | −1.7 | 16.6 | 9.9 | 61.1 |
| No. 21 | −1.8 | −4.4 | −0.8 | 12.7 | −4.8 | 6.4 |
| No. 22 | 26.0 | 38.1 | 13.0 | 14.9 | −1.8 | 28.6 |
| No. 23 | 18.6 | 45.3 | 6.8 | 9.4 | 6.8 | 15.4 |
| No. 24 | −7.5 | 15.4 | 4.1 | 9.7 | 17.1 | 30.9 |
| No. 25 | 5.9 | 13.8 | 5.5 | 7.9 | 25.7 | 29.0 |
| No. 26 | 23.5 | 37.4 | −1.8 | 32.3 | −6.1 | 7.1 |
| No. 27 | 11.2 | 32.3 | 8.5 | 7.2 | −14.4 | 12.2 |
| No. 28 | 2.6 | 18.0 | 12.9 | 16.3 | 1.9 | 16.7 |
| No. 29 | 9.0 | 15.5 | 8.5 | 21.1 | 16.9 | 28.4 |
| No. 30 | 25.4 | 39.7 | 20.2 | 19.1 | −1.2 | 16.3 |
| No. 31 | 12.0 | 39.7 | −0.5 | 5.1 | −1.3 | 10.8 |
| No. 32 | 37.2 | 86.6 | 9.8 | 19.5 | 9.6 | 70.0 |
| No. 33 | 17.6 | 67.3 | 16.3 | 18.7 | 1.9 | 0.1 |
| No. 34 | 12.5 | 64.2 | −1.5 | 25.3 | 15.8 | 100.0 |
| No. 35 | 8.8 | 28.6 | −6.8 | 28.7 | 14.7 | 82.3 |
| No. 36 | 20.7 | 22.4 | −6.8 | 28.7 | −0.9 | 7.6 |
| No. 37 | 9.7 | 21.4 | −0.2 | 9.0 | 9.2 | 22.2 |
| No. 38 | 0.3 | 23.6 | 11.4 | 33.4 | 14.2 | 17.6 |
| No. 39 | 21.1 | 13.2 | 25.0 | 9.5 | 18.5 | 12.8 |
| No. 40 | 15.6 | 25.0 | 13.8 | 5.3 | 3.8 | 16.2 |
| No. 41 | 5.7 | 10.0 | 17.9 | 17.7 | 22.5 | 34.5 |
| No. 42 | 26.8 | 56.0 | −1.9 | −0.5 | 3.2 | 4.0 |
| No. 43 | 12.0 | 23.8 | 18.0 | 15.0 | −2.5 | −0.9 |
| No. 44 | 10.5 | 55.6 | 2.2 | 16.3 | −22.5 | 26.3 |

TABLE 9-continued

% Inhibition of the 17(β-HSD enzymes type 1, type 2 and type 3 by the compounds of the invention

| Compound | HSD1 1 μM | HSD1 10 μM | HSD2 1 μM | HSD2 10 μM | HSD3 1 μM | HSD3 10 μM |
|---|---|---|---|---|---|---|
| No. 45 | −7.7 | −18.3 | 3.5 | 6.5 | −2.2 | 4.1 |
| No. 46 | 32.1 | 72.2 | 44.0 | 20.9 | 31.4 | 37.1 |
| No. 47 | 16.1 | 63.2 | 31.9 | 59.0 | 39.7 | 52.2 |
| No. 48 | 27.4 | 36.5 | 0.8 | 25.6 | 33.7 | 23.4 |
| No. 49 | 24.7 | 86.2 | 20.1 | 36.9 | 12.4 | 52.6 |
| No. 50 | 34.4 | 65.8 | 32.4 | 39.0 | 32.9 | 75.8 |
| No. 51 | 9.9 | 9.1 | 16.6 | 30.7 | n.d. | n.d. |
| No. 52 | 4.7 | 11.6 | 0.1 | 19.1 | −2.4 | 4.3 |
| No. 53 | 52.2 | 71.0 | 22.4 | 60.0 | 32.2 | 52.7 |
| No. 54 | 35.4 | 76.7 | 17.0 | 59.8 | 24.6 | 55.2 |
| No. 55 | 12.6 | 9.6 | 4.8 | 14.8 | n.d. | n.d. |
| No. 56 | 21.3 | 33.2 | 18.8 | 24.5 | 14.7 | 41.9 |
| No. 57 | 23.0 | 47.3 | 17.5 | 28.5 | 19.7 | 57.3 |
| No. 58 | 25.5 | 54.9 | 22.5 | 33.9 | 16.0 | 39.4 |
| No. 59 | 24.0 | 20.8 | 36.7 | 40.0 | 17.6 | 31.7 |
| No. 60 | 16.3 | 36.0 | 44.2 | 76.9 | 10.0 | 45.7 |
| No. 61 | 17.7 | 26.2 | 25.7 | 23.8 | 20.0 | 26.4 |
| No. 62 | 25.8 | 32.0 | 18.9 | 26.4 | 18.0 | 28.0 |
| No. 63 | 28.5 | 23.2 | 32.8 | 48.4 | 21.8 | 25.6 |
| No. 64 | 15.0 | 20.7 | 15.4 | 16.6 | 12.1 | 49.0 |
| No. 65 | 1.2 | 7.8 | 19.2 | 34.6 | 5.0 | 38.0 |
| No. 66 | 7.8 | 8.9 | 27.0 | 37.6 | 0.3 | 7.4 |
| No. 67 | 14.7 | 29.6 | 55.2 | 80.3 | 19.1 | 33.4 |
| No. 68 | 9.0 | 21.5 | 15.5 | 49.0 | 7.3 | 40.7 |
| No. 69 | 4.7 | 10.5 | 10.8 | 11.9 | −1.1 | 3.9 |
| No. 70 | 15.3 | 39.4 | 13.1 | 17.9 | −4.1 | 44.2 |
| No. 71 | 20.7 | 20.8 | 28.9 | 24.5 | 21.9 | 36.0 |
| No. 72 | 15.3 | 15.2 | 18.0 | 53.9 | 16.1 | 64.4 |
| No. 73 | 26.8 | 32.8 | 58.3 | 90.5 | 37.9 | 82.6 |
| No. 74 | 11.7 | 12.2 | 33.2 | 26.1 | 8.3 | 8.3 |
| No. 75 | 14.5 | 11.9 | 20.2 | 23.1 | 5.0 | 17.0 |
| No. 76 | 35.8 | 44.1 | 44.6 | 43.4 | 47.1 | 81.4 |
| No. 77 | 14.9 | 28.6 | 18.5 | 20.5 | 3.1 | 14.7 |
| No. 78 | 7.1 | 28.5 | 9.1 | 7.8 | −4.3 | 27.6 |
| No. 79 | 26.6 | 39.1 | 34.4 | 31.6 | 21.9 | 59.7 |
| No. 80 | 37.0 | 39.3 | 47.3 | 51.0 | 22.7 | 35.4 |
| No. 81 | 33.1 | 16.8 | 32.1 | 35.6 | 7.8 | 26.2 |
| No. 82 | 17.8 | 17.9 | 22.2 | 32.2 | 3.0 | 11.3 |
| No. 83 | 25.4 | 26.3 | 26.1 | 60.1 | 13.5 | 21.0 |
| No. 84 | 10.2 | 22.6 | 26.4 | 63.6 | 4.0 | 33.5 |
| No. 85 | 24.1 | 40.1 | 21.5 | 25.4 | −2.2 | 24.4 |
| No. 86 | 23.6 | 46.6 | 18.9 | 19.5 | 11.3 | 45.7 |
| No. 87 | 26.8 | 67.4 | 24.6 | 23.4 | 13.0 | 31.9 |
| No. 88 | 25.0 | 40.5 | 25.9 | 29.9 | 20.4 | 23.3 |
| No. 89 | 37.7 | 84.7 | 31.2 | 40.1 | 30.9 | 80.0 |
| No. 90 | 15.5 | 24.7 | 16.1 | 22.0 | 4.0 | 11.3 |
| No. 91 | 21.5 | 26.1 | 28.2 | 33.7 | 3.7 | 18.1 |
| No. 92 | 22.0 | 23.3 | 42.7 | 60.9 | 4.7 | 24.3 |
| No. 93 | 13.3 | 11.7 | 43.2 | 57.7 | 19.4 | 26.1 |
| No. 94 | 16.5 | 27.2 | 25.7 | 31.5 | 2.2 | 21.1 |
| No. 95 | 17.0 | 59.6 | 6.9 | 31.2 | 9.9 | 62.4 |
| No. 96 | 19.5 | 65.1 | 17.2 | 21.9 | 13.0 | 37.5 |
| No. 97 | 18.1 | 29.4 | 25.2 | 44.6 | −5.9 | 11.5 |
| No. 98 | 28.2 | 69.1 | 46.6 | 82.8 | 16.6 | 63.3 |
| No. 99 | 21.8 | 64.5 | 46.1 | 85.4 | 15.9 | 68.9 |
| No. 100 | 23.5 | 66.7 | 28.8 | 81.3 | −0.8 | 7.7 |
| No. 101 | 14.1 | 26.0 | 18.0 | 30.0 | 5.7 | 7.8 |
| No. 102 | 14.8 | 57.5 | 13.6 | 18.6 | 6.7 | 51.2 |
| No. 103 | 16.2 | 70.6 | 30.7 | 49.7 | −7.7 | 51.8 |
| No. 104 | 20.2 | 42.6 | 26.6 | 47.9 | −5.0 | 51.4 |
| No. 105 | 29.8 | 61.2 | 50.7 | 85.9 | 17.7 | 67.3 |
| No. 106 | 28.8 | 72.5 | 50.0 | 86.2 | 8.1 | 71.1 |
| No. 107 | −14.2 | 24.7 | 25.4 | 45.7 | 3.2 | 44.3 |
| No. 108 | 5.2 | 11.0 | 9.6 | 7.4 | 0.8 | 9.8 |
| No. 109 | −0.2 | 20.7 | 6.0 | 9.7 | 0.6 | 11.6 |
| No. 110 | 18.1 | 49.0 | 24.1 | 30.3 | 11.8 | 35.5 |
| No. 111 | 23.8 | 56.9 | 24.7 | 48.7 | 7.3 | 41.5 |
| No. 112 | 28.3 | 54.4 | 14.6 | 46.3 | 7.0 | 49.4 |
| No. 113 | 22.2 | 57.6 | 8.2 | 7.7 | 2.7 | 48.9 |
| No. 114 | 15.5 | 55.9 | 15.5 | 25.3 | 2.4 | 32.0 |
| No. 115 | 22.9 | 70.3 | 18.7 | 19.5 | 7.6 | 20.7 |
| No. 116 | 12.5 | 41.4 | 28.0 | 26.1 | 8.1 | 21.2 |
| No. 117 | 39.3 | 62.2 | 19.7 | 20.7 | 19.7 | 44.1 |
| No. 118 | 31.0 | 51.5 | 23.6 | 24.4 | 10.8 | 24.4 |
| No. 119 | 9.6 | 27.9 | 25.1 | 30.1 | 2.3 | 19.1 |
| No. 120 | 17.6 | 52.1 | 19.9 | 35.4 | 12.4 | 38.4 |
| No. 121 | 37.8 | 23.3 | 44.0 | 25.0 | 17.5 | 18.4 |
| No. 122 | 13.9 | 49.0 | 15.4 | 26.2 | 9.4 | 56.2 |
| No. 123 | 19.4 | 62.9 | 24.6 | 40.2 | 1.3 | 29.1 |
| No. 124 | 40.2 | 73.3 | 0.2 | 17.6 | 8.3 | 42.4 |
| No. 125 | 34.7 | 49.9 | 11.7 | 19.8 | 10.9 | 21.0 |
| No. 126 | 27.4 | 59.3 | 6.6 | −9.0 | 8.0 | 36.3 |
| No. 127 | 40.3 | 91.3 | −0.4 | 5.7 | 4.8 | 29.3 |
| No. 128 | 17.9 | 25.9 | −4.9 | 0.0 | 4.7 | 6.3 |
| No. 129 | 46.8 | 85.3 | 23.9 | 53.1 | 34.7 | 78.6 |
| No. 131 | 37.7 | 84.7 | 31.2 | 40.1 | 30.9 | 80.1 |
| No. 132 | 23.8 | 53.9 | 22.8 | 16.9 | 16.9 | 24.9 |
| No. 133 | 18.2 | 58.4 | 6.8 | 24.3 | 18.7 | 37.7 |
| No. 134 | 16.0 | 7.9 | 9.9 | 11.6 | 17.2 | 21.6 |
| No. 135 | 54.0 | 96.6 | 19.1 | 34.6 | 21.8 | 93.1 |
| No. 136 | 3.6 | 8.5 | 23.2 | 8.8 | 3.5 | 11.0 |
| No. 137 | 35.0 | 76.0 | 28.1 | 32.9 | 19.3 | 49.8 |
| No. 138 | 20.6 | 21.5 | 25.7 | 24.8 | 6.8 | 23.0 |
| No. 140 | 39.5 | 81.0 | 10.3 | 36.8 | 8.8 | 63.5 |
| No. 141 | 25.0 | 58.9 | 3.0 | 1.1 | 2.7 | 22.7 |
| No. 142 | 32.8 | 52.7 | 6.2 | 10.5 | 8.0 | 24.1 |
| No. 143 | 40.1 | 74.2 | 4.5 | 17.7 | 12.5 | 52.1 |
| No. 144 | 23.5 | 33.7 | 13.6 | 31.1 | 12.7 | 19.3 |
| No. 145 | 23.6 | 21.2 | 25.9 | 25.7 | 19.2 | 21.6 |
| No. 146 | 7.3 | 50.9 | 14.3 | 5.1 | 14.7 | 37.9 |
| No. 147 | 11.4 | 12.5 | 0.1 | 17.2 | 10.3 | 9.1 |
| No. 148 | 27.0 | 53.2 | 29.1 | 42.0 | 53.7 | 97.9 |
| No. 149 | 17.8 | 18.3 | 34.6 | 29.9 | 31.0 | 59.8 |
| No. 150 | 0.4 | 3.4 | 6.4 | 11.4 | −1.1 | 22.0 |
| No. 151 | 21.2 | 52.7 | 14.6 | 22.1 | n.d. | n.d. |
| No. 627 | 25.2 | 26.6 | 27.1 | 22.6 | 10.7 | 33.9 |
| No. 628 | 11.4 | 32.4 | −0.9 | 22.5 | 12.4 | 36.1 |
| No. 629 | 22.4 | 33.1 | 39.1 | 71.7 | 19.3 | 35.9 |
| No. 630 | 25.1 | 21.0 | 24.7 | 19.9 | 10.9 | 35.4 |
| No. 633 | 30.6 | 60.9 | 33.2 | 64.6 | 62.3 | 91.7 |
| No. 634 | 16.8 | 17.9 | 16.8 | 20.1 | 13.3 | 56.4 |
| No. 635 | 4.9 | 18.9 | 15.4 | 50.8 | 11.6 | 62.5 |
| No. 639 | 22.6 | 39.3 | 18.2 | 24.0 | 33.6 | 76.2 |
| No. 641 | 20.4 | 35.0 | 10.5 | 36.9 | 13.2 | 55.7 |
| No. 643 | 15.7 | 34.2 | 20.1 | 43.3 | 23.4 | 46.1 |
| No. 644 | 29.8 | 28.4 | 27.6 | 26.4 | 13.9 | 19.8 |
| No. 645 | 17.2 | 29.1 | 48.8 | 75.5 | 21.7 | 22.7 |
| No. 648 | 18.0 | 24.6 | 16.0 | 40.2 | 17.7 | 70.1 |
| No. 659 | 14.4 | 35.4 | 16.3 | 33.9 | 22.9 | 76.1 |
| No. 660 | 21.7 | 37.1 | 19.8 | 48.9 | 16.6 | 19.9 |
| No. 663 | 26.3 | 24.6 | 37.4 | 57.6 | 12.4 | 45.6 |
| No. 667 | 20.1 | 51.9 | 20.9 | 63.7 | 16.9 | 37.0 |
| No. 683 | 16.8 | 32.9 | 9.2 | 18.8 | 8.1 | 37.7 |
| No. 684 | 24.6 | 63.3 | 9.2 | 11.0 | 24.7 | 10.5 |
| No. 685 | 16.6 | 31.2 | 22.7 | 19.9 | 5.1 | 13.8 |
| No. 686 | 2.1 | 15.0 | 2.1 | 4.3 | −1.1 | 7.1 |
| No. 687 | −3.3 | 5.5 | 8.3 | 5.6 | 1.7 | 7.3 |
| No. 688 | 21.5 | 21.6 | 25.4 | 14.2 | 14.4 | 22.3 |
| No. 689 | 7.7 | 5.7 | −3.0 | 5.7 | −2.4 | 17.4 |
| No. 690 | 17.3 | 19.2 | 14.2 | 23.5 | −2.7 | 6.4 |
| No. 691 | 7.0 | 22.6 | 2.1 | −6.3 | −5.3 | 11.9 |
| No. 692 | 18.0 | 28.6 | 12.7 | 21.0 | 9.8 | 35.0 |
| No. 693 | 15.0 | 5.7 | 18.1 | 18.2 | 5.2 | 16.8 |
| No. 694 | 12.1 | 10.9 | 6.2 | 15.8 | 5.8 | 21.1 |
| No. 699 | 5.9 | 7.3 | 16.1 | 19.6 | 7.4 | 8.5 |

2. Estrogen Receptor Binding Assay

The binding affinity of the compounds of the invention to the estrogen receptor α and to the estrogen receptor β may be determined according to the in vitro ER binding assays described by Koffmann et al. [Koffmann B et al. (1991) J. Steroid. Biochem. Mol. Biol. 38:135]. Alternatively, an estro- 3. Estrogen Receptor Transactivation Assays Compounds of the invention showing binding affinity towards the estrogen receptor may be further tested with regard to their individual estrogenic or anti-estrogenic potential (agonistic binding or antagonistic binding to the ERα or ERβ). The determination of the estrogen receptor agonist activity may be performed according to an in vitro assay system using the MMTV-ERE-LUC reporter system which is for example described within U.S. patent application Ser. No. 10/289079 (published as US 2003/0170292):

To assay estrogen receptor agonist activity, Hela cells are grown in 24-well microtiter plates and then transiently co-transfected with two plasmids using lipofectamine. The first plasmid comprises DNA encoding human estrogen receptor (either ER-alpha or ER-beta), and the second plasmid comprises an estrogen-driven reporter system comprising: a luciferase reporter gene (LUC) whose transcription is under the control of upstream regulatory elements comprising 4 copies of the vitellogenin estrogen response element (ERE) cloned into the mouse mammary tumor virus (MMTV) promoter (the full name for the reporter system being "MMTV-ERE-LUC"). Cells are exposed to the compounds of the invention in RPMI 1640 medium, supplemented with 10% charcoal-treated fetal calf serum, 2 mM L-glutamine, 0.1 mM non-essential amino acids and 1 mM sodium pyruvate for 42-48 hours at 37° C. in a 5% carbon dioxide incubator. Concurrently, cells exposed to estradiol (1 nM) serve as positive controls. Replicate wells exposed to the solvent in which the compounds of the invention are dissolved (i.e. ethanol or methanol) are used as negative controls. After the 42-48 hr incubation period, cells are rinsed with phosphate buffered saline (PBS), lysis buffer (Promega Corp) is added, and cell lysates are collected for measurement of luciferase activity with a luminometer. Estrogenic activity of the compounds of the invention is expressed as fold-increase in luciferase activity as compared to that observed in negative control cells.

Alternatively, the determination of the estrogen receptor transactivation activity (estrogenicity assay or agonist assay) and of the inhibitory potency of transactivation activity (anti-estrogenicity assay or antagonist assay) may be performed according to international patent application PCT/US/17799 (published as WO 00/07996).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

CITED LITERATURE

The following documents provide background information and are hereby incorporated herein by reference.

Andersson S. (1995) "Molecular genetics of androgenic 17β-Hydroxysteroid Dehydrogenases. J. Steroid Biochem. Molec. Biol., 55:533-534].

Dong Y et al. (1998) "17β-hydroxysteroid dehydrogenases in human bone cells" J. Bone Min. Res., 13:1539-1546

Gadad A K, Kapsi S G, Anegundi R I, Pattan S R, Mahajanshetti C S, Shishoo C J. (1996) "Synthesis and antihyperlipaemic activity of some 2-aminomethyl-3-aryl-5,6, 7,8-tetrahydrobenzo(b)/5,6-dimethylthieno (2,3-d)-pyrimidin-4-ones." Arzneimiftelforschung. 46(10):981-5.

Geissler W M et al. (1994) "Male pseudohermaphroditism caused by mutations of testicular 17beta-hydroxysteroid dehydrogenase 3." Nat Genet., 7:34-9.

Gutschow M, Kuerschner L, Neumann U, Pietsch M, Loser R, Koglin N, Eger K. (1999) "2-(diethylamino)thieno1, 3oxazin-4-ones as stable inhibitors of human leukocyte elastase" J Med Chem. 42(26):5437-47.

JP48042271B

JP62132884

Kapustina M V, Kharizomenova A, Shvedov V I, Fomina A N, Nikolaeva I S, Golovanova E M, Bogdanova G A, Alekseeva L M (1990) "Synthesis and antiviral activity of 7-oxo- and 7-hydroxy-4,5,6,7-tetrahydrobenzo[b]-thiophene derivatives" Chem. Heterocycl. Compd. (Engl. Transl.) 24:1269-271.

Kapustina, M. V, Nikolaeva, I. S., Kharizomenova, I. A., Shvedov, V. I., Pushkina, T. V., Fomina, A. N. (1992) Pharm. Chem. J. 789.

Kapustina, M. V., Kharizomenova, I. A., Shvedov, V. I., (1991) Chem. Heterocycl. Compd. (Engl. Trans.) 425.

Kharizomenova A, Kapustina M V, Grinev A N, Sheinker Y N, Alekseeva L M, Kuleshova E F (1984) "Synthesis and structure of derivatives of 7-oxo-4,5,6,7-tetrahydrobenzo [b]-thiophene and 7-hydroxy [b]thiophene" Chem. Heterocycl. Compd. (Engl. Transl.) 20:1339-1342.

Koeller S & Lellouche J P (1999) "Preparation of Formate Esters from O-TBDMS/O-TES Protected Alcohols. A One-Step Conversion Using the Vilsmeier-Haack Complex POCl3/DMF" Tetrahedron Letters 40(38):7043-7046.

Koffman B, Modarress K J, Beckerman T, Bashirelahi N. (1991) "Evidence for involvement of tyrosine in estradiol binding by rat uterus estrogen receptor." J Steroid Biochem Mol Biol. 38(2):135-9.

Labrie et al. (2000) "Role of 17 beta-hydroxysteroid dehydrogenases in sex steroid formation in peripheral intracrine tissues" Trends Endocrinol Metab., 11:421-7

Labrie F et al. (1997) "The key role of 17 beta-hydroxysteroid dehydrogenases in sex steroid biology." Steroids, 62:148-58

Lidström P, Tierney J, Wathey B, Westman J (2001) "Microwave assisted organic synthesis—a review" Tetrahedron 57(45):9225-9283.

Lipshutz B H, Wilhelm R S, Kozlowski J A (1984) "Conjugate addition reactions of □□-unsaturated ketones with higher order, mixed organocuprate reagents, R2Cu (CN)Li2" J. Org. Chem. 49:3938-3942.

Manhas M S, Sharma S D, Amin S G. (1972) "Heterocyclic compounds. 4. Synthesis and antiinflammatory activity of some substituted thienopyrimidinones." J Med Chem. 15(1):106-7.

Manjunath K S, Mohan S, Naragund L V, Shishoo C J. (1997) "Synthesis and evaluation of 2-chloromethyl-3-N-substituted arylthieno(2,3-d)pyrimidin-4-ones and derivatives for central nervous system depressant activity." Arzneimittelforschung. 47(9):1005-8.

Mitra R B & Joshi V S (1988) "A novel synthesis of ketoprofen, important non-steroidal antiinflammatory agent" Synth. Comm.:18:2259.

Oefelein M G & Cornum R (2000) "Failure to achieve castrate levels of testosterone during luteinizing hormone releasing hormone agonist therapy: the case for monitoring serum testosterone and a treatment decision algorithm." J Urol.; 164:726-9.

Perrissin M, Duc C L, Narcisse G, Bakri-Logeais F, Huguet F (1980) "Tetrahydro-4,5,6,7 benzo-[b] et tetrahydro-5,6,7,8 (4H)-cyclohepta[b]thiophene; Eur. J. Med. Chem. Chim. Ther. 15:413-418.

Poirier D. (2003) "Inhibitors of 17 beta-hydroxysteroid dehydrogenases" Curr Med Chem. 10:453-77

Samanta S S, Ghosh S C, De A (1997) "Studies in sulfur heterocycles. Part 12.1 Use of 5,6-dihydrobenzo[b] thiophen-7(4H)-one in the synthesis of condensed sulfur heterocycles" J. Chem. Soc.; Perkin Trans. I, 3673-3677.

Tamaya et al. (1985) "Comparison of cellular levels of steroid receptors in uterine leiomyoma and myometrium." Acta Obstet Gynecol Scand., 64:307-9

Tani M, Ariyasu T, Ohtsuka M, Koga T, Ogawa Y, Yokoyama Y, Murakami Y (1996) "New Strategy for indole synthesis from ethyl pyrrole-2-carboxylate (Synthetic Studies on Indoles and Realted Compounds. XXXIX)" Chem. Pharm. Bull. 44:55-61.

US 2003/0170292
U.S. Pat. No. 5,597,823
WO 00/07996
WO 01/42181
WO 02/26706
WO 2004/085457
WO 98/30556
WO 98/32724
WO 99/12540

What is claimed is:

1. A method of treating or inhibiting a steroid hormone dependent disease or disorder selected from the group consisting of breast cancer, prostate carcinoma, ovarian cancer, uterine cancer, endometrial cancer, endometrial hyperplasia, endometriosis, uterine fibroids, uterine leiomyoma, adenomyosis, dysmenorrhea, menorrhagia, metrorrhagia, prostadyna, benign prostatic hyperplasia, prostatitis, acne, seborrhoea, hirsutism, androgenic alopecia, precocious puberty, adrenal hyperplasia, polycystic ovarian syndrome and osteoporosis, said method comprising administering to a patient in need thereof an effective amount of a compound corresponding to formula (I)

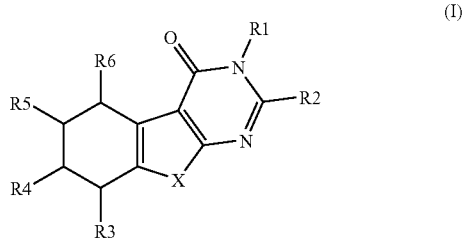

wherein
X is S, SO or $SO_2$
R1 and R2 are individually selected from the group consisting of alkyl, substituted alkyl, aryl, substituted aryl, heteroaryl, substituted heteroaryl, cycloheteroalkyl, substituted cycloheteroalkyl, arylalkyl, substituted arylalkyl, heteroarylalkyl, substituted heteroarylalkyl, cycloheteroalkyl-alkyl, substituted cycloheteroalkyl-alkyl,
whereby the cycloheteroalkyl moiety of cycloheteroalkyl-alkyl and substituted cycloheteroalkyl-alkyl is a four- to eight-membered heterocyclic ring containing at least one heteroatom selected from N, O and S, the number of N atoms being 0-3 and the number of O and S atoms each being 0-1, which ring may be saturated, partly unsaturated or hydroaromatic;
whereby the cycloheteroalkyl moiety is optionally substituted by up to three substituents independently selected from the group consisting of oxo, alkyl, aryl or aryl-($C_1$-$C_4$)-alkyl both optionally substituted in the aryl moiety, hydroxyl, ($C_1$-$C_6$)alkoxy, halogenated ($C_1$-$C_6$)alkyl, halogenated ($C_1$-$C_6$)alkoxy, carboxyl-($C_1$-$C_6$)alkyl, thiol, nitrile, sulfamoyl, sulphonamide, carboxyl, aryloxy or arylalkyloxy both optionally substituted in the aryl moiety, ($C_1$-$C_6$)alkylthio, arylthio or arylalkyloxy both optionally substituted in the aryl moiety, ($C_1$-$C_6$)alkylthio, arylthio or arylalkylthio both optionally substituted in the aryl moiety, amino, amido, acyl, and acylamino;
or R2 itself may be independently selected from acyl, carboxyl, or amido,
wherein R1 and R2 cannot be simultaneously unsubstituted alkyl,
the hydrocarbon chain —C(R3)-C(R4)-C(R5)-C(R6)- of the six-membered ring is saturated or contains one or two double bonds between the carbon atoms;
R3 and R4 are individually selected from the group consisting of hydrogen, oxo, halogen or dihalogen, acyl, alkyl, substituted alkyl, hydroxyl, carboxyl, amido, amino, nitrile, thio, alkoxy, acyloxy, aryloxy, alkylthio and arylthio;
R5 and R6 are individually selected from the group consisting of hydrogen, halogen, alkyl, substituted alkyl, arylalkyl, substituted arylalkyl, hydroxyl, alkoxy, aryloxy, acyl or carboxyl,
or a pharmaceutically acceptable salt thereof.

2. A method according to according to claim 1, wherein R1 and R2 are individually selected from the group consisting of
(i) —$C_1$-$C_{12}$-alkyl, which alkyl can be linear, cyclic, branched or partially unsaturated,
and which can be optionally substituted with one, two or three substituents individually selected from the group consisting of hydroxyl, $C_1$-$C_{12}$-alkoxy, thiol, $C_1$-$C_{12}$-alkylthio, aryloxy, arylacyl, —CO—OR, —O—CO—R, heteroaryl-acyloxy, and —N(R)$_2$;
wherein said aryl group is phenyl or naphthyl, and can be optionally substituted with one, two or three halogen atoms;
wherein said heteroaryl group is thienyl, furyl or pyridinyl
(ii) aryl and aryl-$C_1$-$C_{12}$-alkyl,
wherein the alkyl moiety can be optionally substituted with one or two hydroxyl groups, and
wherein the aryl moiety can be optionally substituted with one to five substituents individually selected from the group consisting of halogen, hydroxyl, $C_1$-$C_{12}$-alkoxy, nitro, nitrile, $C_1$-$C_{12}$-alkyl, halogenated $C_1$-$C_{12}$-alkyl, —$SO_2$—N(R)$_2$, and $C_1$-$C_{12}$-alkylsulphonyl;
or which aryl may be optionally substituted by two groups which are attached to adjacent carbon atoms and are combined into a saturated cyclic 5, 6 or 7 membered ring system, optionally containing one, two or three heteroatoms, such as N or 0, the number of N atoms being 0-3 and the number of 0 atoms each being 0-2, wherein the cyclic ring system may optionally be further substituted by an oxo group;
(iii) heteroaryl and heteroaryl-$C_1$-$C_{12}$-alkyl,
wherein the heteroaryl group can be optionally substituted with one, two or three substituents individually selected from the group consisting of halogen, $C_1$-$C_{12}$-alkyl, halogenated $C_1$-$C_8$-alkyl, —CO—OR, aryl and aryloxy,
wherein the aryl group is selected from phenyl or naphthyl and can be optionally substituted with one, two or three halogen atoms;
(iv) cycloheteroalkyl and cycloheteroalkyl-$C_1$-$C_8$-alkyl,
wherein the cycloheteroalkyl moiety can be optionally substituted with one or two substituents individually selected from the group consisting of oxo, $C_1$-$C_{12}$-alkyl, hydroxyl, $C_1$-$C_{12}$-alkoxy and aryl-$C_1$-$C_{12}$-alkyl;
or R2 itself may be independently selected from —CO—R, —CO—O—R, or —CO—N(R)$_2$;
R3 and R4 are individually selected from the group consisting of hydrogen, oxo, thio, halogen or dihalogen, nitrile, —CO—N(R)$_2$, —O—CO—R, —O—R, —S—R, —N(R)$_2$, and —$C_1$-$C_{12}$-alkyl,
which alkyl can be linear, cyclic, branched or partially unsaturated, and which alkyl can be optionally substituted with one, two or three substituents individually selected from the group consisting of hydroxyl, $C_1$-$C_{12}$-alkoxy, thiol, and —N(R)$_2$; and
R5 and R6 are individually selected from the group consisting of hydrogen, halogen, —O—R, —CO—O—R, —CO—R,
$C_1$-$C_{12}$-alkyl, which alkyl can be linear, cyclic, branched or partially unsaturated, and which alkyl can be optionally substituted with one, two or three substituents individually selected from the group consisting of hydroxyl, $C_1$-$C_{12}$-alkoxy, thiol, $C_1$-$C_{12}$-alkylthio, —CO—OR and —CO—NHR; and
aryl and aryl-$C_1$-$C_{12}$-alkyl, wherein the aryl moiety can be optionally substituted with one to five substituents individually selected from the group consisting of halogen, hydroxyl, $C_1$-$C_{12}$-alkoxy, nitro, nitrile, $C_1$-$C_{12}$-alkyl, halogenated $C_1$-$C_{12}$-alkyl,
wherein R represents hydrogen, $C_1$-$C_{12}$-alkyl, phenyl-$C_1$-$C_4$-alkyl or phenyl, optionally substituted in the phenyl moiety with one, two or three substituents selected from the group consisting of halogen, hydroxyl, and $C_1$-$C_4$-alkoxy.

3. A compound corresponding to formula (I)

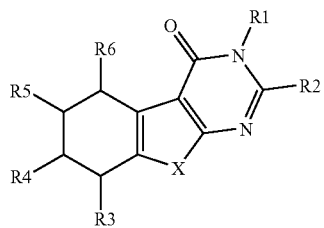

(I)

wherein
X is S, SO or SO$_2$
R1 and R2 are individually selected from the group consisting of alkyl, substituted alkyl, aryl, substituted aryl, heteroaryl, substituted heteroaryl, cycloheteroalkyl, substituted cycloheteroalkyl, arylalkyl, substituted arylalkyl, heteroarylalkyl, substituted heteroarylalkyl, cycloheteroalkyl-alkyl, and substituted cycloheteroalkyl-alkyl,
whereby the cycloheteroalkyl moiety of cycloheteroalkyl-alkyl and substituted cycloheteroalkyl-alkyl is a four- to eight-membered heterocyclic ring containing at least one heteroatom selected from N, O and S, the number of N atoms being 0-3 and the number of O and S atoms each being 0-1, which ring may be saturated, partly unsaturated or hydroaromatic;
whereby the cycloheteroalkyl moiety is optionally substituted by up to three substituents independently selected from the group consisting of oxo, alkyl, aryl or aryl-($C_1$-$C_4$)-alkyl both optionally substituted in the aryl moiety, hydroxyl, ($C_1$-$C_6$)alkoxy, halogenated ($C_1$-$C_6$)alkyl, halogenated ($C_1$-$C_6$)alkoxy, carboxyl-($C_1$-$C_6$)alkyl, thiol, nitrile, sulfamoyl, sulphonamide, carboxyl, aryloxy or arylalkyloxy both optionally substituted in the aryl moiety, ($C_1$-$C_6$)alkylthio, arylthio or arylalkyloxy both optionally substituted in the aryl moiety, ($C_1$-$C_6$)alkylthio, arylthio or arylalkylthio both optionally substituted in the aryl moiety, amino, amido, acyl, and acylamino;
or R2 itself may be independently selected from acyl, carboxyl, or amido,
wherein R1 and R2 cannot be simultaneously unsubstituted alkyl, and
wherein if R3, R5 and R6 all simultaneously represent hydrogen and R4 represents hydrogen or methyl, then R2 is different from methyl;
R3 and R4 are individually selected from the group consisting of hydrogen, oxo, halogen or dihalogen, acyl, alkyl, substituted alkyl, hydroxyl, carboxyl, amido, amino, nitrile, thio, alkoxy, acyloxy, aryloxy, alkylthio and arylthio;
R5 and R6 are individually selected from the group consisting of hydrogen, halogen, alkyl, substituted alkyl, arylalkyl, substituted arylalkyl, hydroxyl, alkoxy, aryloxy, acyl and carboxyl;
the hydrocarbon chain —C(R3)-C(R4)-C(R5)-C(R6)- of the six-membered ring is saturated or contains one or two double bonds between the carbon atoms; and wherein if all the substituents R3, R4, R5 and R6 are simultaneously hydrogen, then the six-membered ring comprising the hydrocarbon chain —C(R3)-C(R4)-C(R5)-C(R6)- is an aromatic ring.

4. A compound according to claim 3, wherein
R1 and R2 are individually selected from the group consisting of
(i) —$C_1$-$C_{12}$-alkyl, which alkyl can be linear, cyclic, branched or. partially unsaturated,
and which can be optionally substituted with one, two or three substituents individually selected from the group consisting of hydroxyl, $C_1$-$C_{12}$-alkoxy, thiol, $C_1$-$C_{12}$-alkylthio, aryloxy, arylacyl, —CO—OR, —O—CO—R, heteroaryl-acyloxy, and —N(R)$_2$;
wherein said aryl group is phenyl or naphthyl, and can be optionally substituted with one, two or three halogens;
wherein said heteroaryl group is thienyl, furyl or pyridinyl
(ii) aryl and aryl-$C_1$-$C_{12}$-alkyl,
wherein the alkyl moiety can be optionally substituted with one or two hydroxyl groups, and
wherein the aryl moiety can be optionally substituted with one to five substituents individually selected from the group consisting of halogen, hydroxyl, $C_1$-$C_{12}$-alkoxy, nitro, nitrile, $C_1$-$C_{12}$-alkyl, halogenated $C_1$-$C_{12}$-alkyl, —$SO_2$—$N(R)_2$, and $C_1$-$C_{12}$-alkylsulphonyl;
or which aryl may be optionally substituted by two groups which are attached to adjacent carbon atoms and are combined into a saturated cyclic 5, 6 or 7 membered ring system, optionally containing one, two or three heteroatoms, the number of N atoms being 0-3 and the number of O atoms each being 0-2, wherein the cyclic ring system may optionally be further substituted by an oxo group;
(iii) heteroaryl and heteroaryl-$C_1$-$C_{12}$-alkyl,
wherein the heteroaryl group can be optionally substituted with one, two or three substituents individually selected from the group consisting of halogen, $C_1$-$C_{12}$-alkyl, halogenated $C_1$-$C_8$-alkyl, —CO—OR, aryl or aryloxy,
wherein the aryl group is selected from phenyl or naphthyl and can be optionally substituted with one, two or three halogen atoms;
(iv) cycloheteroalkyl and cycloheteroalkyl-$C_1$-$C_8$-alkyl,
wherein the cycloheteroalkyl moiety can be optionally substituted with one or two substituents individually selected from the group consisting of oxo, $C_1$-$C_{12}$-alkyl, hydroxyl, $C_1$-$C_{12}$-alkoxy and aryl-$C_1$-$C_{12}$-alkyl;
or R2 itself may be independently selected from —CO—R, —CO—O—R, or —CO—N(R)$_2$;
R3 and R4 are individually selected from the group consisting of hydrogen, oxo, thio, halogen or dihalogen, —CO—R, —CO—O—R, nitrile, —CO—N(R)$_2$, —O—CO—R, —O—R, —S—R, —N(R)$_2$, —$C_1$-$C_{12}$-alkyl,
which alkyl can be linear, cyclic, branched or partially unsaturated, and which alkyl can be optionally substituted with one, two or three substituents individually selected from the group consisting of hydroxyl, $C_1$-$C_{12}$-alkoxy, thiol, and —N(R)$_2$; and
R5 and R6 are individually selected from the group consisting of hydrogen, halogen, —O—R, —CO—O—R, —CO—R,
$C_1$-$C_{12}$-alkyl, which alkyl can be linear, cyclic, branched or partially unsaturated, and which alkyl can be optionally substituted with one, two or three substituents individually selected from the group consisting of hydroxyl, $C_1$-$C_{12}$-alkoxy, thiol, $C_1$-$C_{12}$-alkylthio, —CO—OR and —CO—NHR; and
aryl and aryl-$C_1$-$C_{12}$-alkyl, wherein the aryl moiety can be optionally substituted with one to five substituents individually selected from the group consisting of halogen, hydroxyl, $C_1$-$C_{12}$-alkoxy, nitro, nitrile, $C_1$-$C_{12}$-alkyl, and halogenated $C_1$-$C_{12}$-alkyl,
wherein R represents hydrogen, $C_1$-$C_{12}$-alkyl, phenyl-$C_1$-$C_4$-alkyl or phenyl, optionally substituted in the phenyl moiety with one, two or three substituents selected from the group consisting of halogen, hydroxyl, and $C_1$-$C_4$-alkoxy.

5. A compound according to claim 4, wherein aryl represents phenyl, biphenyl, naphthyl, indanyl, indenyl or fluorenyl,
heteroaryl represents pyrrolyl, thienyl, furyl, imidazolyl, thiazolyl, isothiazolyl, oxazolyl, isoxazolyl, pyrazolyl, pyridinyl, pyrimidinyl, pyrazinyl, indolyl, quinolinyl, isoquinolinyl, benzoimidazolyl, 1,3-dihydro-benzoimidazolyl, benzofuran, or benzo[b]thiophene, and
cycloheteroalkyl represents piperidinyl, pyrrolidinyl, tetrahydrofuryl, dioxolyl, morpholinyl, tetrahydrothiophenyl, tetrahydropyridinyl, azetidinyl, thiazolidinyl, oxazolidinyl, thiomorpholinyl, piperazinyl, azepanyl, diazepanyl, oxazepanyl, thiazepanyl, dihydro-1H-pyrrolyl, or 1,3-dihydro-benzoimidazolyl.

6. A compound corresponding to formula (I)

(I)

wherein
X is S, SO or $SO_2$
R1 and R2 are individually selected from the group consisting of alkyl, substituted alkyl, aryl, substituted aryl, heteroaryl, substituted heteroaryl, cycloheteroalkyl, substituted cycloheteroalkyl, arylalkyl, substituted arylalkyl, heteroarylalkyl, substituted heteroarylalkyl, cycloheteroalkyl- alkyl, substituted cycloheteroalkylalkyl,
whereby the cycloheteroalkyl moiety of cycloheteroalkyl-alkyl and substituted cycloheteroalkyl-alkyl is a four- to eight-membered heterocyclic ring containing at least one heteroatom selected from N, O and S, the number of N atoms being 0-3 and the number of O and S atoms each being 0-1, which ring may be saturated, partly unsaturated or hydroaromatic;
whereby the cycloheteroalkyl moiety is optionally substituted by up to three substituents independently selected from the group consisting of oxo, alkyl, aryl or aryl-($C_1$-$C_4$)-alkyl both optionally substituted in the aryl moiety, hydroxyl, ($C_1$-$C_6$)alkoxy, halogenated ($C_1$-$C_6$)alkyl, halogenated ($C_1$-$C_6$)alkoxy, carboxyl-($C_1$-$C_6$)alkyl, thiol, nitrile, sulfamoyl, sulphonamide, carboxyl, aryloxy or arylalkyloxy both optionally substituted in the aryl moiety, ($C_1$-$C_6$)alkylthio, arylthio or arylalkyloxy both optionally substituted in the aryl moiety, ($C_1$-$C_6$)alkylthio, arylthio or arylalkylthio both optionally substituted in the aryl moiety, amino, amido, acyl, and acylamino;
or R2 itself may be independently selected from acyl, carboxyl, or amido,
wherein R1 and R2 cannot be simultaneously unsubstituted alkyl, and
wherein if R3, R5 and R6 all simultaneously represent hydrogen and R4 represents hydrogen or methyl, then R2 is different from methyl;
R3 and R4 are individually selected from the group consisting of hydrogen, oxo, halogen or dihalogen, acyl, alkyl, substituted alkyl, hydroxyl, carboxyl, amido, amino, nitrile, thio, alkoxy, acyloxy, aryloxy, alkylthio and arylthio;
R5 and R6 are individually selected from the group consisting of hydrogen, halogen, alkyl, substituted alkyl, arylalkyl, substituted arylalkyl, hydroxyl, alkoxy, aryloxy, acyl or carboxyl,
the hydrocarbon chain —C(R3)-C(R4)-C(R5)-C(R6)- of the six-membered ring is saturated or contains one or two double bonds between the carbon atoms;

wherein if R3, R4, R5 and R6 are all simultaneously hydrogen, then the six membered ring comprising the hydrocarbon chain —C(R3)-C(R4)-C(R5)═C(R6)- is an aromatic ring;

provided that said compound is not (3-Benzyl-7-tert-butyl-4-oxo-3,4,5,6,7,8-hexahydro-benzo[4,5]thieno[2,3-d]pyrimidin-2-yl)-acetic acid methyl ester or 2,3-Dibenzyl-7-tert-butyl-5,6,7,8-tetrahydro-3H-benzo[4,5]thieno[2,3-d]pyrimidin-4-one.

7. A compound according to claim 6, wherein the six-membered ring comprising the hydrocarbon chain —C(R3)-C(R4)-C(R5)-C(R6)- is an aromatic ring.

8. A compound according to claim 6, wherein the six-membered ring comprising the hydrocarbon chain —C(R3)-C(R4)-C(R5)-C(R6)- is non-aromatic ring and at least one of R3 to R6 is different from hydrogen.

9. A compound according to claim 3, wherein
R1 and R2 are individually selected from the group consisting of
(i) —$C_1$-$C_{12}$-alkyl, which alkyl can be linear, cyclic, branched or partially unsaturated,
and which can be optionally substituted with one, two or three substituents individually selected from the group consisting of hydroxyl, $C_1$-$C_{12}$-alkoxy, thiol, $C_1$-$C_{12}$-alkylthio, aryloxy, arylacyl, —CO—OR, —O—CO—R, heteroaryl-acyloxy, and —N(R)$_2$;
wherein said aryl group is phenyl or naphthyl, and can be optionally substituted with one, two or three halogens;
wherein said heteroaryl group is thienyl, furyl or pyridinyl
(ii) aryl and aryl-$C_1$-$C_{12}$-alkyl,
wherein the alkyl moiety can be optionally substituted with one or two hydroxyl groups, and
wherein the aryl moiety can be optionally substituted with one to five substituents individually selected from the group consisting of halogen, hydroxyl, $C_1$-$C_{12}$-alkoxy, nitro, nitrile, $C_1$-$C_{12}$-alkyl, halogenated $C_1$-$C_{12}$-alkyl, —SO$_2$—N(R)$_2$, $C_1$-$C_{12}$-alkyl-sulphonyl;
or which aryl may be optionally substituted by two groups which are attached to adjacent carbon atoms and are combined into a saturated cyclic 5, 6 or 7 membered ring system, optionally containing one, two or three heteroatoms, the number of N atoms being 0-3 and the number of O atoms each being 0-2, wherein the cyclic ring system may optionally be further substituted by an oxo group;
(iii) heteroaryl and heteroaryl-$C_1$-$C_{12}$-alkyl,
wherein the heteroaryl group can be optionally substituted with one, two or three substituents individually selected from the group consisting of halogen, $C_1$-$C_{12}$-alkyl, halogenated $C_1$-$C_8$-alkyl, —CO—OR, aryl or aryloxy,
wherein the aryl group is selected from phenyl or naphthyl and can be optionally substituted with one, two or three halogen atoms;
(iv) cycloheteroalkyl and cycloheteroalkyl-$C_1$-$C_8$-alkyl,
wherein the cycloheteroalkyl moiety can be optionally substituted with one or two substituents individually selected from the group consisting of oxo, $C_1$-$C_{12}$-alkyl, hydroxyl, $C_1$-$C_{12}$-alkoxy and aryl-$C_1$-$C_{12}$-alkyl;
or R2 itself may be independently selected from —CO—R, —CO—O—R, or —CO—N(R)$_2$;
R3 and R4 are individually selected from the group consisting of hydrogen, oxo, thio, halogen or dihalogen, —CO—R, —CO—O—R, nitrile, —CO—N(R)$_2$, —O—CO—R, —O—R, —S—R, —N(R)$_2$, and —$C_1$-$C_{12}$-alkyl,
which alkyl can be linear, cyclic, branched or partially unsaturated, and
which alkyl can be optionally substituted with one, two or three substituents individually selected from the group consisting of hydroxyl, $C_1$-$C_{12}$-alkoxy, thiol, and —N(R)$_2$; and
R5 and R6 are individually selected from the group consisting of
hydrogen, halogen, —O—R, —CO—O—R, —CO—R, and $C_1$-$C_{12}$-alkyl,
which alkyl can be linear, cyclic, branched or partially unsaturated, and
which alkyl can be optionally substituted with one, two or three substituents individually selected from the group consisting of hydroxyl, $C_1$-$C_{12}$-alkoxy, thiol, $C_1$-$C_{12}$-alkylthio, —CO—OR and —CO—NHR; and
aryl and aryl-$C_1$-$C_{12}$-alkyl, wherein the aryl moiety can be optionally substituted with one to five substituents individually selected from the group consisting of halogen, hydroxyl, $C_1$-$C_{12}$-alkoxy, nitro, nitrile, $C_1$-$C_{12}$-alkyl, halogenated $C_1$-$C_{12}$-alkyl,
wherein R represents hydrogen, $C_1$-$C_{12}$-alkyl, phenyl-$C_1$-$C_4$-alkyl or phenyl, optionally substituted in the phenyl moiety with one, two or three substituents selected from the group consisting of halogen, hydroxyl, and $C_1$-$C_4$-alkoxy.

10. A compound according to claim 9, wherein the six-membered ring comprising the hydrocarbon chain —C(R3)-C(R4)-C(R5)-C(R6)- is an aromatic ring.

11. A compound according to claim 9, wherein the six-membered ring comprising the hydrocarbon chain —C(R3)-C(R4)-C(R5)-(R6)- is non-aromatic ring and at least one of R3 to R6 is different from hydrogen.

12. A compound according to claim 6, wherein R2 is selected from the group consisting of
(i) —$C_1$-$C_8$-alkyl, which alkyl can be linear, cyclic, branched or partially unsaturated,
which can be optionally substituted with one, two or three substituents individually selected from the group consisting of hydroxyl, $C_1$-$C_8$-alkoxy, thiol, $C_1$-$C_8$-alkylthio, aryloxy, —CO—O—$C_1$-$C_8$-alkyl, and —O—CO—R';
wherein said aryl group is phenyl or naphthyl, and can be optionally substituted with one, two or three halogens;
(ii) aryl and aryl-$C_1$-$C_8$-alkyl,
wherein the aryl moiety can be optionally substituted with one to five substituents individually selected from the group consisting of halogen, hydroxyl, $C_1$-$C_8$-alkoxy, nitro, nitrile, halogenated $C_1$-$C_8$-alkyl, and —SO$_2$—N(R')$_2$,
(iii) heteroaryl and heteroaryl-$C_1$-$C_8$-alkyl,
wherein the heteroaryl group can be optionally substituted with one, two or three substituents individually selected from the group consisting of halogen, $C_1$-$C_8$-alkyl, halogenated $C_1$-$C_8$-alkyl, aryl or aryloxy,
wherein the aryl group is selected from phenyl or naphthyl and can be optionally substituted with one, two or three halogen atoms;
(iv) —CO—R',
(v) —CO—N(R')$_2$, and
(vi) —CO—O—R';
wherein R' represents hydrogen or $C_1$-$C_8$-alkyl.

13. A compound according to claim 6, wherein R2 is
a) a residue of formula (II)

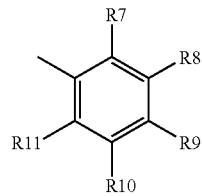

(II)

wherein
R7 is hydrogen, halogen, hydroxyl or $C_1$-$C_4$-alkoxy;
R8 is hydrogen, $C_1$-$C_4$-alkoxy, hydroxyl, nitrile, halogen, or halogenated $C_1$-$C_4$-alkyl;
R9 is hydrogen, $C_1$-$C_4$-alkoxy, hydroxyl, nitrile, halogen, or N,N-di-$C_1$-$C_4$-alkyl-sulphonamide;
R10 is hydrogen, $C_1$-$C_4$-alkoxy, hydroxyl, nitrile, halogen, or halogenated $C_1$-$C_4$-alkyl; and
R11 is hydrogen, halogen, hydroxyl or $C_1$-$C_4$-alkoxy;
or b)
(i) —$C_1$-$C_8$-alkyl, which alkyl can be linear, cyclic, branched or partially unsaturated;
(ii) —$C_1$-$C_4$-alkyl, substituted with one or two substituents selected from the group consisting of
—CO—O—R";
—O—Ar, wherein Ar is phenyl optionally substituted with halogen;
—O—CO—R",
phenyl or biphenyl, optionally substituted in the phenyl moiety with one, two or three $C_1$-$C_4$-alkoxy groups;
(iii) —CO—O—R",
(iv) —CO—R",
(v) -naphthyl,
(vi) -heteroaryl,
wherein the heteroaryl group can be optionally substituted by one or two substituents individually selected from the group consisting of halogen, $C_1$-$C_4$-alkyl, halogenated $C_1$-$C_4$-alkyl, phenyl and phenoxy, wherein the phenyl group can be optionally substituted with one, two or three halogens;
wherein R" represents hydrogen or $C_1$-$C_4$-alkyl.

14. A compound according to claim 13, wherein R2 is selected from the group consisting of
(i) —$C_3$-$C_8$-alkyl, which alkyl is linear, cyclic or branched,
(ii) —$C_1$-$C_4$-alkyl, optionally substituted with one or two substituents independently selected from the group consisting of $C_1$-$C_4$-alkoxy and hydroxyl,
(iii) phenyl-$C_1$-$C_4$-alkyl,
wherein the phenyl group is optionally substituted with one or two $C_1$-$C_4$-alkoxy groups,
(iv) heteroaryl,
which heteroaryl moiety is selected from the group consisting of furyl, pyridinyl, thienyl, thiazolyl, benzothienyl, pyrazoloyl and pyrimidinyl, and (v) a residue of formula (II)

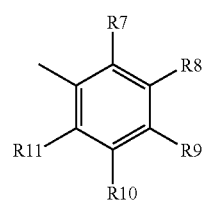

(II)

wherein
R7 is hydrogen, $C_1$-$C_4$-alkoxy or halogen,
R8 is hydrogen, halogen, $C_1$-$C_4$-alkoxy, or hydroxyl,
R9 is hydrogen, hydroxyl or $C_1$-$C_4$-alkoxy,
R10 is hydrogen, halogen, $C_1$-$C_4$-alkoxy, or hydroxyl, and
R11 is hydrogen, $C_1$-$C_4$-alkoxy or halogen.

15. A compound according to claim 13, wherein R2 is selected from the group consisting of phenyl, methoxyphenyl, trimethoxyphenyl, trihydroxyphenyl, 3,5-dihydroxy-4-methoxyphenyl, 2-bromo-3,4,5-trimethoxyphenyl, 2-bromo-5-methoxyphenyl, 2-chloro-3,4, 5-trimethoxyphenyl, cyanophenyl, fluorophenyl, di-trifluoromethylphenyl, difluorophenyl, dichlorophenyl, 4-N, N-dipropylsulphonamide, methyl, cyclopropyl, cyclopentylethyl, 1-ethylpentyl, 2-methylprop-1-enyl, propyl, benzyl, phenethyl, biphenylmethyl, dimethoxybenzyl, naphthyl, thienyl, furyl, pyridinyl, benzothienyl, bromothienyl, 1-phenyl-5-trifluoromethyl-4H-pyrazol-4-yl, 2-(4-Chloro-phenoxy)-pyridin-3-yl, hydroxymethyl, acetyl-oxymethyl, methoxymethyl, methoxy-acyl-methyl, ethoxy-acyl-methyl, ethoxy-acyl-ethyl, 1-(3-Chloro-phenoxy)-1-methyl-ethyl, carbonyl, and methoxyacyl.

16. A compound of formula (I) according to claim 15, wherein R2 is methoxyphenyl, trimethoxyphenyl, 2-bromo-3,4,5-trimethoxyphenyl, 2-chloro-3,4,5-trimethoxyphenyl, thienyl, or propyl.

17. A compound according to claim 6, wherein R1 is selected from the group consisting of
(i) —$C_1$-$C_8$-alkyl, which alkyl can be linear, cyclic, branched or partially unsaturated,
which can be optionally substituted with one, two or three substituents individually selected from the group consisting of hydroxyl, $C_1$-$C_8$-alkoxy, thiol, —$NH_2$, $C_1$-$C_8$-alkylthio, aryloxy, arylacyl, —CO—O—$C_1$-$C_8$-alkyl, $C_1$-$C_8$-alkylacyloxy, heteroarylacyloxy, and $C_1$-$C_8$-alkylamino;
wherein said aryl group is phenyl or naphthyl, and can be optionally substituted with one, two or three halogens;
wherein said heteroaryl group is thienyl, furyl or pyridinyl,
(ii) aryl and aryl-$C_1$-$C_8$-alkyl,
wherein the alkyl moiety can be optionally substituted with one or two hydroxyl groups, and
wherein the aryl moiety can be optionally substituted with one to five substituents individually selected from the group consisting of halogen, hydroxyl, $C_1$-$C_8$-alkoxy, $C_1$-$C_8$-alkylsulphonyl, —$SO_2$—N($C_1$-$C_8$-alkyl)$_2$, $C_1$-$C_8$-alkyl, halogenated $C_1$-$C_8$-alkyl;
or which aryl may be optionally substituted by two groups which are attached to adjacent carbon atoms and are combined into a saturated cyclic 5 or 6 membered ring system, optionally containing one, two or three heteroatoms, the number of N atoms being 0-3 and the number of O atoms each being 0-2,
wherein the cyclic ring system may optionally be further substituted by an oxo group;
(iii) heteroaryl and heteroaryl-$C_1$-$C_8$-alkyl,
wherein the heteroaryl group can be optionally substituted with one, two or three substituents individually selected from the group consisting of halogen, $C_1$-$C_8$-alkyl, and —CO—O—$C_1$-$C_8$-alkyl;
(iv) cycloheteroalkyl and cycloheteroalkyl-$C_1$-$C_8$-alkyl,
wherein the cycloheteroalkyl moiety can be optionally substituted with one or two substituents individually selected from the group consisting of oxo, $C_1$-$C_8$-alkyl, hydroxyl, $C_1$-$C_8$-alkoxy and aryl-$C_1$-$C_8$-alkyl.

18. A compound according to claim 17, wherein R1 is selected from the group consisting of
(i) —$C_1$-$C_8$-alkyl, which alkyl can be linear, cyclic or branched,
(ii) —$C_1$-$C_4$-alkyl, substituted with one or two substituents independently selected from the group consisting of —O—R"; —O—Ar, —O—CO-HetAr, —CO—Ar, —CO—O—R", and —N(R")$_2$,
(iii) aryl and aryl-$C_1$-$C_4$-alkyl,
wherein the alkyl moiety can be optionally substituted with a hydroxyl group; and
wherein the aryl moiety can be optionally substituted with one, two or three substituents individually selected from the group consisting of halogen, —O—R"; —SO$_2$—R", —SO$_2$—N(R")$_2$,
or which aryl may be optionally substituted by two groups which are attached to adjacent carbon atoms and are combined into a saturated cyclic 5 or 6 membered ring system, optionally containing one or two O atoms,
wherein the cyclic ring system may optionally be further substituted by an oxo group;
(iii) heteroaryl and heteroaryl-C 1-$C_4$-alkyl,
wherein the heteroaryl group can be optionally substituted with one or two substituents individually selected from the group consisting of halogen, —$C_1$-$C_4$-alkyl, and —CO—O—R";
(iv) cycloheteroalkyl and cycloheteroalkyl-$C_1$-$C_4$-alkyl,
wherein the cycloheteroalkyl moiety can be optionally substituted with one or two substituents individually selected from the group consisting of oxo, $C_1$-$C_4$-alkyl, and —$C_1$-$C_4$-alkyl-Ar;
wherein
Ar represents phenyl, optionally substituted with halogen or $C_1$-$C_4$-alkoxy,
HetAr represents thienyl, furyl, pyridinyl, and
R" represents hydrogen or $C_1$-$C_4$-alkyl.

19. A compound according to claim 17, wherein R1 is selected from the group consisting of cyclopropyl, butyl, isobutyl, 3-methylbutyl, cyclohexyl, benzyl, phenethyl, 2-hydroxy-2-phenyl-ethyl, methoxybenzyl, 5-bromo-2-methoxybenzyl, 5-bromo-2-hydroxybenzyl, 3,4-dichlorobenzyl, 3,4-dihydroxybenzyl, 4-methylsulfonylbenzyl, 4-aminosulfonyiphenethyl, 2,3-dihydrobenzofuranyl, Benzo[1,3]dioxolyl, phenyl, fluorenyl, indanyl, 3-oxo-2,3-dihydrobenzofuranyl, quinolinyl, methyl-thiazolyl, 2-methoxyacyl-pyrazinyl, furylmethyl, pyridinylmethyl, thienylethyl, thienylmethyl, pyridinylethyl, bromo-furylmethyl, benzylpiperidinyl, morpholinylethyl, 2-oxo-pyrrolidinylpropyl, tetrahydrofurylmethyl, 2,2-dimethyl-[1,3]dioxolan-4-ylmethyl, hydroxyethyl, methoxyethyl, 2-oxo-2-phenyl-ethyl, methoxy-acyl-propyl, phenoxyethyl, thiophene-2-carboxylic acid ethyl ester, and dimethylaminoethyl.

20. A compound according to claim 19, wherein R1 is selected from the group consisting of isobutyl, 3-methylbutyl, benzyl, tetrahydrofurylmethyl, furylmethyl, 5-bromo-furan-2-ylmethyl, 5-bromo-2-methoxybenzyl, thiophene-2-carboxylic acid ethyl ester, and methoxyethyl.

21. A compound according to claim 6, wherein R3 is selected from the group consisting of hydrogen, oxo, —O—R', —O—Ar, —O—CO—R', halogen, thio, —S—R', and —S—Ar,
wherein
R' represents hydrogen or $C_1$-$C_8$-alkyl, and
Ar represents phenyl, optionally substituted with one or more substituents selected from the group consisting of halogen, hydroxy or $C_1$-$C_4$-alkoxy.

22. A compound according to claim 21, wherein R3 is selected from the group consisting of hydrogen, hydroxyl, oxo, halogen, phenoxy, phenylthio, $C_1$-$C_4$-alkoxy, $C_1$-$C_4$-alkylthio, and —O—CO—$C_1$-$C_4$-alkyl.

23. A compound according to claim 22, wherein R3 is selected from the group consisting of hydrogen, hydroxyl, chioro, bromo, oxo, —O—CO—$CH_3$, and —S-ethyl.

24. A compound according to claim 6, wherein R4 is selected from the group consisting of hydrogen, $C_1$-$C_8$-alkyl optionally substituted with hydroxyl, —CO—R', —CO—O—R', halogen and dihalogen, wherein R' represents hydrogen or $C_1$-$C_8$-alkyl.

25. A compound according to claim 24, wherein R4 is selected from the group consisting of hydrogen, $C_1$-$C_4$-alkyl, carbonyl, ethoxyacyl, bromo, dibromo, chloro, dichloro, and hydroxymethyl.

26. A compound according to claim 25, wherein R4 is selected from the group consisting of hydrogen, bromo and carbonyl.

27. A compound according to claim 6, wherein R5 is selected from the group consisting of hydrogen, —COOR', phenyl-$C_1$-$C_4$-alkyl, $C_1$-$C_4$-alkyl, and $C_1$-$C_4$-alkyl substituted with —COOR', wherein R' represents H or $C_1$-$C_4$-alkyl.

28. A compound according to claim 27, wherein R5 is selected from the group consisting of hydrogen, —COOH, benzyl, $C_1$-$C_4$-alkyl, and $C_1$-$C_4$-alkyl substituted with —COOR', wherein R' represents H or $C_1$-$C_4$-alkyl.

29. A compound according to claim 6, wherein R6 is selected from the group consisting of hydrogen, halogen, —O—R', phenyl-$C_1$-$C_4$-alkyl, $C_1$-$C_4$-alkyl, and $C_1$-$C_4$-alkyl substituted with —COOR', wherein R' represents H or $C_1$-$C_4$-alkyl.

30. A compound according to claim 29, wherein R6 is selected from the group consisting of hydrogen, halogen, hydroxyl, benzyl, $C_1$-$C_4$-alkyl, and $C_1$-$C_4$-alkyl substituted with —COOR', wherein R' represents H or $C_1$-$C_4$-alkyl.

31. A compound of formula (I) according to claim 7,

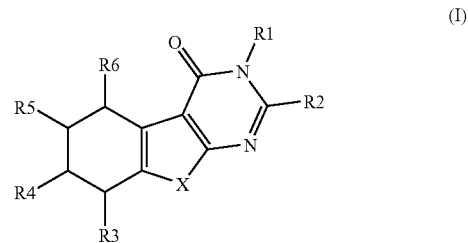

(I)

wherein
X is S, SO or $SO_2$

R1 is selected from the group consisting of:
(i) —$C_1$-$C_8$-alkyl, which alkyl can be linear, cyclic or branched,
(ii) —$C_1$-$C_4$-alkyl, substituted with one or two substituents independently selected from the group consisting of —O—R"; —O—Ar, —O—CO-HetAr, —CO—Ar, —CO—O—R", and —N(R")$_2$,
(iii) aryl and aryl-$C_1$-$C_4$-alkyl,
wherein the alkyl moiety can be optionally substituted with one hydroxyl group; and
wherein the aryl moiety can be optionally substituted with one, two or three substituents individually selected from the group consisting of halogen, —O—R"; —SO$_2$—R", —SO$_2$—N(R")$_2$,
or which aryl may be optionally substituted by two groups which are attached to adjacent carbon atoms and are combined into a saturated cyclic 5 or 6 membered ring system, optionally containing one or two O atoms,
wherein the cyclic ring system may optionally be further substituted by an oxo group;
(iv) heteroaryl and heteroaryl-$C_1$-$C_4$-alkyl,
wherein the heteroaryl group can be optionally substituted with one or two substituents individually selected from the group consisting of halogen, —$C_1$-$C_4$-alkyl, and —CO—O—R";
(v) cycloheteroalkyl and cycloheteroalkyl-$C_1$-$C_4$-alkyl,
wherein the cycloheteroalkyl moiety can be optionally substituted with one or two substituents individually selected from the group consisting of oxo, $C_1$-$C_4$-alkyl, and —$C_1$-$C_4$-alkyl-Ar;
R2 is selected from the group consisting of
a) a residue of formula (II)

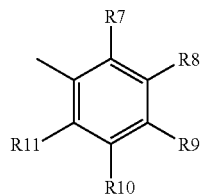

(II)

wherein
R7 is hydrogen, halogen, hydroxyl or $C_1$-$C_4$-alkoxy;
R8 is hydrogen, $C_1$-$C_4$-alkoxy, hydroxyl, nitrile, halogen, or halogenated $C_1$-$C_4$-alkyl;
R9 is hydrogen, $C_1$-$C_4$-alkoxy, hydroxyl, nitrile, halogen, or N,N-di-$C_1$-$C_4$-alkyl-sulphonamide;
R10 is hydrogen, $C_1$-$C_4$-alkoxy, hydroxyl, nitrile, halogen, or halogenated $C_1$-$C_4$-alkyl;
R11 is hydrogen, halogen, hydroxyl or $C_1$-$C_4$-alkoxy, and b)
(i) —$C_1$-$C_8$-alkyl, which alkyl can be linear, cyclic, branched or partially unsaturated;
(ii) —$C_1$-$C_4$-alkyl substituted with one or two substituents selected from the group consisting of
—CO—O—R"; —O—R"; —O—Ar, wherein Ar is phenyl optionally substituted with halogen;
—O—CO—R", and -phenyl or biphenyl, optionally substituted in the phenyl moiety with one, two or three $C_1$-$C_4$-alkoxy groups;
(iii) —CO—O—R",
(iv) —CO—R",
(v) -naphthyl, and (vi) -heteroaryl
wherein the heteroaryl group can be optionally substituted by one or two substituents individually selected from the group consisting of halogen, $C_1$-$C_4$-alkyl, halogenated $C_1$-$C_4$-alkyl, phenyl and phenoxy,
wherein the phenyl group can be optionally substituted with one, two or three halogens;
R3 is selected from the group consisting of hydrogen, oxo, —O—R", —O—Ar, —O—CO—R", halogen, thio, —S—R", and —S—Ar;
R4 is selected from the group consisting of hydrogen, $C_1$-$C_4$-alkyl optionally substituted with hydroxyl, —CO—R", —CO—O—R", halogen and dihalogen,
R5 is selected from the group consisting of hydrogen, —COOR", phenyl-$C_1$-$C_4$-alkyl, $C_1$-$C_4$-alkyl, and $C_1$-$C_4$-alkyl substituted with —COOR",
R6 is selected from the group consisting of hydrogen, halogen, —O—R", phenyl-$C_1$-$C_4$-alkyl, $C_1$-$C_4$-alkyl, and $C_1$-$C_4$-alkyl substituted with —COOR";
wherein
Ar represents phenyl optionally substituted with one or more substituents selected from the group consisting of halogen, hydroxy and methoxy,
HetAr represents thienyl, furyl or pyridinyl, and
R" represents hydrogen or $C_1$-$C_4$-alkyl, preferably methyl or ethyl.

32. A compound according to claim 31, wherein
aryl represents phenyl, biphenyl, naphthyl, indanyl, indenyl or fluorenyl,
heteroaryl represents pyrrolyl, thienyl, furyl, imidazolyl, thiazolyl, isothiazolyl, oxazolyl, isoxazolyl, pyrazolyl, pyridinyl, pyrimidinyl, pyrazinyl, indolyl, quinolinyl, isoquinolinyl, benzoimidazolyl, 1, 3-dihydro-benzoimidazolyl, benzofuran, or benzo[b]thiophene, and
cycloheteroalkyl represents piperidinyl, pyrrolidinyl, tetrahydrofuryl, dioxolyl, morpholinyl, tetrahydrothiophenyl, tetrahydropyridinyl, azetidinyl, thiazolidinyl, oxazolidinyl, thiomorpholinyl, piperazinyl, azepanyl, diazepanyl, oxazepanyl, thiazepanyl, dihydro-1H-pyrrolyl, or 1,3-dihydro-benzoimidazolyl.

33. A compound according to claim 31, wherein
R1 is selected from the group consisting of:
(i) —$C_3$-$C_8$-alkyl, which alkyl can be linear, cyclic or branched,
(ii) —$C_1$-$C_4$-alkyl, optionally substituted with one or two substituents independently selected from the group consisting of $C_1$-$C_4$-alkoxy, hydroxyl, and —O—CO-HetAr,
(iii) phenyl-$C_1$-$C_4$-alkyl,
wherein the aryl moiety is optionally substituted with one, two or three substituents individually selected from the group consisting of halogen, $C_1$-$C_4$-alkoxy, and hydroxyl,
(iv) heteroaryl or heteroaryl-$C_1$-$C_4$-alkyl,
which heteroaryl moiety is selected from the group consisting of pyrimidinyl, furyl, pyridinyl, and thienyl,
wherein the heteroaryl group can be optionally substituted with one or two substituents individually selected from the group consisting of halogen, $C_1$-$C_4$-alkoxy, and hydroxyl, and
(v) cycloheteroalkyl-$C_1$-$C_4$-alkyl,
which cycloheteroalkyl moiety is selected from the group consisting of tetrahydrofuryl, piperidinyl, morpholinyl, and pyrrolidinyl, R2 is selected from the group consisting of
(i) $C_3$-$C_8$-alkyl, which alkyl is linear, cyclic or branched, optionally substituted with an —O—CO—($C_1$-$C_4$)-alkyl or —CO—O—($C_1$-$C_4$)-alkyl group
(ii) —$C_1$-$C_4$-alkyl, optionally substituted with one or two substituents independently selected from the group consisting of $C_1$-$C_4$-alkoxy and hydroxyl,
(iii) phenyl-$C_1$-$C_4$-alkyl,
wherein the phenyl group is optionally substituted with one or two $C_1$-$C_4$-alkoxy groups,
(iv) heteroaryl,
which heteroaryl moiety is selected from the group consisting of furyl, pyridinyl, thienyl, thiazolyl, benzothienyl, pyrimidinyl and pyrazoloyl;
(v) a residue of formula (II)

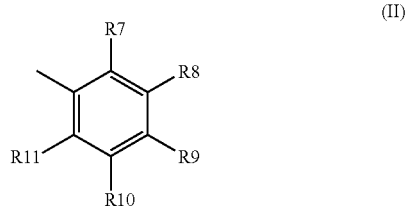

(II)

wherein
R7 is hydrogen, halogen or $C_1$-$C_4$-alkoxy,
R8 is hydrogen, halogen, $C_1$-$C_4$-alkoxy, or hydroxyl,
R9 is hydrogen, hydroxyl or $C_1$-$C_4$-alkoxy,
R10 is hydrogen, halogen, $C_1$-$C_4$-alkoxy, or hydroxyl, and
R11 is hydrogen, halogen or $C_1$-$C_4$-alkoxy;
R3 is selected from the group consisting of hydrogen, oxo, hydroxyl, $C_1$-$C_4$-alkoxy, —O—CO—$C_1$-$C_4$-alkyl, and $C_1$-$C_4$-alkylthio;
R4 is selected from the group consisting of hydrogen, halogen, carbonyl, —CO—$C_1$-$C_4$-alkyl,
R5 is selected from the group consisting of hydrogen, -COOH, benzyl, $C_1$-$C_4$-alkyl, and $C_1$-$C_4$-alkyl substituted with —COOR', wherein R' represents H or $C_1$-$C_4$-alkyl; and
R6 is selected from the group consisting of hydrogen, bromo, hydroxyl, benzyl, $C_1$-$C_4$-alkyl, and $C_1$-$C_4$-alkyl substituted with —COOR', wherein R' represents H or $C_1$-$C_4$-alkyl.

34. A compound according to claim 33, wherein R2 is a residue of formula (II)

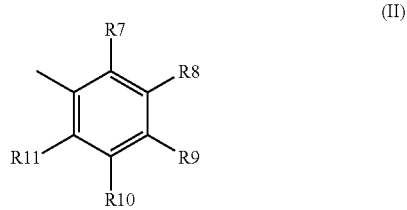

(II)

wherein
R7 is hydrogen, bromo, chioro, or fluoro,
R8 is hydrogen, $C_1$-$C_4$-alkoxy, or hydroxyl,
R9 is hydrogen, $C_1$-$C_4$-alkoxy, or hydroxyl,
R10 is hydrogen, $C_1$-$C_4$-alkoxy, or hydroxyl,
R11 is hydrogen.

35. A compound according to claim 33, wherein
R1 is selected from the group consisting of isobutyl, 3-methylbutyl, benzyl, tetrahydrofurylmethyl, furylmethyl, 5-bromo-furan-2-ylmethyl, 5-bromo-2-methoxybenzyl, thiophene-2-carboxylic acid ethyl ester, and methoxyethyl;
R2 is selected from the group consisting of methoxyphenyl, trimethoxyphenyl, 2-bromo-3,4,5-trimethoxyphenyl, 2-chloro-3,4,5-trimethoxyphenyl, thienyl, and propyl;
R3 is selected from the group consisting of hydroxyl, oxo, —O—CO—$CH_3$, and —S-ethyl;
R4 is selected from the group consisting of hydrogen, bromo and carbonyl;
R5 is hydrogen, benzyl or $C_1$-$C_4$-alkyl, and
R6 is hydrogen, halogen, benzyl or $C_1$-$C_4$-alkyl.

36. A compound according to claim 6, wherein X represents S.

37. A method of treating or inhibiting a steroid hormone dependent disease or disorder selected from the group consisting of breast cancer, prostate carcinoma, ovarian cancer, uterine cancer, endometrial cancer, endometrial hyperplasia, endometriosis, uterine fibroids, uterine leiomyoma, adenomyosis, dysmenorrhea, menorrhagia, metrorrhagia, prostadyna, benign prostatic hyperplasia, prostatitis, acne, seborrhoea, hirsutism, androgenic alopecia, precocious puberty, adrenal hyperplasia, polycystic ovarian syndrome and osteoporosis, said method comprising administering to a patient in need thereof an effective amount of a compound according to claim 6.

38. A pharmaceutical composition comprising a compound according to claim 3 and at least one pharmaceutically acceptable carrier or adjuvant.

39. A method for reducing the fertility of a male, said method comprising administering to a patient an effective amount of a compound according to claim 6.

40. A pharmaceutical composition comprising a compound according to claim 6 and at least one pharmaceutically acceptable carrier or adjuvant.

* * * * *